United States Patent
Williams et al.

(10) Patent No.: US 10,138,255 B2
(45) Date of Patent: Nov. 27, 2018

(54) PIPERAZINE DERIVATIVES AS HIV PROTEASE INHIBITORS

(71) Applicants: Merck Sharp & Dohme Corp., Rahway, NJ (US); MSD R&D (China) Co., Ltd., Shanghai (CN)

(72) Inventors: Peter D. Williams, Harleysville, PA (US); John A. McCauley, Maple Glen, PA (US); Christopher J. Bungard, Lansdale, PA (US); David Jonathan Bennett, Winchester, MA (US); Sherman T. Waddell, Westfield, NJ (US); Gregori J. Morriello, Randolph, NJ (US); Lehua Chang, Ramsey, NJ (US); Michael P. Dwyer, Scotch Plains, NJ (US); M. Katharine Holloway, Lansdale, PA (US); Alejandro Crespo, Edison, NJ (US); Xin-Jie Chu, Shanghai (CN); Catherine Wiscount, Allentown, PA (US); H. Marie Loughran, Perkasie, PA (US); Jesse J. Manikowski, Norristown, PA (US); Jurgen Schulz, Motherwell (GB); Kartik M. Keertikar, East Windsor, NJ (US); Bin Hu, Shanghai (CN); Bin Zhong, Shanghai (CN); Tao Ji, Shanghai (CN)

(73) Assignees: Merck Sharp & Dohme Corp., Rahway, NJ (US); MSD R&D (China) Co., Ltd., Shanghai (CN)

( * ) Notice: Subject to any disclaimer, the term of this patent is extended or adjusted under 35 U.S.C. 154(b) by 0 days.

(21) Appl. No.: 15/124,635

(22) PCT Filed: Mar. 6, 2015

(86) PCT No.: PCT/US2015/019083
§ 371 (c)(1),
(2) Date: Sep. 8, 2016

(87) PCT Pub. No.: WO2015/138220
PCT Pub. Date: Sep. 17, 2015

(65) Prior Publication Data
US 2017/0073354 A1 Mar. 16, 2017

Related U.S. Application Data

(60) Provisional application No. 62/001,281, filed on May 21, 2014.

(30) Foreign Application Priority Data

Mar. 10, 2014 (WO) .............. PCT/CN2014/000227

(51) Int. Cl.
*A61K 31/554* (2006.01)
*C07D 513/08* (2006.01)
*A61K 45/06* (2006.01)

(52) U.S. Cl.
CPC .......... *C07D 513/08* (2013.01); *A61K 31/554* (2013.01); *A61K 45/06* (2013.01)

(58) Field of Classification Search
CPC ........................... A61K 31/554; C07D 513/08
USPC ....................................... 514/211.1; 540/552
See application file for complete search history.

(56) References Cited

U.S. PATENT DOCUMENTS

| | | | |
|---|---|---|---|
| 5,196,438 A | 3/1993 | Martin et al. | |
| 5,413,999 A | 5/1995 | Vacca et al. | |
| 5,484,801 A | 1/1996 | Al-Razzak et al. | |
| 5,484,926 A | 1/1996 | Dressman et al. | |
| 5,506,355 A | 4/1996 | Jadhav et al. | |
| 5,650,412 A | 7/1997 | Kim et al. | |
| 5,852,195 A | 12/1998 | Romines et al. | |
| 5,858,397 A | 1/1999 | Lim et al. | |
| 7,112,683 B2 | 9/2006 | Bertenshaw et al. | |

(Continued)

FOREIGN PATENT DOCUMENTS

| | | |
|---|---|---|
| IN | 960DEL2010 | 10/2012 |
| WO | 200138332 A1 | 5/2001 |

(Continued)

OTHER PUBLICATIONS

Daniel E. Patterson, et al, "Developement of a Practical Large-Scale Synthesis of Denagliptin Tosylate", Organic Process Research & Dev., 2009, pp. 900-906, vol. 13.

(Continued)

*Primary Examiner* — Brenda L Coleman
(74) *Attorney, Agent, or Firm* — Carol S. Quagliato; John C. Todaro

(57) ABSTRACT

The present invention is directed to compounds of Formula I pharmaceutical compositions comprising the same, and their use in the inhibition of HIV protease, the inhibition of HIV replication, the prophylaxis of infection by HIV, the treatment of infection by HIV, and the prophylaxis, treatment, and delay in the onset or progression of AIDS.

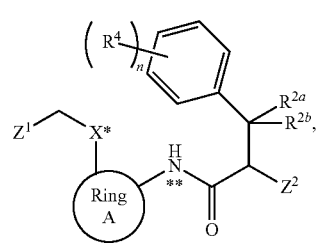

19 Claims, No Drawings

(56) References Cited

U.S. PATENT DOCUMENTS

| | | |
|---|---|---|
| 7,273,863 B1 | 9/2007 | Andrews, III et al. |
| 8,497,383 B2 | 7/2013 | Coburn et al. |
| 9,315,475 B2 | 4/2016 | Beaulieu et al. |
| 2004/0147512 A1 | 7/2004 | Konradi et al. |
| 2005/0203093 A1 | 9/2005 | Konradi et al. |
| 2014/0018325 A1 | 1/2014 | Boyd et al. |
| 2014/0018326 A1 | 1/2014 | Moradei et al. |
| 2014/0303171 A1 | 10/2014 | Boyd et al. |

FOREIGN PATENT DOCUMENTS

| | | |
|---|---|---|
| WO | 200230930 A2 | 4/2002 |
| WO | 2006130426 A2 | 12/2006 |
| WO | 2009042093 A2 | 4/2009 |
| WO | 2009042094 A2 | 4/2009 |
| WO | 2012030685 A2 | 3/2012 |
| WO | 2015017393 A2 | 2/2015 |
| WO | 2015095265 A1 | 6/2015 |
| WO | 2015095276 A1 | 6/2015 |
| WO | 2015134366 A1 | 9/2015 |

OTHER PUBLICATIONS

Hiroyuki Toh, et al, "Lose Structural Resemblance Between Putative Polymerase of a *Drosophila* Transposable Genetic Element 17.5 and Pol Gene Product of Moloney Murine Leukaemia Virus", The EMBO Journal, 1985, pp. 1267-1272, vol. 4, No. 5.

J.P. Vacca, et al, "L-735,524: An Orally Bioavailable Human Immunodeficiency Virus Type 1 Protease Inhibitor", Proc. Natl. Acad. Sci., Apr. 1994, pp. 4096-4100, vol. 91.

Laurence H. Pearl, et al, "A Structural Model for the Retroviral Proteases", Nature, 1987, pp. 351-354, vol. 329.

Lee Ratner, et al, Complete Nucleotide Sequence of AIDS Virus, HTLV-III, Nature, 1985, pp. 277-284, vol. 313.

Michael D. Power, et al, "Nucleotide Sequence of SRV-1, a Type D Simian", Science, 1986, pp. 1567-1572, vol. 231.

Nancy E. Kohl., et al, "Active Human Immunodeficiency Virus Protease Is Required for Viral Infectivity", Proc. Natl. Acad. Sci., 1988, pp. 4686-4690, vol. 85.

Roy M. Gulick, et al, "Treatment With Indinavir, Zidovudine, and Lamivudine in Adults With Human Immunodeficiency Virus Infection and Prior Antiretroviral Therapy", New England Journal of Medicine, 1997, pp. 734-739, vol. 337.

Scott M. Hammer, et al, "A Controlled Trial of Two Nucleoside Analogues Plus Indinavir in Persons With Human Immunodeficiency Virus Infection and CD4 Cell Counts of 200 Per Cubic Millimeter or Less", The New England Journal of Medicine, 1997, pp. 725-733, vol. 337, No. 11.

PIPERAZINE DERIVATIVES AS HIV PROTEASE INHIBITORS

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., *Proc. Nat'l Acad. Sci.* 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, an endonuclease, HIV protease and gag, which encodes the core proteins of the virion (Toh et al., *EMBO J.* 1985, 4: 1267; Power et al., *Science* 1986, 231: 1567; Pearl et al., *Nature* 1987, 329: 351].

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

There is a continuing need for new compounds which are capable of inhibiting HIV protease and suitable for use in the treatment or prophylaxis of infection by HIV and/or for the treatment or prophylaxis or delay in the onset or progression of AIDS.

SUMMARY OF THE INVENTION

The present invention is directed to piperazine derivatives, pharmaceutical compositions comprising the same, and their use in the inhibition of HIV protease, the inhibition of HIV replication, the prophylaxis of infection by HIV, the treatment of infection by HIV, and the prophylaxis, treatment, and delay in the onset or progression of AIDS.

DETAILED DESCRIPTION OF THE INVENTION

The invention encompasses compounds of structural Formula I

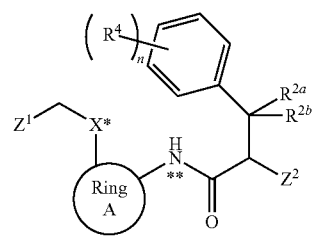

or a pharmaceutically acceptable salt thereof, wherein:
X is O or $CH_2$;
Ring A is

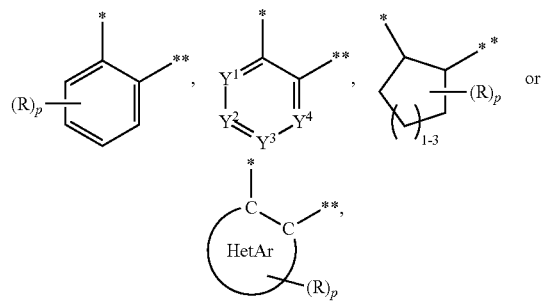

wherein * indicates the point of attachment to X* in Formula I and  indicates the point of attachment to N in Formula I;
one, two or three of $Y^1$, $Y^2$, $Y^3$ and $Y^4$ are N and the others are C(R);
HetAr is:
  (a) a 5-membered (including the two carbons that are the points of attachment to X and N in Formula I) monocyclic heteroaromatic ring containing from 1 to 3 heteroatoms independently selected from N, O and S, or
  (b) a 9-, 10- or 11-membered (including the two carbons that are the points of attachment to X* and N** in Formula I) bicyclic heteroaromatic ring system containing from 1 to 4 heteroatoms independently selected from N, O and S;
p is an integer selected from 1, 2 or 3;
R is independently selected at each occurrence from
  (a) —H,
  (b) halo, —OH, —SH, —CN, —$NO_2$, or —N($R^{3a}$)$_2$,
  (c) —$C_{1-6}$alkyl unsubstituted or substituted with (i) 1 to 6 of F, or (ii) —OH, —C(O)O$C_{1-6}$alkyl, —O—$C_{1-6}$alkyl or —O—$C_{1-3}$alkyl-phenyl,
  (d) —O—$C_{1-6}$alkyl unsubstituted or substituted with (i) 1 to 6 of F, or (ii) —OH, —C(O)O$C_{1-6}$alkyl, —O—$C_{1-6}$alkyl or —O—$C_{1-3}$alkyl-phenyl, (e) —C$_{1-6}$alkyl-O—C$_{1-3}$alkyl unsubstituted or substituted with 1 to 6 of —F,
(f) —C(O)OC$_{1-6}$alkyl unsubstituted or substituted with 1-6 of —F, or
(g) —C(O)C$_{1-6}$alkyl unsubstituted or substituted with 1-6 of —F;

Z$^1$ is

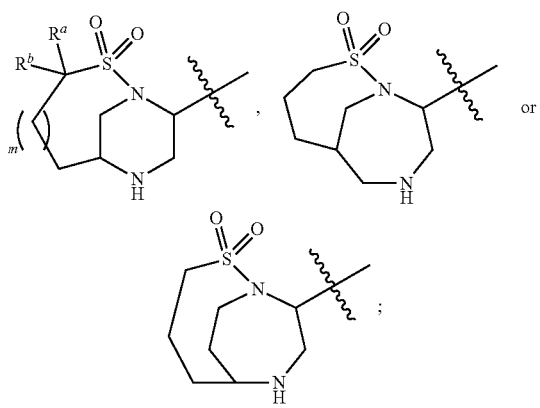

R$^a$ and R$^b$ are independently selected from —H and —C$_{1-3}$alkyl;
R$^c$ is —C$_{1-3}$alkyl or —C$_{3-6}$cyclolkyl and R$^c$ is unsubstituted or substituted with 1-3 of —F;
R$^d$ is —C$_{1-6}$alkyl unsubstituted or substituted with 1-6 of —F or —C$_{3-6}$cyclolkyl unsubstituted or substituted with 1-3 of —F;
m is an integer selected from 0 (zero), 1 or 2;
Z$^2$ is —H or —NHR$_3$;
R$^{2a}$ is
(a) —C$_{1-6}$alkyl unsubstituted or substituted with one to four substituents independently selected at each occurrence from halo; —OH; —C$_{1-6}$alkyl unsubstituted or substituted with 1-3 of —F; or —OR$^c$;
(b) —C$_{3-6}$cycloalkyl unsubstituted or substituted with one to four substituents independently selected at each occurrence from halo; —OH; —C$_{1-6}$alkyl unsubstituted or substituted with 1-6 of —F; —C$_{1-3}$alkyl-OR$^c$; —OR$^d$; —COOH; or —C(O)OR$^d$;
(c) phenyl unsubstituted or substituted with one to four substituents independently selected at each occurrence from halo; —OH; —C$_{1-6}$alkyl unsubstituted or substituted with 1-6 of —F; —C$_{1-3}$alkyl-O—R$^c$; —OR$^d$; —COOH; —C(O)OR$^d$; or C$_{3-6}$cycloalkyl unsubstituted or substituted with 1-3 of —F;
(d)

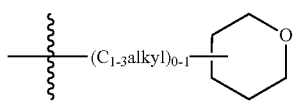

wherein the tetrahydropyran is unsubstituted or substituted with one to four substituents independently selected at each occurrence from halo —OH; —C$_{1-6}$alkyl unsubstituted or substituted with 1-6 of —F; or —OC$_{1-6}$alkyl unsubstituted or substituted with 1-6 of —F;
(e) pyridinyl unsubstituted or substituted with one to four substituents independently selected at each occurrence from
(i) halo, (ii) —OH,
(iii) —C$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$alkyl-phenyl,
(iv) —OC$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$alkyl-phenyl,
(v) —C$_{1-6}$alkyl-O—C$_{1-3}$alkyl unsubstituted or substituted with 1 to 6 of —F,
(vi) =O (oxo),
(vii) —C(O)OC$_{1-6}$alkyl optionally substituted with 1-6 of —F, or
(viii) —C(O)C$_{1-6}$alkyl optionally substituted with 1-6 of —F;
(f) pyrimidinyl, unsubstituted or substituted with one to four substituents independently selected at each occurrence from
(i) halo, (ii) —OH,
(iii) —C$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$alkyl-phenyl,
(iv) —OC$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$alkyl-phenyl,
(v) —C$_{1-6}$alkyl-O—C$_{1-3}$alkyl unsubstituted or substituted with 1 to 6 of —F,
(vi) =O (oxo),
(vii) —C(O)OC$_{1-6}$alkyl optionally substituted with 1-6 of —F, or
(viii) —C(O)C$_{1-6}$alkyl optionally substituted with 1-6 of —F;
(g)

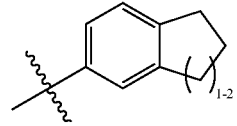

unsubstituted or substituted with one to four substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C$_{3-6}$cycloalkyl unsubstituted or substituted with 1-3 of —F;
(h)

(i) morpholinyl;
(j) piperidinyl, unsubstituted or substituted with one to four substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C(O)OR$^1$;
(k) pyrazinyl, unsubstituted or substituted with one to four substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C(O)OR$^1$;

(l) thiazolyl, unsubstituted or substituted with one to three substituents independently selected at each occurrence from halo; —OH; —$C_{1-6}$alkyl unsubstituted or substituted with 1-6 of —F; —O$C_{1-6}$alkyl unsubstituted or substituted with 1-6 of —F; or —C(O)O$R^1$;

(m) pyrazolyl, unsubstituted or substituted halo; —OH; —$C_{1-6}$alkyl unsubstituted or substituted with 1-6 of —F; —O$C_{1-6}$alkyl unsubstituted or substituted with 1-6 of —F; or —C(O)O$R^1$; or (n)

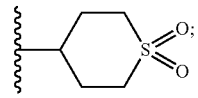

$R^1$ is (i) —$C_{1-6}$alkyl unsubstituted or substituted with 1-6 of —F, phenyl or —$C_{3-6}$cycloalkyl, or (ii) —S(O)$_2$—$C_{1-6}$alkyl;

$R^{2b}$ is —H, —$C_{1-6}$alkyl or —O$C_{1-6}$alkyl, wherein each of —$C_{1-6}$alkyl or —O$C_{1-6}$alkyl is unsubstituted or substituted with 1 to 3 substituents independently selected from halo, —OH, or —O$C_{1-6}$alkyl;

or $R^{2a}$ and $R^{2b}$ are joined together with the carbon to which they are both attached to form (a) —$C_{3-6}$cycloalkyl, (b) piperidinyl, or (c) tetrahydro-(2H)-furanyl;
  wherein each of cycloalkyl, piperidinyl and tetrahydro-(2H)-furan is unsubstituted or substituted with one to four substituents independently selected at each occurrence from halo; —OH; —$C_{1-6}$alkyl unsubstituted or substituted with 1-6 of —F; —O$C_{1-6}$alkyl unsubstituted or substituted with 1-6 of —F; or —COO$C_{1-3}$alkyl unsubstituted or substituted with 1-6 of —F;

$R^3$ and $R^{3a}$ are independently selected at each occurrence from
(a) —H,
(b) —$C_{1-6}$alkyl unsubstituted or substituted with (i) 1 to 6 of —F, (ii) —OH, (iii) —C(O)O$C_{1-3}$alkyl, (iv) —O—$C_{1-3}$alkyl, or (v) —O—$C_{1-3}$alkyl-phenyl,
(c) —C(O)O$C_{1-6}$alkyl unsubstituted or substituted with (i) 1-6 of —F, (ii) —$C_{3-6}$cycloalkyl or (iii) —NH$_2$, or
(d) —C(O)$C_{1-6}$alkyl unsubstituted or substituted with (i) 1-6 of —F, (ii) —$C_{3-6}$cycloalkyl or (iii) —NH$_2$;

n is an integer selected from 1, 2 or 3;

$R^4$ is independently selected at each occurrence from:
(a) —H, —OH, halo, —CN, —$C_{1-6}$alkyl, —O—$C_{1-6}$alkyl, —$C_{3-6}$cycloalkyl, —O—$C_{3-6}$cycloalkyl, —$C_{2-6}$alkenyl-S$R^5$, —S—$C_{3-6}$cycloalkyl, —SO$_2R^5$, —N($R^5$)$_2$, —N(H)C(O)—$C_{1-6}$alkyl, —C(O)O$R^5$, —C(O)—$C_{1-6}$alkyl, —$C_{1-6}$haloalkyl, —O—$C_{1-6}$haloalkyl, —S—$C_{1-6}$haloalkyl, —NO$_2$, —N(H)CH(O), —CH(O), —C(O)N($R^5$)$_2$, —C(O)N(H)C(O)$R^5$, or trimethylsilyl,
(b) phenyl, benzyl or phenoxy, each being unsubstituted or substituted with 1 to 5 substituents selected from halogen and, —OH, halo, —CN, —$C_{1-6}$alkyl, —$C_{1-6}$haloalkyl, —O—$C_{1-6}$alkyl, —O—$C_{1-6}$haloalkyl, —S—$C_{1-6}$haloalkyl, —NO$_2$, —SO$_2R^5$, —N($R^5$)$_2$, —C(O)O$R^5$, or —C(O)—$C_{1-6}$alkyl, or
(c) HetA, —O-HetA or —CH$_2$-HetA, optionally substituted with 1 to 5 substituents selected from halogen and $C_{1-6}$alkyl;

wherein —$C_{1-6}$ alkyl when present within any $R^4$ group is unsubstituted or substituted with 1-6 substituents independently selected at each occurrence from:

-halo, —CF$_3$, —CN, —NO$_2$, —OH, —O—$C_{1-6}$alkyl, —O—$C_{1-6}$haloalkyl, —O—$C_{3-6}$cycloalkyl, —S$R^5$, —N($R^5$)$_2$, —C(O)—$C_{1-6}$alkyl, —C(O)O$R^5$, or —SO$_2$—$C_{1-6}$alkyl;

$R^5$ is independently selected at each occurence from —H and $C_{1-6}$alkyl; and HetA is independently selected from (i) a 5- or 6-membered monocyclic heteroaromatic ring containing from 1 to 3 heteroatoms independently selected from N, O and S, or (ii) a 9-, 10- or 11-membered bicyclic fused heteroaromatic ring system containing from 1 to 4 heteroatoms independently selected from N, O and S.

In another embodiment of this invention are compounds of Formula I having structural Formula II, or the pharmaceutically acceptable salts thereof, wherein Ring A is

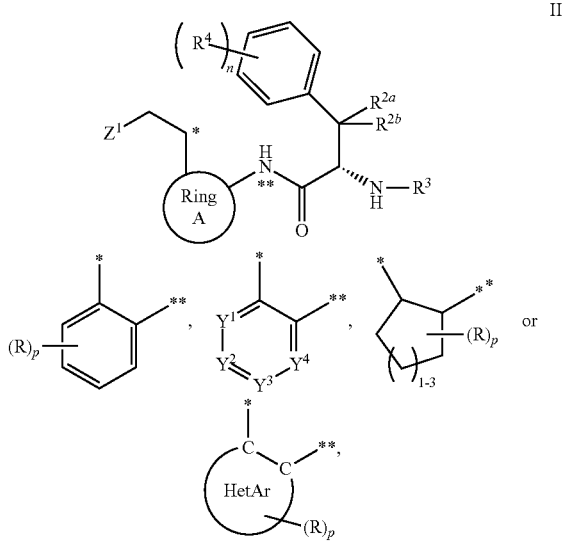

wherein * indicates the point of attachment to C* in Formula II and  indicates the point of attachment to N in Formula II; and the remaining variables in Formula II, e.g., $Z^1$, $R^{2a}$, $R^{2b}$, $R^3$, $R^4$, and all additional variables therein, are defined as in Formula I.

In another embodiment of this invention are compounds of Formula I or II having structural Formula III, or the pharmaceutically acceptable salts thereof,

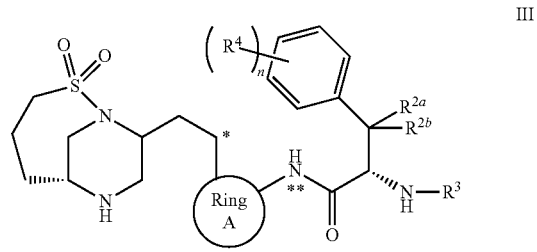

wherein Ring A is as defined in Formula I or II, and the remaining variables in Formula III, e.g., $R^{2a}$, $R^{2b}$, $R^3$, $R^4$, and all additional variables therein, are defined as in Formula I.

In another embodiment of this invention, referred to herein as Embodiment A, are compounds of Formula I, Formula II or Formula III, or the pharmaceutically acceptable salts thereof, wherein:

Ring A is

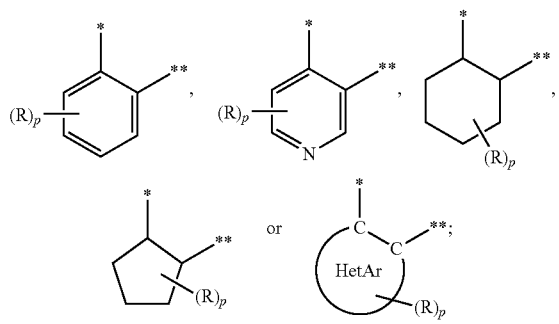

and R and p are as defined in Formula I.

In another embodiment of this invention, referred to herein as Embodiment B, are compounds of Formula I, Formula II, Formula III or Embodiment A, or the pharmaceutically acceptable salts thereof, wherein:

p is 1, 2 or 3, or more particularly p is 1 or 2;

R is independently selected at each occurrence from H, halo or —$C_{1-6}$alkyl substituted with 1 to 6 of —F; or p is particularly —H, halo or —$C_{1-3}$alkyl substituted with 1 to 3 of —F; and more particularly p is —H, —F or —$CF_3$;

HetAr is defined as in Formula I, or particularly HetAr is a 5-membered monocyclic heteroaromatic ring containing from 1 to 3 heteroatoms independently selected from N, O and S, and more particularly wherein HetAr is:

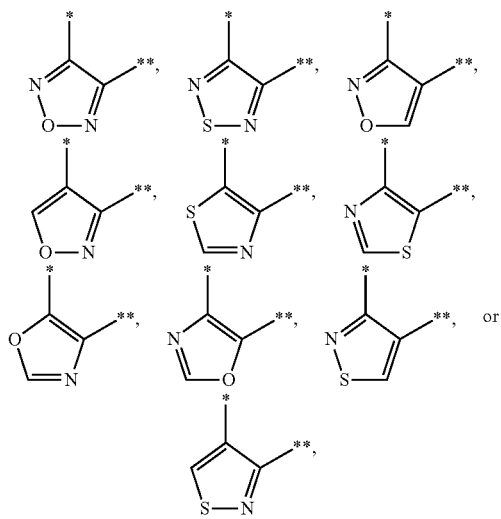

wherein the ring is unsubstituted or susbtituted with R;

$R^{2a}$ is as defined in Formula I, or particularly it is (a) —$C_{1-6}$alkyl unsubstituted or substituted, and particularly it is —$C_{1-3}$alkyl unsubstituted or substituted, wherein the susbtituents are independently selected at each occurrence from one or two of halo (particularly —F); —OH; —$C_{1-3}$alkyl unsubstituted or substituted with 1-3 of —F; or —$OC_{1-3}$alkyl unsubstituted or substituted with 1-3 of —F;

(b) —$C_{3-6}$cycloalkyl unsubstituted or substituted with one or two substituents independently selected at each occurrence from one or two of halo (particularly —Cl or —F); —OH; —$C_{1-3}$alkyl unsubstituted or substituted with 1-3 of —F; or —$OC_{1-3}$alkyl unsubstituted or substituted with 1-3 of —F;

(c) phenyl unsubstituted or substituted with one or two substituents independently selected at each occurrence from halo (particularly —F); —OH; —$C_{1-3}$alkyl unsubstituted or substituted with 1-3 of —F; or —$OC_{1-3}$alkyl unsubstituted or substituted with 1-3 of —F;

(d)

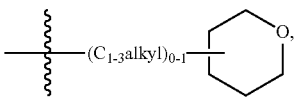

and particularly

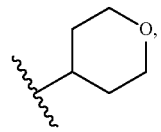 [SMILES: *C1CCOCC1]

wherein the tetrahydropyran is unsubstituted or substituted with one or two substituents independently selected at each occurrence from halo (particularly —F); —OH; —$C_{1-3}$alkyl unsubstituted or substituted with 1-3 of —F; or —$OC_{1-3}$alkyl unsubstituted or substituted with 1-3 of —F;

(e) pyridinyl unsubstituted or substituted with one or two substituents independently selected at each occurrence from halo (particularly —F); —OH; —$C_{1-3}$alkyl unsubstituted or substituted with 1-3 of —F; or —$OC_{1-3}$alkyl unsubstituted or substituted with 1-3 of —F;

(f) pyrimidinyl unsubstituted or substituted with one or two substituents independently selected at each occurrence from halo (particularly —F); —OH; —$C_{1-3}$alkyl unsubstituted or substituted with 1-3 of —F; or —$OC_{1-3}$alkyl unsubstituted or substituted with 1-3 of —F; or (g)

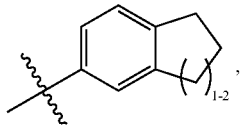

and particularly

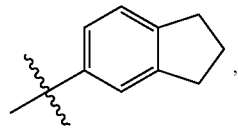

unsubstituted or substituted with one or two substituents independently selected at each occurrence from halo (particularly —F); —OH; —$C_{1-3}$alkyl unsubstituted or substituted with 1-3 of —F; or —$OC_{1-3}$alkyl unsubstituted or substituted with 1-3 of —F;

$R^{2b}$ is as defined in Formula I, or particularly it is —H;

or $R^{2a}$ and $R^{2b}$ are joined together with the carbon to which they are both attached and defined as in Formula I, or particularly together they form cyclohexyl or piperidinyl, wherein each is unsubstituted or substituted with one or two substituents independently selected at each occurrence from halo (particularly —F); OH; —C$_{1-3}$ alkyl unsubstituted or substituted with 1-3 of —F; —OC$_{1-3}$ alkyl unsubstituted or substituted with 1-3 of —F; or —C(O)OC$_{1-3}$alkyl unsubstituted or substituted with 1-3 of —F;

R$^3$ is as defined in Formula I, or particularly it is —H or —C(O)OC$_{1-3}$alkyl;

R$^4$ and n are as defined in Formula I, or particularly n is 1 or 2 and R$^4$ is independently selected at each occurrence from halo, particularly —F or —Cl; and more particularly one of the one or two halo substituents is at the para position on the phenyl to which it is attached; and R$^5$ is independently selected at each occurence from —H and —C$_{1-6}$ alkyl.

In another embodiment of this invention are compounds of Formula I, II or III or Embodiment A or Embodiment B, wherein Ring A is unsubstituted or substituted and is selected from

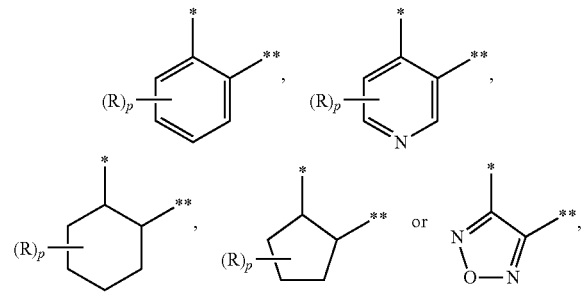

and more particularly it is

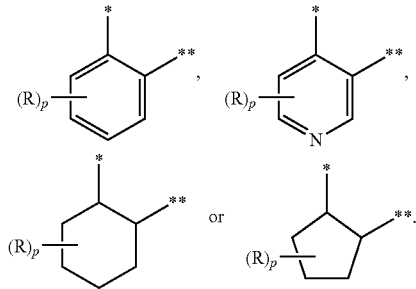

In another embodiment Ring A is

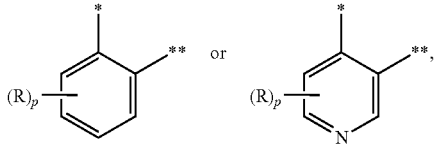

and more particularly it is

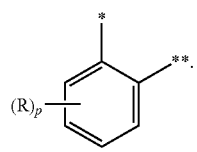

In another embodiment Ring A is

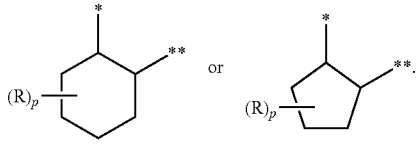

In each embodiment, p is 1 to 3 and more particularly p is 1 to 2; and R is independently selected at each occurrence from —H, halo and —C$_{1-6}$alkyl substituted with 1 to 6 of —F, particularly R is —H, halo or —C$_{1-3}$alkyl substituted with 1 to 3 of —F, and more particularly R is —H, —F or —CF$_3$.

In another embodiment of this invention are compounds of Formula I, II or III or Embodiment A or Embodiment B, wherein HetAr is a 5-membered monocyclic heteroaromatic ring containing from 1 to 3 heteroatoms independently selected from N, O and S; and particularly HetAr is

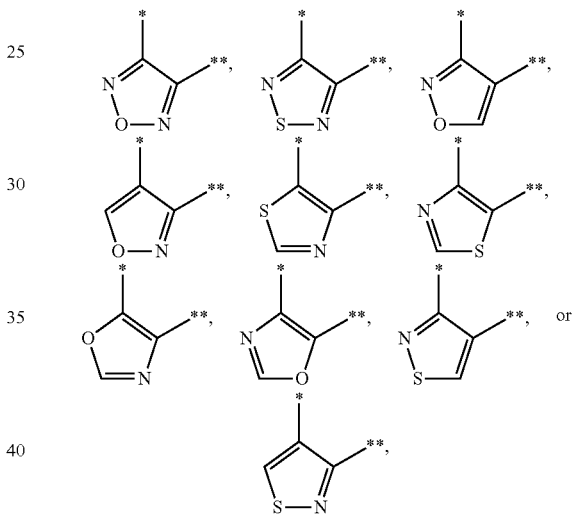

wherein the ring is unsubstituted or susbtituted with R; and more particularly HetAr is

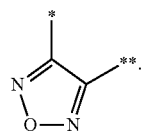

In another embodiment of this invention are compounds of Formula I or II or Embodiment A or Embodiment B, wherein Z$^1$ is

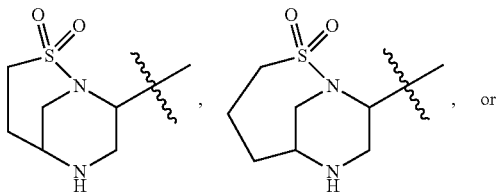

-continued

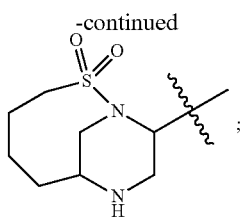

and particularly it is

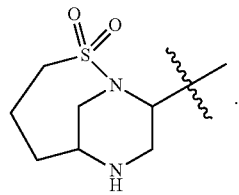 [SMILES: *C1CNC2CCCS(=O)(=O)N1C2]

In another embodiment of this invention are compounds of Formula I or II or Embodiment A or Embodiment B, wherein $R^a$ and $R^b$ are each —H or —CH$_3$, or particularly $R^a$ and $R^b$ are each —H.

In another embodiment of this invention are compounds of Formula I, II or III or Embodiment A or Embodiment B, wherein $Z^2$ is —NHR$^3$, and particularly it is NH$_2$ or —NHC(O)C$_{1-6}$alkyl.

In another embodiment of this invention are compounds of Formula I, II or III or Embodiment A or Embodiment B wherein R$^3$ is:
(a) —H, (b) —C$_{1-6}$alkyl unsubstituted or substituted with (i) —OH, (ii) 1 to 3 of —F, (iii) —C(O)OC$_{1-3}$alkyl, (iv) —O—C$_{1-3}$alkyl or (v) —O—C$_{1-3}$alkyl-phenyl;
(c) —C(O)OC$_{1-3}$alkyl unsubstituted or substituted with with 1-3 of —F or —C$_{3-6}$cycloalkyl; or
(d) —C(O)C$_{1-3}$alkyl unsubstituted or substituted with 1-3 of —F or —NH$_2$.
Particularly R$^3$ is —H or —C(O)OC$_{1-6}$alkyl, and particularly it is —H or —C(O)OCH$_3$.

In another embodiment of this invention are compounds of Formula I, II or III or Embodiment A or Embodiment B, wherein R$^{2a}$ is:
(a) —C$_{1-6}$alkyl, (b) —C$_{3-6}$cycloalkyl, (c) phenyl, (d)

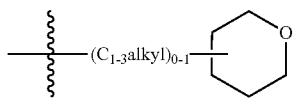

and particularly

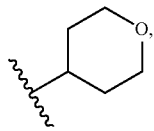 [SMILES: *C1CCOCC1]

(e) pyridinyl, (f) pyrimidinyl or
(g)

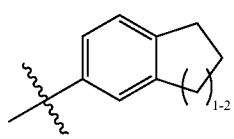

and particularly

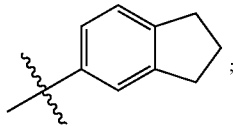 [SMILES: *c1ccc2c(c1)CCC2]

wherein each group is unsubstituted or substituted with one or two substituents as defined in Formula I or Embodiment B.

In another embodiment of this invention are compounds of Formula I, II or III or Embodiment A or Embodiment B, wherein R$^{2b}$ is —H, —C$_{1-3}$alkyl or —OC$_{1-3}$alkyl wherein each of —C$_{1-3}$alkyl or —OC$_{1-3}$alkyl is unsubstituted or substituted with 1 to 3 substituents independently selected from halo, —OH, or —OC$_{1-6}$alkyl, and particularly R$^{2b}$ is —H.

In another embodiment of this invention are compounds of Formula I, II or III or Embodiment A or Embodiment B, wherein R$^{2a}$ and R$^{2b}$ are joined together with the carbon to which they are both attached to form (a) cyclohexyl, (b) piperidinyl, or (c) tetrahydro-(2H)-furan; wherein each group is unsubstituted or substituted with one or two substituents independently selected at each occurrence from halo (particularly —F); —OH; —C$_{1-3}$alkyl unsubstituted or substituted with 1-3 of —F; —OC$_{1-3}$alkyl unsubstituted or substituted with 1-3 of —F; or —C(O)OC$_{1-3}$alkyl unsubstituted or substituted with 1-3 of —F.

In another embodiment of this invention are compounds of Formula I, II or III or Embodiment A or Embodiment B, wherein n is 1 to 3, and R$^4$ is independently selected at each occurrence from halo, and more particularly from —F or —Cl. It is preferred for at least one R$^4$ to be halo (preferably —F or —Cl) at the 4- (i.e., para) position on the phenyl to which it is attached, i.e.,

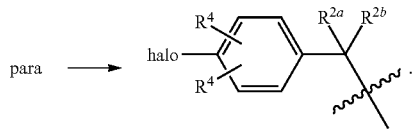

In another embodiment of this invention are compounds of Formula I wherein X is CH$_2$.

In another embodiment of this invention are compounds of Formula I, II or III having structural Formula IV, or a pharmaceutically acceptable salt thereof,

IV

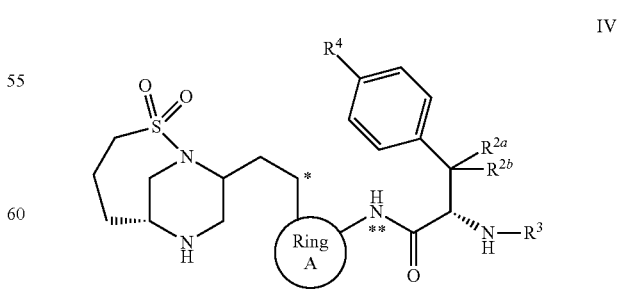

wherein R$^{2a}$ is:
(a) —C$_{1-4}$alkyl unsubstituted or substituted with (a) 1 to 3 of —F, (b) —OH or —OC$_{1-3}$alkyl;

(b) cyclohexyl unsubstituted or substituted with (a) 1 to 3 of F, or (b) —OH or —OC$_{1-3}$alkyl;

(c) phenyl unsubstituted or substituted with 1 to 2 of halo, and particularly 1 to 2 of —F (d) pyridyl unsubstituted or substituted with —F, —OC$_{1-3}$ alkyl, —C$_{1-3}$alkyl substituted with 1-3 of —F, and particularly it is substituted with —OCH(CH$_3$)$_2$, —CF$_2$CH$_3$ or —CF$_3$; or (e)

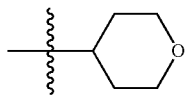

unsubstituted or substituted with 1 to 3 of —C$_{1-3}$alkyl;

R$^{2b}$ is —H;

or R$^{2a}$ and R$^{2b}$ are joined together with the carbon to which they are both attached to form cyclohexyl unsubstituted or substituted with —OC$_{1-3}$alkyl;

R$^3$ is —H or —C(O)OC$_{1-3}$ alkyl;

R$^4$ is —F or —Cl; and

Ring A is (a) cyclohexyl, (b) phenyl substituted with 1-2 of —F, or (c) pyridyl substituted with F.

All structural Formulas, embodiments and classes thereof described herein include the pharmaceutically acceptable salts of the compounds defined therein. Reference to the compounds of Formula I herein encompasses the compounds of Formulas I, II, and III and all embodiments and classes thereof. Reference to the compounds of this invention as those of a specific formula or embodiment, e.g., Formula I, II, and III or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise The present invention includes each of the Examples desribed herein, and pharmaceutically acceptable salts thereof. The invention also encompasses pharmaceutical compositions comprising an effective amount of a compound of the invention or a pharmaceutically acceptable salt thereof, and a pharmaceutically acceptable carrier.

As used herein, the term "alkyl" refers to a straight or branched chain, saturated aliphatic hydrocarbon radical having a number of carbon atoms in the specified range. Thus, for example, "—C$_{1-6}$ alkyl" (or "—C$_1$-C$_6$ alkyl") means linear or branched chain alkyl groups, including all isomers, having the specified number of carbon atoms and includes each of the hexyl and pentyl isomers as well as each of n-, iso-, sec- and tert-butyl (butyl, s-butyl, i-butyl, t-butyl; Bu=butyl), n- and i-propyl (Pr=propyl), ethyl (Et) and methyl (Me). As another example, "—C$_{1-4}$ alkyl" refers to each of n-, iso-, sec- and t-butyl; n- and iso-propyl; ethyl and methyl. As another example, "—C$_{1-3}$ alkyl" refers to each of n-propyl, iso-propyl, ethyl and methyl. An alkyl group, when viewed in context within a chemical structure, may be univalent (e.g., when R$^{2a}$ is unsubstituted —C$_{1-6}$alkyl), bivalent (e.g., when R$^{2a}$ is mono-substituted —C$_{1-6}$alkyl), or multi-valent (e.g., when R$^{2a}$ is —C$_{1-6}$alkyl having two or more substituents).

The term "halogen" (or "halo") refers to fluorine, chlorine, bromine and iodine (alternatively referred to as fluoro, chloro, bromo, and iodo). Fluoro or chloro are preferred.

"Cycloalkyl" is a cyclized alkyl ring having the indicated number of carbon atoms. Thus, for example, "—C$_{3-6}$ cycloalkyl" (or "—C$_3$-C$_6$ cycloalkyl") refers to each of cyclopropyl, cyclobutyl, cyclopentyl, and cyclohexyl.

The term "haloalkyl" refers to an alkyl group as defined above in which one or more of the hydrogen atoms have been replaced (i.e., substituted) with a halogen (i.e., F, Cl, Br and/or I). Thus, for example, "—C$_{1-6}$ haloalkyl" (or "—C$_1$-C$_6$ haloalkyl") refers to a —C$_1$ to C$_6$ linear or branched alkyl group as defined above with one or more halogen substituents; particularly 1-6 halogen substituents; and more particularly 1-3 halogen substituents. The term "fluoroalkyl" has an analogous meaning except that the halogen substituents are restricted to fluoro. Suitable fluoroalkyls include the series —(CH$_2$)$_{0-4}$CF$_3$ (i.e., trifluoromethyl, 2,2,2-trifluoroethyl, 3,3,3-trifluoro-n-propyl, etc.). A fluoroalkyl of particular interest is CF$_3$.

The term "C(O)" refers to carbonyl. The terms "S(O)$_2$" and "SO$_2$" each refer to sulfonyl. The term "S(O)" refers to sulfinyl.

A heteroaromatic ring or ring system means a monoaromatic ring or a bicyclic fused aromatic ring system having the specified number of total atoms and specificed number of heteroatoms in the ring or ring system. A heteroaromatic bicyclic fused ring system includes an aromatic heterocyclic ring fused to an aromatic or partially unsaturated heterocyclic ring, and an aromatic heterocyclic ring fused to a cycloalkyl ring. Suitable 5-membered heteroaromatic rings within the definition of each of HetAr or HetA include, for example, pyrrolyl, pyrazolyl, triazolyl, imidazolyl, furanyl, thienyl, thiazolyl, isothiazolyl, oxazolyl, isooxazolyl, oxadiazolyl including 1,3,4-oxadiazolyl, oxatriazolyl, and thiadiazolyl. Suitable 6-membered heteroaromatic rings within the definition of each of HetA include, for example, pyridyl (also referred to as pyridinyl), pyrimidinyl, pyrazinyl, pyridazinyl, and triazinyl. Suitable 9-, 10- or 11-membered heteroaromatic rings within the definition of HetAr or HetA include, for example, bezimidazolyl, ondolyl, purinyl, quinolinyl, isoquinolinyl, benzofuranyl, 2H-1-benzopyran, and 2-benzofuran-1(3H)-one.

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Each Ring A may be unsubstituted, when all R groups on the ring are H, or substituted, when at least one R group on the ring is not H.

Unless expressly stated to the contrary, all ranges cited herein are inclusive. For example, a heteroaromatic ring described as containing from "1 to 3 heteroatoms" means the ring can contain 1, 2 or 3 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. As another example, a moeity described as optionally substituted with "from 1 to 3 substituents" is intended to include as aspects thereof, such moeity substituted with 1 to 3 substituents, 2 or 3 substituents, 3 substituents, 1 or 2 substituents, 2 substituents, or 1 substituent.

When any variable (e.g., $R^3$ or $R^{3a}$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly depicted or described otherwise, variables depicted in a structural formula with a "floating" bond attached to a ring, such as $R^4$, are permitted to be a substituent on any available carbon or nitrogen atom in the ring to which the variable is attached. When a moiety is noted as being "optionally substituted" in Formula I or any embodiment thereof, it means that Formula I or the embodiment thereof encompasses compounds that are substituted with the noted substituent (or substituents) on the moiety and compounds that do not contain the noted substituent (or substituents) on the moiety (i.e., wherein the moiety is unsubstituted).

Unless expressly stated to the contrary, substitution by a named substituent is permitted on any atom in a chain or ring provided such substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof).

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The compounds of the invention have two or more asymmetric centers and can occur as mixtures of stereoisomers. It is understood that a substantially pure compound can be either a substantially pure mixture of stereoisomers or a substantially pure individual diastereomer or enantiomer. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The invention also encompasses methods for the treatment or prophylaxis of infection by HIV or for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the inhibition of HIV protease, for the treatment or prophylaxis of infection by HIV, or for the treatment, prophylaxis, or delay in the onset of AIDS in a subject in need thereof.

The invention also encompasses a pharmaceutical composition comprising an effective amount of a compound of the invention, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Compounds of Formula II and III each form a subset of the compounds included in Formula I. Any description which follows that refers to a compound of Formula I also applies to a compound of Formula II and III and all embodiments thereof.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c) or (d) or the combination of (e) or (f).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

In general, compounds that are HIV protease inhibitors can be identified as those compounds which, when tested in the "Cell-based HIV Infection Assay using a Reporter" assay described below, have an inflection point (IP) of 10 $\mu$M, particulalry 5 $\mu$M or less, preferably 1 $\mu$M or less, and more preferably 0.25 $\mu$M or less.

The term "administration" and variants thereof (e.g., "administering" a compound) in reference to a compound of Formula I mean providing the compound to the individual in need of treatment or prophylaxis and includes both self-administration and administration to the patient by another person. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" which is an amount effective for inhibiting HIV protease (wild type and/or mutant strains thereof), inhibiting HIV replication (either of the foregoing which may also be referred to herein as an "inhibition effective amount"), treating HIV infection, treating AIDS, delaying the onset of AIDS and/or slowing progression of AIDS. In another embodiment, the effective amount is a "prophylactically effective amount" which is an amount effective for prophylaxis of HIV infection or prophylaxis of AIDS. It is understood that an effective amount can simultaneously be both a therapeutically effective amount, e.g., for treatment HIV infection, and a prophylactically effective amount, e.g., for prevention or reduction of risk of developing AIDS. When the active compound (i.e., active ingredient) is administered as the salt, references to the amount of active ingredient are to the free form (i.e., the non-salt form) of the compound.

In the methods of the present invention (e.g., inhibiting HIV protease, treating or prophylaxis of HIV infection, inhibiting HIV replication, treating or prophylaxis of AIDS, delaying the onset of AIDS, or delaying or slowing progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the follwing routes: orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences,* 18th edition, edited by A. R. Gennaro, Mack Publishing Co., 1990 and in *Remington—The Science and Practice of Pharmacy,* 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given daily dose. Furthermore, the compound may be formulated for immediate or modified release such as extended or controlled release.

As noted above, the present invention is also directed to use of a compound of Formula I with one or more additional anti-HIV agents. An "anti-HIV agent" is any agent which is directly or indirectly effective in the inhibition of HIV reverse transcriptase, protease, or another enzyme required for HIV replication or infection, the inhibition of HIV replication, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nuRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be used for these purposes.

Abbreviations and acronymns employed herein include the following: Bn=benzyl; BOC (or Boc)=t-butyloxycarbonyl; $Boc_2O$=di-t-butyl carbonate; BOP=benzotriazol-1-yloxytris-(dimethylamino)phosphonium; BSA=bovine serum albumin; CBS=Corey, Bakshi, Shibata chiral oxazaborolidine mediated ketone reduction; Cbz=benzyloxycarbonyl; DBU=1,8-diazabicyclo[5.4.0]undec-7-one; DCAD=di-(4-chlorobenzyl) azodicarboxylate; DCE=1,2-dichloroethane; DCM=dichloromethane; DEAD=diethyl azodicarboxylate; DIAD=diisopropylazodicarboxylate; Dibal-H=diisobutylaluminum hydride; DMAP=4-dimethylaminopyridine; DMF=dimethylformamide; DMSO=dimethyl sulfoxide; e.g.=for example (but not limited to); EDC=1-ethyl-3-(3-dimethylaminopropyl) carbodiimide; Et=ethyl; EtOAc=ethyl acetate; EtOH=ethanol; G-2G=Grubbs catalyst, $2^{nd}$ generation; HOAt=1-hydroxy-7-azabenzotriazole; HPLC=high performance liquid chromatography; HSU=hydroxysuccinimide; i-PrOH=isopropanol; LAH=lithium aluminum hydride; LCMS=liquid chromatography-mass spectroscopy; Me=methyl; MeOH=methanol; MOC=methoxycarbonyl; Ms=mesyl or methanesulfonyl; NMR=nuclear magnetic resonance; Ph=phenyl; RCM=ring closing metathesis; Piv=pivaloyl; PPTS=pyridinium p-toluene sulfonate; PyBrOP=bromo-tris-pyrrolidinophosphonium hexafluorophosphate;); rt, r.t. or RT=room temperature; SCX=strong cation exchange resin; STP=standard temperature and pressure (i.e., 25° C. & 1 atmosphere); TBS=tert-butyldimethylsilyl; TBDPS=tert-butyl(diphenyl)silyl; TBDPSCl=tert-butyl(dimethyl)silyl chloride; TEA=triethylamine; TFA=trifluoroacetic acid; THF=tetrahydrofuran; TLC=thin layer chromatography; TMAF=tetramethyl ammonium fluoride; $TMSCHN_2$=trimethylsilyl diazomethane; TPAP=tetrapropylammonium perruthenate; TPP=triphenylphosphine.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. In the examples that follow, when a nitrogen atom is depicted without the necessary hydrogen atoms to complete the valence, it is assumed those hydrogen atoms are present unless specifically stated to the contrary.

SCHEME 1

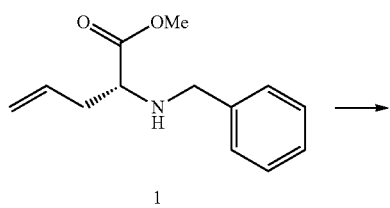

1

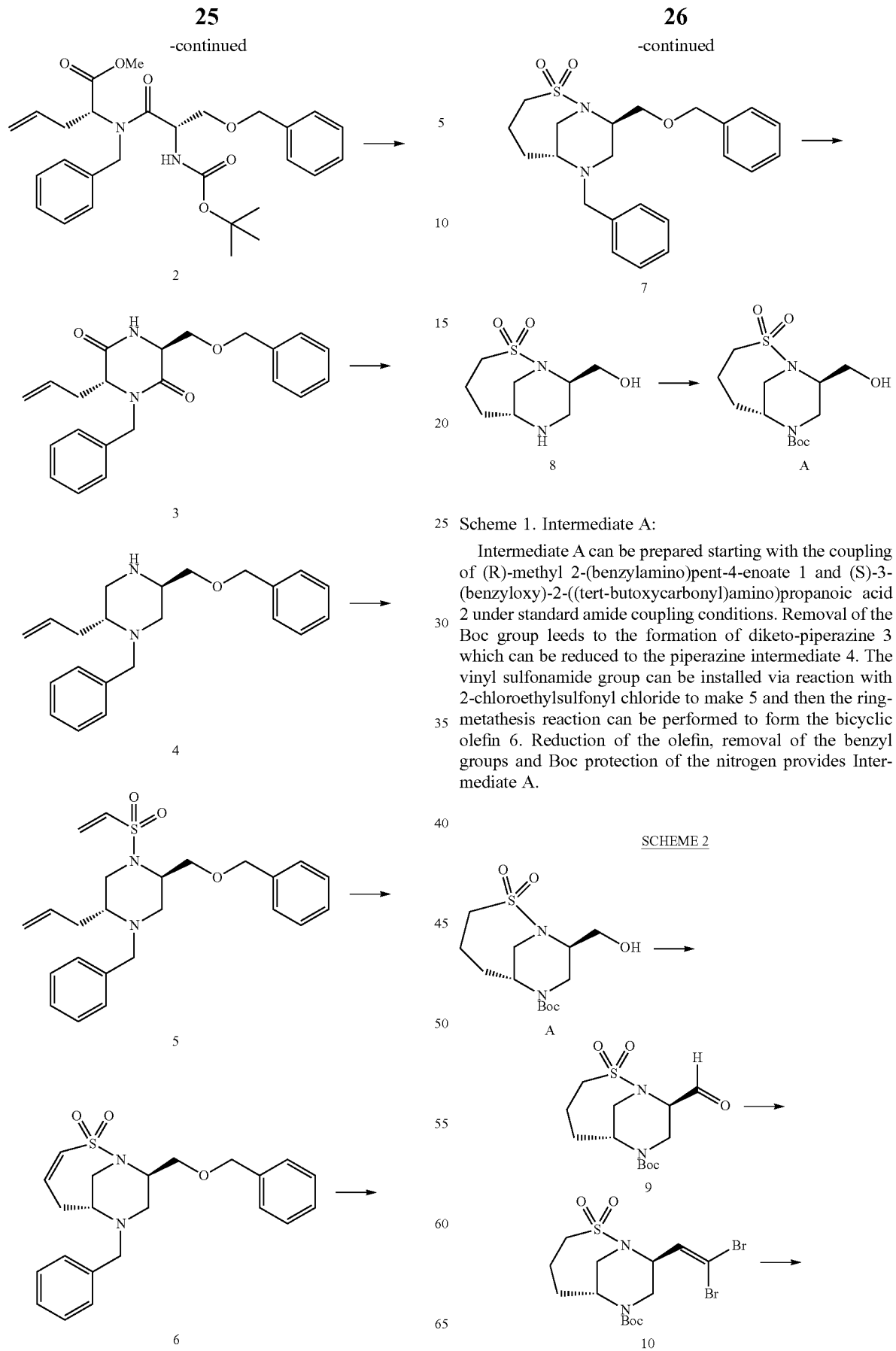

Scheme 1. Intermediate A:

Intermediate A can be prepared starting with the coupling of (R)-methyl 2-(benzylamino)pent-4-enoate 1 and (S)-3-(benzyloxy)-2-((tert-butoxycarbonyl)amino)propanoic acid 2 under standard amide coupling conditions. Removal of the Boc group leeds to the formation of diketo-piperazine 3 which can be reduced to the piperazine intermediate 4. The vinyl sulfonamide group can be installed via reaction with 2-chloroethylsulfonyl chloride to make 5 and then the ring-metathesis reaction can be performed to form the bicyclic olefin 6. Reduction of the olefin, removal of the benzyl groups and Boc protection of the nitrogen provides Intermediate A.

SCHEME 2

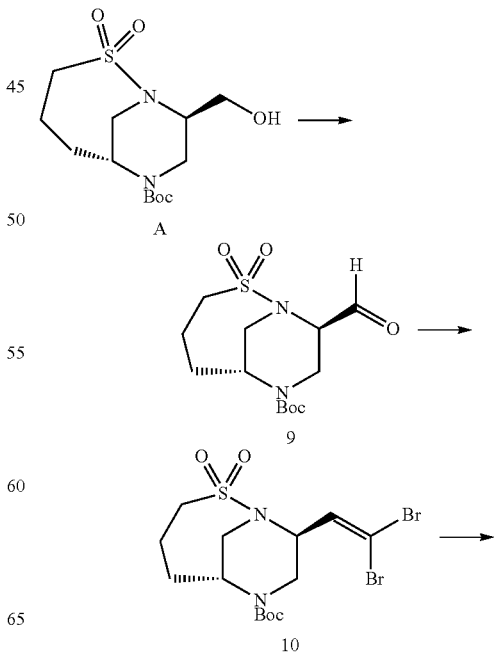

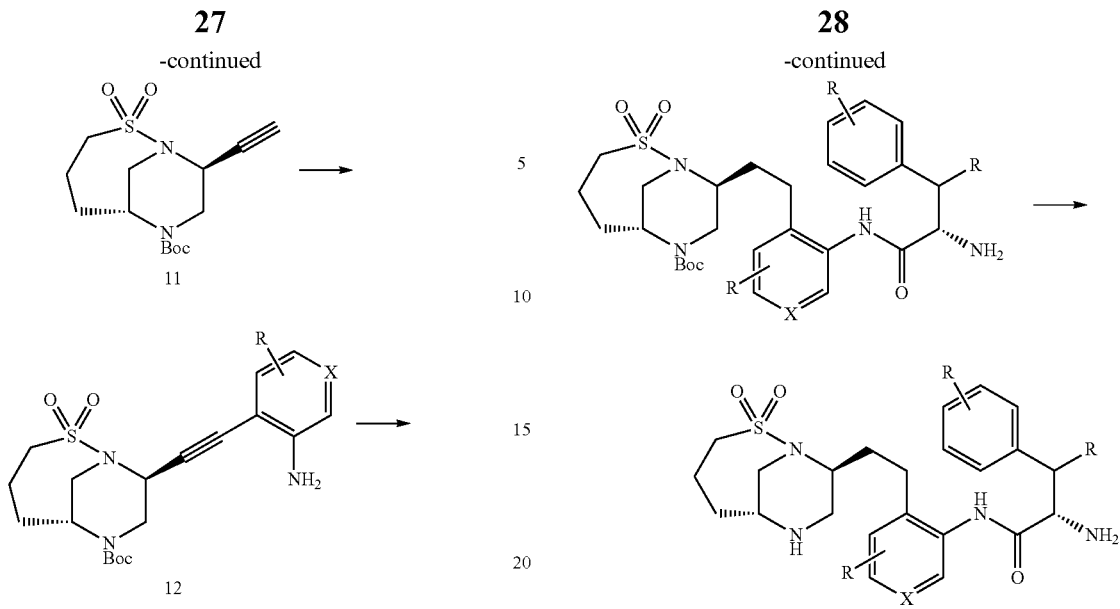

Scheme 2:

The alkyne 11 can be obtained by oxidation of the alcohol of Intermediate A via two-step conversion under standard conditions. Coupling to the linker fragment under a variety of conditions can then be achieved to obtain 12. Reduction of the alkyne gives intermediate 13.

SCHEME 3

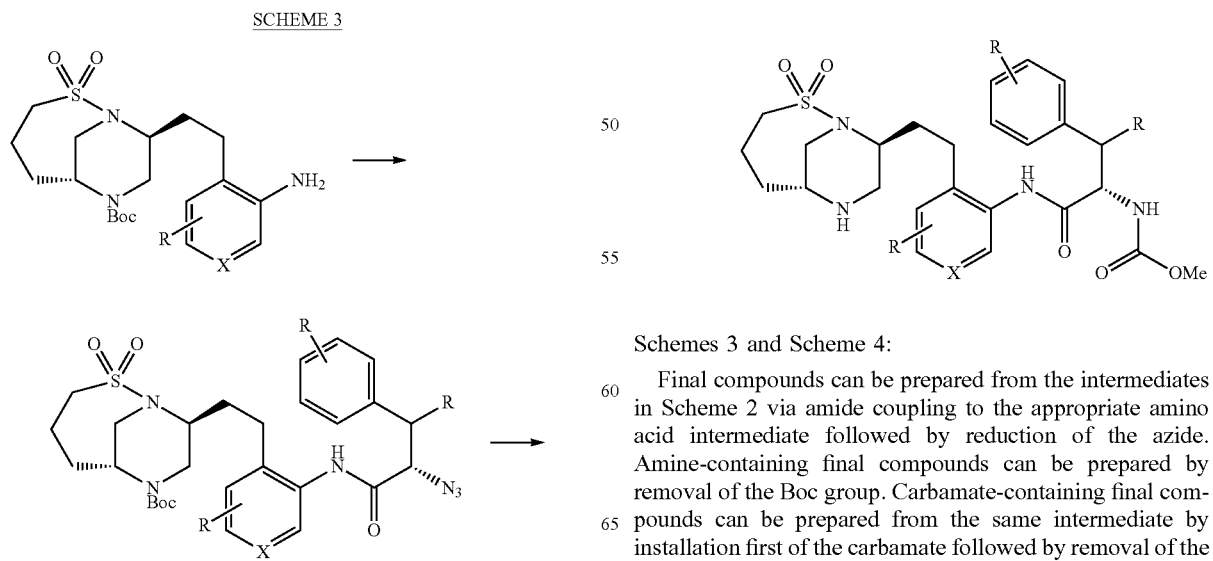

Schemes 3 and Scheme 4:

Final compounds can be prepared from the intermediates in Scheme 2 via amide coupling to the appropriate amino acid intermediate followed by reduction of the azide. Amine-containing final compounds can be prepared by removal of the Boc group. Carbamate-containing final compounds can be prepared from the same intermediate by installation first of the carbamate followed by removal of the Boc protecting group.

Intermediate 1

(S)-2-((tert-Butoxycarbonyl)amino)-3,3-bis(4-fluorophenyl)propanoic acid

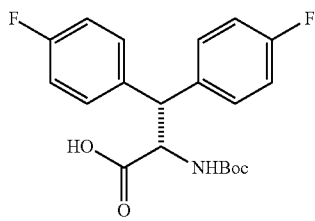

[Patterson, D. E., et al. *Org. Proc. Res. Dev.* 2009, 13, 900-906.] MS: m/z=378 (M+H)+.

Intermediate 2

(2S,3S)-2-Azido-3-(3,5-difluorophenyl)-3-(4-fluorophenyl)propanoic acid

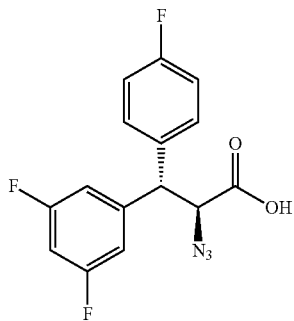 [SMILES: [N-]=[N+]=N[C@H](C(=O)O)[C@@H](c1ccc(F)cc1)c1cc(F)cc(F)c1]

Step 1. (4R)-3-[(2E)-3-(3,5-Difluorophenyl)prop-2-enoyl]-4-phenyl-1,3-oxazolidin-2-one

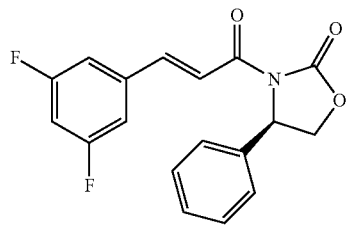 [SMILES: O=C(/C=C/c1cc(F)cc(F)c1)N1C(=O)OC[C@H]1c1ccccc1]

To a slurry of 3,5-difluorocinammic acid (6.3 g, 34 mmol) in CH$_2$Cl$_2$ (130 mL) was added thionyl chloride (6.2 mL, 85 mmol). The mixture was heated to reflux under a nitrogen atmosphere for 5 h, at which time all solids had dissolved. The solvents were removed in vacuo to give the acid chloride as a solid. A solution of (4R)-4-phenyl-1,3-oxazolidin-2-one (5.6 g, 34 mmol) in THF (100 mL) under an atmosphere of nitrogen was cooled to −10° C. in an ice-acetone bath. To the stirred solution was added nBuLi (13.6 mL of a 2.5 M solution in hexane, 34 mmol) dropwise over a period of 10 min. To this solution was added a solution of the acid chloride in 40 mL of THF dropwise over 10 min. The resulting solution was stirred at 0° C. in an ice-water bath for 1 h. The reaction was quenched with the addition of aqueous NaHCO$_3$, and the mixture was extracted three times with EtOAc. The combined organic extracts were washed with water and brine, then dried (MgSO$_4$), filtered, and the solvent was removed in vacuo. The residue was chromatographed on a 330 g SiO$_2$ column using a gradient elution of 0-50% EtOAc:A, where A=1:1 hexanes:CHCl$_3$. Fractions containing product were combined and the solvents were removed in vacuo to give the title compound.

Step 2. (4R)-3-[(3S)-3-(3,5-Difluorophenyl)-3-(4-fluorophenyl)propanoyl]-4-phenyl-1,3-oxazolidin-2-one

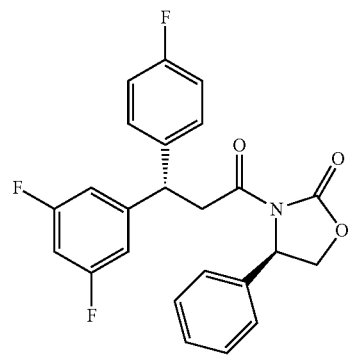 [SMILES: O=C(C[C@@H](c1ccc(F)cc1)c1cc(F)cc(F)c1)N1C(=O)OC[C@H]1c1ccccc1]

A solution of 4-fluorophenylmagnesium bromide (29 mL of a 2.0 M solution in THF, 58 mmol) and copper(I) bromide-dimethylsulfide complex (12 g, 59 mmol) in THF (100 mL) under an atmosphere of nitrogen was cooled to −40° C. in a dry ice-acetonitrile bath. To the stirred solution was added a solution of (4R)-3-[(2E)-3-(3,5-difluorophenyl) prop-2-enoyl]-4-phenyl-1,3-oxazolidin-2-one (7.7 g, 23 mmol) in 100 mL of THF dropwise over 15 min. The resulting mixture was stirred at −40° C. for 1.5 h, then the cooling bath was removed and the stirred mixture was allowed to warm to RT. The reaction was quenched by the addition of aqueous NH$_4$Cl solution. The resulting mixture was stirred for 15 min then extracted with two portions of EtOAc. The combined organic phases were washed with water and brine, then dried (MgSO$_4$), filtered, and the solvents were removed in vacuo. The residue was chromatographed on a 330 g SiO$_2$ column using a gradient elution of 0-50% EtOAc:A, where A=1:1 hexanes:CHCl$_3$. Fractions containing product were combined and the solvents were removed in vacuo to give the title compound.

Step 3. (3S)-3-(3,5-Difluorophenyl)-3-(4-fluorophenyl)propanoic acid

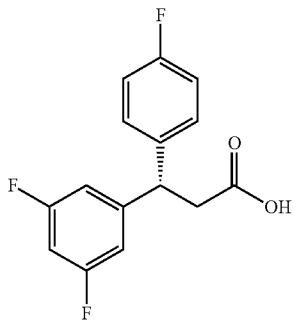 [SMILES: O=C(O)C[C@@H](c1ccc(F)cc1)c1cc(F)cc(F)c1]

A solution of (4R)-3-[(3S)-3-(3,5-difluorophenyl)-3-(4-fluorophenyl)propanoyl]-4-phenyl-1,3-oxazolidin-2-one (7.3 g, 17 mmol) in 90 mL of THF and 30 mL of water was cooled to 0° C. in an ice-water bath. To the solution was added hydrogen peroxide (7.0 mL of a 30% solution in water, 69 mmol) and LiOH (0.83 g g, 35 mmol). After 45 min, a solution of sodium sulfite (8.7 g, 69 mmol) in 30 mL of water was added, followed by 170 mL of a 0.5 M solution of aqueous NaHCO$_3$ (86 mmol). The stirred mixture was warmed to RT and most of the THF was removed in vacuo. The aqueous mixture was extracted with two portions of CH$_2$Cl$_2$ to remove the chiral auxiliary. The aqueous phase was then acidified to pH 1 with the addition of 6 N HCl and extracted with two portions of EtOAc. The combined EtOAc layers were dried (MgSO$_4$), filtered, and the solvent was removed in vacuo to give the title compound.

Step 4. (4S)-3-[(3S)-3-(3,5-Difluorophenyl)-3-(4-fluorophenyl)propanoyl]-4-phenyl-1,3-oxazolidin-2-one

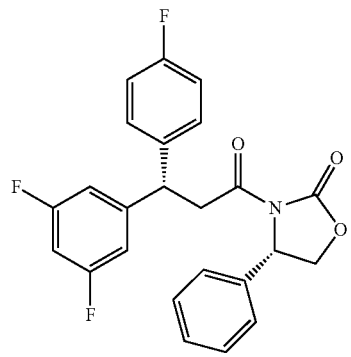 [SMILES: O=C(C[C@@H](c1ccc(F)cc1)c1cc(F)cc(F)c1)N1C(=O)OC[C@@H]1c1ccccc1]

To a solution of (3S)-3-(3,5-difluorophenyl)-3-(4-fluorophenyl)propanoic acid (Step 3) (3.0 g, 11 mmol) in CH$_2$Cl$_2$ (70 mL) was added thionyl chloride (2.0 mL, 27 mmol). The mixture was heated to reflux under a nitrogen atmosphere for 1 h. The solvents were removed in vacuo to give the acid chloride as a gum. A solution of (4S)-4-phenyl-1,3-oxazolidin-2-one (1.7 g, 11 mmol) in THF (60 mL) under an atmosphere of nitrogen was cooled to −10° C. in an ice-acetone bath. To the stirred solution was added nBuLi (4.3 mL of a 2.5 M solution in hexane, 11 mmol) dropwise over a period of 5 min. To this solution was added a solution of the acid chloride in 20 mL of THF dropwise over 5 min. The resulting solution was stirred at 0° C. in an ice-water bath for 1 h. The reaction was quenched with the addition of aqueous NaHCO$_3$, and the mixture was extracted three times with EtOAc. The combined organic extracts were washed with water and brine, then dried (MgSO$_4$), filtered, and the solvent was removed in vacuo. The residue was chromatographed on a 120 g SiO2 column using a gradient elution of 0-50% EtOAc:A, where A=1:1 hexanes:CHCl$_3$. Fractions containing product were combined and the solvents were removed in vacuo.

Step 5. (4S)-3-[(2S,3S)-2-Azido-3-(3,5-difluorophenyl)-3-(4-fluorophenyl)propanoyl]-4-phenyl-1,3-oxazolidin-2-one

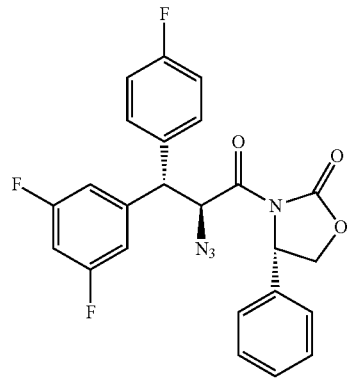 [SMILES: [N-]=[N+]=N[C@H](C(=O)N1C(=O)OC[C@@H]1c1ccccc1)[C@@H](c1ccc(F)cc1)c1cc(F)cc(F)c1]

10 mL of THF under an atmosphere of nitrogen was cooled to −78° C. in a dry ice-acetone bath and to the stirred solution was added sodium hexamethyldisilazide (9.1 mL of a 1.0 M solution in THF, 9.1 mmol). A solution of (4S)-3-[(3S)-3-(3,5-difluorophenyl)-3-(4-fluorophenyl)propanoyl]-4-phenyl-1,3-oxazolidin-2-one (3.5 g, 8.2 mmol) in 20 mL of THF under nitrogen atmosphere was cooled to −78° C. in a dry ice-acetone bath and added via cannula to the cold sodium hexamethyldisilazide solution. The resulting mixture was stirred at −78° C. for 30 min when trisyl azide (3.3 g, 11 mmol) was added as a solid. The solids dissolved and the cold solution was stirred for 2 min. To the cold solution was added HOAc (2.8 mL, 49 mmol) and solid tetramethylammonium acetate (4.4 g, 33 mmol). The cooling bath was removed and the mixture was stirred at RT for 4 h. The reaction was diluted with EtOAc and washed with brine. The aqueous phase was extracted with EtOAc, and the combined EtOAc layers were washed with aqueous NaHCO$_3$ and brine, then dried (MgSO$_4$), filtered, and the solvents were removed in vacuo. The residue was chromatographed on a 120 g SiO$_2$ column using a gradient elution of 0-40% EtOAc in hexanes. Fractions containing product were combined and the solvents were removed in vacuo to give the title compound.

Step 6. (2S,3S)-2-Azido-3-(3,5-difluorophenyl)-3-(4-fluorophenyl)propanoic acid

A solution of (4S)-3-[(2S,3S)-2-azido-3-(3,5-difluorophenyl)-3-(4-fluorophenyl)propanoyl]-4-phenyl-1,3-oxazolidin-2-one (3.1 g, 6.7 mmol) in 45 mL of THF and 15 mL of water was cooled to 0° C. in an ice-water bath. To the stirred solution was added hydrogen peroxide (2.7 mL of a 30% solution in water, 27 mmol) and LiOH (0.32 g, 13 mmol), and the mixture was stirred at 0° C. for 45 min. The reaction was quenched by the addition of a solution of sodium sulfite (3.4 g, 27 mmol) in 20 mL of water, followed by 67 mL of a 0.5 M solution of aqueous NaHCO$_3$ (33 mmol). The stirred mixture was warmed to RT and most of the THF was removed in vacuo. The aqueous mixture was extracted with two portions of CH2Cl2 to remove the chiral auxiliary. The aqueous phase was then acidified to pH 1 with the addition of 6 N HCl and extracted with two portions of EtOAc. The combined EtOAc layers were dried (MgSO$_4$), filtered, and the solvent was removed in vacuo to give a gum.

Intermediate 3

(2S,3R)-2-Azido-3-(4-fluorophenyl)-3-(tetrahydro-2H-pyran-4-yl)propanoic acid

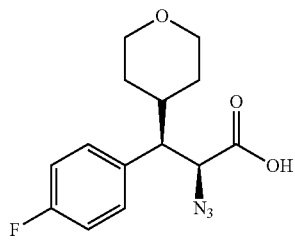 [SMILES: [N-]=[N+]=N[C@H](C(=O)O)[C@@H](c1ccc(F)cc1)C1CCOCC1]

Step 1. (R,E)-4-Phenyl-3-(3-(tetrahydro-2H-pyran-4-yl)acryloyl)oxazolidin-2-one

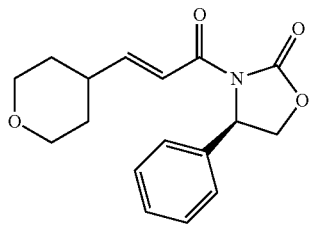 [SMILES: O=C(/C=C/C1CCOCC1)N1C(=O)OC[C@H]1c1ccccc1]

To a solution of dimethyl (2-oxo-2-((4R)-2-oxo-4-phenyltetrahydrofuran-3-yl)ethyl)phosphonate (31.8 g, 98.0 mmol) in THF (140 mL) was added t-BuOK (1M solution in THF (96.0 mL, 96.0 mmol) and stirred at RT for 1 h. A solution of 4-tetrahydropyran carboxaldehyde (10.0 g, 87.0 mmol) in THF (70.0 mL) was added drop wise and continued stirring at RT for 1 h. The reaction mixture was quenched with saturated solution of NH$_4$Cl (150 mL) and extracted with EtOAc (2×500 mL). The combined EtOAc extracts were washed with water (250 mL), brine (100 mL), dried (Na$_2$SO$_4$), filtered and concentrated under reduced pressure to provide the title product.

Step 2. (R)-3-((R)-3-(4-Fluorophenyl)-3-(tetrahydro-2H-pyran-4-yl)propanoyl)-4-phenyloxazolidin-2-one

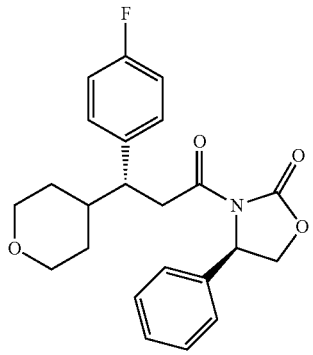 [SMILES: O=C(C[C@@H](c1ccc(F)cc1)C1CCOCC1)N1C(=O)OC[C@H]1c1ccccc1]

To a precooled (−40° C.) solution of copper (I) bromide methylsulfide complex (17.7 g, 82.5 mmol) in anhydrous THF (100 mL) was added dimethylsulfide (82.5 mL), followed by the slow addition of 4-fluorophenylmagnesium-bromide (1M solution in THF, 82.5 mL, 82.5 mmol). The reaction mixture was allowed to warm to −20° C. and stirred for 20 min. A solution of (R,E)-4-phenyl-3-(3-(tetrahydro-2H-pyran-4-yl)acryloyl)oxazolidin-2-one (15.0 g, 55.0 mmol) in THF (100 mL) was added drop wise over 20 min. The resulting solution was stirred at −20° C. for 1 h and continued stirring at RT for 16 h. The reaction mixture was quenched with saturated solution of NH$_4$Cl (250 mL) and extracted with EtOAc (2×500 mL). The combined EtOAc extracts were washed with brine (250 mL), dried (Na$_2$SO$_4$), filtered and concentrated under reduced pressure. The residue was purified on 80 g SiO$_2$ column using a gradient elution of 0-20% EtOAc in hexanes. Fractions containing the compound were combined and concentrated in vacuo to provide title product. MS: m/z=370 (M+H)$^+$.

Step 3. (R)-3-(4-Fluorophenyl)-3-(tetrahydro-2H-pyran-4-yl)propanoic acid

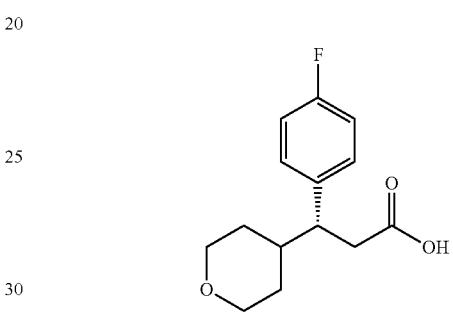

To a precooled (0° C.) solution of (R)-3-((R)-3-(4-fluorophenyl)-3-(tetrahydro-2H-pyran-4-yl)propanoyl)-4-phenyloxazolidin-2-one (16.5 g, 45.0 mmol) in THF (100 mL) and water (20 mL) was added 30% hydrogen peroxide (30.0 mL) drop wise and stirred for 10 min. A solution of LiOH (4.16 g, 99.0 mmol) in water (30.0 mL) was added at 0° C. and reaction mixture was stirred at 0° C. for 2 h. The reaction mixture was quenched with saturated solution of sodium sulphite (100 mL), water (500 mL) and extracted with EtOAc (2×250 mL). The aqueous phase was acidified to pH 3 with 6 N HCl extracted with EtOAc (2×300 mL). The combined EtOAc extracts were washed with brine (200 mL), dried (Na$_2$SO$_4$), filtered and concentrated under reduced pressure to provide the title product. MS: m/z=251 (M+H)$^+$.

Step 4. (S)-3-((R)-3-(4-Fluorophenyl)-3-(tetrahydro-2H-pyran-4-yl)propanoyl)-4-phenyloxazolidin-2-one

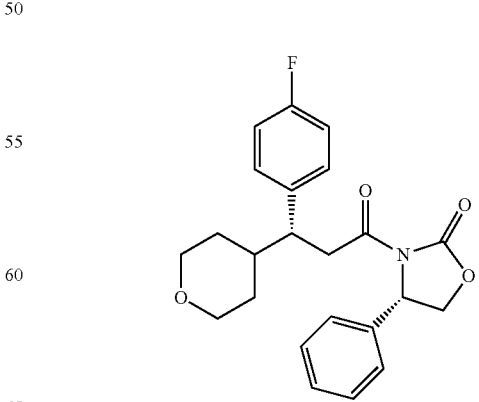

To a precooled (0° C.) solution of (R)-3-(4-fluorophenyl)-3-(tetrahydro-2H-pyran-4-yl)propanoic acid (10.1 g, 40.4 mmol) in THF (30.0 mL) was added thionyl chloride (14.7 mL, 202 mmol) and the reaction mixture was heated at reflux for 1 h. In another precooled (0° C.) suspension of 60% NaH (1.45 g, 60.6 mmol) in THF (20.0 mL), was added a solution of (S)-4-phenyloxazolidin-2-one (6.50 g, 40.4 mmol) in THF (10.0 mL) dropwise and stirred at 0° C. for 1 h. A solution of the above acid chloride in THF (10.0 mL) was added and stirred for additional 5 h. The reaction mixture was quenched with water (30.0 mL) and extracted with EtOAc (2×300 mL). The combined EtOAc extracts were washed with brine (150 mL), dried (Na$_2$SO$_4$), filtered, and concentrated under reduced pressure. The residue was purified on using a gradient elution of 0-20% EtOAc in hexanes. Fractions containing the product were combined and concentrated under reduced pressure to provide the title product. MS: m/z=352 (M+H)$^+$.

Step 5. (S)-3-((2S,3R)-2-Azido-3-(4-fluorophenyl)-3-(tetrahydro-2H-pyran-4-yl)propanoyl)-4-phenyloxazolidin-2-one

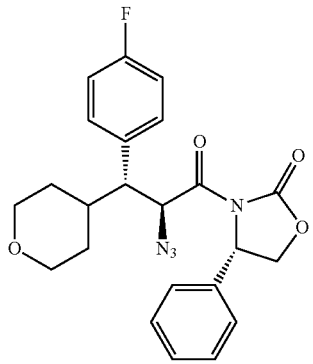 [SMILES: [N-]=[N+]=N[C@H](C(=O)N1C(=O)OC[C@@H]1c1ccccc1)[C@@H](c1ccc(F)cc1)C1CCOCC1]

To a precooled (−78° C.) solution of (S)-3-((R)-3-(4-fluorophenyl)-3-(tetrahydro-2H-pyran-4-yl)propanoyl)-4-phenyloxazolidin-2-one (5.60 g, 15.6 mmol) in dry THF (100 mL) was added NaHMDS (1M solution in THF, 23.9 mL, 23.9 mmol) at −78° C. slowly and stirred for 1 h when trisyl azide (6.42 g, 20.7 mmol) was added as a solid. To the cold solution was added tetramethyl ammonium acetate (4.22 g, 31.9 mmol) and acetic acid (5.47 mL, 95.7 mmol). The cooling bath was removed and stirred at RT for 1 h. The reaction mixture was diluted with water (200 mL) and extracted with EtOAc (2×500 mL). The combined EtOAc extracts were washed with brine (300 mL), dried (Na$_2$SO$_4$), filtered and concentrated under reduced pressure. The residue was purified on 40 g SiO$_2$ column using a gradient elution of 0-60% EtOAc in hexanes. Fractions containing the product were combined and concentrated under reduced pressure to provide the to give the title compound. MS: m/z=393 (M+H)$^+$.

Step 6. (2S,3S)-2-Azido-3-(4-fluorophenyl)-3-(tetrahydro-2H-pyran-4-yl)propanoic acid To a precooled (0° C.) solution of (S)-3-((2S, 3R)-2-azido-3-(4-fluorophenyl)-3-(tetrahydro-2H-pyran-4-yl)propanoyl)-4-phenyloxazolidin-2-one (3.90 g, 9.95 mmol) in THF (45.0 mL) and water (9.00 mL) was added 30% hydrogen peroxide (6.76 mL) drop wise and stirred for 10 min. A solution of LiOH (919 mg, 21.9 mmol) in water (12.0 mL) was added dropwise at 0° C. and stirred for 2 h. The reaction mixture was quenched with saturated solution of sodium sulfite (200 mL), water (400 mL) and extracted with EtOAc (2×300 mL). The aqueous phase was acidified to pH 3 and extracted with EtOAc (2×300 mL). The combined EtOAc extracts were washed with brine (200 mL), dried (Na$_2$SO$_4$), filtered and concentrated under reduced pressure to provide the to give the title compound. MS: m/z=262 (M+H)$^+$.

Intermediate 4

(2S,3R)-2-Azido-3-(4-chlorophenyl)-4-methylpentanoic acid

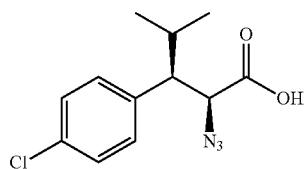 [SMILES: CC(C)[C@H](c1ccc(Cl)cc1)[C@H](N=[N+]=[N-])C(=O)O]

Step 1. (S,E)-3-(3-(4-Chlorophenyl)acryloyl)-4-phenyloxazolidin-2-one

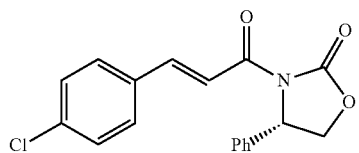 [SMILES: O=C(/C=C/c1ccc(Cl)cc1)N1C(=O)OC[C@@H]1c1ccccc1]

To a stirred solution of (S)-dimethyl 2-oxo-2-(2-oxo-4-phenyloxazolidin-3-yl)ethylphosphonate (20.0 g, 63.8 mmol) in dry THF (100 mL) was added potassium tert-butoxide (76.6 mL, 76.6 mmol, 1.0 M solution in THF) under an atmosphere of N$_2$ at 0° C. over a period of 10 min and the reaction mixture stirred at 0° C. for 30 min. A solution of 4-chloro benzaldehyde (8.98 g, 63.8 mmol) in dry THF (50.0 mL) was added over a period of 20 min and the reaction mixture was stirred at RT for 2 h. The reaction mixture was quenched with saturated solution of NH$_4$Cl (250 mL) and diluted with EtOAc (500 mL). The biphasic system was stirred at RT for 10 min and the layers were separated. The organic layer was washed with brine (250 mL), dried (Na$_2$SO$_4$), filtered and concentrated under reduced pressure. The residue was purified by recrystallization from MTBE/Hexanes to give the title product.

Step 2. (S)-3-4R)-3-(4-Chlorophenyl)-4-methylpentanoyl)-4-phenyloxazolidin-2-one

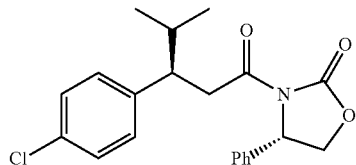 [SMILES: CC(C)[C@@H](CC(=O)N1C(=O)OC[C@@H]1c1ccccc1)c1ccc(Cl)cc1]

To a precooled (−40° C.) solution of copper (I) bromide methylsulfide complex (3.76 g, 18.3 mmol), in dry THF (120 mL), was added dimethyl sulfide (20.0 mL), followed by a solution of isopropyl magnesium bromide (9.20 mL, 2.90M solution) and stirred for 1 h. A solution of (S, E)-3-(3-(4-chlorophenyl)acryloyl)-4-phenyloxazolidin-2-one (4.00 g, 12.2 mmol) in dry THF (40.0 mL) was added slowly at −45° C. and stirred for 3 h. Quenched the reaction mixture with saturated solution of NH$_4$Cl (150 mL) and extracted with EtOAc (200 mL). The EtOAc extract was washed with brine (200 mL), dried (Na$_2$SO$_4$), filtered and concentrated under reduced pressure. The residue was purified by 120 g SiO$_2$ column using a gradient elution of 0-20% EtOAc in hexanes. Fractions containing product were combined and the solvents were removed in vacuo to provide the title product. MS: m/z=372 (M+H)$^+$.

Step 3. (S)-3-((2S,3R)-2-Azido-3-(4-chlorophenyl)-4-methylpentanoyl)-4-phenyloxazolidin-2-one

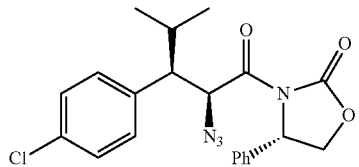 [SMILES: CC(C)[C@H](c1ccc(Cl)cc1)[C@H](N=[N+]=[N-])C(=O)N1C(=O)OC[C@@H]1c1ccccc1]

To a precooled (−78° C.) solution of (S)-3-((R)-3-(4-chlorophenyl)-4-methylpentanoyloxazolidin-2-one (3.00 g, 8.0 mmol) in dry THF (120 mL) was added NaHMDS (16.9 mL, 1M solution in THF) slowly and the resulting solution was stirred for 1 h at −75° C. when trisyl azide (3.30 g, 10.5 mmol) was added as a solid. To the cold solution was added tetramethyl ammonium acetate (2.15 g, 16.7 mmol) and acetic acid (2.77 mL, 48.5 mmol). The cooling bath was removed and the reaction mixture was stirred at RT for an additional for 1 h. Diluted the reaction mixture with water (150 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-20% EtOAc in hexanes. Fractions containing product were combined and the solvents were removed in vacuo to provide the title product.

Step 4. (2S,3R)-2-Azido-3-(4-chlorophenyl)-4-methylpentanoic acid

To a precooled (0° C.) solution of (S)-3-((2S, 3R)-2-azido-3-(4-chlorophenyl)-4-methylpentanoyl)-4-phenyloxazolidin-2-one (4.1 g, 9.9 mmol) in a mixture of THF (160 mL), and water (120 mL) added 30% hydrogen peroxide solution (6.76 mL) and stirred for 10 min. A solution of LiOH (525 mg, 21.8 mmol) in water (2.00 mL) was added at 0° C. and stirred for 3 h. The reaction mixture was quenched with saturated solution of sodium sulfite (40.0 mL) and stirred for at RT for additional 20 min. The reaction mixture was acidified to pH 3 using 6N HCl and extracted with EtOAc (250 mL). The organic layer was dried (Na$_2$SO$_4$), filtered and concentrated under reduced pressure. The residue was purified by 80 g SiO$_2$ column using a gradient elution of 0-20% EtOAc in hexanes. Fractions containing product were combined and the solvents were removed in vacuo to provide the title product. MS: m/z=266 (M−H)$^+$.

Intermediate 5

(2S,3S)-2-Azido-3-(4-chlorophenyl)-3-(6-methoxypyridin-3-yl)propanoic acid

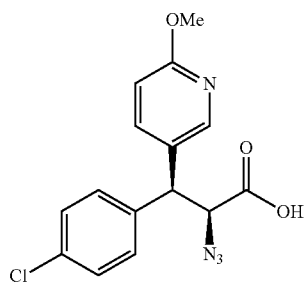 [SMILES: COc1ccc([C@H](c2ccc(Cl)cc2)[C@H](N=[N+]=[N-])C(=O)O)cn1]

Step 1. (R,E)-3-(3-(6-Methoxypyridin-3-yl)acryloyl)-4-phenyloxazolidin-2-one

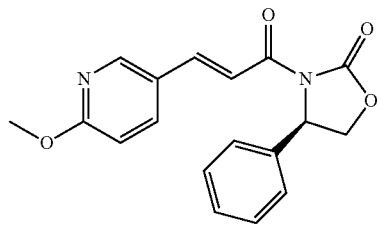 [SMILES: COc1ccc(/C=C/C(=O)N2C(=O)OC[C@H]2c2ccccc2)cn1]

To a solution of dimethyl (2-oxo-2-((4R)-2-oxo-4-phenyltetrahydrofuran-3-yl)ethyl)phosphonate (17.4 g, 52.5 mmol) in THF (70.0 mL) was added t-BuOK (1M solution in THF, 65.6 mL, 65.6 mmol) and stirred at RT for 1 h. A solution of 6-methoxynicitinaldehyde (6.00 g, 43.4 mmol) in THF (30.0 mL) was added drop-wise and continued stirring at RT for 1 h. The reaction mixture was quenched with saturated solution of NH$_4$Cl (75.0 mL) and extracted with EtOAc (2×200 mL). The combined EtOAc extracts were washed with water (100 mL), brine (50.0 mL), dried (Na$_2$SO$_4$), filtered and concentrated under reduced pressure to provide the title product. MS: m/z=325 (M+H)$^+$.

Step 2. (R)-3-(4-Chlorophenyl)-3-(6-methoxypyridin-3yl)propanoyl)-4-phenyloxazolidi-2-one

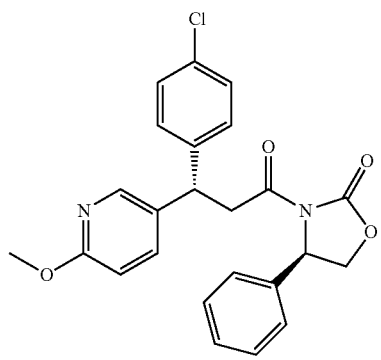 [SMILES: COc1ccc([C@@H](CC(=O)N2C(=O)OC[C@H]2c2ccccc2)c2ccc(Cl)cc2)cn1]

To a precooled (−40° C.) solution of copper (I) bromide methylsulfide complex (5.40 g, 26.4 mmol) in anhydrous THF (30.0 mL) was added dimethylsulfide (15.0 mL), followed by the slow addition of 4-chlorophenylmagnesiumbromide (1M solution in THF, 8.83 mmol). The reaction mixture was allowed to warm to −20° C. and stirred for 20 min. A solution of (R,E)-3-(3-(6-methoxypyridin-3-yl)acryloyl)-4-phenyloxazolidin-2-one (5.70 g, 17.6 mmol) in THF (25.0 mL) was added drop wise over 20 min. The resulting solution was stirred at −20° C. for 1 h and continued stirring at RT for 16 h. The reaction mixture was quenched with saturated solution of NH₄Cl (250 mL) and extracted with EtOAc (2×200 mL). The combined EtOAc extracts were washed with brine (200 mL), dried (Na₂SO₄), filtered and concentrated under reduced pressure. The residue was purified on 40 g SiO₂ column using a gradient elution of 0-20% EtOAc in hexanes. Fractions containing the product were combined and concentrated in vacuo to provide the title product. MS: m/z=437 (M+H)⁺.

Step 3. (S)-3-(4-Chlorophenyl)-3-(6-methoxypyidin-3-yl)propanoic acid

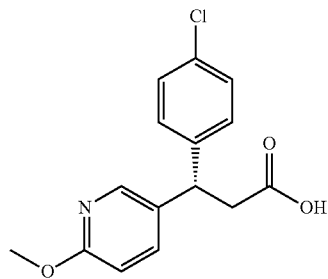 [SMILES: COc1ccc([C@@H](CC(=O)O)c2ccc(Cl)cc2)cn1]

To a precooled (0° C.) solution of (R)-3-(4-chlorophenyl)-3-(6-methoxypyridin-3yl)propanoyl)-4-phenyloxazolidi-2-one (5.50 g, 12.6 mmol) in THF (25.0 mL) and water (5 mL) was added 30% hydrogen peroxide (8.50 mL) drop-wise and stirred for 10 min. A solution of LiOH (906 mg, 37.8 mmol) in water (3.00 mL) was added at 0° C. and reaction mixture was stirred at 0° C. for 2 h. The reaction mixture was quenched with saturated solution of sodium sulphite (100 mL), water (500 mL) and extracted with EtOAc (2×100 mL). The aqueous phase was acidified to pH 3 and extracted with EtOAc (2×150 mL). The combined EtOAc extracts were washed with brine (100 mL), dried (Na₂SO₄), filtered and concentrated under reduced pressure to provide the title product. MS: m/z=292 (M+H)⁺.

Step 4. (S)-3-((S)-3-(4-Chlorophenyl)-3-(6-methoxypyridin-3-yl)propanoyl)-4-phenyloxazolidin-2-one

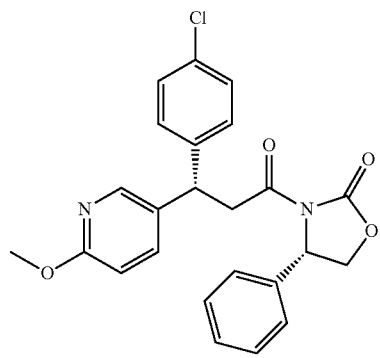 [SMILES: COc1ccc([C@@H](CC(=O)N2C(=O)OC[C@@H]2c2ccccc2)c2ccc(Cl)cc2)cn1]

To a precooled (0° C.) solution of (S)-3-(4-chlorophenyl)-3-(6-methoxypyidin-3-yl)propanoic acid (3.30 g, 11.3 mmol) in THF (30.0 mL) was added pivolyl chloride (1.39 mL, 11.3 mmol), DMAP (cat) and triethylamine (3.15 mL, 22.6 mmol) drop-wise and stirred for 1 h. In another precooled (−78° C.) suspension of (S)-4-phenyloxazolidin-2-one (2.03 g, 12.4 mmol) in THF (10.0 mL) was added n-BuLi (2.50 M solution in hexanes, 9.30 mL, 14.9 mmol) drop-wise and stirred at −20° C. for 1 h. The solution of the above mixed anhydride was added slowly and stirred for additional 3 h. The reaction mixture was quenched with saturated solution of NH₄Cl (250 mL) and extracted with EtOAc (2×200 mL). The combined EtOAc extracts were washed with brine (200 mL), dried (Na₂SO₄), filtered and concentrated under reduced pressure. The residue was purified on 40 g SiO₂ column using using a gradient elution of 0-40% EtOAc in hexanes. Fractions containing the product were combined and concentrated under reduced pressure to provide the the title product. MS: m/z=437 (M+H)⁺.

Step 5. (S)-3-((2S,3S)-2-Azido-3-(4-chlorophenyl)-3-(6-methoxypyridin-3-yl)propanoyl)-4-phenyloxazolidin-2-one

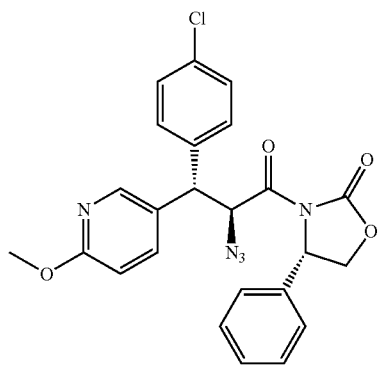 [SMILES: COc1ccc([C@H](c2ccc(Cl)cc2)[C@H](N=[N+]=[N-])C(=O)N2C(=O)OC[C@@H]2c2ccccc2)cn1]

To a precooled (−78° C.) solution of (S)-3-((S)-3-(4-chlorophenyl)-3-(6-methoxypyridin-3-yl)propanoyl)-4-phenyloxazolidin-2-one (2.10 g, 4.81 mmol) in dry THF (30.0 mL) was added NaHMDS (1M solution in THF, 7.20 mL, 7.20 mmol) at −78° C. slowly stirred for 1 h, when trisyl azide (1.93 g, 6.25 mmol) was added as a solid. To the cold solution was added tetramethyl ammonium acetate (1.28 g, 9.61 mmol) and acetic acid (1.73 mL, 28.8 mmol). The cooling bath was removed and stirred at RT for 1 h. The reaction mixture was diluted with water (80.0 mL) and extracted with EtOAc (2×100 mL). The combined organic extracts were washed with brine (100 mL), dried (Na₂SO₄), filtered and concentrated under reduced pressure. The residue was purified on 24 g SiO₂ column using a gradient elution of 0-60% EtOAc in hexanes. Fractions containing the product were combined and concentrated under reduced pressure to provide the the title product. MS: m/z=478 (M+H)⁺.

Step 6. (2S,3R)-2-Azido-3-(4-chlorophenyl)-3-(6-methoxypyridin-3-yl)propanoic acid To a precooled (0° C.) solution of (S)-3-((2S, 3S)-2-azido-3-(4-chlorophenyl)-3-(6-methoxypyridin-3-yl)propanoyl)-4-phenyloxazolidin-2-one (1.64 g, 3.42 mmol) in THF (15.0 mL) and water (3.00 mL) was added 30% hydrogen peroxide (1.10 mL) drop wise and stirred for 10 min. A solution of LiOH (245 mg, 10.2 mmol) in water (4.00 mL) was added dropwise at 0° C. and stirred for 2 h. The reaction mixture was quenched with saturated solution of sodium sulphite (10.0 mL), water (40.0 mL) and extracted with EtOAc (2×50.0 mL). The aqueous phase was acidified to pH 3 with 6 N HCl and extracted with EtOAc (2×150 mL). The combined EtOAc extracts were washed with brine (100 mL), dried (Na$_2$SO$_4$), filtered and concentrated under reduced pressure to provide the the title product. MS: m/z=292 (M+H)$^+$.

Intermediate 6

(2S,3S)-2-Azido-3-(4-chlorophenyl)-3-(6-isopropoxypyridin-3-yl)propanoic acid

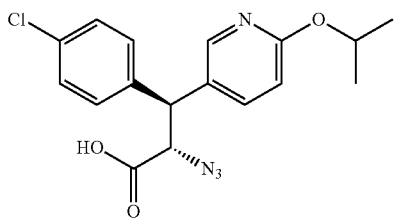 [SMILES: CC(C)Oc1ccc([C@H](c2ccc(Cl)cc2)[C@H](N=[N+]=[N-])C(=O)O)cn1]

Step 1: 6-isopropoxynicotinaldehyde

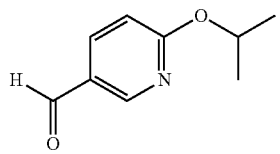

To a solution of 5-bromo-2-isopropoxypyridine (2.6 g, 12 mmol) in 50 mL dry THF under nitrogen atmosphere at −78° C. was added nBuLi (4.8 mL of a 2.5 M solution in hexane, 12 mmol) dropwise. The mixture was stirred at −78° C. for 30 min. To the solution was then added a solution of N-methoxy-N-methylformamide (2.1 g, 24 mmol) in 5 mL dry THF dropwise. The mixture was stirred at −78° C. for 30 min. The reaction was quenched with 20% NH$_4$Cl and extracted with two portions of EtOAc. The organic phases were combined, washed with with water and brine, dried over MgSO$_4$, filtered, and the solvents were removed in vacuo. The crude product was chromatographed on a 12 g SiO$_2$ column using a gradient elution of 0-30% EtOAc:hexanes. Fractions containing product were combined and the solvents were removed in vacuo to give the title compound.

Step 2: (R,E)-3-(3-(6-isopropoxypyridin-3-yl)acryloyl)-4-phenyloxazolidin-2-one

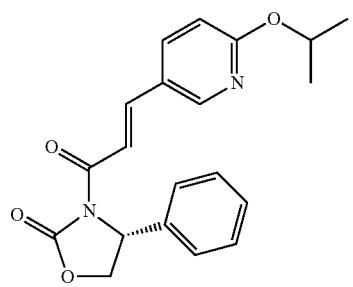 [SMILES: CC(C)Oc1ccc(/C=C/C(=O)N2C(=O)OC[C@H]2c2ccccc2)cn1]

To a solution of (R)-dimethyl (2-oxo-2-(2-oxo-4-phenyloxazolidin-3-yl)ethyl)-phosphonate (1.74 g, 5.56 mmol) in THF (25 mL) under nitrogen at 0° C. was added t-BuOK (1.0 M in THF, 5.6 mL, 5.6 mmol) dropwise. The mixture was stirred at 0° C. for 30 min. A solution of 6-isopropoxynicotinaldehyde (0.92 g, 5.56 mmol) in THF (5 mL) was added dropwise to the reaction mixture. The cooling bath was removed and the resulting mixture was stirred at RT for 18 h. Water was added and the mixture was extracted with ethyl acetate. The organic layer was washed with brine, dried over sodium sulfate, filtered, and concentrated in vacuo. The residue was purified on a 40 g SiO$_2$ column chromatography eluting with a gradient of 0-40% EtOAc:hexanes. Fractions containing product were combined and the solvents were removed in vacuo to give the title compound as a foam. LCMS m/z=353.2 (M+H)$^+$.

Step 3: (R)-3-((S)-3-(4-chlorophenyl)-3-(6-isopropoxypyridin-3-yl)propanoyl)-4-phenyloxazolidin-2-one

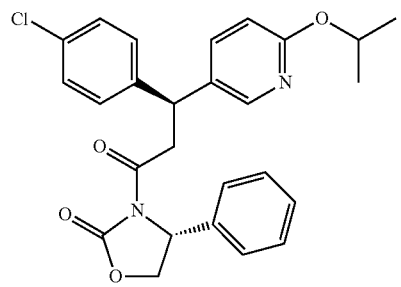 [SMILES: CC(C)Oc1ccc([C@@H](CC(=O)N2C(=O)OC[C@H]2c2ccccc2)c2ccc(Cl)cc2)cn1]

A stirred suspension of copper bromide dimethylsulfide complex (2.3 g, 11 mmol) in 20 mL THF under nitrogen atmosphere was cooled to −40° C. A solution of (4-chlorophenyl)magnesium bromide (1.0 M in ether, 11 mL, 11 mmol) was added dropwise and the resulting mixture was stirred at −40° C. for 10 min. A solution of (R,E)-3-(3-(6-isopropoxypyridin-3-yl)acryloyl)-4-phenyloxazolidin-2-one (1.57 g, 4.44 mmol) in 10 mL THF was added dropwise to reaction and the mixture was stirred at −40° C. for 1 h. The reaction was quenched with 20% NH4Cl, the cooling bath was removed, and the mixture was stirred at RT for 15 min. The mixture was extracted with two portions of EtOAc. The EtOAc extracts were combined, washed with water and brine, dried over MgSO$_4$, and the solvents were removed in vacuo. The crude product was chromatographed on an 80 g SiO$_2$ column using a gradient elution of 0-50% EtOAc:hexanes. Fractions containing product were combined and the solvents were removed in vacuo to give the title compound. LCMS m/z=464.9 (M+H)$^+$.

Step 4: (S)-3-(4-chlorophenyl)-3-(6-isopropoxypyridin-3-yl)propanoic acid

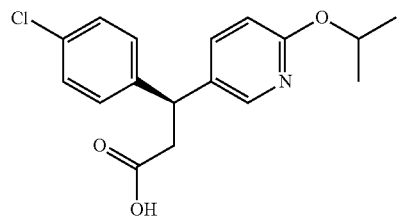 [SMILES: CC(C)Oc1ccc([C@@H](CC(=O)O)c2ccc(Cl)cc2)cn1]

A solution of (R)-3-((S)-3-(4-chlorophenyl)-3-(6-isopropoxypyridin-3-yl)-propanoyl)-4-phenyloxazolidin-2-one (1.32 g, 2.84 mmol) in 18 mL THF and 6 mL water was cooled to 0° C. To the stirred solution was added hydrogen peroxide (1.0 mL of a 30% solution in water, 11 mmol) and solid LiOH (0.14 g, 5.7 mmol). The mixture was stirred at 0° C. for 60 min. A solution of sodium sulfite (1.4 g, 11 mmol) in water (10 mL) was added to the mixture. A solution of NaHCO$_3$ (34 mL of a 0.5 M solution, 17 mmol) was added and the mixture was stirred for 5 min. Most of the THF was removed in vacuo and the remaining aqueous phase was extracted twice with DCM to remove the oxazolidinone. The aqueous phase was acidified to pH 5 with citric acid and the resulting solution was extracted with two portions of EtOAc. The combined organic layers were washed with brine, dried over sodium sulfate, filtered, and concentrated in vacuo to give the title compound. LCMS m/z=320.0 (M+H)$^+$.

Step 5: (S)-3-((S)-3-(4-chlorophenyl)-3-(6-isopropoxypyridin-3-yl)propanoyl)-4-phenyloxazolidin-2-one

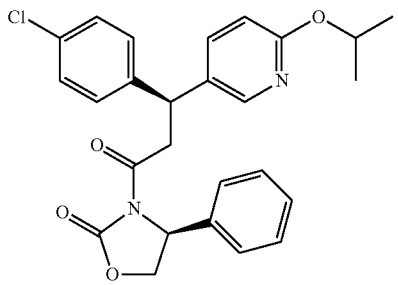 [SMILES: CC(C)Oc1ccc([C@@H](CC(=O)N2C(=O)OC[C@@H]2c2ccccc2)c2ccc(Cl)cc2)cn1]

To a stirred solution of (S)-3-(4-chlorophenyl)-3-(6-isopropoxypyridin-3-yl)propanoic acid (899 mg, 2.81 mmol) and TEA (0.47 mL, 3.37 mmol) in THF (15 mL) −10° C. under nitrogen atmosphere was added pivaloyl chloride (0.36 mL, 2.95 mmol) dropwise. The mixture was stirred at −10° C. for 30 min (mixture A). In a separate flask, n-butyl lithium (1.13 mL of a 2.5 M solution in hexanes, 2.81 mmol) was added dropwise to a stirred solution of of (S)-4-phenyloxazolidin-2-one (459 mg, 2.81 mmol) in 10 mL dry THF at −10° C. under nitrogen atmosphere. The mixture was stirred for 10 min at −10° C. and then added to mixture A. The resulting mixture was stirred at −10° C. for 1 h. Aqueous NaHCO$_3$ was added, the cooling bath was removed, and the mixture was stirred for 10 min at RT. The mixture was diluted with water and extracted with two portions of EtOAc. The EtOAc extracts were combined, washed with brine, dried over MgSO$_4$, filtered, and the solvents were removed in vacuo. The crude product was chromatographed on a 40 g SiO$_2$ column using a gradient elution of 0-50% EtOAc in hexanes. Fractions containing product were combined and the solvents were removed in vacuo to give the title compound. LCMS m/z=664.9 (M+H)$^+$.

Step 6: (S)-3-((2S,3S)-2-azido-3-(4-chlorophenyl)-3-(6-isopropoxypyridin-3-yl)propanoyl)-4-phenyloxazolidin-2-one

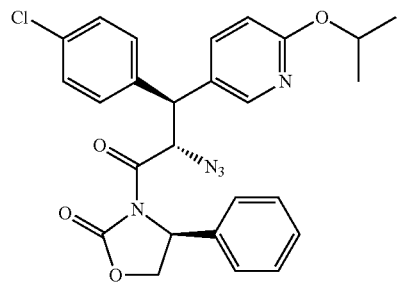 [SMILES: CC(C)Oc1ccc([C@H](c2ccc(Cl)cc2)[C@H](N=[N+]=[N-])C(=O)N2C(=O)OC[C@@H]2c2ccccc2)cn1]

A solution of sodium hexamethyldisilazide (2.15 mL of a 1.0 M solution in THF, 2.15 mmol) was added to 3 mL of dry THF at −78° C. under nitrogen atmosphere. (S)-3-((S)-3-(4-Chlorophenyl)-3-(6-isopropoxypyridin-3-yl)propanoyl)-4-phenyl-oxazolidin-2-one (907 mg, 1.95 mmol) in 12 mL of dry THF under nitrogen atmosphere was cooled to −78° C. and added via cannula to the solution of NaHMDS. The resulting solution was stirred at −78° C. for 30 min. Solid trisyl azide (785 mg, 2.54 mmol) was added and the mixture was stirred at −78° C. for 15 min. To the reaction was then added acetic acid (0.67 mL, 11.7 mmol) followed by solid Me$_4$NOAc (1.04 g, 7.8 mmol). The cooling bath was removed and the mixture was stirred at RT for 18 h. The mixture was diluted with brine and EtOAc. The layers were separated and the aqueous phase was extracted with EtOAc. The EtOAc extracts were combined, washed with aqueous NaHCO$_3$ and brine, dried over MgSO$_4$, filtered, and the solvents were removed under reduced pressure. The crude product was chromatographed on a 40 g SiO$_2$ column using a gradient elution of 0-100% EtOAc in hexanes. Fractions containing product were combined and the solvents were removed in vacuo to give the title compound. LCMS m/z=506.1 (M+H)$^+$.

Step 7: (2S,3S)-2-azido-3-(4-chlorophenyl)-3-(6-isopropoxypyridin-3-yl)propanoic acid A solution of (S)-3-((2S,3S)-2-azido-3-(4-chlorophenyl)-3-(6-isopropoxy-pyridin-3-yl)propanoyl)-4-phenyloxazolidin-2-one (661 mg, 1.31 mmol) in 9 mL of THF and 3 mL of water was cooled in an ice bath. To the stirred solution was added a solution of hydrogen peroxide (0.46 mL of a 35% solution in water, 5.2 mmol) followed by solid LiOH (62.6 mg, 2.61 mmol). The mixture was stirred at 0° C. for 1 h. A solution of sodium sulfite (659 mg, 5.23 mmol) in water (10 mL) was added, followed by a solution of NaHCO$_3$ (15.7 mL of a 0.5 M solution un water, 7.84 mmol). The mixture was stirred at RT for 5 min, then most of the THF was removed in vacuo. The remaining aqueous phase was extracted with two portions of DCM to remove the oxazolidinone, acidified to pH 5 with 10% aqueous citric acid, and extracted with two portions of EtOAc. The EtOAc extracts were combined, dried over MgSO$_4$, filtered, and the solvents were removed in vacuo to give the title compound. LCMS m/z=361.2 (M+H)$^+$.

Intermediate 7

(2S,3R)-2-Azido-3-(4-chlorophenyl)-3-((S)-2,2-dimethyltetrahydro-2H-pyran-4-yl)propanoic acid

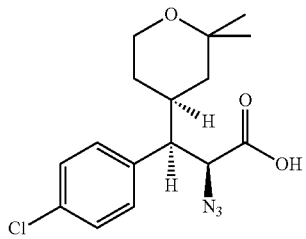 [SMILES: CC1(C)C[C@@H]([C@H](c2ccc(Cl)cc2)[C@H](N=[N+]=[N-])C(=O)O)CCO1]

Step 1. 2,2-dimethyltetrahydro-2H-pyran-4-carbaldehyde

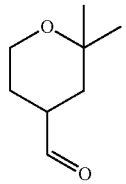

To a stirred solution of (2,2-dimethyltetrahydro-2H-pyran-4-yl)methanol (8 g, 55.5 mmol) in 260 mL DCM cooled to 0° C. in an ice/water bath was added Dess-Martin Periodinane (29.4 g, 69.3 mmol) in portions over 3 min and the resulting mixture was stirred for 1 h at 0° C. The mixture was quenched with solid calcium hydroxide (excess) and stirred vigorously for 45 min. The solids were filtered off and washed with DCM (2×100 mL). The organic phases were combined and the solvent was removed under reduced pressure to give the title product. $^1$HNMR (CD$_3$OD) δ: 9.56 (s, 1H); 4.16 (dd, J=3.3 and 16.1 Hz, 1H); 3.80-3.62 (m, 2H); 2.76-2.66 (m, 1H); 1.90-1.85 (m, 1H); 1.72-1.64 (m, 1H); 1.62-1.52 (m, 1H); 1.24 (s, 3H); 1.22 (s, 3H) ppm.

Step 2. (E)-tert-butyl 3-(2,2-dimethyltetrahydro-2H-pyran-4-yl)acrylate

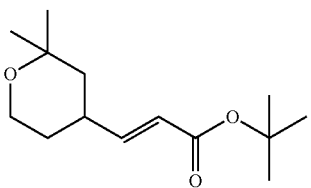 [SMILES: CC(C)(C)OC(=O)/C=C/C1CCOC(C)(C)C1]

To a stirred solution of 2,2-dimethyltetrahydro-2H-pyran-4-carbaldehyde (7.11 g, 50.0 mmol) in anhydrous DCM (500 mL) under nitrogen atmosphere was added solid tert-butyl 2-(triphenylphosphoranylidene)acetate (19.39 g, 51.5 mmol) and the resulting solution was stirred overnight at RT. The solution was concentrated to dryness and the residue purified on a 220 g silica gel column eluting with a gradient of 0-100% ethyl acetate in hexanes. The fractions containing product were combined and the solvents were removed in vacuo to afford the title product. MS: m/z=241 (M+H)$^+$.

Step 3. (E)-3-(2,2-dimethyltetrahydro-2H-pyran-4-yl)acrylic acid

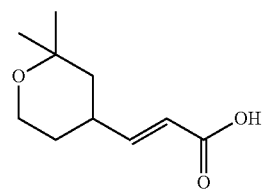

To a stirred solution of (E)-tert-butyl 3-(2,2-dimethyltetrahydro-2H-pyran-4-yl)acrylate (11.6 g, 48.3 mmol) in DCM (150 mL) cooled to 0° C. in an ice-water bath was added TFA (45 mL). After 5 min, the cooling bath was removed and the mixture was stirred at RT for 2 h. The solvent was removed under reduced pressure and the residue was dissolved in 50 mL DCM and 50 mL of toluene. The solvents were removed under reduced pressure to afford the title product. $^1$HNMR (CD$_3$OD) δ: 6.85 (dd, J=6.6 and 16.3 Hz, 1H); 5.80 (dd, J=1.5 and 16.3 Hz, 1H); 3.80-3.71 (m, 2H); 2.68-2.60 (m, 1H); 1.70-1.62 (m, 2H); 1.42-1.32 (m, 1H); 1.26 (s, 3H); 1.22 (s, 3H) ppm.

Step 4. (R,E)-4-Phenyl-3-(3-(2,2-dimethyltetrahydro-2H-pyran-4-yl)acryloyl)oxazolidin-2-one

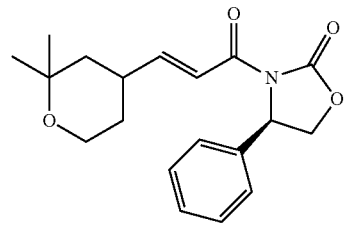 [SMILES: CC1(C)CC(/C=C/C(=O)N2C(=O)OC[C@H]2c2ccccc2)CCO1]

To a stirred solution of (E)-3-(2,2-dimethyltetrahydro-2H-pyran-4-yl)acrylic acid (9 g, 48.9 mmol) in 350 mL of THF was added TEA (7.49 mL, 53.7 mmol). The resulting solution was stirred under N$_2$ atmosphere and cooled to −10° C. (ice/salt water bath). Pivaloyl chloride (6.37 mL, 51.8 mmol) was added dropwise over 5 min and a thick precipitate formed. This suspension (A) was stirred at −10° C. for 15 min then cooled to −78° C. In a separate flask, (R)-4-phenyloxazolidin-2-one (9.01 g, 55.2 mmol) was dissolved in THF (150 mL) and the solution was stirred and cooled to −78° C. under N$_2$ atmosphere. n-BuLi (20.52 mL of a 2.5 M solution in hexane) was added dropwise over 5 min and a precipitate formed. This suspension (B) was stirred at −78° C. for 10 min. Suspension A (cooled at −78° C.) was added to suspension B via cannula over a period of 5 min. The resulting mixture was stirred at −78° C. for 10 min, then the cooling bath was removed and the mixture was stirred for 1.5 h while it gradually warmed to RT. The reaction mixture was poured into a 1000 mL Erlenmeyer flask and was diluted with EtOAc (400 mL). The resulting solution was extracted with water (2×300 mL), brine (300 mL), then dried over sodium sulfate, filtered, and concentrated in vacuo. The crude product was purified on a 220 g silica gel column eluting with a gradient of 0-60% ethyl acetate in hexanes. The fractions containing product were combined and the solvents were removed under reduced pressure to afford to give the title compound, MS: m/z=330 (M+H)$^+$.

Step 5. (R)-3-((R)-3-(4-chlorophenyl)-3-((S)-2,2-dimethyltetrahydro-2H-pyran-4-yl)propanoyl)-4-phenyloxazolidin-2-one

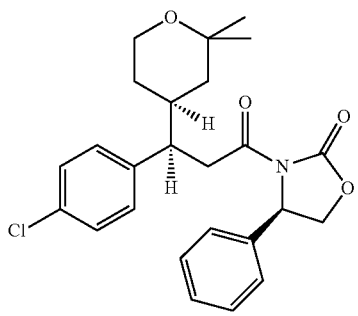 [SMILES: CC1(C)C[C@@H]([C@@H](CC(=O)N2C(=O)OC[C@H]2c2ccccc2)c2ccc(Cl)cc2)CCO1]

Copper(I) bromide dimethylsulfide complex (4.31 g, 21.35 mmol) was suspended in 200 mL of anhydrous THF under an N$_2$ atmosphere and the stirred suspension was cooled to −78° C. in a dry ice-acetone bath. (4-Chlorophenyl)magnesium bromide (21.3 mL of a 1.0 M solution in THF, 21.3 mmol) was added dropwise over 3 min and the resulting mixture was stirred for 10 min at −78° C. The cooling bath was removed and the mixture was stirred for 10 min. The mixture was again placed in the cooling bath and stirred for 5 min. A solution of (R,E)-4-phenyl-3-(3-(2,2-dimethyltetrahydro-2H-pyran-4-yl)acryloyl)oxazolidin-2-one (7 g, 21.25 mmol) in 35 mL of THF cooled to 0° C. was then added to the −78° C. Cu/Grignard solution via cannula over 3 min. The resulting mixture was stirred for 10 min, then the cooling bath was removed and the mixture was stirred for 3 h at RT. The reaction was quenched by the addition of saturated NH$_4$Cl aqueous solution (150 mL) and water (150 mL) and extracted with EtOAc (2×150 mL). The aqueous phase was removed. The organic phase was washed with brine, dried (NaSO$_4$), filtered, and concentrated in vacuo and the residue was purified on a 220 g silica gel column eluting with 20-80% ethyl acetate in hexanes. Two components were isolated, both with the same mass spectrum. The fractions containing the second eluting more polar isomer were combined and the solvents were removed in vacuo to give the title product. MS: m/z=442 (M+H)$^+$.

Step 6. (R)-3-(4-chlorophenyl)-3-((S)-2,2-dimethyltetrahydro-2H-pyran-4-yl)propanoic acid

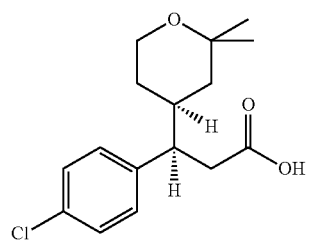 [SMILES: CC1(C)C[C@@H]([C@@H](CC(=O)O)c2ccc(Cl)cc2)CCO1]

To a solution of (R)-3-((R)-3-(4-chlorophenyl)-3-((S)-2,2-dimethyltetrahydro-2H-pyran-4-yl)propanoyl)-4-pheny-loxazolidin-2-one (3.0 g, 6.79 mmol) in THF/water (75 mL/25 mL) cooled to 0° C. in an ice-water bath was added hydrogen perioxide (2.38 mL of a 30% solution in water, 27.2 mmol) followed by solid LiOH (325 mg, 13.58 mmol) and the resulting solution was stirred for 1 h at 0° C. A solution of sodium sulfite (3.42 g) in 10 mL of water was added to the reaction and the cooling bath was removed. The mixture was stirred for 30 min at RT. Saturated aqueous sodium bicarbonate solution was added and the mixture was stirred for 10 min. The THF was removed under reduced pressure and the resulting aqueous solution was diluted with water (100 mL) and washed with DCM (2×100 mL) to remove the oxazolidinone by-product. The aqueous layer was acidified to pH 3 with addition of 6N HCl solution (caution, gas evolution). The acidic aqueous phase was extracted with ethyl acetate (2×150 mL). The organic phases were combined, dried over sodium sulfate, filtered, and the solvent was removed under reduced pressure to afford a gum, MS: m/z=297 (M+H)$^+$.

Step 7. (S)-3-((R)-3-(4-chlorophenyl)-3-((S)-2,2-dimethyltetrahydro-2H-pyran-4-yl)propanoyl)-4-phenyloxazolidin-2-one

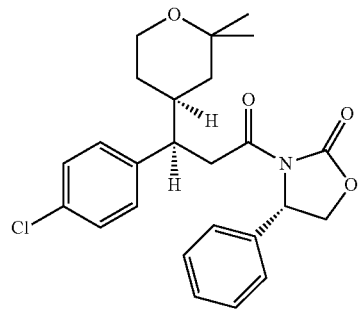 [SMILES: CC1(C)C[C@@H]([C@@H](CC(=O)N2C(=O)OC[C@@H]2c2ccccc2)c2ccc(Cl)cc2)CCO1]

To a solution of (3R)-3-(4-chlorophenyl)-3-((S)-2,2-dimethyltetrahydro-2H-pyran-4-yl)propanoic acid (1.62 g, 5.46 mmol) in 30 mL of THF was added TEA (0.84 mL, 6.0 mmol) and the resulting solution was stirred under N$_2$ atmosphere and cooled to −10° C. (ice/salt water bath). To the solution was added pivaloyl chloride (0.71 mL, 5.79 mmol) dropwise over 2 min. A thick precipitate formed and the suspension (A) was stirred at −10° C. for 15 min and then cooled to −78° C. In a separate flask, (S)-4-phenyloxazolidin-2-one (1.01 g, 6.17 mmol) was dissolved in THF (10 mL) and the resulting solution was stirred and cooled to −78° C. under N$_2$ atmosphere. n-BuLi (2.29 mL of a 2.5 M solution in hexane) was added dropwise over 2 min and a precipitate formed. This suspension (B) was stirred at −78° C. for 10 min. Suspension A (−78° C.) was then added to suspension B via cannula over a period of 2 min. The resulting mixture was stirred at −78° C. for 10 min. The cooling bath was removed and the mixture was stirred for 1.5 h while it gradually warmed to RT. The reaction mixture was poured into a 500 mL Erlenmeyer flask and was diluted with EtOAc (100 mL). The resulting solution was washed with water (2×100 mL), brine (100 mL), then dried over sodium sulfate, filtered, and concentrated in vacuo. The resulting material was purified on a 220 g silica gel column eluting with a gradient of 0-60% ethyl acetate in hexanes. Fractions containing product were combined and the solvents were removed under reduced pressure to give the title compound, MS: m/z=442 (M+H)+.

Step 8. (S)-3-((2S,3R)-2-azido-3-(4-chlorophenyl)-3-((S)-2,2-dimethyltetrahydro-2H-pyran-4-yl)propanoyl)-4-phenyloxazolidin-2-one

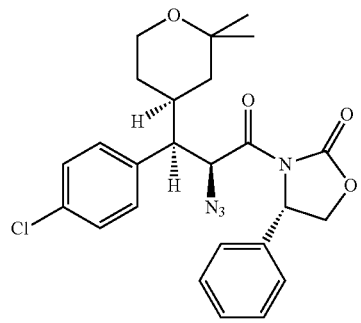 [SMILES: CC1(C)C[C@@H]([C@H](c2ccc(Cl)cc2)[C@H](N=[N+]=[N-])C(=O)N2C(=O)OC[C@@H]2c2ccccc2)CCO1]

To a −78° C. solution of (S)-3-((R)-3-(4-chlorophenyl)-3-((S)-2,2-dimethyltetrahydro-2H-pyran-4-yl)propanoyl)-4-phenyloxazolidin-2-one (2.10 g, 4.75 mmol) in 20 mL of anhydrous THF under $N_2$ atmosphere was added NaHMDS (1.0 M solution in THF, 6.0 mL, 6.0 mmol) and the resulting solution was stirred at −78° C. for 25 min. Solid trisyl azide (1.55 g, 6.32 mmol) was added in one portion and the resulting mixture was stirred for 30 min. A mixture of tetramethyl ammonium acetate (633 mg, 4.75 mmol) in HOAc (0.343 mL) was then added and the resulting mixture was stirred at RT for 3 h. The mixture was diluted with EtOAc (25 mL) and washed with aqueous $NaHCO_3$ (2×15 mL) and brine (15 mL). The aqueous layers were combined and extracted with EtOAc (25 mL). The EtOAc layers were combined and dried over sodium sulfate, filtered, and concentrated in vacuo to give a foam. The residue was purifed on an 80 g silica gel column eluting with a gradient of 0-70% ethyl acetate in hexanes. The fractions containing product were combineded and the solvents were removed under reduced pressure to give to give the title compound, MS: m/z=455 (M−$N_2$+H)+ and m/z 505 (M+Na)+.

Step 9. (2S,3R)-2-Azido-3-(4-chlorophenyl)-3-((S)-2,2-dimethyltetrahydro-2H-pyran-4-yl)propanoic acid To a 0° C. solution of (4S)-3-((2S,3R)-2-azido-3-(4-chlorophenyl)-3-((S)-2,2-dimethyltetrahydro-2H-pyran-4-yl) propanoyl)-4-phenyloxazolidin-2-one (1.1 g, 2.28 mmol) in THF (25.0 mL) and water (3.00 mL) was added 30% aqueous hydrogen peroxide (0.8 mL, 9.11 mmol) dropwise. The mixture was stirred at 0° C. for 10 min. A solution of LiOH (109 mg, 4.56 mmol) in water (1.0 mL) was added dropwise and the mixture was stirred for 2 h. The reaction mixture was quenched with a solution of sodium sulfite (1.15 g) in 5 mL of water and the resulting mixture was stirred for 30 min at RT. Saturated aqueous sodium bicarbonate (15 mL) was added and the mixture stirred for 10 min. The THF was removed under reduced pressure and the remaining aqueous solution was diluted with water (15 mL) and washed with DCM (2×25 mL) to remove the oxazolidinone by-product. The aqueous phase was acidified to pH 3 with 6N HCl solution. The acidic solution was extracted with ethyl acetate (2×100 mL). The organic phases were combined, dried over sodium sulfate, filtered, and the solvents were removed under reduced pressure to give a dense gum, MS: m/z=310 (M−$N_2$+H)+ and m/z 338 (M+H)+.

Intermediate 8

(2S,3R)-2-azido-3-(4-fluorophenyl)-3-((1r,4R)-4-methoxycyclohexyl)propanoic acid

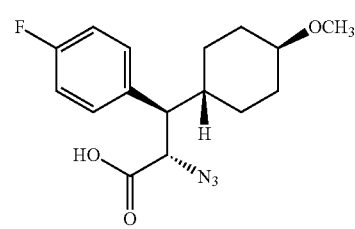 [SMILES: CO[C@H]1CC[C@H]([C@H](c2ccc(F)cc2)[C@H](N=[N+]=[N-])C(=O)O)CC1]

Step 1: (1r,4r)-methyl 4-hydroxycyclohexanecarboxylate

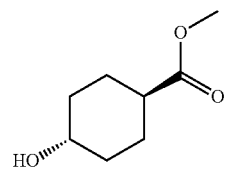

To a stirred solution of trans-4-hydroxycyclohexane carboxylic acid (20 g, 139 mmol) in MeOH (400 mL) at 0° C. was added $SOCl_2$ (20 mL, 278 mmol) dropwise. When the addition was complete, the mixture was heated at 70° C. for 16 h. The mixture was cooled to RT and the solvent was removed in vacuo. The residue was dissolved in ethyl acetate, washed with aqueous $NaHCO_3$ and brine, dried over sodium sulfate, filtered, and concentrated in vacuo to give the title compound MS (ESI) m/z (M+H)+: 158.09

Step 2: (1r,4r)-methyl 4-((tert-butyldiphenylsilyl)oxy)cyclohexanecarboxylate

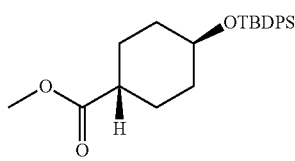

To a solution of (1r,4r)-methyl 4-hydroxycyclohexanecarboxylate (21.2 g, 134 mmol) and imidazole (10.9 g, 161 mmol) in DCM (300 mL) at 0° C. was added tert-butyldiphenylchlorosilane (44 g, 161 mmol). The mixture was stirred at RT for 16 h. The reaction was diluted with water and stirred for 30 min. The organic layer was collected and washed with brine, dried over sodium sulfate, filtered, and concentrated in vacuo. The crude product was purified by column chromatography on silica gel, eluting with 1% ethyl acetate in petroleum ether to give the title compound. MS (ESI) m/z (M+H)+: 396.2

Step 3: ((1r,4r)-4-((tert-butyldiphenylsilyl)oxy)cyclohexyl)methanol

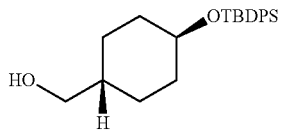

To a solution of LiAlH₄ (10.2 g, 268 mmol) in THF (600 mL) at 0° C. was added a solution of (1r,4r)-methyl 4-((tert-butyldiphenylsilyl)oxy)cyclohexanecarboxylate (53 g, 134 mmol) in THF (100 mL) dropwise. When the addition was complete the mixture was stirred at 0° C. for 30 min. A solution of NaOH (10.2 g) in water (80 mL) was added to quench the reaction. The resulting mixture was stirred at RT for 20 min and then the solids were removed by filtration. The filtrate solvent was removed in vacuo. The residue was dissolved in DCM and the solution was washed with brine, dried over sodium sulfate, filtered, and the solvent was removed in vacuo to give the title compound. MS (ESI) m/z $(M+H)^+$: 368.2

Step 4: (1r,4r)-4-((tert-butyldiphenylsilyl)oxy)cyclohexanecarbaldehyde

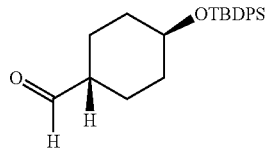

To a solution of oxalyl chloride (13.2 mL, 139 mmol) in DCM (300 mL) at −78° C. was added a solution of DMSO (13.5 g, 174 mmol) in DCM (100 mL) and the resulting mixture was stirred at −78° C. for 30 min. A solution of ((1r,4r)-4-((tert-butyl-diphenylsilyl)oxy)cyclohexyl)methanol (42.6 g, 116 mmol) in DCM (200 mL) was added dropwise over 1 h and the resulting mixture was stirred at −78° C. for 30 min. Triethylamine (84 mL, 579 mmol) was added dropwise over 40 min. The mixture was allowed to warm to RT with stirring for 30 min. Aqueous NH₄Cl (200 mL) was added to quench the reaction. The organic layer was separated and washed with brine, dried over sodium sulfate, filtered, and concentrated in vacuo to give the title compound. MS (ESI) m/z $(M+H)^+$: 366.2.

Step 5: (R)-3-((E)-3-((1r,4R)-4-((tert-butyldiphenylsilyl)oxy)cyclohexyl)acryloyl)-4-phenyloxazolidin-2-one

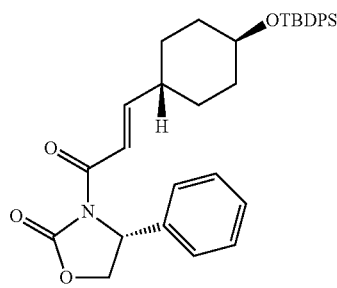

To a solution of (R)-dimethyl (2-oxo-2-(2-oxo-4-phenyloxazolidin-3-yl)ethyl)-phosphonate (0.3 g, 0.88 mmol) in THF (8 mL) under nitrogen at 0° C. was added t-BuOK (1.0 M in THF, 0.98 mL, 0.98 mmol) dropwise. The mixture was stirred at 0° C. for 30 min. A solution of (1r,4r)-4-((tert-butyldiphenylsilyl)oxy)cyclohexane-carbaldehyde (0.3 g, 0.82 mmol) in THF (1 mL) was added dropwise over a period of 10 min at 0° C. The cooling bath was removed and the resulting mixture was stirred at RT for 2 h. Aqueous NH₄Cl was added to quench the reaction and the mixture was extracted with ethyl acetate. The organic layer was washed with brine, dried over sodium sulfate, filtered, and concentrated in vacuo. The residue was purified by SiO₂ column chromatography eluting with 1:5 ethyl acetate in petroleum ether to give the title compound. MS (ESI) m/z $(M+H)^+$: 553.3.

Step 6: (R)-3-((R)-3-((1r,4R)-4-((tert-butyldiphenylsilyl)oxy)cyclohexyl)-3-(4-fluorophenyl)propanoyl)-4-phenyloxazolidin-2-one

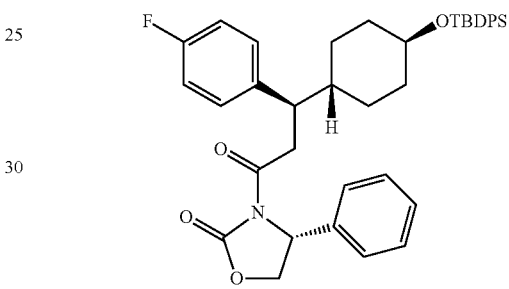

To a solution of (R)-3-((E)-3-((1r,4R)-4-((tert-butyldiphenylsilyl)oxy)cyclohexyl)-acryloyl)-4-phenyloxazolidin-2-one (2 g, 3.62 mmol) and CuBr/SMe₂ (0.745 g, 3.62 mmol) in THF (20 mL) under nitrogen at 0° C. was added (4-fluorophenyl)magnesium bromide (0.5 M in THF, 22 mL, 11 mmol) dropwise. The mixture was stirred at 0° C. for 1 h. Aqueous NH₄Cl was added to quench the reaction and the mixture was extracted with ethyl acetate. The organic layer was washed with brine, dried over sodium sulfate, filtered, and concentrated in vacuo. The residue was purified by column chromatography on silica gel eluting with 1:1 ethyl acetate in petroleum ether to give the title compound. MS (ESI) m/z $(M+H)^+$: 649.3.

Step 7: (R)-3-((1r,4R)-4-((tert-butyldiphenylsilyl)oxy)cyclohexyl)-3-(4-fluoro-phenyl)propanoic acid

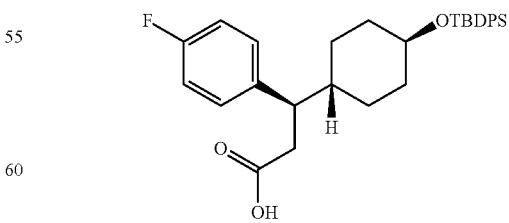

A solution of (R)-3-((R)-3-((1r,4R)-4-((tert-butyldiphenylsilyl)oxy)cyclohexyl)-3-(4-fluorophenyl)propanoyl)-4-phenyloxazolidin-2-one (13.43 g, 20.7 mmol) in 150 mL THF and 50 mL water was cooled to 0° C. To the stirred solution was added hydrogen peroxide (82.8 mmol of a 30% solution in water) and solid LiOH (1.74 g, 41.4 mmol). The mixture was stirred at 0° C. for 40 min. A solution of sodium sulfite (10.4 g, 82.8 mmol) in water (100 mL) was added to the mixture. A solution of $NaHCO_3$ (8.69 g, 103.5 mmol) in water (50 mL) was added and the mixture was stirred for 5 min. Most of the THF was removed in vacuo and the remaining aqueous phase was extracted with DCM to remove the oxazolidinone. The aqueous phase was acidified to pH 2 with dilute HCl and then extracted with two portions of EtOAc. The EtOAc extracts were combined, washed with brine, dried over sodium sulfate, filtered, and concentrated in vacuo to give the title compound. MS (ESI) m/z (M+H)$^+$: 504.2.

Step 8: (S)-3-((R)-3-((1r,4R)-4-((tert-butyldiphenyl-silyl)oxy)cyclohexyl)-3-(4-fluorophenyl)propanoyl)-4-phenyloxazolidin-2-one

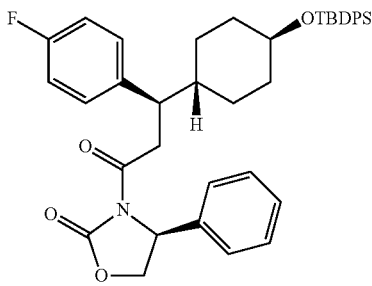

To a solution of (R)-3-((1r,4R)-4-((tert-butyldiphenylsi-lyl)oxy)cyclohexyl)-3-(4-fluorophenyl)propanoic acid (5.7 g, 11.3 mmol) and DMF (0.1 mL) in DCM (60 mL) 0° C. under nitrogen was added (COCl)$_2$ (3.2 mL, 33.9 mmol) dropwise. The mixture was stirred at 0° C. for 1 h, then concentrated in vacuo to give the crude acid chloride. To a stirred solution of (S)-4-phenyloxazolidin-2-one (2.03 g, 12.4 mmol) in 100 mL dry THF at −5° C. under nitrogen atmosphere was added n-BuLi (2.5 M in hexane, 5 mL, 12.5 mmol) dropwise. The mixture was stirred for 30 min, then a solution of the crude acid chloride in 10 mL dry THF was added dropwise. The mixture was stirred at 0° C. for 1 h, then quenched with aqueous NH$_4$Cl and extracted with EtOAc. The organic phase was washed with brine, dried over Na$_2$SO$_4$, filtered, and concentrated in vacuo. The crude product was purified by column chromatography on silica gel eluted with 1:10 ethyl acetate in petroleum ether to give the title compound. MS (ESI) m/z (M+H)$^+$: 649.3.

Step 9: (S)-3-((R)-3-(4-fluorophenyl)-3-((1r,4R)-4-hydroxycyclohexyl)propanoyl)-4-phenyloxazolidin-2-one

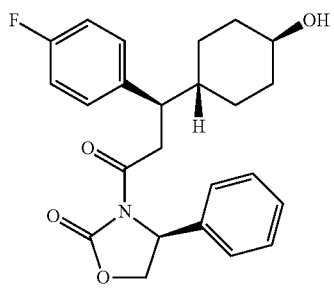 [SMILES: O=C(C[C@@H](c1ccc(F)cc1)[C@H]1CC[C@H](O)CC1)N1C(=O)OC[C@@H]1c1ccccc1]

To a solution of (S)-3-((R)-3-((1r,4R)-4-((tert-butyldiphenylsilyl)oxy)cyclohexyl)-3-(4-fluorophenyl)-propanoyl)-4-phenyloxazolidin-2-one (2.2 g, 3.39 mmol) in DCM (30 mL) at 0° C. was added a solution of HCl (6 M in MeOH, 30 mL). The cooling bath was removed and the mixture was stirred at RT for 16 h. The solvents were removed in vacuo and the crude product was purified by column chromatography on silica gel eluting with 1:1 ethyl acetate in hexanes to give the title compound. MS (ESI) m/z (M+H)$^+$: 411.2.

Step 10: (S)-3-((R)-3-(4-fluorophenyl)-3-((1r,4R)-4-methoxycyclohexyl)propanoyl)-4-phenyloxazolidin-2-one A solution of (S)-3-((R)-3-(4-fluorophenyl)-3-((1r,4R)-4-hydroxycyclohexyl)propanoyl)-4-phenyloxazolidin-2-one (770 mg, 1.87 mmol), Me$_3$OBF$_4$ (1.66 g, 11.2 mmol) and 1,2-bis(dimethylamino)naphthalene (2.4 g, 11.2 mmol) in DCM (40 mL) was stirred at RT for 6 h. The reaction was quenched with 1 M aqueous HCl and extracted with EtOAc. The combined organic phases were washed with water, aqueous NaHCO$_3$ and brine, then dried over Na$_2$SO$_4$, filtered and concentrated in vacuo. The crude product was purified by column chromatography on silica gel eluted with 1:2 ethyl acetate in petroleum ether to give the title compound. MS (ESI) m/z (M+H)$^+$: 425.2.

Step 11: (S)-3-((2S,3R)-2-azido-3-(4-fluorophenyl)-3-((1r,4R)-4-methoxycyclohexyl)propanoyl)-4-phenyloxazolidin-2-one To a solution of (S)-3-((R)-3-(4-fluorophenyl)-3-((1r,4R)-4-methoxycyclohexyl)propanoyl)-4-phenyloxazolidin-2-one (630 mg, 1.48 mmol) in THF (20 mL) at −78° C. under nitrogen was added NaHMDS (1 M in THF, 1.63 mL, 1.63 mmol) dropwise. The mixture was stirred at −78° C. for 45 min, then solid trisyl azide (595 mg, 1.93 mmol) was added and the mixture was stirred for 15 min. The reaction was quenched with HOAc (534 mg, 8.89 mmol) and solid Bu$_4$NOAc (1.64 g, 5.93 mmol). The cooling bath was removed and the mixture was stirred at RT for 16 h. The mixture was diluted with brine and extracted with ethyl acetate. The organic phase was washed with aqueous NaHCO₃ and brine, dried over Na₂SO₄, filtered, and concentrated in vacuo. The crude product was purified by column chromatography on silica gel eluting with 1:5 ethyl acetate in petroleum ether to give the title compound. MS (ESI) m/z (M+H)⁺: 466.2.

Step 12: (2S,3R)-2-azido-3-(4-fluorophenyl)-3-((1r, 4R)-4-methoxycyclohexyl)propanoic acid To a 0° C. solution of (S)-3-((2S,3R)-2-azido-3-(4-fluorophenyl)-3-((1r,4R)-4-methoxycyclohexyl)propanoyl)-4-phenyloxazolidin-2-one (360 mg, 0.822 mmol) in 6 mL THF and 2 mL water was added hydrogen peroxide (3.29 mmol of a 30% solution in water) and solid LiOH (69 mg, 1.64 mmol). The mixture was stirred at 0° C. for 40 min. Sodium sulfite (414 mg, 3.29 mmol) in water (10 mL) was added followed by NaHCO₃ (345 mg, 4.11 mmol), and the mixture was stirred for 5 min. Most of the THF was removed in vacuo and the remaining aqueous solution was extracted with DCM to remove the oxazolidinone. The aqueous phase was acidified with 6 N HCl to pH 1 and extracted with two portions of EtOAc. The organic phases were combined, dried over Na₂SO₄, filtered, and the solvent was removed in vacuo to give the title compound. MS (ESI) m/z (M+H)⁺: 321.2.

Intermediate 9

(2S,3R)-2-Azido-3-(4-chlorophenyl)-3-((1r,4R)-4-methoxycyclohexyl)propanoic acid

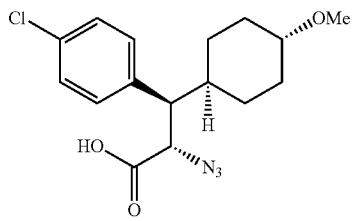 [SMILES: CO[C@H]1CC[C@H]([C@H](c2ccc(Cl)cc2)[C@H](N=[N+]=[N-])C(=O)O)CC1]

Intermediate 9 was prepared from using the procedure described for Intermediate 8 using (4-chlorophenyl)magnesium bromide.

Intermediate 10

(S)-2-Azido-2-((2R,4r,6S)-4-(4-chlorophenyl)-2,6-dimethyltetrahydro-2H-pyran-4-yl)acetic acid

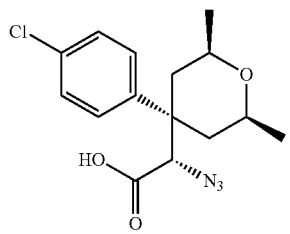 [SMILES: C[C@@H]1C[C@](c2ccc(Cl)cc2)([C@H](N=[N+]=[N-])C(=O)O)C[C@H](C)O1]

Step 1. (2R,6S)-4-(4-chlorophenyl)-2,6-dimethyltetrahydro-2H-pyran-4-ol

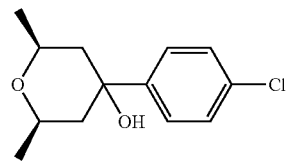 [SMILES: C[C@@H]1CC(O)(c2ccc(Cl)cc2)C[C@H](C)O1]

n-BuLi (30 mL, 75 mmol) was dropwise added to a solution of 4-chlorobromobenzene (14.24 g, 75 mmol) in THF (200 mL) at −78° C. and then stirred for 30 min. (2R,6S)-2,6-Dimethyldihydro-2H-pyran-4(3H)-one (8 g, 62.5 mmol) was added dropwise to the solution and then stirred additional 1 h. The reaction mixture was quenched with saturated NH₄Cl, and extracted with EtOAc three times, the combined organic extracts were washed with brine, dried over Na₂SO₄, concentrated in vacuo. The residual was purified by chromatography on silica gel (PE:EA=20:1) to afford the title compound.

Step 2. (2R,4s,6S)-4-allyl-4-(4-chlorophenyl)-2,6-dimethyltetrahydro-2H-pyran

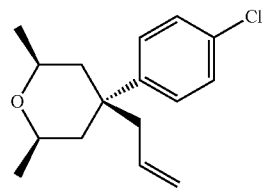 [SMILES: C=CC[C@@]1(c2ccc(Cl)cc2)C[C@@H](C)O[C@@H](C)C1]

To an ice-cooled solution of (2R,6S)-4-(4-chlorophenyl)-2,6-dimethyltetrahydro-2H-pyran-4-ol (4.5 g, 18.75 mmol) and allyltrimethylsilane (3.75 mL, 22.5 mmol) in DCM (50 mL) was added BF₃.OEt₂ (3 mL, 22.5 mmol). The resulting mixture was stirred at RT for 15 h. Then the reaction mixture was concentrated in vacuo and partitioned between H₂O and EtOAc, the organic layers were washed successively with saturated sodium bicarbonate solution and brine, dried over Na₂SO₄ and evaporated in vacuo. The residual was purified by pre-HPLC to afford the title compound. MS (ESI) m/z (M+H)⁺: 265.

Step 3. 2-((2R,4s,6S)-4-(4-chlorophenyl)-2,6-dimethyltetrahydro-2H-pyran-4-yl)acetic acid

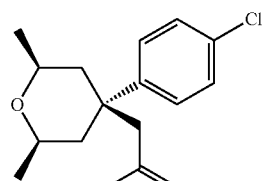

To a solution of (2R,4s,6S)-4-allyl-4-(4-chlorophenyl)-2,6-dimethyltetrahydro-2H-pyran (2.5 g, 9.47 mmol) in acetone (50 mL) was added a solution of KMnO₄ (838 mg, 5.303 mmol) and NaIO₄ (7.17 g, 33.523 mmol) in water (50 mL) at RT and the mixture was stirred for 2 h at RT. The precipitate was removed by filtration and the acetone was removed under reduced pressure. The residue was basified to pH 13 by addition of 1M aqueous sodium hydroxide, and then extracted with ether. The aqueous phase was acidified to pH 1 by addition of aqueous 1M HCl and then extracted with EtOAc. The combined organic layers were washed with brine, dried over Na$_2$SO$_4$ and then concentrated in vacuo to afford the title compound. $^1$H NMR (400 MHz, CDCl$_3$) δ 7.34-7.27 (m, 2H), 7.25-7.18 (m, 2H), 3.59-3.35 (m, 2H), 2.47 (s, 4H), 1.58-1.38 (m, 2H), 1.17 (d, J=6.3 Hz, 6H) ppm.

Step 4. (S)-3-(2-((2R,4s,6S)-4-(4-chlorophenyl)-2,6-dimethyltetrahydro-2H-pyran-4-yl)acetyl)-4-phenyloxazolidin-2-one

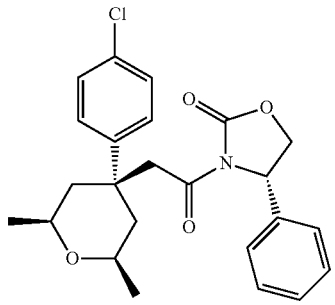 [SMILES: C[C@@H]1C[C@@](CC(=O)N2C(=O)OC[C@@H]2c2ccccc2)(c2ccc(Cl)cc2)C[C@H](C)O1]

To a solution of 2-((2R,4s,6S)-4-(4-chlorophenyl)-2,6-dimethyltetrahydro-2H-pyran-4-yl)acetic acid (1.8 g, 6.383 mmol) in DCM (20 mL) was added DMF (0.5 mL) at 0° C. under N$_2$. After 5 min, oxalyl chloride (973 mg, 7.66 mmol) was added to the mixture, after 2 h, the mixture was concentrated and used directly. A solution of chiral control groups in dry THF (20 mL) was cooled to −10° C. Then nBuLi (3.06 mL, 7.65 mmol) was added dropwise thereto, and stirred for 30 min. A solution of acyl chloride (1.914 g, 6.38 mmol) in THF (10 mL) was added dropwise. The resulting mixture was stirred for 1 h at 0° C. The reaction was quenched with 20% NH$_4$Cl and extracted with EtOAc. The combined organics were washed with water, aqueous NaHCO$_3$ and brine. It was dried over anhydrous Na$_2$SO$_4$ and concentrated in vaccuo. The resulting material was purified by column chromatograph on silicon to afford the title compound. MS (ESI) m/z (M+H)$^+$: 428.

Step 5. (S)-3-((S)-2-azido-2-((2R,4r,6S)-4-(4-chlorophenyl)-2,6-dimethyltetrahydro-2H-pyran-4-yl)acetyl)-4-phenyloxazolidin-2-one

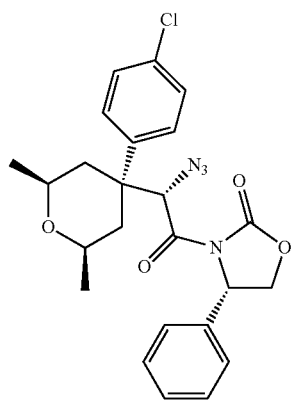 [SMILES: C[C@@H]1C[C@](c2ccc(Cl)cc2)([C@H](N=[N+]=[N-])C(=O)N2C(=O)OC[C@@H]2c2ccccc2)C[C@H](C)O1]

A solution of NaHMDS in 10 mL dry THF was cooled to −78° C. Then it was added dropwise to a solution of (S)-3-(2-((2R,4s,6S)-4-(4-chlorophenyl)-2,6-dimethyltetrahydro-2H-pyran-4-yl)acetyl)-4-phenyloxazolidin-2-one (2.4 g, 5.621 mmol) in 40 mL dry THF at −78° C. Then the resulting mixture was stirred for 45 min at this temperature. TosN$_3$ was added thereto. The resulting mixture was stirred for 15 min. Then HOAc and Bu$_4$NOAc were added. The bath was removed and stirred overnight. It was partitioned between EtOAc and brine. The organic layer was washed with saturated NaHCO$_3$ and brine. The organics was dried over Na$_2$SO$_4$ and concentrated in vaccuo to give crude product which was purified by column chromatography on silicon (PE:EA=10:1) to afford the title compound.

Step 6. (S)-2-azido-2-((2R,4r,6S)-4-(4-chlorophenyl)-2,6-dimethyltetrahydro-2H-pyran-4-yl)acetic acid A solution of (S)-3-((S)-2-azido-2-((2R,4r,6S)-4-(4-chlorophenyl)-2,6-dimethyltetrahydro-2H-pyran-4-yl)acetyl)-4-phenyloxazolidin-2-one (780 mg, 1.667 mmol) in 15 mL THF and 5 mL water was cooled in an ice bath. Add hydrogen peroxide, then solid LiOH. Stir at 0° C. for 40 min. Dissolve sodium sulfite in water and add to reaction. Then add NaHCO$_3$ solution and stir for 5 min. Rotovap off THF and dilute with water. Wash with DCM to remove the chiral auxiliary. Acidify aqueous with 6N HCl and extracted with EtOAc. Dry combined organics over Na$_2$SO$_4$ and rotovap off solvent to afford the title compound (350 mg). $^1$H NMR (400 MHz, CDCl$_3$) δ 7.31-7.25 (m, 2H), 7.19-7.10 (m, 2H), 3.95-3.84 (m, 1H), 3.45-3.24 (m, 2H), 2.49-2.29 (m, 2H), 1.66-1.41 (m, 2H), 1.13 (d, J=5.9 Hz, 6H) ppm.

Intermediate 11

(S)-2-Azido-2-(4-(4-chlorophenyl)tetrahydro-2H-pyran-4-yl)acetic acid

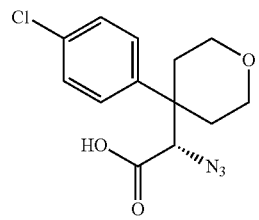 [SMILES: [N-]=[N+]=N[C@H](C(=O)O)C1(c2ccc(Cl)cc2)CCOCC1]

Step 1. ethyl 2-cyano-2-(dihydro-2H-pyran-4(3H)-ylidene)acetate

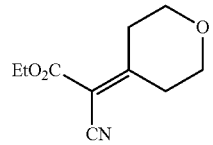

Dihydro-2H-pyran-4(3H)-one (5.0 g, 50 mmol) was dissolved in toluene (50 mL) and ethyl 2-cyanoacetate (5.65 g, 50 mmol), ammonium acetate (0.77 g, 10 mmol), and acetic acid (2.4 mL, 40 mmol) were added. Piperidine (3 drops) was then added and the stirred mixture was heated to reflux for 3.5 h. The mixture was cooled to RT and the solvent was removed in vacuo. The crude material was dissolved in EtOAc and extracted with water, saturated aquepous NaHCO₃, and brine. The organic phase was dried over MgSO₄ and the solvent was removed in vacuo and the crude product was chromatographed on a 120 g SiO₂ column using 0-40% EtOAc:hexane over 30 min at 85 mL/min. Pure fractions were combined and the solvents were removed in vacuo to give the title compound.

Step 2. Ethyl 2-(4-(4-chlorophenyl)tetrahydro-2H-pyran-4-yl)-2-cyanoacetate

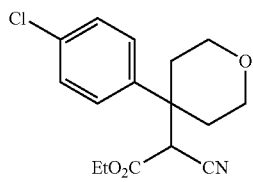

Ethyl 2-cyano-2-(dihydro-2H-pyran-4(3H)-ylidene)acetate (5.8 g, 30 mmol) was dissolved in 120 mL of dry ether and to the stirred solution was added 4-chlorophenylmagnesium bromide (37 mL of a 1.0 M solution in THF, 37 mmol) dropwise over a period of 10 min. A thick suspension formed and the mixture was heated to reflux for 2.5 h. The mixture was then cooled in an ice bath and quenched with the addition of 25 mL 1M HCl. The reaction was diluted with water and extract with ether. The organic phase was dried over MgSO₄ and the solvents were removed under reduced pressure to provide crude product. The crude product was chromatographed on a 120 g SiO₂ column using 0-50% EtOAc:hexane over 30 min at 85 mL/min. Pure fractions were combined and the solvents were removed in vacuo to give the title compound.

Step 3. 2-(4-(4-chlorophenyl)tetrahydro-2H-pyran-4-yl)acetic acid

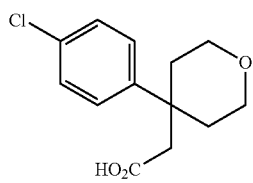 [SMILES: O=C(O)CC1(c2ccc(Cl)cc2)CCOCC1]

Ethyl 2-(4-(4-chlorophenyl)tetrahydro-2H-pyran-4-yl)-2-cyanoacetate (5.9 g, 19 mmol) was dissolved in 100 mL of ethylene glycol and to the stirred solution was added a solution of KOH (9.1 g, 160 mmol) in 20 mL water. The mixture was heated to reflux for 18 h. The mixture was cooled to RT and the solvents were removed in vacuo. The residue was dissolved in water and the solution was extracted with ether. The aqueous phase was acidified to pH 1 with conc. HCl and extracted with three portions of ether. The combined organic phases were washed with brine, died over MgSO₄, and the solvent was removed under reduced pressure to give the title compound.

Step 4. 2-(4-(4-chlorophenyl)tetrahydro-2H-pyran-4-yl)acetyl chloride

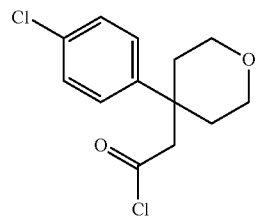 [SMILES: O=C(Cl)CC1(c2ccc(Cl)cc2)CCOCC1]

2-(4-(4-Chlorophenyl)tetrahydro-2H-pyran-4-yl)acetic acid (390 mg, 1.5 mmol) was dissolved in 15 mL of DCM and to the solution was added thionyl chloride (0.54 g, 4.6 mmol). The stirred solution was heated to reflux for 4 h. The reaction was cooled to RT and the solvent was removed in vacuo to give a dense gum.

Step 5. (S)-3-(2-(4-(4-chlorophenyl)tetrahydro-2H-pyran-4-yl)acetyl)-4-phenyloxazolidin-2-one

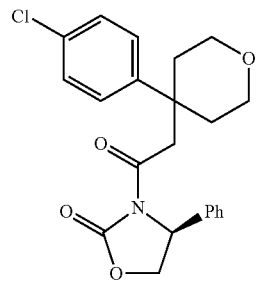 [SMILES: O=C(CC1(c2ccc(Cl)cc2)CCOCC1)N1C(=O)OC[C@@H]1c1ccccc1]

(S)-4-Phenyloxazolidin-2-one (250 mg, 1.5 mmol) was dissolved in 15 mL of dry THF and cooled to −10° C. under an atmosphere of nitrogen. To the stirred solution was added n-BuLi (1.5 mL of a 1.0 M solution in hexanes, 1.5 mmol) dropwise and the resulting solution was stirred for 10 min. 2-(4-(4-Chlorophenyl)tetrahydro-2H-pyran-4-yl)acetyl chloride (420 mg, 1.5 mmol) was dissolved in 6 mL of dry THF and added dropwise to oxazolidinone anion solution. The reaction mixture was stirred at 0° C. for 1 h, then quenched with 20% NH₄Cl and extracted with EtOAc. The organic phase was washed with water, saturated aquoeus NaHCO₃, and brine, then dried over MgSO₄. The solvents were removed in vacuo and the crude product was chromatograph on a 12 g SiO₂ column using 0-70% hexane:EtOAc over 15 min at 30 mL/min. Pure fractions were combined and the solvents were removed in vacuo to give the title product.

Step 6. (S)-3-((S)-2-azido-2-(4-(4-chlorophenyl)tetrahydro-2H-pyran-4-yl)acetyl)-4-phenyloxazolidin-2-one

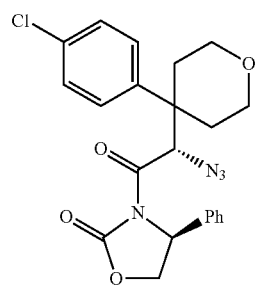 [SMILES: [N-]=[N+]=N[C@H](C(=O)N1C(=O)OC[C@@H]1c1ccccc1)C1(c2ccc(Cl)cc2)CCOCC1]

NaHMDS (13.7 mL of a 1.0 M solution in THF, 13.8 mmol) was added to 14 mL of dry THF under nitrogen atmosphere and cooled to −78° C. (S)-3-(2-(4-(4-chlorophenyl)tetrahydro-2H-pyran-4-yl)acetyl)-4-phenyloxazolidin-2-one (5.0 g, 12.5 mmol) was dissolved in 60 mL of dry THF under nitrogen atmosphere, the solution was cooled to −78° C. and transferred by cannula into the stirred solution of NaHMDS. The resulting solution was stirred at −78° C. for 45 min. Trisyl azide (5.0 g, 16 mmol) was added as a solid and the mixture was stirred for 15 min at −78° C. Acetic acid (4.5 mL, 75 mmol) and solid Me$_4$NOAc (6.7 g, 50 mmol) were then added to the mixture. The cooling bath was removed and the mixture was stirred at RT overnight. The reaction was diluted with EtOAc and brine. The layers were separated and the aqueous phase was extracted with EtOAc. The combined organic extracts were washed with saturated aqueous NaHCO$_3$ and brine, then dried over MgSO$_4$ and the solvents were removed in vacuo. The crude product was chromatographed on a 120 g SiO$_2$ column using 0-40% EtOAc:hexane over 30 min at 85 mL/min. Pure fractions were combined and the solvents were removed in vacuo to give a dense gum, LCMS: m/z=400.3 (M+H)$^+$.

Step 7. (S)-2-azido-2-(4-(4-chlorophenyl)tetrahydro-2H-pyran-4-yl)acetic acid (S)-3-((S)-2-Azido-2-(4-(4-chlorophenyl)tetrahydro-2H-pyran-4-yl)acetyl)-4-phenyloxazolidin-2-one (265 mg, 0.60 mmol) was dissolved in 4.5 mL THF and 1.5 mL water and cooled in an ice-water bath. To the solution was added 30% aqueous hydrogen peroxide (0.21 mL, 2.4 mmol) and solid LiOH (29 mg, 1.2 mmol). The mixture was stirred for 45 min. Sodium sulfite (300 mg, 2.4 mmol) in 3 mL of water and NaHCO$_3$ solution (6 mL of a 0.5 M solution, 3 mmol) were added and the reaction mixture was stirred for 5 min. Most of the THF was removed under reduced pressure and the resulting solution was diluted with water. The solution was washed with two portions of DCM to remove the chiral auxiliary. The aqueous phase was then acidified with 6N aqueous HCl to pH 2 and extracted with two portions of EtOAc. The EtOAc phases were combined, dried over MgSO$_4$, and the solvent was removed in vacuo to give a dense gum. LCMS m/z=296.2 (M+H)$^+$.

Intermediate 12

(2S,3S)-2-Azido-3-(4-chlorophenyl)-3-(3,5-difluorophenyl)propanoic acid

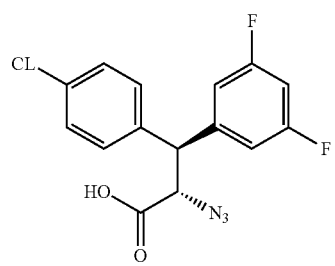

The title compound was prepared from 4-chlorobenzaldehyde and 3,5-difluorophenylmagnesium bromide using the procedures given for Intermediate 4.

Intermediate 13

(2S,3R)-2-Azido-3-(4-chlorophenyl)-3-(tetrahydro-2H-pyran-4-yl)propanoic acid

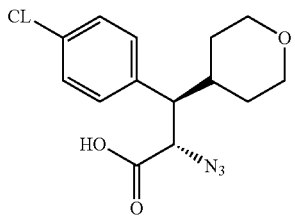

The title compound was prepared from tetrahydropyran-4-carboxaldehyde and 4-chlorophenylmagnesium bromide using the procedures given for Intermediate 3.

Intermediate 14

(2S,3R)-2-Azido-3-(4-chloro-3-fluorophenyl)-5-(tetrahydro-2H-pyran-4-yl)pentanoic acid

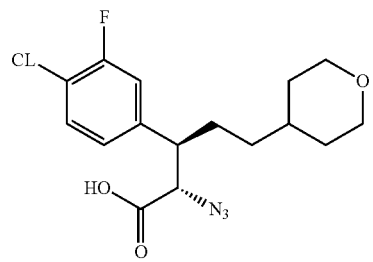

The title compound was prepared from 3-(tetrahydropyran-4-yl)propanal and 4-chloro-3-fluorophenylmagnesium bromide using the procedures given in Intermediate 3.

Intermediate 15

(2S,3R)-2-Azido-3-(4-fluorophenyl)-3-(4-(trifluoromethyl)phenyl)propanoic acid

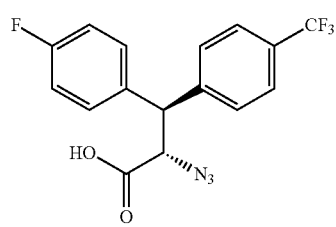 [SMILES: [N-]=[N+]=N[C@H](C(=O)O)[C@@H](c1ccc(F)cc1)c1ccc(C(F)(F)F)cc1]

The title compound was prepared from 4-fluorobenzaldehyde and (4-(trifluoromethyl)phenyl)magnesium bromide using the procedures given in Intermediate 3.

Intermediate 16

(2S,3S)-2-Azido-3-(4-fluorophenyl)-3-(3-(trifluoromethyl)phenyl)propanoic acid

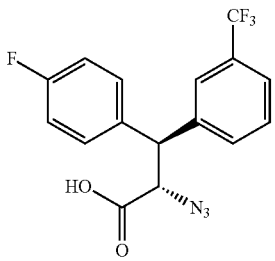 [SMILES: [N-]=[N+]=N[C@H](C(=O)O)[C@@H](c1ccc(F)cc1)c1cccc(C(F)(F)F)c1]

The title compound was prepared from 4-fluorobenzaldehyde and (3-(trifluoromethyl)phenyl)magnesium bromide using the procedures given in Intermediate 3.

Intermediate 17

(2S,3S)-2-Azido-3-(2,3-dihydro-1H-inden-5-yl)-3-(4-fluorophenyl)propanoic acid

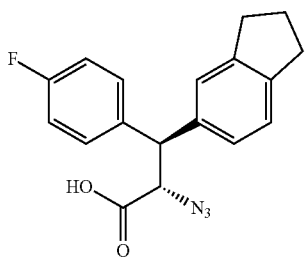 [SMILES: [N-]=[N+]=N[C@H](C(=O)O)[C@@H](c1ccc(F)cc1)c1ccc2c(c1)CCC2]

The title compound was prepared from 4-fluorobenzaldehyde and (2,3-dihydro-1H-inden-5-yl)magnesium bromide using the procedures given in Intermediate 4.

Intermediate 18

(2S,3R)-2-Azido-3-(4-chlorophenyl)-3-(3,3-difluorocyclobutyl)propanoic acid

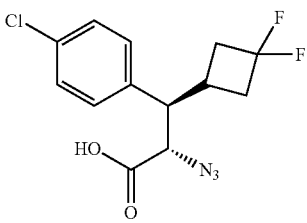 [SMILES: [N-]=[N+]=N[C@H](C(=O)O)[C@@H](c1ccc(Cl)cc1)C1CC(F)(F)C1]

The title compound was prepared from 3,3-difluorocyclobutanecarbaldehyde and 4-chlorophenylmagnesium bromide using the procedures given for Intermediate 3.

Intermediate 19

(2S,3R)-2-Azido-3-(4-chlorophenyl)-3-(4,4-difluorocyclohexyl)propanoic acid

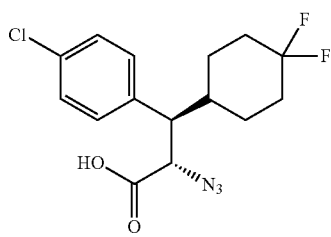 [SMILES: [N-]=[N+]=N[C@H](C(=O)O)[C@@H](c1ccc(Cl)cc1)C1CCC(F)(F)CC1]

The title compound was prepared from 4,4-difluorocyclohexanecarbaldehyde and 4-chlorophenylmagnesium bromide using the procedures given for Intermediate 3.

Intermediate 20

(2S,3R)-2-Azido-3-(4-chlorophenyl)-3-((2R,4r,6S)-2,6-dimethyltetrahydro-2H-pyran-4-yl)propanoic acid

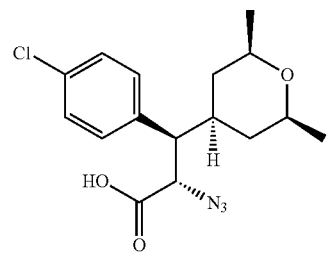 [SMILES: C[C@@H]1C[C@H]([C@H](c2ccc(Cl)cc2)[C@H](N=[N+]=[N-])C(=O)O)C[C@H](C)O1]

Step 1.
(2R,4r,6S)-2,6-Dimethyltetrahydro-2H-pyran-4-ol

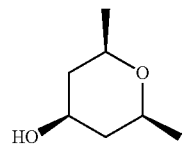

A mixture of 2,6-dimethyl-4H-pyran-4-one (50 g, 0.4 mol) and 10% Pd/C (25 g, 24 mmol) in methanol (400 mL) was stirred under 50 psi of $H_2$ at 50° C. for 24 h. The catalyst was removed by filtration and the filtrate solvent was removed in vacuo to give the title compound. $^1$H NMR δ 3.82-3.89 (m, 1H), 3.67-3.74 (m, 1H), 3.36-3.43 (m, 2H), 1.83-1.87 (dd, 2H), 1.54-1.59 (m, 1H), 1.29-1.39 (m, 1H), 1.16-1.17 (d, 6H) ppm.

Step 2. (2R,6S)-2,6-Dimethyldihydro-2H-pyran-4(3H)-one

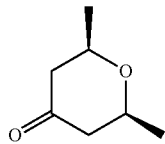

To a solution of (2R,4r,6S)-2,6-dimethyltetrahydro-2H-pyran-4-ol (28 g, 0.214 mol) in 200 mL of DCM was added a solution of NaHCO₃ (1.81 g, 21.54 mmol) and KBr (2.56 g, 21.54 mmol) in water (30 mL). Then TEMPO (0.34 g, 2.15 mmol) was added. The mixture was cooled to 0° C. and stirred while aqueous NaClO (21.56 g, 0.24 mol, 5% solution in water) was slowly added over a period of 1 h. The cooling bath was removed and the mixture was stirred at RT for 24 h. The DCM phase was collected and the aqueous phase was extracted with DCM. The organic layers were combined, washed with brine, dried over anhydrous Na₂SO₄, filtered, and concentrated in vacuum. The residue was purified by silica gel column chromatography using 10% ethyl acetate in petroleum ether as the mobile phase. Fractions containing product were combined and the solvents were removed in vacuo to give the title compound. ¹H NMR δ 3.65-3.76 (m, 2H), 3.32-3.36 (m, 2H), 2.17-2.24 (m, 2H), 1.31-1.33 (m, 6H) ppm.

Step 3. (2R,4r,6S)-2,6-Dimethyltetrahydro-2H-pyran-4-carboxylic acid

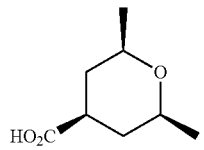

To a solution of (2R,6S)-2,6-dimethyldihydro-2H-pyran-4(3H)-one (20 g, 156 mmol) in 400 mL of DME was added tosylmethylisocyanide (39.8 g, 203 mmol) and t-BuOH (19.6 g, 265 mmol). The mixture was cooled in an ice/brine bath so that the internal temperature was below 0° C., and potassium tert-butoxide (43.68 g, 390 mmol) was added in portions at a rate which maintained the reaction temperature below 10° C. The stirred mixture was heated to 35° C. for 16 h. The mixture was cooled to RT, 200 mL of t-BuOMe was added, the mixture was filtered and the filter cake was washed with t-BuOMe. The filtrate solvents were removed in vacuo. The residue was suspended in 200 mL of 2.25 M KOH and the stirred mixture was heated to reflux for 17 h. The mixture was cooled to RT and transferred to a separatory funnel. The aqueous layer was extracted with 3×250 mL of CH₂Cl₂. The aqueous phase was transferrd to a flask and cooled to 0° C. and stirred. Concentrated aqueous HCl was slowly added to obtain a reading of pH 2. The aqueous layer was extracted with EtOAc. The organic layer was washed with brine, dried over anhydrous Na₂SO₄, filtered, and the filtrate solvent was removed in vacuo to provide the title compound. ¹H NMR δ 3.45-3.50 (m, 2H), 2.54-2.62 (m, 1H), 1.85-1.88 (d, 2H), 1.26-1.36 (q, 2H), 1.20-1.21 (d, 6H) ppm.

Step 4. (2R,4r,6S)—N-Methoxy-N,2,6-trimethyltetrahydro-2H-pyran-4-carboxamide

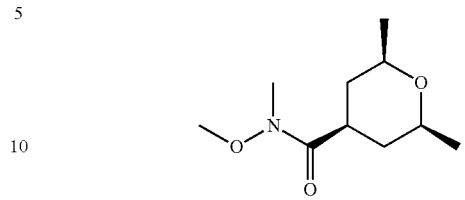

A solution of (2R,4r,6S)-2,6-dimethyltetrahydro-2H-pyran-4-carboxylic acid (12 g, 75.95 mmol), EDCI (19.9 g, 104.4 mmol) and HOBT (14.1 g, 104.4 mmol) in 220 mL of DCM was stirred at 0° C. for 0.5 h, then N,O-dimethylhydroxylamine hydrochloride (10.1 g, 104.4 mmol) and Et₃N (46 mL, 332 mmol) were added to the mixture. The mixture was stirred at RT for 4 h. The solvent was removed in vacuo and the residue was purified by SiO₂ column chromatography using a gradient elution of 10-20% ethyl acetate in petroleum ether. Fractions containing product were combined and the solvent was removed in vacuo to give the title compound. ¹H NMR δ 3.69 (s, 3H), 3.48-3.55 (m, 2H), 3.17 (s, 3H), 2.91-2.97 (t, 1H), 1.63-1.66 (d, 2H), 1.35-1.46 (m, 2H), 1.19-1.21 (d, 6H) ppm.

Step 5. (2R,4r,6S)-2,6-dimethyltetrahydro-2H-pyran-4-carbaldehyde

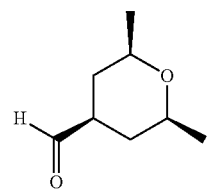

To a solution of (2R,4r,6S)—N-methoxy-N,2,6-trimethyltetrahydro-2H-pyran-4-carboxamide (10.5 g, 52.2 mmol) in 180 mL of dry THF at −78° C. under N₂ atmosphere was added LiAlH₄ (1.98 g, 52.2 mmol) in portions. The mixture was stirred at −78° C. for 1 h. The mixture was quenched with water (caution, gas evolution). The mixture was warmed to RT and diluted with water and EtOAc. The organic phase was collected and the aqueous layer was extracted with another portion of EtOAc. The organic layers were combined, washed with brine, dried over anhydrous Na₂SO₄, filtered, and the filtrate solvents were removed in vacuo to give the title compound. ¹H NMR δ 3.48-3.55 (m, 2H), 2.50-2.56 (m, 1H), 1.82-1.85 (d, 2H), 1.22-1.24 (d, 6H), 1.13-1.19 (m, 2H) ppm.

Step 6: (E)-3-((2R,4r,6S)-2,6-Dimethyltetrahydro-2H-pyran-4-yl)acrylic acid

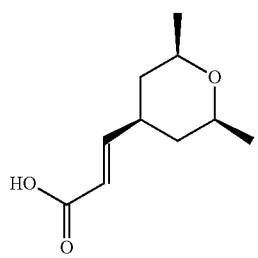

To a stirred solution of (2R,4r,6S)-2,6-dimethyltetrahydro-2H-pyran-4-carbaldehyde (6.36 g, 44.8 mmol) and malonic acid (5.13 g, 49.3 mmol) in 100 mL of pyridine was added piperidine (0.6 mL). The mixture was heated at 110° C. for 4 h. The mixture was cooled to RT and the solvent was removed in vacuo. The residue was treated with 2 N aqueous HCl to obtain a pH 1.5 solution, and the aqueous phase was extracted with two portions of EtOAc. The organic phases were combined, dried over anhydrous $Na_2SO_4$, filtered, and the filtrate solvents were removed in vacuo to obtain the crude product. The crude product was suspended in petroleum ether and filtered to give the title compound. $^1H$ NMR δ 6.94-6.99 (dd, 1H), 5.76-5.80 (d, 1H), 3.47-3.53 (m, 2H), 2.44-2.46 (m, 1H), 1.66-1.69 (d, 2H), 1.20-1.21 (d, 6H), 1.03-1.12 (m, 2H) ppm.

Step 7: (R)-3-((E)-3-((2R,4r,6S)-2,6-Dimethyltetrahydro-2H-pyran-4-yl)acryloyl)-4-phenyloxazolidin-2-one

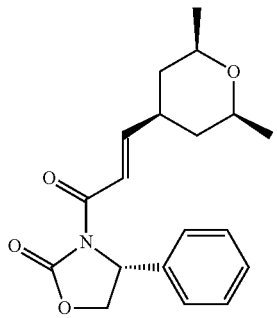 [SMILES: C[C@@H]1C[C@H](/C=C/C(=O)N2C(=O)OC[C@H]2c2ccccc2)C[C@H](C)O1]

To a stirred solution of (E)-3-((2R,4r,6S)-2,6-dimethyltetrahydro-2H-pyran-4-yl)acrylic acid (5.33 g, 28.9 mmol) and DMF (0.9 mL) in DCM (100 mL) under $N_2$ at 0° C. was added oxalyl chloride (4.42 g, 34.7 mmol) dropwise. The mixture was stirred for 2 h. The solution was concentrated in vacuo to give the crude acid chloride. In a separate flask, (R)-4-phenyloxazolidin-2-one (4.96 g, 30.4 mmol) was dissolved in dry THF (110 mL) and cooled to −78° C. with stirring under $N_2$ atmosphere. n-BuLi (12.1 mL of a 2.5 M solution in hexane, 30.4 mmol) was added dropwise and the resulting solution was stirred for 30 min. To this solution was added a solution of the crude acid chloride in THF (60 mL) dropwise over a period of 10 min. The mixture was stirred at −78° C. for 2 h. The reaction was quenched with 20% aqueous $NH_4Cl$ and extracted with two portions of EtOAc. The organic phases were combined, washed with water, aqueous $NaHCO_3$, and brine, then dried over $Na_2SO_4$, filtered, and the solvents were removed under reduced pressure. The residue was purified by silica gel column chromatography using a gradient elution of 10-20% ethyl acetate in petroleum ether. Fractions containing product were combined and the solvents were removed in vacuo to afford the title compound. MS (ESI) m/z (M+H)$^+$: 330.1.

Step 8: (R)-3-((R)-3-(4-chlorophenyl)-3-((2R,4r,6S)-2,6-dimethyltetrahydro-2H-pyran-4-yl)propanoyl)-4-phenyloxazolidin-2-one

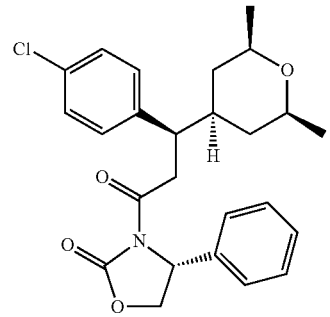 [SMILES: C[C@@H]1C[C@H]([C@@H](CC(=O)N2C(=O)OC[C@H]2c2ccccc2)c2ccc(Cl)cc2)C[C@H](C)O1]

A solution of 4-chlorophenylmagnesium bromide (81 mL of a 1.0 M solution in ether, 81 mmol) was added dropwise to a −40° C. suspension of copper(I)bromide dimethylsulfide complex (9.46 g, 45.9 mmol) in 60 mL of dry THF under nitrogen atmosphere. The resulting mixture was stirred at −40° C. for 30 min. To this mixture was added a solution of (R)-3-((E)-3-((2R,4r,6S)-2,6-dimethyltetrahydro-2H-pyran-4-yl)acryloyl)-4-phenyloxazolidin-2-one (8.10 g, 27.05 mmol) in 100 mL of dry THF dropwise over a period of 10 min. The resulting mixture was stirred at −40° C. for 2 h. The reaction was quenched with 20% $NH_4Cl$ and extracted with two portions of EtOAc. The organic phases were combined, washed with water, aqueous $NaHCO_3$ and brine, then dried over $Na_2SO_4$, filtered, and the solvents were removed in vacuo. The residue was purified by $SiO_2$ column chromatography using a gradient elution of 2-6% MeOH in DCM. Fractions containing product were combined and the solvents were removed in vacuo to afford the title compound. MS (ESI) m/z (M+H)$^+$: 442.2.

Step 9: (R)-3-(4-Chlorophenyl)-3-((2R,4r,6S)-2,6-dimethyltetrahydro-2H-pyran-4-yl)propanoic acid

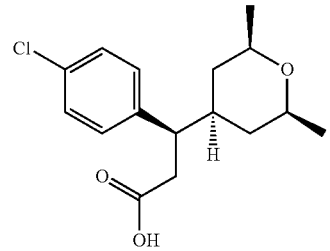 [SMILES: C[C@@H]1C[C@H]([C@@H](CC(=O)O)c2ccc(Cl)cc2)C[C@H](C)O1]

To a solution of (R)-3-((R)-3-(4-chlorophenyl)-3-((2R,4r,6S)-2,6-dimethyltetrahydro-2H-pyran-4-yl)propanoyl)-4-phenyloxazolidin-2-one (8.50 g, 19.2 mmol) in 200 mL of 3:1 THF:$H_2O$ was cooled to 0° C. in an ice-brine bath. To the stirred solution was added $H_2O_2$ (9.03 g, 84.7 mmol, a 30% solution in water) and $LiOH \cdot H_2O$ (1.62 g, 38.5 mmol), and the mixture was stirred at 0° C. for 4 h. The mixture was quenched with $Na_2SO_3$ (19.4 g, 154 mmol) in 100 mL of water, followed by $NaHCO_3$ (12.93 g, 154 mmol) in 180 mL of water. The stirred mixture was warmed to RT and the THF was removed under reduced pressure. The water layer was extracted twice with DCM to remove the oxazolidinone. The aqueous phase was acidified to pH 1 with concentrated HCl and extracted twice with EtOAc. The combined EtOAc layers were dried over anhydrous Na₂SO₄, filtered, and the filtrate solvents were removed in vacuo to give the title compound.

Step 10: (S)-3-((R)-3-(4-Chlorophenyl)-3-((2R,4r, 6S)-2,6-dimethyltetrahydro-2H-pyran-4-yl)propanoyl)-4-phenyloxazolidin-2-one

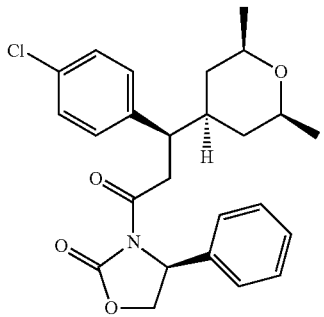 [SMILES: C[C@@H]1C[C@H]([C@@H](CC(=O)N2C(=O)OC[C@@H]2c2ccccc2)c2ccc(Cl)cc2)C[C@H](C)O1]

To a stirred solution of (R)-3-(4-chlorophenyl)-3-((2R,4r, 6S)-2,6-dimethyltetrahydro-2H-pyran-4-yl)propanoic acid (4.90 g, 16.5 mmol) and DMF (0.1 mL) in DCM (100 mL) under N₂ atmosphere at 0° C. was added oxalyl chloride (2.82 g, 22.1 mmol) dropwise. The mixture was stirred for 2 h. The solution was concentrated in vacuo to give the crude acid chloride. (S)-4-Phenyloxazolidin-2-one (3.32 g, 20.3 mmol) was dissolved in dry THF (110 mL) and cooled to −78° C. under N₂ atmosphere. To the stirred solution was added n-BuLi (8.0 mL of a 2.5 M solution in hexane, 20 mmol) dropwise over 3 min and the resulting solution was stirred for 0.5 h. To the solution was added a solution of the crude chloride in THF (60 mL) dropwise. The mixture was stirred at −78° C. for 2 h. The reaction was quenched with 20% NH₄Cl and extracted with two portions of EtOAc. The combined organic phases were washed with water, aqueous NaHCO₃, and brine, then dried over Na₂SO₄, filtered, and the solvents were removed in vacuo. The residue was purified by SiO2 column chromatography using a gradient elution of 10-20% EtOAc in petroleum ether. Fractions containing product were combined and the solvents were removed under reduced pressure to give the title compound. MS (ESI) m/z (M+H)⁺: 442.2.

Step 11: (S)-3-((2S,3R)-2-Azido-3-(4-chlorophenyl)-3-((2R,4r,6S)-2,6-dimethyltetrahydro-2H-pyran-4-yl)propanoyl)-4-phenyloxazolidin-2-one

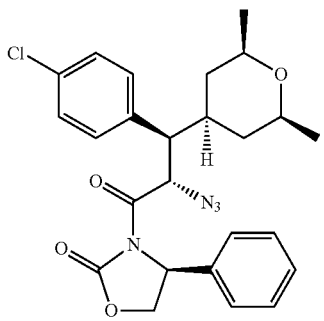 [SMILES: C[C@@H]1C[C@H]([C@H](c2ccc(Cl)cc2)[C@H](N=[N+]=[N-])C(=O)N2C(=O)OC[C@@H]2c2ccccc2)C[C@H](C)O1]

To a stirred solution of dry THF (20 mL) cooled to −78° C. under N₂ atmosphere was added a solution of sodium hexamethyldisilazide (19.3 mL of a 1.0 M solution in THF, 19.3 mmol) followed by the dropwise addition of a solution of (S)-3-((R)-3-(4-chlorophenyl)-3-((2R,4r,6S)-2,6-dimethyltetrahydro-2H-pyran-4-yl)propanoyl)-4-phenyloxazolidin-2-one (4.98 g, 11.7 mmol) in dry THF (60 mL). The resulting solution was stirred at −78° C. for 45 min. Trisyl azide (4.7 g, 15 mmol) was added as a solid and the resulting mixture was stirred for 15 min at −78° C. The reaction was quenched with the addition of AcOH (4.64 g, 77.2 mmol) and Me₄NOAc (15.50 g, 51.52 mmol). The cooling bath was removed and the mixture was stirred at RT for 18 h. EtOAc (120 mL) and water (100 mL) were added. The layers were separated and the aqueous phase was extracted with EtOAc. The organic phases were combined, washed with aqueous NaHCO₃ and brine, then dried over Na₂SO₄, filtered, and the solvents were removed in vacuo. The residue was purified by SiO₂ column chromatography using a gradient elution of 10-20% EtOAc in petroleum ether. Fractions containing product were combined and the solvents were removed under reduced pressure to give the title compound. MS (ESI) m/z (M+H)⁺: 483.1.

Step 12: (2S,3R)-2-Azido-3-(4-chlorophenyl)-3-((2R,4r,6S)-2,6-dimethyltetrahydro-2H-pyran-4-yl)propanoic acid To a solution of (S)-3-((2S,3R)-2-azido-3-(4-chlorophenyl)-3-((2R,4r,6S)-2,6-dimethyltetrahydro-2H-pyran-4-yl)propanoyl)-4-phenyloxazolidin-2-one (5.30 g, 10.9 mmol) in 120 mL of 3:1 THF:H₂O was cooled to 0° C. in an ice-brine bath. To the stirred solution was added H₂O₂ (6.54 g, 57.6 mmol, a 30% solution in water) and LiOH.H₂O (1.27 g, 28.8 mmol), and the mixture was stirred at 0° C. for 4 h. The mixture was quenched with Na₂SO₃ (14.5 g, 115 mmol) in 80 mL of water, followed by NaHCO₃ (9.70 g, 115 mmol) in 70 mL of water. The stirred mixture was warmed to RT and the THF was removed in vacuo. The water layer was extracted with two portions of DCM to remove the oxazolidinone. The aqueous phase was acidified to pH 1 with concentrated HCl and extracted with two portions of EtOAc. The EtOAc phases were combined and dried over anhydrous Na₂SO₄, filtered, and the filtrate solvents were removed in vacuo to give the title compound. ¹H NMR (400 MHz, CDCl₃) δ 7.21-7.33 (m, 2H), 7.07-7.17 (m, 2H), 4.17 (d, J=5.48 Hz, 1H), 3.50 (dd, J=5.87, 9.39 Hz, 1H), 3.40 (dd, J=5.87, 9.78 Hz, 1H), 2.94 (dd, J=5.48, 8.61 Hz, 1H), 2.11-2.26 (m, 1H), 1.74 (d, J=12.52 Hz, 1H), 1.25 (d, J=7.43 Hz, 1H), 1.14 (d, J=6.26 Hz, 3H), 1.05 (d, J=5.87 Hz, 3H), 0.88 (q, J=12.00 Hz, 1H), 0.66-0.81 (m, 1H) ppm.

Intermediate 21

(2S,3R)-2-Azido-3-((2R,4r,6S)-2,6-dimethyltetrahydro-2H-pyran-4-yl)-3-(4-fluorophenyl)propanoic acid

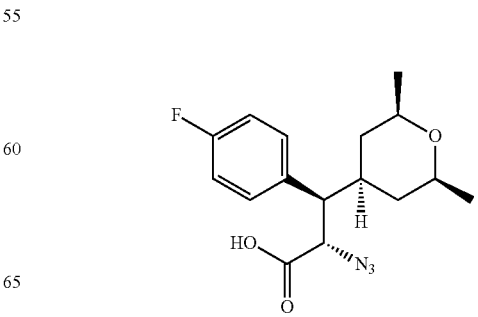

The title compound was prepared using the procedures given in Intermediate 20 using (4-fluorophenyl)magnesium bromide.

Intermediate 22

(2S,3R)-2-Azido-3-(4-chloro-3-fluorophenyl)-3-((2R,4r,6S)-2,6-dimethyltetrahydro-2H-pyran-4-yl)propanoic acid

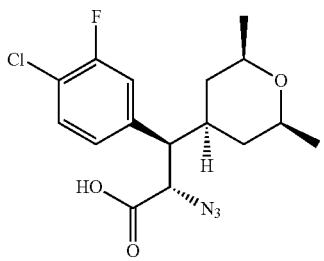 [SMILES: C[C@@H]1C[C@H]([C@H](c2ccc(Cl)c(F)c2)[C@H](N=[N+]=[N-])C(=O)O)C[C@H](C)O1]

The title compound was prepared using the procedures given in Intermediate 20 using (4-chloro-3-fluorophenyl) magnesium bromide.

Intermediate 23

(2S,3R)-2-azido-3-(4-chlorophenyl)-3-((2R,4S)-2-(2,2,2-trifluoroethyl)tetrahydro-2H-pyran-4-yl)propanoic acid

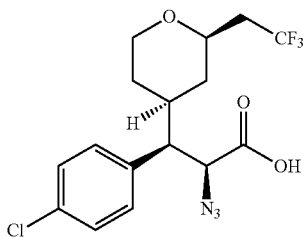 [SMILES: [N-]=[N+]=N[C@H](C(=O)O)[C@@H](c1ccc(Cl)cc1)[C@H]1CCO[C@@H](CC(F)(F)F)C1]

Step 1. 2-(2,2,2-Trifluoroethyl)-2H-pyran-4(3H)-one

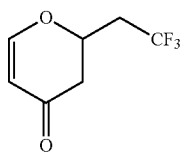 [SMILES: O=C1C=COC(CC(F)(F)F)C1]

To a solution of 3,3,3-trifluoropropane-1,1-diol (7.55 g, 58 mmol) in 150 mL dry THF under nitrogen atmosphere at 0° C. was added ZnCl₂ (7.91 g, 58 mmol) in portions. The mixture was stirred for 20 min and (E)-((4-methoxybuta-1,3-dien-2-yl)oxy)trimethylsilane (5.65 mL, 29 mmol) was added. The cooling bath was removed and the mixture was stirred at RT for 18 h. More 3,3,3-trifluoropropane-1,1-diol (2.5 g, 19 mmol) and ZnCl₂ (3.4 g, 25 mmol) were added and the mixture was stirred at RT for 24 h. Water (50 mL) was added and the mixture was stirred at RT for 1 h. 1N HCl (50 mL) was added and the mixture was stirred at RT for 2 h. The mixture was diluted with EtOAc (200 mL) and the solution was washed with 1N HCl, water, and brine, then dried over MgSO₄, filtered, and the solvents were removed in vacuo. The crude product was chromatographed on a 120 g SiO₂ column using 0-40% EtOAc:hexane over 30 min at 85 mL/min. Fractions containing product were combined and the solvents were removed in vacuo to give to give the title compound.

Step 2. 2-(2,2,2-Trifluoroethyl)dihydro-2H-pyran-4(3H)-one

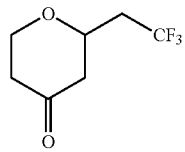 [SMILES: O=C1CCOC(CC(F)(F)F)C1]

A suspension 20% Pd(OH)2 on carbon (300 mg) and 2-(2,2,2-trifluoroethyl)-2H-pyran-4(3H)-one (3.0 g, 16.7 mmol) in 60 mL EtOAc was stirred under an atmosphere of hydrogen (1 atm) for 30 min. Nitrogen gas was bubbled through the solution to purge excess hydrogen and the mixture was filtered to remove the catalyst. The filtrate solvent was removed in vacuo and the crude product was dissolved in CH₂Cl₂ (25 mL) and stirred with pyridinium chlorochromate (3.59 g, 16.7 mmol) for 2 h at RT. Diethyl ether (100 mL) was added and the solvent was decanted. The remaining solids were slurried in diethyl ether (50 mL) and the solvent was decanted. The slurry/decant procedure was repeated two more times. The organic phases were combined and the solvents were removed in vacuo. The crude product was filtered through a pad of silica gel eluting with 1:1 EtOAc:hexanes. The solvents were removed in vacuo to give the title compound.

Step 3. 4-(Methoxymethylene)-2-(2,2,2-trifluoroethyl)tetrahydro-2H-pyran

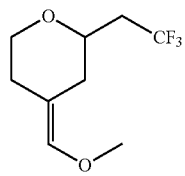

A stirred suspension of (methoxymethyl)triphenylphosphonium chloride (8.7 g, 25 mmol) in 100 mL dry THF under nitrogen atmosphere was cooled in an ice-acetone bath. A solution of NaN(TMS)2 (25 mL of a 1.0 M solution in THF, 25 mmol) was added dropwise and the resulting solution was stirred for 20 min. A solution of 2-(2,2,2-trifluoroethyl)dihydro-2H-pyran-4(3H)-one (3.1 g, 17 mmol) in 20 mL THF was add dropwise over a period of 5 min. The mixture was stirred for 3 h during which time the cooling bath had warmed to RT. The reaction was diluted with water and diethyl ether. The aqueous phase was collected and washed with ether. The organic phases were combined, dried over MgSO₄, filtered, and the solvents were removed in vacuo and the crude product was chromatographed on an 80 g SiO₂ column using 0-30% EtOAc:hexane over 30 min at 60 mL/min. Fractions containing product were combined and the solvents were removed in vacuo to give to give the title compound.

Step 4. 2-(2,2,2-Trifluoroethyl)tetrahydro-2H-pyran-4-carbaldehyde

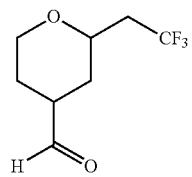

A stirred solution of 4-(methoxymethylene)-2-(2,2,2-trifluoroethyl)tetrahydro-2H-pyran (2.7 g, 12.9 mmol) in 20 mL water and 40 mL formic was heated at 90° C. for 3 h. The solution was cooled to RT and and adjusted to pH 7 with with 5N NaOH. The solution was extracted with ether, dried over MgSO₄, and the solvent was removed in vacuo. The crude product was chromatographed on a 40 g SiO₂ column using 0-50% EtOAc:hexane over 20 min at 40 mL/min. Fractions containing product were combined and the solvents were removed in vacuo to give the title compound (cis:trans ratio=3.5:1 by NMR).

Step 5. (4R)-4-Phenyl-3-((E)-3-(2-(2,2,2-trifluoroethyl)tetrahydro-2H-pyran-4-yl)acryloyl)oxazolidin-2-one

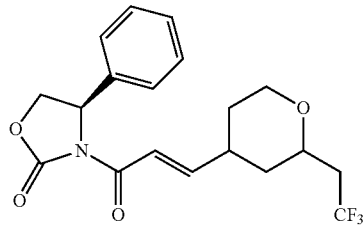 [SMILES: O=C(/C=C/C1CCOC(CC(F)(F)F)C1)N1C(=O)OC[C@H]1c1ccccc1]

To a stirred suspension of (R)-dimethyl (2-oxo-2-(2-oxo-4-phenyloxazolidin-3-yl)ethyl)phosphonate (2.71 g, 8.67 mmol) in 50 mL THF under nitrogen atmosphere at 0° C. was added a solution of potassium tert-butoxide (8.7 mL of a 1.0 M solution in THF, 8.7 mmol) dropwise over 5 min. A solution of 2-(2,2,2-trifluoroethyl)tetrahydro-2H-pyran-4-carbaldehyde (1.7 g, 8.67 mmol) in 10 mL of THF was added dropwise. The solution was stirred at 0° C. for 10 min then at RT for 18 h. The mixture was diluted with water and EtOAc. The organic phase was collected and washed with water and brine, then dried (MgSO₄), filtered, and the solvents were removed in vacuo. The crude product was chromatographed on an 80 g SiO₂ column using 0-40% EtOAc:hexane over 30 min at 60 mL/min. Fractions containing the faster eluting component were combined to give the title compound. LCMS m/z (M+H)⁺=384.3.

Step 6. (R)-3-((R)-3-(4-Chlorophenyl)-3-((2R,4S)-2-(2,2,2-trifluoroethyl)tetrahydro-2H-pyran-4-yl)propanoyl)-4-phenyloxazolidin-2-one

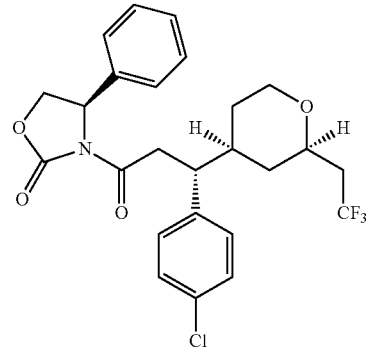 [SMILES: O=C(C[C@@H](c1ccc(Cl)cc1)[C@H]1CCO[C@@H](CC(F)(F)F)C1)N1C(=O)OC[C@H]1c1ccccc1]

To a stirred suspension of copper bromide dimethylsulfide complex (2.1 g, 10.4 mmol) in 20 mL of THF under nitrogen atmosphere at −40° C. was added a solution of 4-chlorophenylmagnesium bromide (10.4 mL of a 1.0 M solution in ether, 10.4 mmol) over a period of 5 min. The mixture was stirred for 10 min and then a solution of (4R)-4-phenyl-3-((E)-3-(2-(2,2,2-trifluoroethyl)tetrahydro-2H-pyran-4-yl)acryloyl)oxazolidin-2-one (1.6 g, 4.17 mmol) in 10 mL THF was added dropwise over a period of 5 min. The mixture was stirred at −40° C. for 45 min, then quenched with the addition of 20% aqueous NH4Cl. The cooling bath was removed and the mixture was stirred for 15 min. The mixture was extracted twice with EtOAc. The organic phases were combined and washed with water and brine, then dried (MgSO₄), filtered, and the solvents were removed in vacuo. The crude product was chromatographed on an 80 g SiO₂ column using 0-40% EtOAc:hexane over 30 min at 60 mL/min. Fractions containing the slower eluting isomer were combined and the solvents were removed in vacuo to give the title compound. LCMS m/z (M+H)⁺=496.3.

Step 7. (R)-3-(4-chlorophenyl)-3-((2R,4S)-2-(2,2,2-trifluoroethyl)tetrahydro-2H-pyran-4-yl)propanoic acid

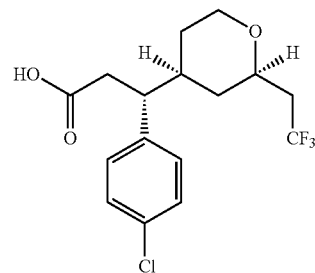 [SMILES: O=C(O)C[C@@H](c1ccc(Cl)cc1)[C@H]1CCO[C@@H](CC(F)(F)F)C1]

(R)-3-((R)-3-(4-Chlorophenyl)-3-((2R,4S)-2-(2,2,2-trifluoroethyl)tetrahydro-2H-pyran-4-yl)propanoyl)-4-phenyloxazolidin-2-one (890 mg, 1.8 mmol) was dissolved in 15 mL THF and 3 mL water and the solution was cooled in an ice bath. Hydrogen peroxide (0.63 mL of a 35% solution in water, 7.2 mmol) was added, followed by LiOH (86 mg, 3.6 mmol). The resulting mixture was stirred at 0° C. for 45 min.

A solution of sodium sulfite (905 mg, 7.2 mmol) in 10 mL water was added to the mixture followed by a solution of aqueous NaHCO₃ (21.5 mL of a 0.5 M solution, 10.8 mmol). The mixture was stirred for 5 min, then the THF was removed in vacuo. Then remaining aqueous solution was washed with two portions of DCM to remove the oxazolidinone. The aqueous phase was acidified to pH 1 with aqueous 1M HCl and extracted with three portions of EtOAc. The EtOAc extracts were combined, dried over MgSO4, filtered, and the solvents were removed in vacuo to give the title compound.

Step 8. (S)-3-((R)-3-(4-chlorophenyl)-3-((2R,4S)-2-(2,2,2-trifluoroethyl)tetrahydro-2H-pyran-4-yl)propanoyl)-4-phenyloxazolidin-2-one

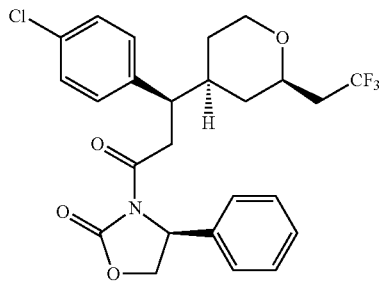 [SMILES: O=C(C[C@@H](c1ccc(Cl)cc1)[C@H]1CCO[C@@H](CC(F)(F)F)C1)N1C(=O)OC[C@@H]1c1ccccc1]

(R)-3-(4-chlorophenyl)-3-((2R,4S)-2-(2,2,2-trifluoroethyl)tetrahydro-2H-pyran-4-yl)propanoic acid (521 mg, 1.48 mmol) was dissolved in 10 mL DCM and SOCl2 (0.27 mL, 3.7 mmol) was added. The solution was heated to reflux for 2 h. The solvents were removed in vacuo to give the crude acid chloride. (S)-4-Phenyloxazolidin-2-one (242 mg, 1.48 mmol) was dissolved in 10 mL dry THF under N2 atmosphere and the solution was cooled to −10° C. nBuLi (0.59 mL of a 2.5 M solution in hexane, 1.48 mmol) was added dropwise and the resulting mixture was stirred for 10 min. To the reaction mixture was then added a solution of the crude acid chloride in 2 mL THF dropwise and the resulting mixture was stirred for 45 min at −10° C. The reaction was diluted with water and extracted with two portions of EtOAc. The EtOAc extracts were combined, washed with water and brine, dried (MgSO₄), filtered, and the solvents were removed in vacuo. The crude product was chromatographed on a 12 g SiO₂ column using 0-45% EtOAc:hexane over 15 min at 30 mL/min to give the title compound. LCMS m/z (M+H)⁺=496.3.

Step 9. (S)-3-((2S,3R)-2-azido-3-(4-chlorophenyl)-3-((2R,4S)-2-(2,2,2-trifluoroethyl)tetrahydro-2H-pyran-4-yl)propanoyl)-4-phenyloxazolidin-2-one

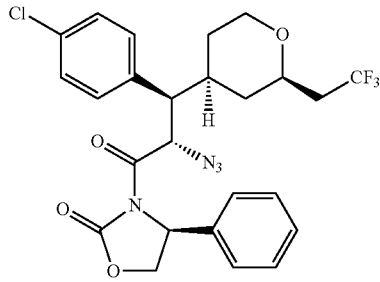 [SMILES: [N-]=[N+]=N[C@H](C(=O)N1C(=O)OC[C@@H]1c1ccccc1)[C@@H](c1ccc(Cl)cc1)[C@H]1CCO[C@@H](CC(F)(F)F)C1]

Sodium hexamethyldisilazide (1.27 mL of a 1.0 M solution in THF, 1.27 mmol) was added to 2 mL of dry THF under N2 atmosphere and the solution was cooled to −78° C. To this stirred solution was added a solution of (S)-3-((R)-3-(4-chlorophenyl)-3-((2R,4S)-2-(2,2,2-trifluoroethyl)tetrahydro-2H-pyran-4-yl)propanoyl)-4-phenyloxazolidin-2-one (572 mg, 1.15 mmol) 10 mL dry THF under N2 atmosphere at −78° C. by cannula. The resulting solution was stirred at −78° C. for 15 min. Solid trisyl azide (464 mg, 1.5 mmol) was added and the resulting mixture was stirred at −78° C. for 15 min. Acetic acid (0.4 mL, 6.9 mmol) and solid Me₄NOAc (614 mg, 4.6 mmol) were added to the reaction mixture. The cooling bath was removed and the mixture was stirred at RT for 18 h. The mixture was diluted with water and EtOAc. The EtOAc layer was collected and the aqueous phase was extracted with another portion of EtOAc. The EtOAc extracts were combined, washed with aqueous NaHCO₃ and brine, dried (MgSO₄), filtered, and the solvents were removed in vacuo. The crude product was chromatographed on a 24 g SiO₂ column using 0-40% EtOAc:hexane over 16 min at 35 mL/min to give the title compound as a gum. LCMS m/z (M−28+H)⁺=509.3.

Step 10. (2S,3R)-2-azido-3-(4-chlorophenyl)-3-((2R,4S)-2-(2,2,2-trifluoroethyl)tetrahydro-2H-pyran-4-yl)propanoic acid (S)-3-((2S,3R)-2-Azido-3-(4-chlorophenyl)-3-((2R,4S)-2-(2,2,2-trifluoroethyl)tetrahydro-2H-pyran-4-yl)propanoyl)-4-phenyloxazolidin-2-one (342 mg, 0.64 mmol) was dissolved in 3 mL THF and 1 mL water and the solution was cooled in an ice bath. Hydrogen peroxide (0.22 mL of a 35% aqueous solution, 2.6 mmol) was added followed by LiOH (31 mg, 1.3 mmol) and the resulting mixture was stirred at 0° C. for 45 min. Sodium sulfite (321 mg, 2.6 mmol) in water (5 mL) and NaHCO3 (7.6 mL of a 0.5 M aqueous solution, 3.8 mmol) were added and the mixture was stirred for 5 min. The THF was removed in vacuo and the remaining aqueous solution was extracted with two portions of DCM to remove the oxazolidinine. The aqueous phase was acidified to pH 1 with 1 M HCl and extracted with two portions of EtOAc. The EtOAc extracts were combined, dried over MgSO4, filtered, and the solvents were removed to give the title compound.

Intermediate 24

(2S,3S)-2-azido-3-(4-chlorophenyl)-3-(2-(trifluoromethyl)pyridin-4-yl)propanoic acid

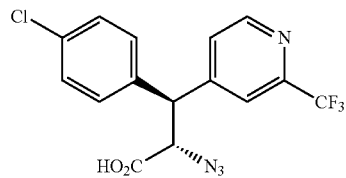 [SMILES: [N-]=[N+]=N[C@H](C(=O)O)[C@@H](c1ccc(Cl)cc1)c1ccnc(C(F)(F)F)c1]

Step 1. (2-(trifluoromethyl)pyridin-4-yl)methanol

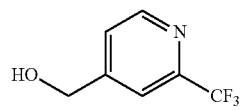 [SMILES: OCc1ccnc(C(F)(F)F)c1]

To a stirred solution of 2-(trifluoromethyl)isonicotinic acid (3.9 g, 20.4 mmol) in 50 mL of THF at 0° C. was added a solution of borane (45 mL of a 1.0 M solution in THF, 45 mmol) dropwise over a period of 5 min. The cooling bath was removed and the mixture was stirred at RT for 18 h. The reaction was quenched with the slow addition of water (100 mL). The mixture was extracted with two portions of EtOAc. The EtOAc extracts were combined, washed with brine, dried over MgSO₄, filtered, and the solvents were removed in vacuo. The crude product was chromatographed on a 40 g SiO₂ column using 0-80% EtOAc:hexane over 15 min at 30 mL/min. Fractions containing product were combined and the solvents were removed in vacuo to give the title compound. LCMS m/z=178.0 (M+H)⁺.

Step 2. 2-(trifluoromethyl)isonicotinaldehyde

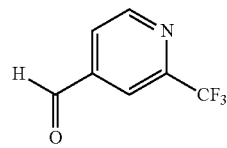

To a stirred solution of (2-(trifluoromethyl)pyridin-4-yl)methanol (3.4 g, 18 mmol) in 180 mL of CH₂Cl₂ and 18 mL of pyridine was added Dess-Martin periodoindane (10.6 g, 25 mmol) in several portions. The mixture was stirred at RT for 45 min. Water was added (70 mL) and the layers were separated. The aqueous phase was extracted with CH₂Cl₂. The organic phases were combined, washed with brine, dried over Na₂SO₄, filtered, and the solvents were removed in vacuo. The crude product was chromatographed on an 80 g SiO2 column using 0-50% EtOAc:hexane over 30 min at 60 mL/min. Fractions containing product were combined and the solvents were removed in vacuo to give the title compound.

Step 3: (2S,3S)-2-azido-3-(4-chlorophenyl)-3-(2-(trifluoromethyl)pyridin-4-yl)propanoic acid The title compound was prepared using the above intermediate and following the procedures described for Intermediate 6.

Intermediate 25

(2S,3S)-2-Azido-3-(4-chloro-3-fluorophenyl)-3-(5-(trifluoromethyl)pyridin-3-yl)propanoic acid

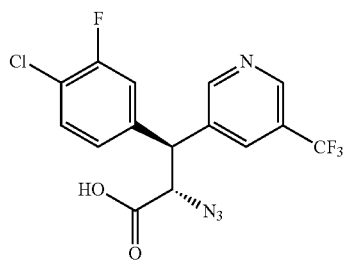 [SMILES: [N-]=[N+]=N[C@H](C(=O)O)[C@H](c1cncc(C(F)(F)F)c1)c1ccc(Cl)c(F)c1]

The title compound was prepared from 3-bromo-5-(trifluoromethyl)pyridine using the procedures given in Intermediate 24.

Intermediate 26

(2S,3S)-2-azido-3-(4-chlorophenyl)-3-(2-isopropoxypyridin-4-yl)propanoic acid

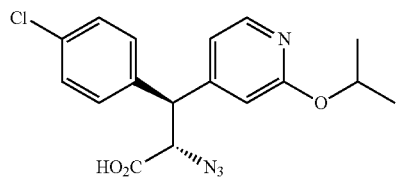 [SMILES: CC(C)Oc1cc([C@H](c2ccc(Cl)cc2)[C@H](N=[N+]=[N-])C(=O)O)ccn1]

Step 1: 2-isopropoxy-4-vinylpyridine

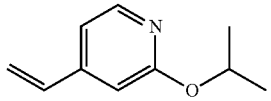

To a stirred solution of 4-bromo-2-isopropoxypyridine (3.0 g, 13.9 mmol) in 90 mL toluene was added vinyl tri-n-butylstannane (4.7 mL, 16 mmol) and the solution was sparged with nitrogen gas. Bis(triphenylphosphine)palladium(II) chloride (975 mg, 1.4 mmol) was added and the mixture was heated to 100° C. for 1.5 h. The mixture was cooled to RT and the solvent was removed in vacuo. The crude product was chromatographed on a 80 g SiO₂ column using 0-30% EtOAc:hexane over 30 min at 60 mL/min. Fractions containing product were combined and the solvents were removed in vacuo to give the title compound.

Step 2: 2-isopropoxyisonicotinaldehyde

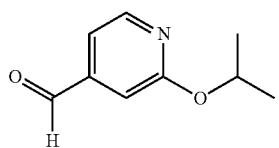

To a stirred solution of 2-isopropoxy-4-vinylpyridine (3.08 g, 178.9 mmol) in 80 mL THF and 20 mL water was added add osmium tetroxide (11.9 mL of a 2.5% in tert-butanol, 0.94 mmol). The mixture was stirred for 5 min, then NaIO₄ (12.1 g, 56.6 mmol) was added in several portions. The mixture was stirred for 30 min then diluted with water and EtOAc. The organic phase was separated, washed with brine, dried (MgSO₄), filtered, and the solvents were removed in vacuo. The crude product was chromatographed on an 80 g SiO₂ column using 0-30% EtOAc:hexane over 30 min at 60 mL/min. Fractions containing product were combined and the solvents were removed in vacuo to give the title compound.

Step 3: (2S,3S)-2-azido-3-(4-chlorophenyl)-3-(2-isopropoxypyridin-4-yl)propanoic acid The title compound was prepared using the above intermediate and following the procedures described for Intermediate 6.

Intermediate 27

(2S,3S)-2-Azido-3-(4-fluorophenyl)-3-(2-(trifluoromethyl)pyrimidin-5-yl)propanoic acid

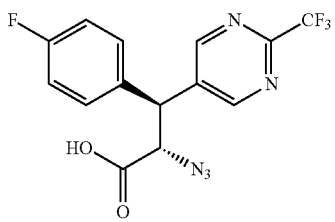 [SMILES: [N-]=[N+]=N[C@H](C(=O)O)[C@@H](c1ccc(F)cc1)c1cnc(C(F)(F)F)nc1]

Step 1: (E)-methyl 3-(2-(trifluoromethyl)pyrimidin-5-yl)acrylate

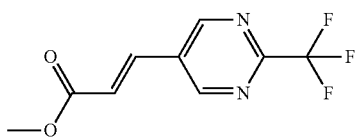 [SMILES: COC(=O)/C=C/c1cnc(C(F)(F)F)nc1]

A solution of 5-bromo-2-(trifluoromethyl)pyrimidine (8.5 g, 37.4 mmol), methyl acrylate (4.84 g, 56.2 mmol), tri-o-tolylphosphine (2.28 g, 7.49 mmol), triethylamine (10.44 mL, 74.9 mmol) and PALLADIUM(II) ACETATE (0.420 g, 1.872 mmol) in dry DMF (10 mL) was stirred at 130° C. for 1 h under $N_2$ protection. After cooling to RT, water was added and extracted by EA. The organic layer was separated, washed with brine, dried over $Na_2SO_4$ and concentrated in vacuo. The residue was purified by column chromatography on silica gel eluted with petroleum ether/ethyl acetate=20:1>10:1 to afford the title compound. MS (ESI) m/z (M+H)$^+$: 233.

Step 2: (E)-3-(2-(trifluoromethyl)pyrimidin-5-yl)acrylic acid

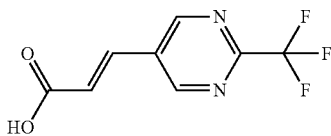 [SMILES: O=C(O)/C=C/c1cnc(C(F)(F)F)nc1]

A solution of (E)-methyl 3-(2-(trifluoromethyl)pyrimidin-5-yl)acrylate (6.5 g, 28.0 mmol) and lithium hydroxide (1.34 g, 56.0 mmol) in MeOH/$H_2O$ (2:1, 150 mL) was stirred at 30° C. for 2 h. The solvent was removed in vacuo. The water phase was extracted with DCM, then acidified pH to about 4 with 1M HCl. The water phase was extracted with EA three times. The organic phases were washed with brine, dried with $Na_2SO_4$, filtered and concentrated in vacuo to give the title compound. $^1$H NMR (400 MHz, chloroform-d) δ 9.05 (s, 2H), 7.76 (d, J=16.0 Hz, 1H), 6.70 (d, J=16.0 Hz, 1H) ppm.

Step 3: (R,E)-4-phenyl-3-(3-(2-(trifluoromethyl)pyrimidin-5-yl)acryloyl)oxazolidin-2-one

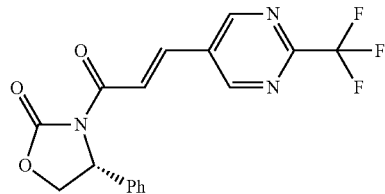 [SMILES: O=C(/C=C/c1cnc(C(F)(F)F)nc1)N1C(=O)OC[C@H]1c1ccccc1]

To a solution of (E)-3-(2-(trifluoromethyl)pyrimidin-5-yl) acrylic acid (5.3 g, 24.30 mmol) and DMF (0.1 mL) in $CH_2Cl_2$ (50 mL) was added OXALYL CHLORIDE (2.55 mL, 29.2 mmol) dropwise under $N_2$ at 0° C. The mixture was stirred for 1 h. The solution was concentrated in vacuum to give (E)-3-(2-(trifluoromethyl)pyrimidin-5-yl)acryloyl chloride. Dissolve (R)-4-phenyloxazolidin-2-one (7.59 g, 46.5 mmol) in dry THF (70 mL) was cooled to −78° C. Then n-BuLi (20.46 mL, 51.1 mmol) was added dropwise thereto. The resulting mixture was stirred for 1 h. A solution of (E)-3-(2-(trifluoromethyl) pyrimidin-5-yl) acryloyl chloride in THF (30 mL) was added dropwise to the above solution. The solution was stirred at −78° C. for 1 h. The reaction was quenched with 20% $NH_4Cl$ and extracted with EtOAc. The combined organic layers were washed with brine, dried over $Na_2SO_4$. The solvent was removed in vacuo and the residue was purified by column chromatography on silica gel eluted with petroleum ether/ethyl acetate=1:20→10:1 to afford the title compound. MS (ESI) m/z (M+H)$^+$: 364.

Step 4: (R)-3-((S)-3-(4-fluorophenyl)-3-(2-(trifluoromethyl)pyrimidin-5-yl)propanoyl)-4-phenyloxazolidin-2-one

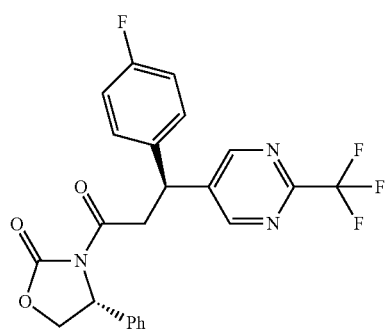 [SMILES: O=C(C[C@@H](c1ccc(F)cc1)c1cnc(C(F)(F)F)nc1)N1C(=O)OC[C@H]1c1ccccc1]

To a solution of (R,E)-4-phenyl-3-(3-(2-(trifluoromethyl) pyrimidin-5-yl)acryloyl)oxazolidin-2-one (6 g, 16.52 mmol) and CuBr/$Me_2S$ (5.08 g, 24.7 mmol) in THF (50 mL) was added dropwise a solution of (4-fluorophenyl) magnesium bromide (49.5 mmol) under $N_2$ at 0° C. The mixture was stirred for 2 h. The reaction was quenched with 20% $NH_4Cl$ and extracted with EtOAc. The combined organic layers were washed with brine, dried over $Na_2SO_4$. The solvent was removed in vacuo and the residue was purified by column chromatography on silica gel eluted with PE/EA=50:1→10:1 to afford the title compound. MS (ESI) m/z (M+H)$^+$: 460.

Step 5: (R)-3-((2R,3S)-2-bromo-3-(4-fluorophenyl)-3-(2-(trifluoromethyl)pyrimidin-5-yl)propanoyl)-4-phenyloxazolidin-2-one

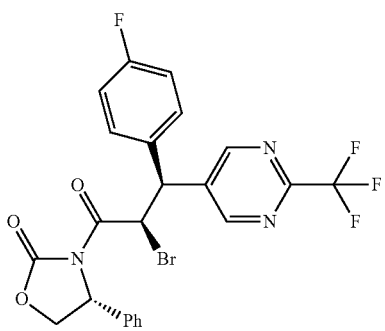 [SMILES: O=C1OC[C@@H](c2ccccc2)N1C(=O)[C@H](Br)[C@@H](c1ccc(F)cc1)c1cnc(C(F)(F)F)nc1]

To a solution of (R)-3-((S)-3-(4-fluorophenyl)-3-(2-(trifluoromethyl)pyrimidin-5-yl)propanoyl)-4-phenyloxazolidin-2-one (2.3 g, 5.01 mmol) and DIPEA (1.312 mL, 7.51 mmol) in $CH_2Cl_2$ (40 mL) was added dropwise dibutyl (((trifluoromethyl)sulfonyl)oxy)borane (1.510 g, 5.51 mmol) at −78° C. The resulting solution was stirred at −78° C. for 15 min and then at 0° C. for 1 h. To a flame-dried flask equipped with magnetic stirring bar was added NBS (0.980 g, 5.51 mmol)). The flask was flushed with nitrogen and cooled to −78° C. Freshly distilled $CH_2Cl_2$ (0.5-2.0 mL/mmol NBS) is added to form a slurry (NBS is completely insoluble in $CH_2Cl_2$ at this temperature). The boron enolate solution, precooled to −78° C., was added rapidly by Teflon cannula to the NBS slurry. The resulting purple slurry was stirred at −78° C. for 2 h and then at 0° C. for 1 h. The reaction was quenched by pouring into 0.5 N aqueous sodium bisulfate-brine. The solution was extracted three times with DCM, and the combined organic layers were washed twice with 0.5 N aqueous sodium thiosulfate and once with brine, dried over anhydrous sodium sulfate, and concentrated in vacuo. The residual was purified by chromatography on silica gel eluted with PE:EA=8:1 to give the title compound. MS (ESI) m/z (M+H)$^+$: 538. $^1$H NMR (400 MHz, CDCl$_3$-d) δ 8.81 (s, 2H), 7.39 (s, 3H), 7.35-7.27 (m, 4H), 7.08 (s, 2H), 6.61 (d, J=11.7 Hz, 1H), 5.38-5.22 (m, 1H), 4.73 (s, 2H), 4.38-4.21 (m, 1H) ppm.

Step 6: (R)-3-((2S,3S)-2-azido-3-(4-fluorophenyl)-3-(2-(trifluoromethyl)pyrimidin-5-yl)propanoyl)-4-phenyloxazolidin-2-one

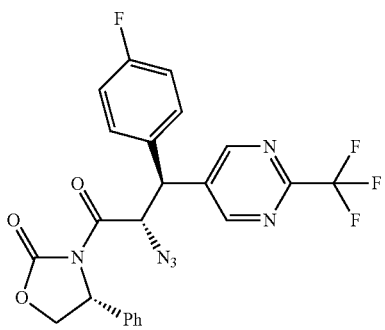 [SMILES: [N-]=[N+]=N[C@H](C(=O)N1C(=O)OC[C@H]1c1ccccc1)[C@@H](c1ccc(F)cc1)c1cnc(C(F)(F)F)nc1]

To a solution of (R)-3-((2R,3S)-2-bromo-3-(4-fluorophenyl)-3-(2-(trifluoromethyl)pyrimidin-5-yl)propanoyl)-4-phenyloxazolidin-2-one (1.5 g, 2.79 mmol) in DMSO (12 mL) was added sodium azide (0.181 g, 2.79 mmol). After addition, the mixture was treated at RT for 45 min, the solution was quenched with water. Extracted with EA, The organic layers were washed with brine, dried over $Na_2SO_4$, filtered and rotovap off solvent to give residue. The residual was purified by pre-HPLC to afford the title compound. MS (ESI) m/z (M+H)$^+$: 501. $^1$H NMR (400 MHz, CDCl$_3$-d) δ 8.92-8.74 (m, 2H), 7.31-7.24 (m, 2H), 7.22-7.16 (m, 2H), 7.13-7.05 (m, 2H), 6.92-6.78 (m, 4H), 6.05 (d, J=9.4 Hz, 1H), 5.39 (dd, J=3.9, 8.6 Hz, 1H), 4.72 (t, J=8.8 Hz, 1H), 4.56 (d, J=9.8 Hz, 1H), 4.29 (dd, J=3.7, 9.2 Hz, 1H) ppm.

Step 7: (2S,3S)-2-azido-3-(4-fluorophenyl)-3-(2-(trifluoromethyl)pyrimidin-5-yl)propanoic acid A solution of (R)-3-((2S,3S)-2-azido-3-(4-fluorophenyl)-3-(2-(trifluoromethyl)pyrimidin-5-yl)propanoyl)-4-phenyloxazolidin-2-one (300 mg, 0.600 mmol) in THF (9 mL) and Water (3 mL) was cooled in an ice bath. $H_2O_2$ (0.210 mL, 2.398 mmol) was added, then LiOH (28.7 mg, 1.199 mmol) was added. The resulting mixture was stirred for 40 min. A solution of sodium sulfite (302 mg, 2.398 mmol) in water was added to reaction. Then $NaHCO_3$ (252 mg, 3.00 mmol) solution was added and stirred for 5 min. THF was removed and diluted with water, washed with DCM to remove the chiral auxiliary. The aqueous was acidified with 6N HCl and extracted with EtOAc. The combined organic layers was dried over $Na_2SO_4$ and concentrated in vacuo to afford the title compound. MS (ESI) m/z (M+H)$^+$: 356. $^1$H NMR (400 MHz, chloroform-d) δ 8.83 (s, 2H), 7.24 (dd, J=5.1, 8.2 Hz, 2H), 7.03 (t, J=8.4 Hz, 2H), 4.83-4.53 (m, 2H) ppm.

Intermediate 28

(2S,3S)-2-Azido-3-(4-fluorophenyl)-3-(2-isopropoxypyrimidin-5-yl)propanoic acid

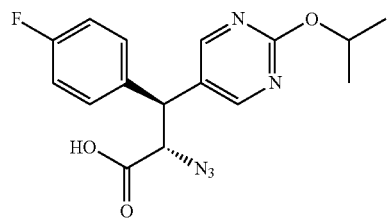 [SMILES: CC(C)Oc1ncc([C@H](c2ccc(F)cc2)[C@H](N=[N+]=[N-])C(=O)O)cn1]

Step 1: 5-bromo-2-isopropoxypyrimidine

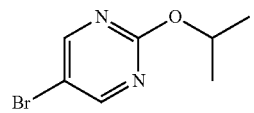

To a solution of iso-propanol (4.5 g, 74.9 mmol) in the anhydrous THF (20 mL) was added the NaH (2.5 g, 60% contained, 62.5 mmol) in portions at 0° C. under $N_2$ atmosphere. Then the mixture was stirred at 0° C. for about 30 min. 5-Bromo-2-chloropyrimidine (10 g, 51.7 mmol) in dry THF (10 mL) was added dropwise into the cold solution, keeping the inner temperature below 0° C. The resulting mixture was stirred at 0° C. for 2 h and warmed to the RT for 0.5 h. The reaction was checked with TLC. Water was added into the flask to quench the reaction, and the aqueous layer was extracted with DCM (20 mL×3). The combined DCM extracts were washed with brine, and then dried with $Na_2SO_4$. The filtrate was concentrated to afford a residue oil, which was purified by column chromatography on silica gel eluted with ethyl acetate/petroleum ether=1:10 to give the the title compound. MS (ESI) m/z (M+H)⁺: 217.1, 219.1. ¹H NMR (Chloroform-d 400 MHz) δ 8.51 (s, 2H), 5.22 (m, J=6.0 Hz, 1H), 1.39 (d, J=6.0 Hz, 6H) ppm.

Step 2: (E)-methyl 3-(2-isopropoxypyrimidin-5-yl)acrylate

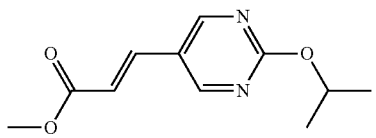 [SMILES: COC(=O)/C=C/c1cnc(OC(C)C)nc1]

5-Bromo-2-isopropoxypyrimidine (450 mg, 2.1 mmol), 3-methoxy-3-oxoprop-1-en-1-ylium (196 mg, 2.3 mmol), tri-o-tolylphosphine (32 mg, 0.11 mmol) and palladium(II) acetate (14.5 mg, 0.06 mmol) were dissolved in dry DMF (5 mL). Triethylamine (319 mg, 3.2 mmol) was added into the solution. The mixture was stirred at 130° C. for overnight under an atmosphere of nitrogen. After cooling to RT, water was added and extracted by EA. The organic layer was separated, washed with brine, dried over Na₂SO₄ and concentrated in vacuo to give a solid. The residue was purified by column chromatography on silica gel eluted with PE/EA=10:1→5:1 to afford the title compound. MS (ESI) m/z (M+H)⁺: 223.2.

Step 3: (E)-3-(2-isopropoxypyrimidin-5-yl)acrylic acid

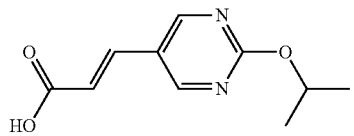

(E)-Methyl 3-(2-isopropoxypyrimidin-5-yl)acrylate (330 mg, 1.5 mmol) was dissolved in THF (5 mL) and water (1 mL). Lithium hydroxide (126 mg, 3.0 mmol) was added into the solution. Then it was stirred at RT for 2 h. The solution was neutralized with 1 N HCl aqueous solution to pH 3-4 and extracted with EA (10 mL×2). The combined extracts were washed with brine, dried over Na₂SO₄, filtered and concentrated in vacuo to give the title compound. MS (ESI) m/z (M+H)⁺: 209.2. ¹H NMR (Chloroform-d 400 MHz) δ 12.47 (br s, 1H), 8.92 (s, 2H), 7.53 (d, J=16.0 Hz, 1H), 6.63 (d, J=16.0 Hz, 1H), 5.22 (m, J=6.4 Hz, 1H), 1.31 (d, J=6.4 Hz, 6H) ppm.

Step 4: (R,E)-3-(3-(2-isopropoxypyrimidin-5-yl)acryloyl)-4-phenyloxazolidin-2-one

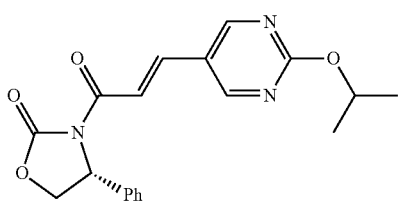 [SMILES: CC(C)Oc1ncc(/C=C/C(=O)N2C(=O)OC[C@H]2c2ccccc2)cn1]

To the cold solution of (E)-3-(2-isopropoxypyrimidin-5-yl)acrylic acid (3.6 g, 17.3 mmol) and DMF (0.5 mL) in dry CH₂Cl₂ (50 mL) was added Oxalyl chloride (2.6 g, 20.8 mmol) dropwise under N₂ at 0° C. The mixture was stirred for 1 h. The solution was concentrated in vacuum to give (E)-3-(2-(isopropoxy)pyrimidin-5-yl)acryloyl chloride. The solution of (R)-4-phenyloxazolidin-2-one (3.1 g, 19.0 mmol) in dry THF (50 mL) was cooled to −78° C. Then it was added n-Butyllithium (8.3 mL, 20.8 mmol) dropwise and stirred for 1 h. (E)-3-(2-(isopropoxy)pyrimidin-5-yl) acryloyl chloride dissolved in THF (50 mL) was added dropwise into the cold solution. The solution was stirred at −78° C. for 1 h. The reaction was quenched with 20% NH₄Cl aqueous solution and extracted with EA. The combined organics were washed with water, sat. NaHCO₃ (aq.), and brine, dried over Na₂SO₄ and concentrated. The residue was purified by column chromatography on silica gel eluted with petroleum ether/ethyl acetate=10:1->5:1 to afford the title compound. MS (ESI) m/z (M+H)⁺: 354.2. 1H NMR (Chloroform-d 400 MHz) δ 8.70 (s, 2H), 7.93 (d, J=16.0 Hz, 1H), 7.65 (d, J=16.0 Hz, 1H), 7.35-7.46 (m, 5H), 5.56 (dd, J=8.6, 3.5 Hz, 1H), 5.33 (dt, J=12.4, 6.2 Hz, 1H), 4.77 (t, J=8.8 Hz, 1H), 4.35 (dd, J=9.0, 3.9 Hz, 1H), 1.42 (d, J=6.4 Hz, 6H) ppm.

Step 5: (R)-3-((S)-3-(4-fluorophenyl)-3-(2-isopropoxypyrimidin-5-yl)propanoyl)-4-phenyloxazolidin-2-one

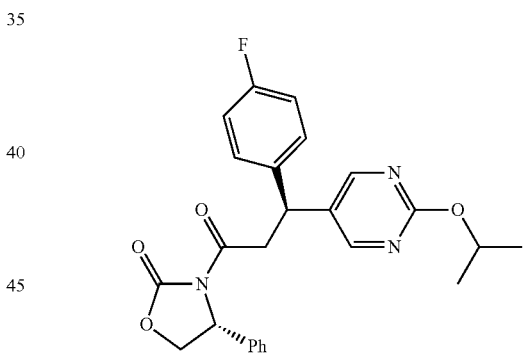

The suspension of (4-fluorophenyl)magnesium bromide (5.3 mL, 4.25 mmol) and copper (I) bromide-dimethylsulfide complex (873 mg, 4.25 mmol) in the dry THF (15 mL) was cooled to −40° C. in the dry ice acetone bath under a nitrogen atmosphere. Then to the above cold stirred solution was added dropwise of a solution of (R,E)-3-(3-(2-isopropoxypyrimidin-5-yl)acryloyl)-4-phenyloxazolidin-2-one (500 mg, 1.42 mmol) in 15 mL of anhydrous THF. The resulting mixture was stirred at −40° C. for 1 h, then the cooling bath was removed and the reaction mixture was stirred at 0° C. for another 1 h. LCMS checked that SM was consumed up. The reaction was quenched with 20% NH₄Cl and extracted with EtOAc. The combined extracts were washed with water and brine, and then dried over Na₂SO₄. The filtrate was evaporated and the residue was purified by column chromatography on silica gel eluted with petroleum ether/ethyl acetate=6:1→3:1 to afford the title compound. MS (ESI) m/z (M+H)⁺: 450.2.

Step 6: (S)-3-(4-fluorophenyl)-3-(2-isopropoxypyrimidin-5-yl)propanoic acid

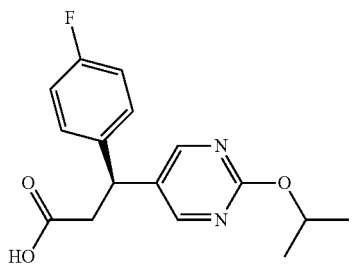 [SMILES: CC(C)Oc1ncc([C@@H](CC(=O)O)c2ccc(F)cc2)cn1]

To a solution of (R)-3-((S)-3-(4-fluorophenyl)-3-(2-isopropoxypyrimidin-5-yl)propanoyl)-4-phenyloxazolidin-2-one (2.0 g, 4.45 mmol) in THF (20 mL) and H$_2$O (4 mL) was added H$_2$O$_2$ (1.8 mL, m=30%, 17.8 mmol) at 0° C., followed with LiOH.H$_2$O (373 mg, 8.9 mmol). The resulting mixture was stirred at RT for 2 h. Then Na$_2$SO$_3$ (2.2 g, 17.8 mmol) in water (6 mL) was added to quench the reaction, followed with sat. NaHCO$_3$. The organic phase was evaporated to afford a residue. The residue was diluted with water and extracted with DCM (10 mL×3). The combined DCM extracts were washed with sat. NaHCO$_3$ (aq.)(10 mL×1). The combined aqueous layer was adjusted to pH 2-3 with conc. HCl and extracted with EA (20 mL×3). The combined EA extracts were washed with brine, dried with MgSO$_4$ and concentrated to give the title compound. MS (ESI) m/z (M+H)$^+$: 305.2

Step 7: (S)-3-((S)-3-(4-fluorophenyl)-3-(2-isopropoxypyrimidin-5-yl)propanoyl)-4-phenyloxazolidin-2-one

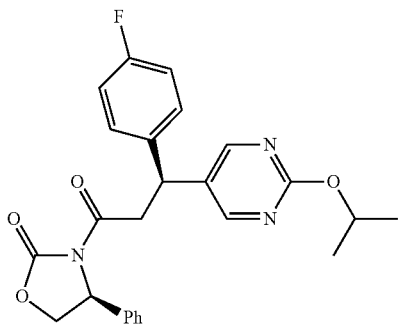 [SMILES: CC(C)Oc1ncc([C@@H](CC(=O)N2C(=O)OC[C@@H]2c2ccccc2)c2ccc(F)cc2)cn1]

To the cold solution of (S)-3-(4-fluorophenyl)-3-(2-isopropoxypyrimidin-5-yl)propanoic acid (1.2 g, 3.94 mmol) and DMF (0.2 mL) in dry CH$_2$Cl$_2$ (20 mL) was added oxalyl chloride (650 mg, 5.13 mmol) dropwise under N$_2$ at 0° C. The mixture was stirred for 1 h. The solution was concentrated in vacuum to give (S)-3-(4-fluorophenyl)-3-(2-isopropoxypyrimidin-5-yl)propanoyl chloride. The solution of (S)-4-phenyloxazolidin-2-one (707 mg, 4.33 mmol) in dry THF (20 mL) was cooled to −78° C. Then it was added n-Butyllithium (1.9 mL, 4.73 mmol) dropwise and stirred for 1 h. (S)-3-(4-fluorophenyl)-3-(2-isopropoxypyrimidin-5-yl)propanoyl chloride dissolved in THF (20 mL) was added dropwise into the cold solution. The solution was stirred at −40° C. for 2 h. The reaction was quenched with 20% NH$_4$Cl aqueous solution and extracted with EA. The combined organics were washed with water, sat. NaHCO$_3$ (aq.), and brine, dried over Na$_2$SO$_4$ and concentrated. The residue was purified by column chromatography on silica gel eluted with (petroleum ether/ethyl acetate=6:13:1) to afford the title compound. MS (ESI) m/z (M+H)$^+$: 450.2.

Step 8: (S)-3-((2S,3S)-2-azido-3-(4-fluorophenyl)-3-(2-isopropoxypyrimidin-5-yl)propanoyl)-4-phenyloxazolidin-2-one

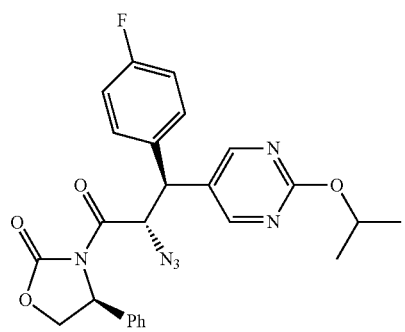 [SMILES: CC(C)Oc1ncc([C@H](c2ccc(F)cc2)[C@H](N=[N+]=[N-])C(=O)N2C(=O)OC[C@@H]2c2ccccc2)cn1]

The stirring solution of NaHMDS (3.33 mL, 3.33 mmol) in dry THF (10 mL) was cooled to −78° C. under the nitrogen atmosphere. Then the dissolved solution of (S)-3-((S)-3-(4-fluorophenyl)-3-(2-isopropoxypyrimidin-5-yl)propanoyl)-4-phenyloxazolidin-2-one (1.0 g, 2.22 mmol) in dry THF (10 mL) was added dropwise into the basic solution. The resulting solution was stirred cold for 45 min. Azide (826 mg, 2.67 mmol) was added into the cold solution as a solid. The solids were dissolved and stirred for 15 min, Then HOAc (800 mg, 13.32 mmol) was added into the cold solution, followed with n-Bu4NOAc (2.67 g, 8.88 mmol) as a solid. The cooling bath was removed and stirred at RT for 3 h. The mixture was diluted with EA and water, and the aqueous layer was extracted with EtOAc. The combined organics were washed with NaHCO$_3$ and brine, dried over MgSO$_4$ and rotovaped off solvent. The crude product was purified on silica gel column, using a gradient elution of 0-5% EA in DCM to give the title compound. MS (ESI) m/z (M+H)$^+$: 491.2.

Step 9: (2S,3S)-2-azido-3-(4-fluorophenyl)-3-(2-isopropoxypyrimidin-5-yl)propanoic acid To a solution of (S)-3-((2S,3S)-2-azido-3-(4-fluorophenyl)-3-(2-isopropoxypyrimidin-5-yl)propanoyl)-4-phenyloxazolidin-2-one (160 mg, 0.33 mmol) in THF (6 mL) and H$_2$O (2 mL) was added H$_2$O$_2$ (0.15 mL, m=30%, 1.31 mmol) at 0° C., followed with LiOH.H$_2$O (27 mg, 0.65 mmol). The resulting mixture was stirred at RT for 1 h. Then Na$_2$SO$_3$ (165 mg, 1.31 mmol) in water (2 mL) was added to quench the reaction, followed with sat. NaHCO$_3$. The organic phase was evaporated to afford a residue. The residue was diluted with water and extracted with DCM (5 mL×2). The combined DCM extracts were washed with sat. NaHCO$_3$ (aq.) (5 mL×1). The combined aqueous layer was adjusted to pH 2-3 with conc. HCl and extracted with EA (10 mL×3). The combined EA extracts were washed with brine, dried with MgSO$_4$ and concentrated to give the title compound. MS (ESI) m/z (M+H)$^+$: 346.2.

87

Intermediate 29

(S)-2-Azido-2-((1r,4S)-1-(4-chlorophenyl)-4-methoxycyclohexyl)acetic acid

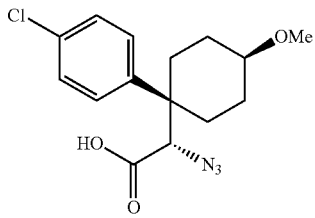 [SMILES: CO[C@H]1CC[C@](c2ccc(Cl)cc2)([C@H](N=[N+]=[N-])C(=O)O)CC1]

Step 1: 8-(benzyloxy)-1,4-dioxaspiro[4.5]decane

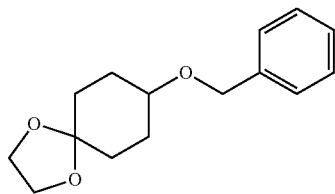 [SMILES: c1ccc(COC2CCC3(CC2)OCCO3)cc1]

To a stirred solution of 1,4-dioxaspiro[4.5]decan-8-ol (30 g, 0.19 mol) in THF (300 mL) at 0° C. was added NaH (8 g, 0.2 mol, 60% in mineral oil) in several portions. After stirring for 0.5 h, benzyl bromide (34.2 g, 0.2 mol) was added to the solution. The mixture was stirred for 1 h at 0° C., quenched with the addition of water (300 mL), and extracted with two portions of EtOAc. The combined EtOAc layers were dried with Na$_2$SO$_4$, filtered, and the solvent was removed in vacuo. The residue was purified by column chromatography on silica gel eluted with 10% ethyl acetate in petroleum ether to give the title compound. MS (M+H)$^+$: 249.

Step 2: 4-(benzyloxy)cyclohexanone

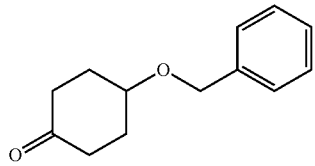 [SMILES: O=C1CCC(OCc2ccccc2)CC1]

To a stirred solution of 8-(benzyloxy)-1,4-dioxaspiro[4.5]decane (32.4 g, 0.13 mol) in THF (200 mL) was added a solution of HCl in MeOH (100 mL of a 4 M solution, 0.4 mol). The solution was stirred for 16 h at ambient temperature. The reaction was concentrated in vacuo, diluted with aqueous NaHCO$_3$, and extracted with teo portions of DCM. The combined DCM layers were dried with Na$_2$SO$_4$, filtered, and the solvent was removed in vacuo to give title. MS (M+H)$^+$: 205.

88

Step 3: methyl 2-(4-(benzyloxy)cyclohexylidene)-2-cyanoacetate

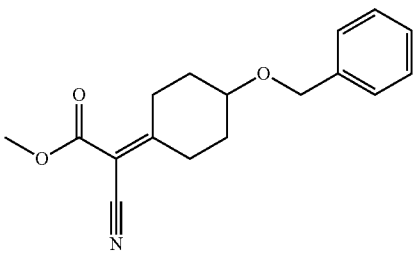 [SMILES: COC(=O)C(C#N)=C1CCC(OCc2ccccc2)CC1]

Acetic acid (635 mg, 8.6 mmol) was added to a stirred mixture of 4-(benzyloxy)cyclohexanone (21.6 g, 106 mmol) and ethyl cyanoacetate (12 g, 106 mmol) at 0° C., followed by piperidine (900 mg, 8.6 mmol). The ice-water bath was removed and 8.6 mmol portions each of acetic acid and piperidine were added. The mixture was stirred for 1.5 h, then partitioned between ethyl acetate and saturated NaHCO$_3$. The organic phase was separated and washed with brine, dried over Na$_2$SO$_4$, and concentrated in vacuo. The crude product was dissolved in ethyl acetate and precipitated with the addition of petroleum ether to give the title compound. MS (M+H)$^+$: 300.

Step 4. ethyl 2-(4-(benzyloxy)-1-(4-chlorophenyl)cyclohexyl)-2-cyanoacetate

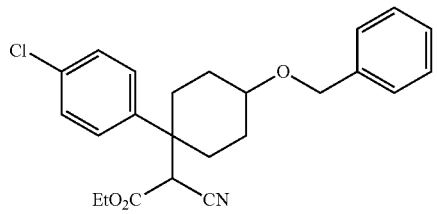 [SMILES: CCOC(=O)C(C#N)C1(c2ccc(Cl)cc2)CCC(OCc2ccccc2)CC1]

To a solution of methyl 2-(4-(benzyloxy)cyclohexylidene)-2-cyanoacetate (26.4 g, 88 mmol) in THF (300 mL) was added CuI (5.5 g, 28.8 mmol) and the solution was cooled to −40° C. A solution of chlorophenylmagnesium bromide (200 mL of a 1.0 M solution in THF, 200 mmol) was added dropwise over 15 min. The reaction mixture was stirred at −40° C. for 1.5 h and then at RT for 1 h. The reaction was quenched by the addition of aqueous NH$_4$Cl solution. The resulting mixture was stirred for 15 min then extracted with two portions of EtOAc. The combined EtOAc extracts were washed with water and brine, then dried over Na$_2$SO$_4$, filtered, and the solvents were removed in vacuo. The crude product was purified by column column chromatography on silica gel eluted with 15% ethyl acetate in petroleum ether to give the title compound. MS (M+H)$^+$: 412.

Step 5: 2-(4-(benzyloxy)-1-(4-chlorophenyl)cyclohexyl)acetic acid

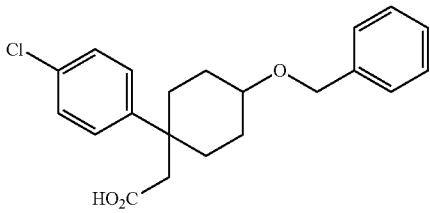 [SMILES: O=C(O)CC1(c2ccc(Cl)cc2)CCC(OCc2ccccc2)CC1]

To a solution of ethyl 2-(4-(benzyloxy)-1-(4-chlorophenyl)cyclohexyl)-2-cyanoacetate (30 g, 73 mmol) in ethylene glycol (300 mL) was added 8 N aqueous KOH solution (48 mL, 0.39 mol). The resulting mixture was heated to 130° C. for 7 days. The mixture was cooled to RT, 200 mL of water was added, and the solution was extracted with EtOAc (400 mL). The aqueous layer was acidified to pH 3 with concentrated HCl and extracted with ethyl acetate (3×200 mL). The ethyl acetate layers were combined, washed with brine, dried over Na$_2$SO$_4$, filtered, and the solvents were removed in vacuo to give the title compound. MS (M+H)$^+$: 359.

Step 6: 2-(4-(benzyloxy)-1-(4-chlorophenyl)cyclohexyl)acetyl chloride

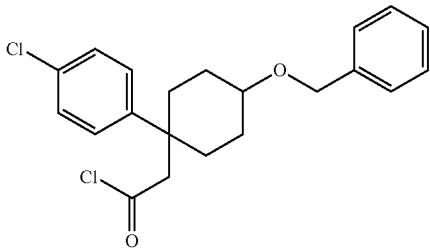 [SMILES: O=C(Cl)CC1(c2ccc(Cl)cc2)CCC(OCc2ccccc2)CC1]

A mixture of 2-(4-(benzyloxy)-1-(4-chlorophenyl)cyclohexyl)acetic acid (10 g, 28 mmol) and oxalyl chloride (5.3 g, 41.7 mmol) in DCM (100 mL) 0° C. was stirred at for 2 h. The solution was concentrated in vacuo to give the title compound.

Step 7: (S)-3-(2-(4-(benzyloxy)-1-(4-chlorophenyl)cyclohexyl)acetyl)-4-phenyl-oxazolidin-2-one

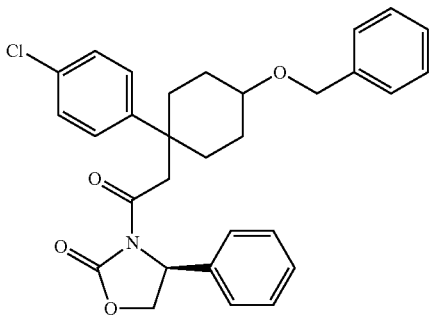 [SMILES: O=C(CC1(c2ccc(Cl)cc2)CCC(OCc2ccccc2)CC1)N1C(=O)OC[C@@H]1c1ccccc1]

To a stirred solution of (S)-4-phenyloxazolidin-2-one (5.05 g, 31 mmol) in dry THF (50 mL) was cooled to −10° C. under nitrogen atmosphere and to the solution was added n-BuLi (12.4 mL of a 2.5 M solution in hexane, 31 mmol) dropwise. The resulting mixture was stirred for 30 min at −10° C. A solution of 2-(4-(benzyloxy)-1-(4-chlorophenyl)cyclohexyl)acetyl chloride (10 g, 26.6 mmol) in dry THF (100 mL) was added dropwise to the above reaction solution. The resulting mixture was stirred at 0° C. for 1 h, then quenched with aqueous NH$_4$Cl and extracted with two portions of EtOAc. The combined organic layers were washed with water and brine, dried over Na$_2$SO$_4$, filtered, and the solvents were removed in vacuo. The crude product was purified by column chromatography on silica gel eluted with 15% EtOAc in petroleum ether to give the title compound. $^1$HNMR (400 MHz, CDCl$_3$) δ 7.22-7.31 (m, 12H), 7.03-7.03 (m, 2H), 5.09-5.12 (m, 1H), 4.46 (s, 1H), 4.30-4.32 (m, 1H), 4.07-4.10 (m, 1H), 3.38-3.43 (m, 1H), 3.23 (s, 2H), 2.46-2.53 (m, 2H), 1.85-1.88 (m, 2H), 1.60-1.68 (m, 2H), 1.35-1.38 (m, 2H) ppm. MS (M+H)$^+$: 504.

Step 8: (S)-3-(2-((1s,4R)-1-(4-chlorophenyl)-4-hydroxycyclohexyl)acetyl)-4-phenyl-oxazolidin-2-one

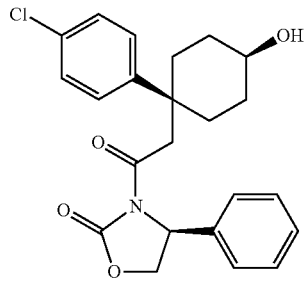 [SMILES: O=C(C[C@]1(c2ccc(Cl)cc2)CC[C@@H](O)CC1)N1C(=O)OC[C@@H]1c1ccccc1]

To a stirred solution of (S)-3-(2-(4-(benzyloxy)-1-(4-chlorophenyl)cyclohexyl)acetyl)-4-phenyloxazolidin-2-one (5.5 g, 10.9 mmol) in MeOH (200 mL) was added 10% Pd/C (500 mg). The solution was stirred under 1 atm H$_2$ at RT for 1 h. The mixture was filtered and concentrated in vacuo. The crude product was purified by preparative reverse phase HPLC to give the title compound. $^1$H NMR (400 MHz, CDCl3): δ 7.21-7.30 (m, 7H), 6.96-6.98 (m, 2H), 5.09-5.12 (m, 1H), 4.31-4.36 (m, 1H), 4.06-4.09 (m, 1H), 3.74-3.75 (m, 1H), 3.31-3.44 (m, 2H), 2.15-2.24 (m, 2H), 1.91-1.93 (m, 2H), 1.69-1.71 (m, 2H), 1.58-1.61 (m, 2H) ppm.

Step 9: (S)-3-(2-((1s,4R)-1-(4-chlorophenyl)-4-methoxycyclohexyl)acetyl)-4-phenyloxazolidin-2-one

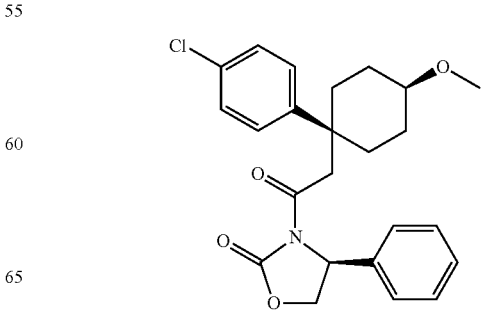

A mixture of (S)-3-(2-((1s,4R)-1-(4-chlorophenyl)-4-hydroxycyclohexyl)-acetyl)-4-phenyloxazolidin-2-one (400 mg, 0.906 mmol), trimethyloxonium tetrafluorborate (720 mg, 4.86 mol) and proton sponge (1.1 g, 5.14 mol) in anhydrous dichloromethane (30 mL) was stirred at RT overnight. The mixture was partitioned between ethyl acetate and 1N aqueous HCl. The EtOAc layer was washed with brine, dried over anhydrous sodium sulfate, and filtered. The filtrate solvents were concentrated in vacuo and the crude product was purified by column chromatography on silica gel eluted with 20% EtOAc in petroleum ether to give the title compound. MS (M+H)+: 428.

Step 10: (S)-3-((S)-2-azido-2-((1r,4S)-1-(4-chlorophenyl)-4-methoxycyclohexyl)-acetyl)-4-phenyloxazolidin-2-one

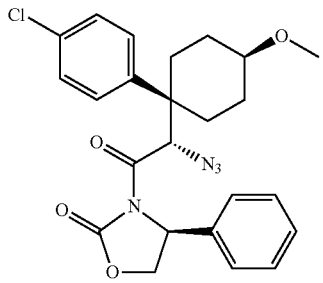 [SMILES: CO[C@H]1CC[C@](c2ccc(Cl)cc2)([C@H](N=[N+]=[N-])C(=O)N2C(=O)OC[C@@H]2c2ccccc2)CC1]

5 mL of THF under an atmosphere of nitrogen was cooled to −78° C. and to the stirred solution was added NaHMDS (1.5 mL of a 1.0 M solution in THF, 1.5 mmol). A solution of (S)-3-(2-((1s,4R)-1-(4-chlorophenyl)-4-methoxycyclohexyl)acetyl)-4-phenyloxazolidin-2-one (400 mg, 0.937 mmol) in 5 mL of THF under nitrogen atmosphere was cooled to −78° C. in a dry ice-acetone bath and added via cannula to the cold sodium hexamethyldisilazide solution. The resulting mixture was stirred at −78° C. for 30 min when trisyl azide (380 mg, 1.21 mmol) was added as a solid. The solids dissolved and the cold solution was stirred for 2 min. To the cold solution was added HOAc (0.33 mL, 5.62 mmol) and solid tetramethylammonium acetate (1.13 g, 3.74 mmol). The cooling bath was removed and the mixture was stirred at RT for 4 h. The reaction was diluted with EtOAc and washed with brine. The aqueous phase was extracted with EtOAc, and the combined EtOAc layers were washed with aqueous NaHCO3 and brine, then dried (Na2SO4), filtered, and the solvents were removed in vacuo. The residue was purified by column chromatography on silica gel eluted with 20% EtOAc in petroleum ether to give the title compound. MS (M+H)+: 469.

Step 11: (S)-2-azido-2-((1r,4S)-1-(4-chlorophenyl)-4-methoxycyclohexyl)acetic acid A solution of (S)-3-((S)-2-azido-2-((1r,4S)-1-(4-chlorophenyl)-4-methoxycyclohexyl)acetyl)-4-phenyloxazolidin-2-one (200 mg, 0.427 mmol) in 5 mL of 4:1 THF:H2O was cooled to 0° C. in an ice-water bath. To the stirred solution was added hydrogen peroxide (0.21 mL of a 30% solution in water, 0.24 mmol) and LiOH (36 mg, 0.855 mmol), and the mixture was stirred at 0° C. for 45 min. The reaction was quenched by the addition of a solution of sodium sulfite (0.8 g, 0.7 mmol) in 5 mL of water, followed by a 0.5 N solution of aqueous NaHCO3 (16 mL, 0.8 mmol). The stirred mixture was warmed to RT and most of the THF was removed in vacuo. The aqueous mixture was extracted with two portions of dichloromethane to remove the chiral auxiliary. The aqueous phase was acidified to pH 1 with the addition of 6 N HCl and extracted with two portions of EtOAc. The combined EtOAc layers were dried with Na2SO4, filtered, and the solvent was removed in vacuo to give the title compound. MS (M+H)+: 324.

Intermediate 30

(S)-2-Azido-2-(4-(4-chlorophenyl)-1-(methoxycarbonyl)piperidin-4-yl)acetic acid

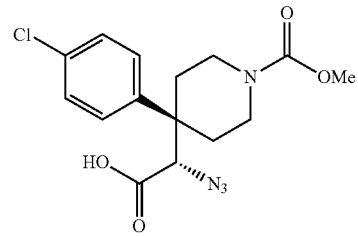

Step 1: tert-butyl 4-(1-cyano-2-ethoxy-2-oxoethylidene)piperidine-1-carboxylate

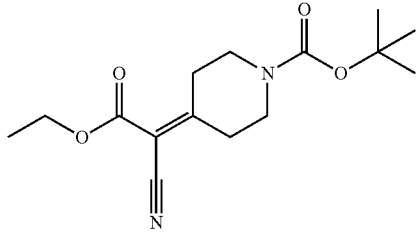 [SMILES: CCOC(=O)C(C#N)=C1CCN(C(=O)OC(C)(C)C)CC1]

To a stirred solution of tert-butyl 4-oxopiperidine-1-carboxylate (25 g, 125 mmol) in ethyl 2-cyanoacetate (15.6 g, 138 mmol), and acetic acid (0.718 mL, 12.5 mmol) was added piperidine (1.24 mL, 12.5 mmol) at 0° C. The resulting mixture was warmed to RT. Acetic acid (0.718 mL, 12.5 mmol) and piperidine (1.24 mL, 12.5 mmol) were added again. After stirring for 25 min, the mixture was diluted with aqueous NaHCO3 and extracted with two portions of EtOAc. The combined organic layers were washed with brine, dried over Na2SO4, filtered, and the solvents were removed in vacuo. The residue was purified by column chromatography on silica gel eluted with 5% EtOAc in petroleum ether to give the title compound. 1H NMR (Chloroform-d, 400 MHz) δ: 4.22 (q, J=7.0 Hz, 2H), 3.55 (t, J=5.7 Hz, 2H), 3.48 (t, J=5.7 Hz, 2H), 3.06 (t, J=5.7 Hz, 2H), 2.71 (t, J=5.7 Hz, 2H), 1.41 (s, 9H), 1.29 (t, J=7.2 Hz, 3H) ppm.

Step 2: tert-butyl 4-(4-chlorophenyl)-4-(1-cyano-2-ethoxy-2-oxoethyl)piperidine-1-carboxylate

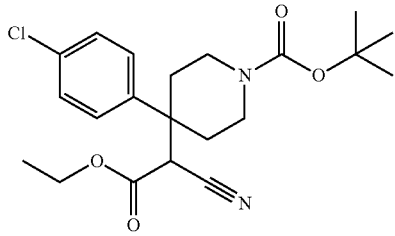 [SMILES: CCOC(=O)C(C#N)C1(c2ccc(Cl)cc2)CCN(C(=O)OC(C)(C)C)CC1]

A suspension of tert-butyl 4-(1-cyano-2-ethoxy-2-oxoethylidene)piperidine-1-carboxylate (28 g, 95 mmol) and copper iodide (7.25 g, 38.1 mmol) in dry THF (200 mL) under $N_2$ atmosphere was cooled to 0° C. A solution of (4-chlorophenyl) magnesium bromide (61.6 g, 285 mmol) in 570 mL THF was added dropwise and the resulting mixture was stirred at 0° C. for 1 h. The cooling bath was removed and the stirred mixture was allowed to warm to RT over 1 h. The reaction was quenched by the addition of aqueous $NH_4Cl$ solution and extracted with ethyl acetate. The combined organic layers were washed with water and brine, then dried over $Na_2SO_4$, filtered, and the solvents were removed in vacuo. The residue was purified by column chromatography on silica gel eluted with 20% EtOAc in petroleum ether to give the title compound. MS (ESI) m/z $(M+H-56+41)^+$: 392.1.

Step 3: 2-(1-(tert-butoxycarbonyl)-4-(4-chlorophenyl)piperidin-4-yl)acetic acid

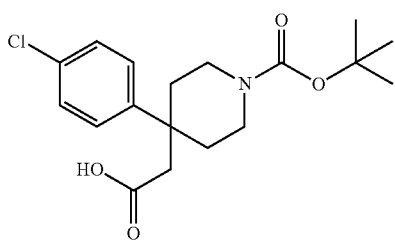 [SMILES: CC(C)(C)OC(=O)N1CCC(CC(=O)O)(c2ccc(Cl)cc2)CC1]

tert-Butyl 4-(4-chlorophenyl)-4-(1-cyano-2-ethoxy-2-oxoethyl)piperidine-1-carboxylate (28.5 g, 70.0 mmol) and KOH (39.3 g, 700 mmol) was dissolved in ethylene glycol (250 mL) and water (50 mL). The solution was heated to 140° C. for 50 h. The mixture was cooled to RT, diluted with water, and extracted with ethyl acetate. The combined organic layers were washed with brine, dried over anhydrous sodium sulfate, and filtered. The filtrate solvents were removed in vacuo. The crude product was purified by column chromatography on silica gel eluted with 20% EtOAc in petroleum ether to give the title compound. MS (ESI) m/z $(M-56+41)^+$: 339.1

Step 4: (S)-tert-butyl 4-(4-chlorophenyl)-4-(2-oxo-2-(2-oxo-4-phenyloxazolidin-3-yl)-ethyl)piperidine-1-carboxylate

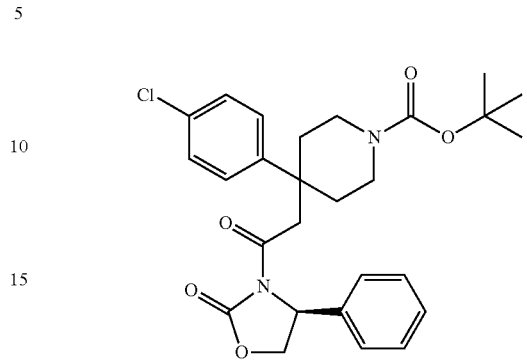

To a stirred solution of 2-(1-(tert-butoxycarbonyl)-4-(4-chlorophenyl)-piperidin-4-yl)acetic acid (7.1 g, 20.0 mmol) in DCM (100 mL) at 0° C., oxalyl chloride (5.27 mL, 60.2 mmol) was added dropwise. The mixture was stirred for 1 h. The solvent was removed in vacuo to give the crude acid chloride. (S)-4-Phenyloxazolidin-2-one (3.29 g, 20.15 mmol) was dissolved in 50 mL dry THF and the solution was cooled to –10° C. n-BuLi (8.06 mL of a 2.5 M solution in hexane, 20.15 mmol) was added dropwise and the resulting solution was stirred for 30 min. A solution of the crude acid chloride in 30 mL dry THF was added dropwise to the reaction mixture, the temperature was raised to 0° C. and the mixture was stirred for 1 h. The reaction was quenched with 20% aqueous $NH_4Cl$ and extracted with two portions of EtOAc. The combined organic layers were washed with water, aqueous $NaHCO_3$, brine, then dried over anhydrous $Na_2SO_4$ and filtered. The filtrate solvents were removed in vacuo. The residue was purified by column chromatography on silica gel eluted with 20% EtOAc in petroleum ether to give the title compound. MS (ESI) m/z $(M+23)^+$: 521.2.

Step 5: tert-butyl 4-((S)-1-azido-2-oxo-2-((S)-2-oxo-4-phenyloxazolidin-3-yl)ethyl)-4-(4-chlorophenyl)piperidine-1-carboxylate

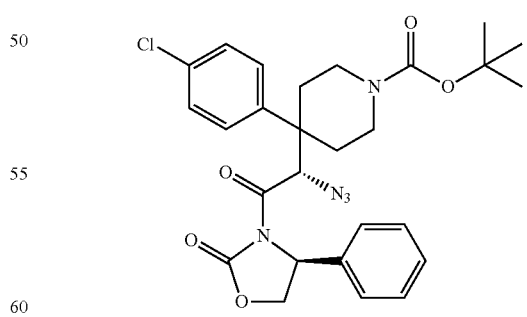

To a stirred mixture of (S)-tert-butyl 4-(4-chlorophenyl)-4-(2-oxo-2-(2-oxo-4-phenyloxazolidin-3-yl)ethyl)piperidine-1-carboxylate (3.9 g, 7.8 mmol) in THF (50 mL) under $N_2$ atmosphere at –70° C. was added NaHMDS (11.7 mL of a 1.0 M solution in THF, 11.7 mmol) dropwise. The mixture was stirred at –70° C. for 1 h. 2,4,6-Triisopropylbenzenesulfonyl azide (3.14 g, 10.1 mmol) was added as a solid and the mixture was stirred at −70° C. for 1 h. Acetic acid (2.82 g, 46.9 mmol) and tetrabutylammonium acetate (9.43 g, 31.3 mmol) were added, the cooling bath was removed, and the mixture was stirred at RT for 18 h. The mixture was diluted with 100 mL of water and extracted with EtOAc (3×50 mL). The EtOAc layers were combined and the solvents were removed in vacuo. The residue was purified by column chromatography on silica gel eluted with 10% EtOAc in petroleum ether to give the title compound. $^1$H NMR (Chloroform-d, 400 MHz) δ 7.37-7.24 (m, 6H), 7.22-7.18 (m, 1H), 7.15-7.07 (m, 2H), 5.51 (s, 1H), 4.91 (d, J=5.5 Hz, 1H), 4.16-4.10 (m, 1H), 4.09-4.05 (m, 1H), 3.93 (br. s., 2H), 2.67-2.55 (m, 1H), 2.46 (d, J=14.1 Hz, 1H), 2.20-2.13 (m, 1H), 2.07 (dt, J=3.7, 13.0 Hz, 1H), 1.89 (dt, J=3.9, 13.7 Hz, 1H), 1.36 (s, 9H), 1.22 (d, J=6.7 Hz, 2H), 1.19 (d, J=7.0 Hz, 2H) ppm. MS (ESI) m/z (M+23)$^+$: 562.3

Step 6: (S)-2-azido-2-(1-(tert-butoxycarbonyl)-4-(4-chlorophenyl)piperidin-4-yl)-acetic acid

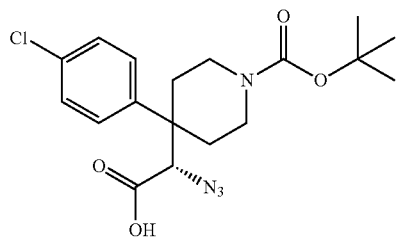 [SMILES: CC(C)(C)OC(=O)N1CCC(c2ccc(Cl)cc2)([C@H](N=[N+]=[N-])C(=O)O)CC1]

To a stirred solution of tert-butyl 4-((S)-1-azido-2-oxo-2-((S)-2-oxo-4-phenyl-oxazolidin-3-yl)ethyl)-4-(4-chlorophenyl)piperidine-1-carboxylate (2.2 g, 4.0 mmol) in THF (30 mL) and water (9 mL) 0° C. was added hydrogen peroxide (0.55 g of a 30% solution in water, 16.3 mmol) and lithium hydroxide (0.19 g, 8.1 mmol). The mixture was stirred at 0° C. for 1 h. Sodium sulfite (2.05 g, 16.3 mmol) in 25 mL of water and sodium bicarbonate (1.71 g, 20.3 mmol) were added, and the mixture was stirred at RT for 15 min. THF was removed in vacuo and the aqueous layer was extracted with DCM (2×30 mL) to remove the oxazolidinone. The aqueous layer was acidified pH 1 with dilute HCl and extracted with EtOAc (3×20 mL). The EtOAc layers were combined and concentrated in vacuo to give the title compound. $^1$H NMR (Chloroform-d, 400 MHz) δ 7.36-7.29 (m, 2H), 7.28-7.23 (m, 2H), 3.87 (br. s., 1H), 3.63 (d, J=12.9 Hz, 1H), 3.15 (t, J=10.6 Hz, 1H), 2.90-2.73 (m, 1H), 2.58 (s, 1H), 2.40 (d, J=14.1 Hz, 1H), 2.23 (d, J=14.1 Hz, 1H), 1.99-1.84 (m, 2H), 1.43 (d, J=2.7 Hz, 9H), 1.23 (br. s., 1H) ppm.

Step 7: (S)-tert-butyl 4-(1-azido-2-methoxy-2-oxo-ethyl)-4-(4-chlorophenyl)piperidine-1-carboxylate

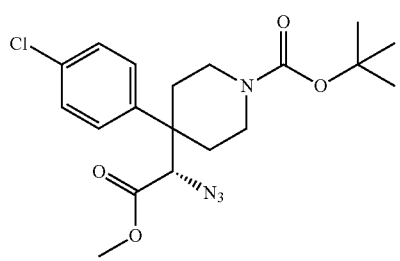 [SMILES: COC(=O)[C@@H](N=[N+]=[N-])C1(c2ccc(Cl)cc2)CCN(C(=O)OC(C)(C)C)CC1]

To a solution of (S)-2-azido-2-(1-(tert-butoxycarbonyl)-4-(4-chlorophenyl)piperidin-4-yl)acetic acid (1.0 g, 2.5 mmol) in THF (10 mL) under N$_2$ atmosphere was added trimethylsilyldoazomethane (17.5 mL, 35.0 mmol). The mixture was stirred at RT for 2 h. The reaction was quenched with acetic acid. The solvents were removed in vacuo to give the title compound. MS (ESI) m/z (M−56+41)$^+$: 394.1.

Step 8: (S)-methyl 2-azido-2-(4-(4-chlorophenyl)piperidin-4-yl)acetate

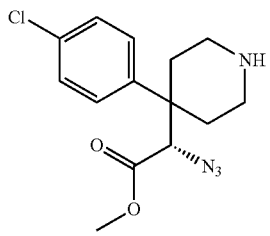 [SMILES: COC(=O)[C@@H](N=[N+]=[N-])C1(c2ccc(Cl)cc2)CCNCC1]

To a solution of (S)-tert-butyl 4-(1-azido-2-methoxy-2-oxoethyl)-4-(4-chlorophenyl)piperidine-1-carboxylate (0.92 g, 2.2 mmol) in CH$_2$Cl$_2$ (10 mL) at RT was added TFA (0.86 mL, 11.25 mmol) and the mixture was stirred for 30 min. The solvents were removed in vacuo to give the TFA salt of the title compound. MS (ESI) m/z (M+H)$^+$: 309.1.

Step 9: (S)-methyl 4-(1-azido-2-methoxy-2-oxo-ethyl)-4-(4-chlorophenyl)piperidine-1-carboxylate

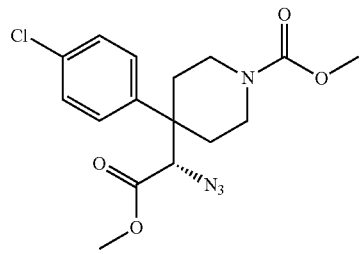 [SMILES: COC(=O)[C@@H](N=[N+]=[N-])C1(c2ccc(Cl)cc2)CCN(C(=O)OC)CC1]

To a solution of (S)-methyl 2-azido-2-(4-(4-chlorophenyl)piperidin-4-yl)acetate (0.21 g, 0.68 mmol) in 10 mL of DCM was added 2,5-dioxopyrrolidin-1-yl methyl carbonate (0.191 g, 1.02 mmol) and TEA (0.114 mL, 0.816 mmol). The mixture was stirred at RT for 4 h. The solvent was removed in vacuo to give compound the title compound. MS (ESI) m/z (M+H)$^+$: 367.1.

Step 10: (S)-2-azido-2-(4-(4-chlorophenyl)-1-(methoxycarbonyl)piperidin-4-yl)acetic acid To a stirred solution of (S)-methyl 4-(1-azido-2-methoxy-2-oxoethyl)-4-(4-chlorophenyl)piperidine-1-carboxylate (0.17 g, 0.463 mmol) in THF (3 mL) and H$_2$O (1 mL) at 0° C. was added hydrogen peroxide (0.12 mL of a 30% solution in water, 1.0 mmol) and solid LiOH (0.022 g, 0.927 mmol). The mixture was stirred for 1 h. The reaction was quenched with the addition of aqueous sodium sulfite and sodium bicarbonate. The THF was removed in vacuo and the aqueous layer was washed with two portions of DCM to remove the oxazolidinone. The aqueous layer was acidified to pH 1 with dilute HCl and extracted with EtOAc (3×10 mL). The EtAOc layers were combined and the solvents were removed in vacuo. The residue was purified by preparative reverse phase HPLC to give the title compound. MS (ESI) m/z (M+H)+: 353.1.

Intermediate 31

(2S,3R)-2-Azido-3-((S)-2,2-dimethyltetrahydro-2H-pyran-4-yl)-3-(4-fluorophenyl)propanoic acid

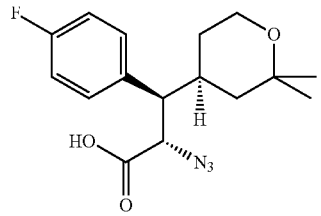 [SMILES: CC1(C)C[C@@H]([C@H](c2ccc(F)cc2)[C@H](N=[N+]=[N-])C(=O)O)CCO1]

The title compound was prepared using the procedures given in Intermediate 7 using (4-fluorophenyl)magnesium bromide.

Intermediate 32

(2S,3S)-2-Azido-3-(4-chlorophenyl)-3-(5-(1,1-difluoroethyl)pyridin-3-yl)propanoic acid

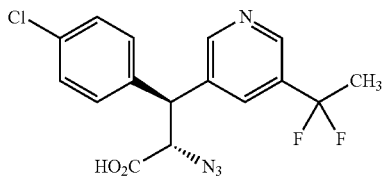 [SMILES: CC(F)(F)c1cncc([C@H](c2ccc(Cl)cc2)[C@H](N=[N+]=[N-])C(=O)O)c1]

Step 1. 3-Bromo-5-(1,1-difluoroethyl)pyridine

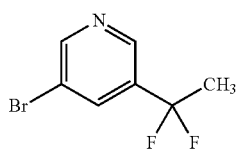

To a stirred solution of 1-(5-bromopyridin-3-yl)ethanone (2.4 g, 12 mmol) in 24 mL of $CH_2Cl_2$ was added DAST (15.5 mL, 96 mmol) dropwise over a period of 10 min. The mixture was heated to 50° C. for 18 h. The mixture was cooled to RT and carefully poured into ice-cold 2N NaOH. The layers were separated and the aqueous phase was extracted with $CH_2Cl_2$. The organic phases were combined, dried over $Na_2SO_4$, and the solvent was removed in vacuo. The crude product was chromatographed on an 80 g $SiO_2$ column using 0-30% EtOAc:hexane over 30 min at 60 mL/min. Fractions containing product were combined and the solvents were removed in vacuo to give the title compound. LCMS m/z (M+H)+=223.9.

Step 2. 3-(1,1-Difluoroethyl)-5-vinylpyridine

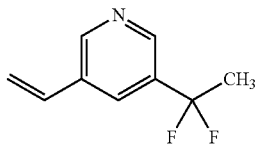

To a stirred solution of 3-bromo-5-(1,1-difluoroethyl) pyridine (1.86 g, 8.38 mmol) in 40 mL toluene was added vinyl tri-n-butylstannane (3.2 mL, 11 mmol) and the solution was sparged with nitrogen gas. Bis(triphenylphosphine) palladium(II) chloride (0.6 g, 0.8 mmol) was added and the mixture was heated to 100° C. for 1.5 h. The mixture was cooled to RT, diluted with EtOAc, and washed with water and brine, then dried ($MgSO_4$), filtered and the solvent was removed in vacuo. The crude product was chromatographed on a 40 g $SiO_2$ column using 0-40% EtOAc:hexane over 20 min at 40 mL/min. Fractions containing product were combined and the solvents were removed in vacuo to give the title compound. LCMS m/z=170.1 (M+H)+.

Step 3. 5-(1,1-Difluoroethyl)nicotinaldehyde

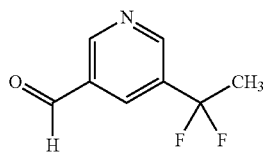

To a stirred solution of 3-(1,1-difluoroethyl)-5-vinylpyridine (1.16 g, 6.86 mmol) in 40 mL THF and 10 mL water was added add osmium tetroxide (8.6 mL of a 2.5% in tert-butanol, 0.67 mmol). The mixture was stirred for 5 min and then $NaIO_4$ (4.4 g, 21 mmol) was added. The mixture was stirred for 30 min then diluted with water and EtOAc. The organic phase was separated, washed with brine, dried ($MgSO_4$), filtered, and the solventes were removed in vacuo to give the title compound. LCMS m/z=172.0 (M+H)+.

Step 4: (2S,3S)-2-Azido-3-(4-chlorophenyl)-3-(5-(1,1-difluoroethyl)pyridin-3-yl)propanoic acid The title compound was prepared using the above intermediate and following the procedures described for Intermediate 6.

Intermediate 33

(2S,3S)-2-Azido-3-(4-chlorophenyl)-3-(6-(trifluoromethyl)pyridin-3-yl)propanoic acid

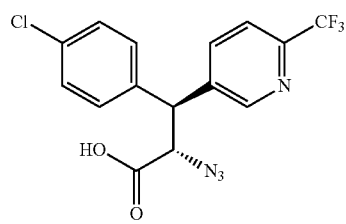 [SMILES: [N-]=[N+]=N[C@H](C(=O)O)[C@@H](c1ccc(Cl)cc1)c1ccc(C(F)(F)F)nc1]

The title compound was prepared from 5-bromo-2-(trifluoromethyl)pyridine using the procedures given in Intermediate 32.

Intermediate 34

(2S,3R)-2-Azido-3-(4-chlorophenyl)-3-(1,1-dioxido-tetrahydro-2H-thiopyran-4-yl)propanoic acid

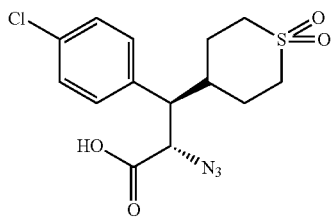 [SMILES: [N-]=[N+]=N[C@H](C(=O)O)[C@@H](c1ccc(Cl)cc1)C1CCS(=O)(=O)CC1]

The title compound was prepared using similar procedure for Intermediate 7, using (4-(hydroxymethyl)tetrahydro-2H-thiopyran 1,1-dioxide as starting material.

Intermediate 35

(2S,3R)-2-Azido-3-(4-chlorophenyl)-3-((1r,4R)-4-ethoxycyclohexyl)propanoic acid

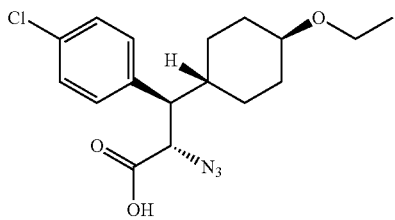 [SMILES: CCO[C@H]1CC[C@H]([C@H](c2ccc(Cl)cc2)[C@H](N=[N+]=[N-])C(=O)O)CC1]

Step 1: 1,4-Dioxaspiro[4.5]decan-8-ol

A solution of 1,4-dioxaspiro[4.5]decan-8-one (300 g, 1920 mmol) in MeOH (2000 mL) was cooled to 0° C. NaBH$_4$ (87 g, 2300 mmol) was added in several portions. The mixture was stirred for 2 h. TLC (petroleum ether:ethyl acetate=5:1) showed the reaction complete, NH$_4$Cl solution was added to quench the reaction. The mixture was concentrated in vacuo to remove MeOH, extracted with DCM (3×250 mL). The combined organic layers were washed with brine, dried over Na$_2$SO$_4$, filtered, and the filtrate was concentrated in vacuo to give the title compound which was used in next Step without further purification.

Step 2: 8-Ethoxy-1,4-dioxaspiro[4.5]decane

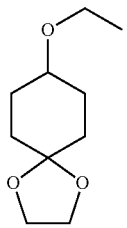

1,4-Dioxaspiro[4.5]decan-8-ol (200 g, 1264 mmol) was dissolved in THF (2000 mL) and the solution was cooled to 0° C. To the stirred solution was added sodium hydride (45.5 g, 1896 mmol) in several portions. The mixture was stirred for 1 h. Iodoethane (296 g, 1896 mmol) was added, and the reaction was stirred for 2 h. NH$_4$Cl solution was added to quench the reaction. The mixture was extracted with EtOAc (3×500 mL). The combined organic layers were washed with brine, dried over Na$_2$SO$_4$, filtered, and the filtrate solvent was removed in vacuo to give the title compound. $^1$H NMR (Chloroform-d, 400 MHz) δ 3.87 (s, 4H), 3.42 (d, J=7.2 Hz, 2H), 3.32 (s, 1H), 1.82-1.75 (m, 5H), 1.72-1.61 (m, 2H), 1.49-1.47 (m, 2H), 1.13 (t, J=7.2 Hz, 3H) ppm.

Step 3: 4-Ethoxycyclohexanone

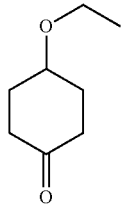

To a stirred solution of 8-ethoxy-1,4-dioxaspiro[4.5]decane (245 g, 1315 mmol) in THF (900 mL) was added HCl (877 mL, 5262 mmol). The mixture was stirred at RT for 2 h. The mixture was basified with aqueous Na$_2$CO$_3$. The mixture was extracted with DCM (3×500 mL). The organic layers were washed with brine, dried over sodium sulfate, filtered, and the filtrate solvents were removed in vacuo to give the title compound. $^1$H NMR (Chloroform-d, 400 MHz) δ 3.67 (s, 1H), 3.18 (q, J=7.2 Hz, 2H), 2.54-2.52 (m, 2H), 2.23-2.20 (m, 2H), 2.03-1.91 (m, 4H), 1.97 (t, J=6.8 Hz, 3H) ppm.

Step 4: 1-Ethoxy-4-(methoxymethylene)cyclohexane

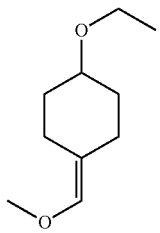

To a stirred mixture of (methoxymethyl)triphenylphosphonium chloride (212 g, 617 mmol) in THF (500 mL) under nitrogen atmosphere at −45° C. was added sodium hexamethyldisilazide (617 mL, 617 mmol) and the resulting mixture was stirred for 30 min. 4-Ethoxycyclohexanone (67.5 g, 475 mmol) in THF (200 mL) was added to the mixture at −45° C. The mixture was warmed to RT and stirred for 16 h. The mixture was quenched with a saturated solution of NH$_4$Cl and extracted with DCM (3×300 mL). The organic layers were washed with brine, dried over sodium sulfate, filtered, and the filtrate solvents were removed in vacuo. The residue was purified by SiO$_2$ column chromatography (petroleum ether:ethyl acetate=100:1) to give the title compound. $^1$H NMR (Chloroform-d, 400 MHz) δ 5.71 (s, 1H), 3.50-3.43 (m, 5H), 3.36-3.28 (m, 1H), 2.62-2.53 (m, 1H), 2.13-2.04 (m, 1H), 1.88-1.78 (m, 4H), 1.35-1.29 (m, 2H), 1.15 (t, J=7.0 Hz, 3H) ppm.

Step 5: 4-Ethoxycyclohexanecarbaldehyde

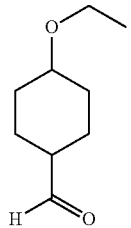

To a stirred solution of 1-ethoxy-4-(methoxymethylene)cyclohexane (145 g, 852 mmol) in acetonitrile (800 mL) was added 2N aqueous HCl (852 mL, 1703 mmol). The mixture was stirred at RT for 2 h. The mixture was basified with 1 M NaHCO$_3$ and extracted with DCM (3×300 mL). The organic layers were combined, washed with brine, dried over sodium sulfate, filtered, and the filtrate solvents wete removed in vacuo to give the title compound. $^1$H NMR (Chloroform-d, 400 MHz) δ 9.58 (d, J=5.1 Hz, 1H), 5.78-5.64 (m, 1H), 3.52-3.35 (m, 3H), 2.27-2.10 (m, 1H), 2.07-1.99 (m, 2H), 1.90-1.77 (m, 1H), 1.72-1.48 (m, 4H), 1.33-1.18 (m, 4H), 1.13 (q, J=6.7 Hz, 4H) ppm.

Step 6: (R)-3-((E)-3-((1r,4S)-4-Ethoxycyclohexyl)acryloyl)-4-phenyl-oxazolidin-2-one

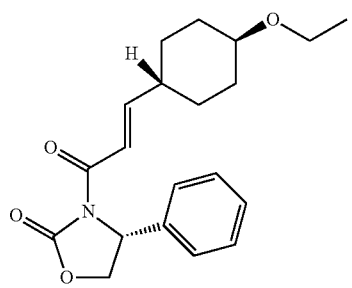 [SMILES: CCO[C@H]1CC[C@H](/C=C/C(=O)N2C(=O)OC[C@H]2c2ccccc2)CC1]

To a stirred solution of (R)-dimethyl (2-oxo-2-(2-oxo-4-phenyloxazolidin-3-yl)ethyl) phosphonate (254 g, 810 mmol) in dry THF (1000 mL) at 0° C. under N$_2$ atmosphere was added potassium tert-butoxide (99 g, 883 mmol). The mixture was stirred for 30 min. 4-Ethoxycyclohexanecarbaldehyde (115 g, 736 mmol) in dry THF (500 mL) was added and the mixture was warmed to RT and stirred for 14 h. The mixture was poured into water, extracted with ethyl acetate (3×400 mL), drived over Na$_2$SO$_4$, filtered, and the filtrate solvents were removed in vacuo. The residue was purified by SiO$_2$ chromatography silica (petroleum ether:ethyl acetate=15:1) to give the title compound. $^1$H NMR (Chloroform-d, 400 MHz) δ 7.40-7.26 (m, 5H), 6.98 (dd, J=7.0, 15.7 Hz, 1H), 5.45 (dd, J=3.9, 8.6 Hz, 1H), 4.67 (t, J=8.8 Hz, 1H), 4.26 (dd, J=3.7, 8.8 Hz, 1H), 3.49 (q, J=7.0 Hz, 2H), 3.24-3.07 (m, 1H), 2.23-2.11 (m, 1H), 2.05 (d, J=11.3 Hz, 2H), 1.83 (d, J=12.1 Hz, 2H), 1.62 (br. s., 2H), 1.28-1.20 (m, 3H), 1.16 (t, J=7.0 Hz, 3H) ppm.

Step 7: (R)-3-((R)-3-(4-Chlorophenyl)-3-((1r,4R)-4-ethoxycyclohexyl)propanoyl)-4-phenyloxazolidin-2-one

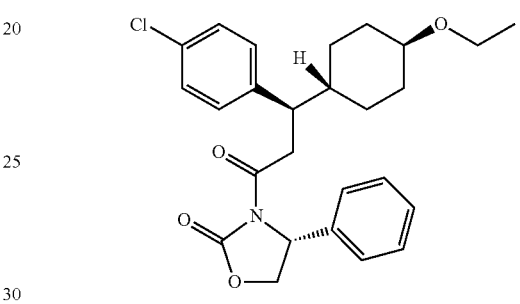

A solution of (4-chlorophenyl) magnesium bromide (114 mL of a 1.0 M solution in THF, 114 mmol) in THF (150 mL) was cooled to −40° C. under nitrogen atmosphere, then CuBrMe2S (13.23 g, 64.4 mmol) was added. The mixture was stirred for 30 min. (R)-3-((E)-3-((1r,4S)-4-Ethoxycyclohexyl)acryloyl)-4-phenyl-oxazolidin-2-one (13 g, 37.9 mmol) in THF (50 mL) was added dropwise to the mixture. The reaction was stirred 40° C. for 2 h. The reaction was quenched by the addition of aqueous NH$_4$Cl solution and then extracted with ethyl acetate (3×200 mL). The combined organic layers were washed with water and brine, dried over Na$_2$SO$_4$, filtered, and the filtrate solvents were removed in vacuo. The residue was purified by SiO$_2$ column chromatography (petroleum ether:ethyl acetate=5:1) to give the title compound. $^1$H NMR (Chloroform-d, 400 MHz) δ 7.23-7.15 (m, 3H), 7.13 (d, J=8.2 Hz, 2H), 6.99 (d, J=8.2 Hz, 2H), 6.78 (d, J=7.0 Hz, 2H), 5.28 (dd, J=3.7, 8.8 Hz, 1H), 4.57 (t, J=8.8 Hz, 1H), 3.73 (dd, J=10.6, 15.7 Hz, 1H), 3.44 (q, J=7.0 Hz, 2H), 3.11-2.98 (m, 2H), 2.93-2.82 (m, 1H), 2.04 (d, J=3.1 Hz, 1H), 1.95-1.83 (m, 2H), 1.60 (br. s., 1H), 1.49-1.35 (m, 2H), 1.19 (br. s., 1H), 1.14 (t, J=7.0 Hz, 3H), 1.10-0.90 (m, 2H), 0.85-0.71 (m, 1H) ppm.

Step 8: (R)-3-(4-Chlorophenyl)-3-((1r,4R)-4-ethoxycyclohexyl)propanoic acid

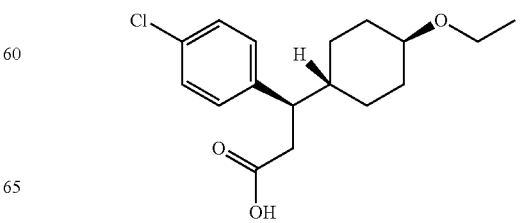

To a stirred solution of (R)-3-((R)-3-(4-chlorophenyl)-3-((1r,4R)-4-ethoxy-cyclohexyl)propanoyl)-4-phenyloxazolidin-2-one (12.5 g, 27.4 mmol) in THF (100 mL) at 0° C. was added H₂O (33 mL), hydrogen peroxide (0.932 g, 27.4 mmol), and lithium hydroxide (0.657 g, 27.4 mmol) The mixture was stirred at 0° C. for 1 h. Sodium sulfite (3.46 g, 27.4 mmol) and sodium bicarbonate (2.303 g, 27.4 mmol) were added and the mixture was stirred at RT for 15 min. The THF solvent was removed in vacuo and the remaining aqueous layer was washed with DCM (2×40 mL) to remove the oxazolidinone. The aqueous layer was acidified to pH=1 with dilute HCl and extracted with ethyl acetate 3×(50 mL). The ethyl acetate layers were combined and concentrated in vacuum to give the title compound. ¹H NMR (Chloroform-d, 400 MHz) δ 7.26-7.19 (m, 2H), 7.03 (d, J=8.2 Hz, 2H), 3.45 (q, J=7.0 Hz, 2H), 3.12-3.01 (m, 1H), 2.88-2.72 (m, 2H), 2.54 (dd, J=9.4, 15.3 Hz, 1H), 2.09-1.79 (m, 3H), 1.50-1.33 (m, 2H), 1.27-1.16 (m, 1H), 1.13 (t, J=6.8 Hz, 3H), 1.11-0.88 (m, 2H), 0.87-0.73 (m, 1H) ppm.

Step 9: (S)-3-((R)-3-(4-Chlorophenyl)-3-((1r,4R)-4-ethoxycyclohexyl)propanoyl)-4-phenyloxazolidin-2-one

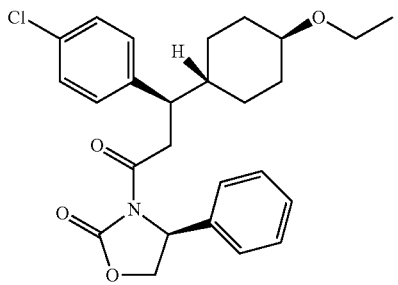 [SMILES: CCO[C@H]1CC[C@H]([C@@H](CC(=O)N2C(=O)OC[C@@H]2c2ccccc2)c2ccc(Cl)cc2)CC1]

To a stirred solution of (R)-3-(4-chlorophenyl)-3-((1r,4R)-4-ethoxycyclohexyl)propanoic acid (7.2 g, 23.16 mmol) in DCM (100 mL) at 0° C. was added oxalyl chloride (4.06 mL, 46.3 mmol) dropwise. The mixture was stirred at 0° C. for 2 h. The solvent was removed in vacuo to give the crude acid chloride. (S)-4-Phenyloxazolidin-2-one (4.52 g, 27.7 mmol) was dissolved in 70 mL of dry THF and cooled to −40° C. BuLi (11.08 mL of a 2.5 M solution in hexane, 27.7 mmol) was added dropwise and resulting mixture was stirred for 30 min. The crude acid chloride in 30 mL dry THF was added dropwise to the mixture. The reaction was stirred at −40° C. for 1 h. The reaction was quenched with the addition of aqueous NH₄Cl and extracted with ethyl acetate (3×80 mL). The combined organic layers were washed with water, saturated aqueous NaHCO₃ and brine, then dried over Na₂SO₄, filtered, and the solvents were removed in vacuo. The crude product was purified by SiO₂ column chromatography (petroleum ether:ethyl acetate=5:1) to give the title compound. ¹H NMR (Chloroform-d, 400 MHz) δ 7.41-7.30 (m, 3H), 7.21 (d, J=7.4 Hz, 4H), 7.06 (d, J=8.2 Hz, 2H), 5.24 (dd, J=3.1, 8.6 Hz, 1H), 4.55 (t, J=8.8 Hz, 1H), 4.23 (dd, J=3.5, 9.0 Hz, 1H), 3.48 (q, J=7.0 Hz, 2H), 3.31-3.23 (m, 1H), 3.13-3.03 (m, 1H), 3.01-2.92 (m, 1H), 2.08-1.82 (m, 3H), 1.64 (s, 1H), 1.50-1.41 (m, 2H), 1.17 (t, J=7.0 Hz, 4H), 1.11-1.02 (m, 1H), 1.01-0.89 (m, 1H), 0.82 (q, J=12.4 Hz, 1H) ppm.

Step 10: (S)-3-((2S,3R)-2-Azido-3-(4-chlorophenyl)-3-((1r,4R)-4-ethoxycyclohexyl)propanoyl)-4-phenyloxazolidin-2-one

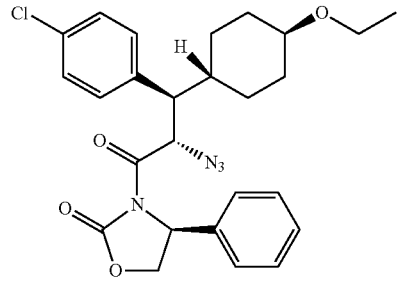 [SMILES: CCO[C@H]1CC[C@H]([C@H](c2ccc(Cl)cc2)[C@H](N=[N+]=[N-])C(=O)N2C(=O)OC[C@@H]2c2ccccc2)CC1]

To a stirred solution of (S)-3-((R)-3-(4-chlorophenyl)-3-((1r,4R)-4-ethoxycyclohexyl)propanoyl)-4-phenyloxazolidin-2-one (8.3 g, 18.20 mmol) in THF (200 mL) at −78° C. under nitrogen atmosphere was added sodium bis(trimethylsilyl)amide (27.3 mL of a 1.0 M solution in THF, 27.3 mmol) dropwise. The mixture was stirred at −78° C. for 1 h. 2,4,6-Triisopropylbenzenesulfonyl azide (8.45 g, 27.3 mmol) was added as a solid and the mixture was stirred at −78° C. for 1 h. Acetic acid (6.56 g, 109 mmol) and tetrabutylammonium acetate (21.95 g, 72.8 mmol) were added, and the mixture was stirred at RT for 18 h. The mixture was poured into 100 mL of water, extracted with ethyl acetate (3×100 mL), and the combined ethyl acetate layers were concentrated in vacuo. The residue was purified by SiO₂ column chromatography (petroleum ether:ethyl acetate=15:1) to give the title compound. ¹H NMR (Chloroform-d, 400 MHz) δ 7.39-7.29 (m, 1H), 7.28-7.22 (m, 1H), 7.19 (d, J=7.0 Hz, 1H), 7.06 (d, J=8.2 Hz, 1H), 5.62 (d, J=11.3 Hz, 1H), 4.97 (dd, J=3.5, 8.6 Hz, 1H), 4.34 (t, J=8.6 Hz, 1H), 4.15 (dd, J=3.7, 8.8 Hz, 1H), 3.43 (q, J=7.0 Hz, 2H), 3.08 (dd, J=4.5, 11.2 Hz, 1H), 3.03-2.92 (m, 1H), 2.02 (t, J=11.9 Hz, 2H), 1.93-1.82 (m, 1H), 1.77 (d, J=12.1 Hz, 2H), 1.28-1.20 (m, 4H), 1.13 (t, J=6.8 Hz, 3H) ppm.

Step 11: (2S,3R)-2-Azido-3-(4-chlorophenyl)-3-((1r,4R)-4-ethoxycyclohexyl)propanoic acid To a stirred solution of (S)-3-((2S,3R)-2-azido-3-(4-chlorophenyl)-3-((1r,4R)-4-ethoxycyclohexyl)propanoyl)-4-phenyloxazolidin-2-one (4.2 g, 8.45 mmol) in THF (45 mL) and water (15 mL) at 0° C. was added hydrogen peroxide (33.8 mmol of a 30% solution in water) and lithium hydroxide (0.405 g, 16.90 mmol). The mixture was stirred at 0° C. for 1 h. Sodium sulfite (4.26 g, 33.8 mmol) and sodium bicarbonate (3.55 g, 42.3 mmol) were added, and resulting mixture was stirred at RT for 15 min. The THF was removed in vacuo and the remaining aqueous solution was washed with DCM 2×(50 mL) to remove the oxazolidinone. The aqueous layer was acidified to pH=1 with dilute aquoeus HCl and extracted with ethyl acetate 3×(50 mL×3). The ethyl acetate extracts were combined and the solvents were removed in vacuo to give the title compound. ¹H NMR (Chloroform-d, 400 MHz) δ 7.30-7.25 (m, 2H), 7.13 (d, J=8.5 Hz, 2H), 4.16 (d, J=6.5 Hz, 1H), 3.49 (q, J=7.0 Hz, 2H), 3.14-3.04 (m, 1H), 2.95 (t, J=6.8 Hz, 1H), 2.00-1.81 (m, 3H), 1.57-1.48 (m, 1H), 1.26 (t, J=7.0 Hz, 2H), 1.15 (t, J=6.8 Hz, 4H), 1.02-0.76 (m, 2H) ppm.

Intermediate A (6R,9R)-tert-Butyl 9-(hydroxymethyl)-2-thia-1,7-diazabicyclo[4.3.1]decane-7-carboxylate 2,2-dioxide

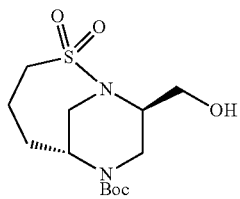 [SMILES: CC(C)(C)OC(=O)N1C[C@H](CO)N2C[C@H]1CCCS2(=O)=O]

Step 1. (R)-methyl 2-(benzylamino)pent-4-enoate

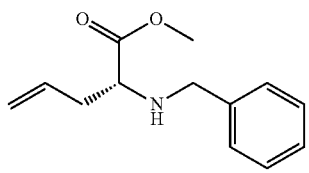 [SMILES: C=CC[C@@H](NCc1ccccc1)C(=O)OC]

(R)-Methyl 2-aminopent-4-enoate (28.8 g, 174 mmol) was stirred in 300 mL of MeOH under an atmosphere of $N_2$. To the stirred solution was added $Et_3N$ (26.7 mL, 191 mmol) followed by benzaldehyde (35.4 mL, 348 mmol). The resulting solution was stirred at RT overnight. The stirred solution was cooled in an ice-water bath under an atmosphere of $N_2$. To the solution was added solid $NaBH_4$ (13 g, 344 mmol) in small portions over a period of about 4 h. 15 min after the final addition of $NaBH_4$ the mixture was stored in a −20° C. freezer overnight. The MeOH was removed in vacuo and the residue was vigorously stirred in a 2-phase system consisting of EtOAc (300 mL) and water (200 mL). 2N aq $H_2SO_4$ (200 mL) was added slowly and the 2-phase system was stirred for 10 min, then transferred to s separatory funnel. The aqueous phase was collected and the organic phase was extracted with another portion of 2N aq $H_2SO_4$ (100 mL). The aqueous phases were combined and washed with EtOAc (150 mL). The aqueous phase was then vigorously stirred in a 2 L rb flask with 200 mL of $CH_2Cl_2$ while solid $K_2CO_3$ (45 g) was slowly added (caution, gas evolution). The 2-phase system was transferred to a separatory funnel and the organic phase was collected. The aqueous phase was extracted with $CH_2Cl_2$ (150 mL) and the combined organic phases were dried ($Na_2SO_4$), filtered, and concentrated in vacuo. The crude product was put through a short pad of silica gel eluting with 20% EtOAc in henxane to give the title compound. LCMS m/z=221.2 (M+H)$^+$.

Step 2. (R)-methyl 2-((S)—N-benzyl-3-(benzyloxy)-2-((tert-butoxycarbonyl)amino)propanamido)pent-4-enoate

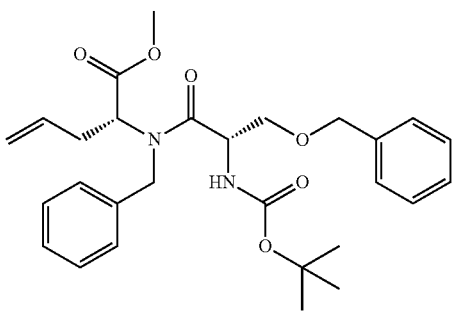 [SMILES: C=CC[C@H](C(=O)OC)N(Cc1ccccc1)C(=O)[C@H](COCc1ccccc1)NC(=O)OC(C)(C)C]

(R)-Methyl 2-(benzylamino)pent-4-enoate (29.6 g, 135 mmol) was dissolved in 75 mL of DMF. The solution was stirred under an atmosphere of nitrogen and Boc-O-benzyl-L-serine (43.9 g, 148 mmol) was added. When all the solids had dissolved HATU (77 g, 202 mmol) was added. The mixture was stirred at ambient temperature for 10 min, then cooled in an ice-water bath. DIEA (25 mL, 143 mmol) was added dropwise over a period of 30 min. The mixture was stirred for 30 min and the cooling bath was removed. The mixture was stirred at ambient temperature for 3 h. The pH of the mixture as determined on a wetted E Merck pH strip was low, pH 2. The stirred mixture was again cooled in an ice-water bath and 1.5 equiv DIEA (37 mL, 211 mmol) was added dropwise over a period of 1 h. The mixture was stirred for 18 h during which time the cooling bath had expired. The stirred mixture was again cooled in an ice-water bath and DIEA (13 mL, 74 mmol) was added dropwise over a period of 30 min. The cooling bath was removed and the dark solution was stirred at ambient temperature for 18 h. The DMF was removed in vacuo and the residue was dissolved in EtOAc (500 mL). The EtOAc solution was washed with 2×300 mL 5% aqueous citric acid, 300 mL $H_2O$, 3×300 mL aq $NaHCO_3$, and 100 mL brine. The EtOAc solution was dried ($MgSO_4$), filtered and concentrated in vacuo. The solids were suspended in ether and removed by filtration. The filtrate solvent was removed in vacuo and the resulting material was dissolved in a small amount of $CH_2Cl_2$ and loaded on a short column of $SiO_2$ and eluted with 15% EtOAc:hexanes to give the title compound. LCMS m/z=497.4 (M+H)$^+$.

Step 3. (3S,6R)-6-allyl-1-benzyl-3-((benzyloxy)methyl)piperazine-2,5-dione

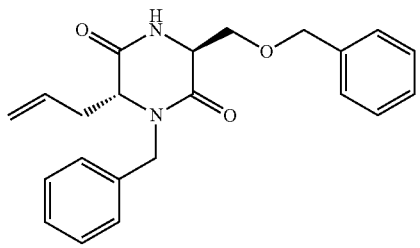 [SMILES: C=CC[C@@H]1C(=O)N[C@@H](COCc2ccccc2)C(=O)N1Cc1ccccc1]

(R)-Methyl 2-((S)—N-benzyl-3-(benzyloxy)-2-((tert-butoxycarbonyl)amino)propanamido)pent-4-enoate (59.5 g, 120 mmol) was dissolved in 100 mL of $CH_2Cl_2$. The solution was stirred and cooled in an ice-water bath. 100 mL of TFA was added and after 5 min of stirring, the cooling bath was removed and the mixture was stirred at RT for 1.5 h. The solvents were removed in vacuo and the residue was dissolved in 400 mL of EtOAc. Saturated aqueous $NaHCO_3$ (200 mL) was added slowly (caution, gas evolution) over a period of 20 min. Water was added (200 mL) and solid $K_2CO_3$ was slowly added (gas evolution) until the aqueous phase was pH 8. The two phase mixture was stirred at RT overnight. The EtOAc layer was collected and the aqueous phase was washed with EtOAc (100 mL). The combined organic phases were washed with brine then dried ($MgSO_4$), filtered, and concentrated in vacuo to give a gum. The crude product was divided in two portions and each portion was chromatographed on a 330 g $SiO_2$ column eluting with 0-100% EtOAc:hexanes. The desired product eluted at 70%

Step 4. (2R,5R)-2-allyl-1-benzyl-5-((benzyloxy)methyl)piperazine

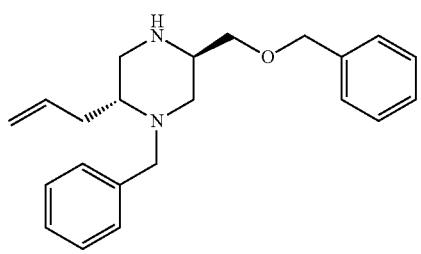 [SMILES: C=CC[C@@H]1CN[C@@H](COCc2ccccc2)CN1Cc1ccccc1]

(3S,6R)-6-Allyl-1-benzyl-3-((benzyloxy)methyl)piperazine-2,5-dione (29.9 g, 82 mmol) was dissolved in 250 mL of THF under an atmosphere of $N_2$. The solution was stirred and cooled in an ice water bath and solid LAH (10 g, 263 mmol) was added in portions over 1 h. The cooling bath was removed and the suspension was stirred at RT for 18 h. The mixture was heated to reflux for 6 h. The mixture was cooled to RT and stirred for 18 h. The mixture was cooled in an ice-water bath and 20 mL of 5N aq NaOH was added dropwise with vigorous stirring (caution, gas evolution). More THF was added to facilitate stirring. To the mixture was added 20 mL of water dropwise. When the addition was complete, CELITE® was added to keep the precipitate granular. Another 10 mL of 5 N NaOH was added dropwise and 200 mL of ether was added. The cooling bath was removed mixture was stirred at ambient temperature for 2 h then filtered through a pad of CELITE®. The salts were washed thoroughly with EtOAc. The filtrate solvents were removed in vacuo to give the title compound. LCMS m/z=337.4 (M+H)$^+$.

Step 5. (2R,5R)-2-allyl-1-benzyl-5-((benzyloxy)methyl)-4-(vinylsulfonyl)piperazine

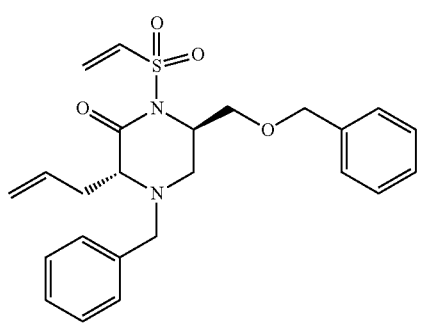 [SMILES: C=CC[C@@H]1C(=O)N(S(=O)(=O)C=C)[C@@H](COCc2ccccc2)CN1Cc1ccccc1]

(2R,5R)-2-Allyl-1-benzyl-5-((benzyloxy)methyl)piperazine (11.1 g, 33 mmol) was dissolved in 75 mL of $CH_2Cl_2$. To the solution was added DIEA (16 mL, 92 mmol) and the resulting solution was added dropwise to a 0° C. solution of 2-chloroethylsulfonyl chloride (4.7 mL, 44.5 mmol) in 150 mL of $CH_2Cl_2$ under an atmosphere of nitrogen over a period of 1 h. The dark mixture was stirred for another 15 min after the addition was complete, then quenched with the addition of aqueous $NaHCO_3$. The $CH_2Cl_2$ layer was collected and dried ($MgSO_4$), filtered, and concentrated in vacuo. The crude product was chromatographed on a 220 g $SiO_2$ column using a gradient of 0-40% EtOAc:hexanes. The peak eluting at 15-20% EtOAc was collected to give the title compound. LCMS m/z=428.2 (M+H)$^+$.

Step 6. (6R,9R)-7-benzyl-9-((benzyloxy)methyl)-2-thia-1,7-diazabicyclo[4.3.1]dec-3-ene 2,2-dioxide

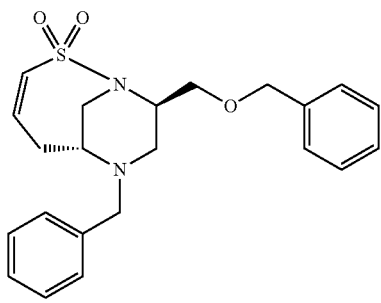 [SMILES: O=S1(=O)C=CC[C@@H]2CN1[C@@H](COCc1ccccc1)CN2Cc1ccccc1]

(2R,5R)-2-Allyl-1-benzyl-5-((benzyloxy)methyl)-4-(vinylsulfonyl)piperazine (7.6 g, 17.8 mmol) was dissolved in 200 mL of dichloroethane and the stirred solution was degassed by bubbling nitrogen gas through the solution for 10 min. To the solution was added [1,3-bis-(2,4,6-trimethylphenyl)-2-imidazolidinylidene]dichloro(phenylmethylene)(tricyclohexyl-phosphine)ruthenium (1.9 g, 2.2 mmol) and the the mixture was heated to reflux under nitrogen atmosphere for 18 h. The mixture was cooled to ambient temperature under $N_2$ atmosphere and more catalyst (1.0 g, 1.2 mmol) was added. The mixture was heated to reflux for 6 h then stirred at RT for 18 h. The solvent was reduced to half the original volume in vacuo and the dark mixture was poured through a pad of SiO2, the pad was washed with 10% EtOAc in $CH_2Cl_2$. The filtrate solvents were removed in vacuo and the residue was chromatographed on a 220 g $SiO_2$ column eluting with a gradient of 0-60% EtOAc-hexanes. The peak eluting at 40% EtOAc was collected to give the title compound. LCMS m/z=399.3 (M+H)$^+$.

Step 7. (6R,9R)-7-benzyl-9-((benzyloxy)methyl)-2-thia-1,7-diazabicyclo[4.3.1]decane 2,2-dioxide

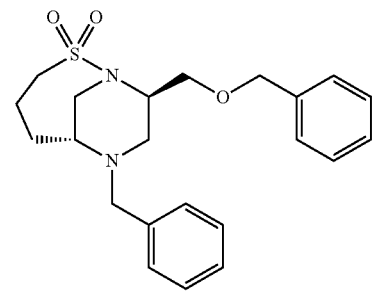 [SMILES: O=S1(=O)CCC[C@@H]2CN1[C@@H](COCc1ccccc1)CN2Cc1ccccc1]

(6R,9R)-7-Benzyl-9-((benzyloxy)methyl)-2-thia-1,7-diazabicyclo[4.3.1]dec-3-ene 2,2-dioxide (8.1 g, 20 mmol) was dissolved in 200 mL EtOAc under nitrogen atmosphere. 10% Pd/C (800 mg, 0.75 mmol) was added and the mixture was stirred under hydrogen atmosphere for 18 h. The hydrogen was removed by flushing with nitrogen gas and the catalyst was removed by filtration. The filtrate solvent was removed in vacuo and the crude product was chromatographed on silica gel eluting using a gradient elution of 0-40% EtOAc in hexanes. Fractions containing product were combined and the solvents were removed in vacuo to give the title compound. LCMS m/z=401.4 (M+H)⁺.

Step 8. (6R,9R)-9-(hydroxymethyl)-2-thia-1,7-diazabicyclo[4.3.1]decane 2,2-dioxide

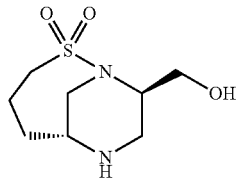 [SMILES: O=S1(=O)CCC[C@@H]2CN1[C@@H](CO)CN2]

(6R,9R)-7-Benzyl-9-((benzyloxy)methyl)-2-thia-1,7-diazabicyclo[4.3.1]decane 2,2-dioxide (7.4 g, 18.5 mmol) was dissolved in 100 mL THF and a solution of aqueous HCl (37 mL of a 1.0 M solution, 37 mmol) was added. The mixture was shaken on a Parr apparatus under 50 psi of hydrogen gas for 18 h. The hydrogen was removed by flushing with nitrogen gas and the catalyst was removed by filtration. The filtrate solvents were removed in vacuo to give the HCl salt of the title compound. LCMS m/z=221.4 (M+H)⁺.

Step 9. (6R,9R)-tert-butyl 9-(hydroxymethyl)-2-thia-1,7-diazabicyclo[4.3.1]decane-7-carboxylate 2,2-dioxide The HCl salt of (6R,9R)-9-(hydroxymethyl)-2-thia-1,7-diazabicyclo[4.3.1]decane 2,2-dioxide (4.74 g, 18.5 mmol) was stirred in a two-phase mixture of water (25 mL) and CH₂Cl₂ (50 mL). NaHCO₃ (3.9 g, 46 mmol) was added followed by di-tert-butyl dicarbonate (4.4 g, 20 mmol). The mixture was stirred at RT for 18 h. The layers were separated and the aqueous phase was extracted with CH₂Cl₂. The organic phases were combined, washed with brine, dried (Na2SO₄), filtered, and the filtrate solvents were removed in vacuo. The crude product was chromatographed on a 120 g SiO₂ column using 0-100% EtOAc:hexane over 30 min at 85 mL/min. Fractions containing product were combined and the solvents were removed in vacuo to give the title compound. LCMS m/z=321.5 (M+H)⁺.

Intermediate B (6R,9S)-tert-Butyl 9-(2-amino-6-fluorophenethyl)-2-thia-1,7-diazabicyclo[4.3.1]decane-7-carboxylate 2,2-dioxide

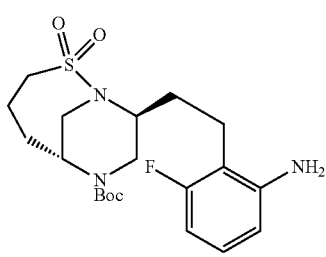 [SMILES: CC(C)(C)OC(=O)N1C[C@H](CCc2c(N)cccc2F)N2C[C@H]1CCCS2(=O)=O]

Step 1. (6R,9R)-tert-butyl 9-formyl-2-thia-1,7-diazabicyclo[4.3.1]decane-7-carboxylate 2,2-dioxide

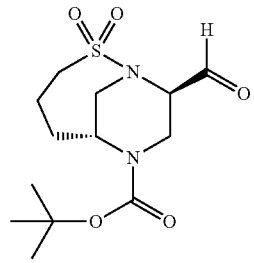 [SMILES: CC(C)(C)OC(=O)N1C[C@H](C=O)N2C[C@H]1CCCS2(=O)=O]

A solution of oxalyl chloride (5.56 mL, 62.4 mmol) in 200 mL DCM under an atmosphere of N₂ was cooled to −78° C. To the stirred solution was added DMSO (4.88 mL, 68.7 mmol) over a period of 10 min (caution, gas evolution). The mixture was stirred at −78° C. for 30 min. (6R,9R)-tert-Butyl 9-(hydroxymethyl)-2-thia-1,7-diazabicyclo[4.3.1]decane-7-carboxylate 2,2-dioxide (10 g, 31.2 mmol) (Intermediate A) was dissolved in 100 mL DCM under N₂ atmosphere and cooled to −78° C. The cold solution was added via cannula to the oxalylchloride/DMSO mixture over a period of 5 min. The resulting solution was stirred at −78° C. for 30 min. Triethylamine (21.3 mL, 156 mmol) was then added dropwise over a period of 10 min and the resulting solution was stirred at −78° C. for 10 minutes. The cooling bath was removed and the stirred mixture was allowed to warm to RT over a period of 1.5 h. The reaction was quenched with the addition of aqueous NaHCO₃. The layers were separated and the CH₂Cl₂ layer was washed with water, then dried (MgSO₄), filtered, and concentrated in vacuo to give the title compound.

Step 2. (6R,9S)-tert-butyl 9-(2,2-dibromovinyl)-2-thia-1,7-diazabicyclo[4.3.1]decane-7-carboxylate 2,2-dioxide

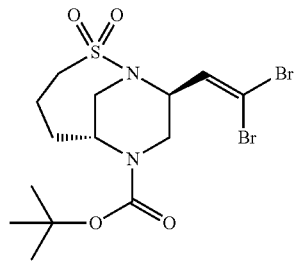 [SMILES: CC(C)(C)OC(=O)N1C[C@H](C=C(Br)Br)N2C[C@H]1CCCS2(=O)=O]

(6R,9R)-tert-Butyl 9-formyl-2-thia-1,7-diazabicyclo[4.3.1]decane-7-carboxylate 2,2-dioxide (10 g, 31.4 mmol) was dissolved in 250 mL CH₂Cl₂ under N₂ atmosphere and cooled to 0° C. To the stirred solution was added PPh₃ (33 g, 126 mmol). When the solids had all dissolved, CBr₄ (20.8 g, 62.8 mmol) was added to the reaction mixture in small portions over a period of 30 min. The cooling bath was removed and the mixture was stirred at ambient temperature for 24 h. The reaction was quenched with the addition of aq NaHCO₃. The CH₂Cl₂ layer was collected and washed with aqueous Na₂SO₃, then dried (MgSO₄), filtered and concentrated in vacuo to give a dark gum. The crude product was split in half and each half was chromatographed on a 220 g SiO$_2$ column eluting with a gradient of 0-70% EtOAc-hexanes. The peak eluting at 45% EtOAc was collected to give the title compound.

Step 3. (6R,9S)-tert-butyl 9-ethynyl-2-thia-1,7-diazabicyclo[4.3.1]decane-7-carboxylate 2,2-dioxide

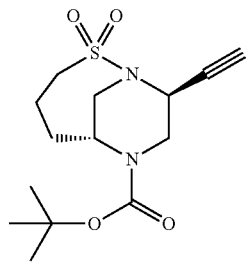 [SMILES: C#C[C@H]1CN(C(=O)OC(C)(C)C)[C@@H]2CCCS(=O)(=O)N1C2]

(6R,9S)-tert-Butyl 9-(2,2-dibromovinyl)-2-thia-1,7-diazabicyclo[4.3.1]decane-7-carboxylate 2,2-dioxide (8.8 g, 18.6 mmol) was dissolved in 150 mL THF under N$_2$ atmosphere and cooled to 0° C. To the stirred solution was added a solution of ethylmagnesium bromide (12.4 mL of a 3.0 M solution in ether, 37.1 mmol) dropwise over a period of 2 min. The solution was stirred at 0° C. for 2 h. The cooling bath was removed and the reaction was stirred at ambient temperature for 30 min, then quenched with the addition of aqueous NH$_4$Cl. EtOAc was added and the layers were separated. The organic phase was washed with brine, dried (MgSO$_4$), filtered, and concentrated in vacuo. The crude product was purified on a 220 g SiO$_2$ column eluting with 0-50% EtOAc-hexanes. The product-containing fractions were combined and the solvents were removed in vacuo to give the title compound.

Step 4. (6R,9S)-tert-butyl 9-((2-amino-6-fluorophenyl)ethynyl)-2-thia-1,7-diazabicyclo[4.3.1]decane-7-carboxylate 2,2-dioxide

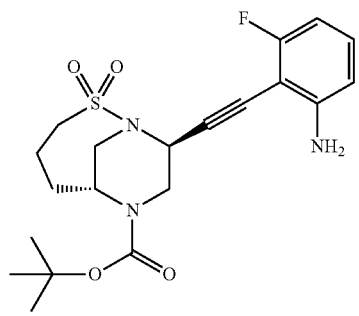 [SMILES: CC(C)(C)OC(=O)N1C[C@H](C#Cc2c(N)cccc2F)N2C[C@H]1CCCS2(=O)=O]

(6R,9S)-tert-Butyl 9-ethynyl-2-thia-1,7-diazabicyclo[4.3.1]decane-7-carboxylate 2,2-dioxide (3.4 g, 10.8 mmol) was dissolved in 100 mL acetonitrile under N$_2$ atmosphere and to the stirred solution was added triethylamine (30 mL, 216 mmol) and 3-fluoro-2-iodoaniline (5.1 g, 22 mmol). The stirred solution was sparged with N$_2$ gas for 10 min, then CuI (0.25 g, 1.3 mmol) and bis-triphenylphosphinepalladium dichloride (0.8 g, 1.1 mmol) were added and the mixture was heated in an oil bath at 70-80° C. for 5 h. The mixture was cooled to RT and the solvents were removed in vacuo. The residue was suspended in EtOAc and saturated aqueous NaHCO$_3$. Undissolved solids were removed by filtration through CELITE®. The EtOAc layer was collected and washed with brine, dried (MgSO$_4$), filtered, and concentrated in vacuo. The crude product was purified on a 120 g SiO$_2$ column eluting with a gradient of 0-60% EtOAc:A where A=1:1 CH$_2$Cl$_2$:hexanes. Product-containing fractions were combined (peak eluting at 45-50% EtOAc) and the solvents were removed in vacuo to give the title compound. LCMS m/z=424.2 (M+H)$^+$.

Step 5

(6R,9S)-tert-butyl 9-(2-amino-6-fluorophenethyl)-2-thia-1,7-diazabicyclo[4.3.1]decane-7-carboxylate 2,2-dioxide: (6R,9S)-tert-Butyl 9-((2-amino-6-fluorophenyl)ethynyl)-2-thia-1,7-diazabicyclo[4.3.1]decane-7-carboxylate 2,2-dioxide (2.7 g, 6.4 mmol) was dissolved in 100 mL THF and the solution was sparged with nitrogen gas. PtO$_2$ (400 mg, 1.8 mmol) and 10% Pd/C (400 mg, 0.38 mmol) were added and the mixture was shaken on a Parr apparatus under 50 psi of hydrogen gas for 18 h. The hydrogen was removed by sparging with nitrogen gas and the catalysts were removed by filtration through CELITE®. The filtrate solvents were removed in vacuo to give the title compound. LCMS m/z=428.4 (M+H)$^+$.

Intermediate C (6R,9S)-tert-Butyl 9-(2-amino-4-fluorophenethyl)-2-thia-1,7-diazabicyclo[4.3.1]decane-7-carboxylate 2,2-dioxide

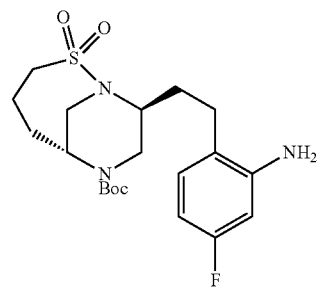 [SMILES: CC(C)(C)OC(=O)N1C[C@H](CCc2ccc(F)cc2N)N2C[C@H]1CCCS2(=O)=O]

The title compound was prepared using 5-fluoro-2-iodoaniline and following the procedures described for Intermediate B. LCMS m/z=428.2 (M+H)$^+$.

Intermediate D (6R,9S)-tert-Butyl 9-(6-amino-2,3-difluorophenethyl)-2-thia-1,7-diazabicyclo[4.3.1]decane-7-carboxylate 2,2-dioxide

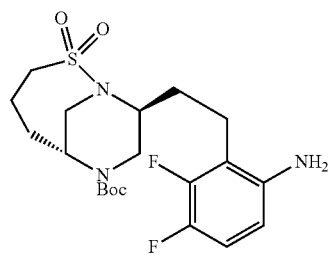 [SMILES: CC(C)(C)OC(=O)N1C[C@H](CCc2c(N)ccc(F)c2F)N2C[C@H]1CCCS2(=O)=O]

The title compound was prepared using 3,4-difluoro-2-iodoaniline and following the procedures described for Intermediate B. LCMS m/z=446 (M+H)⁺.

Intermediate E (6R,9S)-tert-Butyl 9-(2-amino-3,6-difluorophenethyl)-2-thia-1,7-diazabicyclo[4.3.1]decane-7-carboxylate 2,2-dioxide

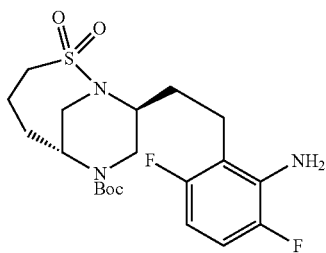 [SMILES: CC(C)(C)OC(=O)N1C[C@H](CCc2c(F)ccc(F)c2N)N2C[C@H]1CCCS2(=O)=O]

The title compound was prepared using 3,6-difluoro-2-iodoaniline and following the procedures described for Intermediate B. LCMS m/z=446.3 (M+H)⁺.

Intermediate F (6R,9S)-tert-Butyl 9-(2-(3-amino-5-fluoropyridin-4-yl)ethyl)-2-thia-1,7-diazabicyclo[4.3.1]decane-7-carboxylate 2,2-dioxide

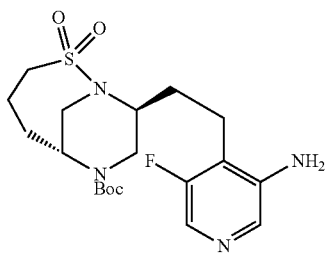 [SMILES: CC(C)(C)OC(=O)N1C[C@H](CCc2c(N)cncc2F)N2C[C@H]1CCCS2(=O)=O]

Step 1. (6R,9S)-tert-butyl 9-((3-amino-5-fluoropyridin-4-yl)ethynyl)-2-thia-1,7-diazabicyclo[4.3.1]decane-7-carboxylate 2,2-dioxide

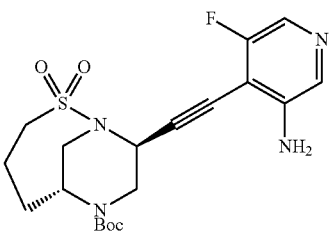 [SMILES: CC(C)(C)OC(=O)N1C[C@H](C#Cc2c(N)cncc2F)N2C[C@H]1CCCS2(=O)=O]

To (6R,9S)-tert-butyl 9-ethynyl-2-thia-1,7-diazabicyclo[4.3.1]decane-7-carboxylate 2,2-dioxide (Intermediate B, Step 3) (0.73 g, 2.33 mmol) in dry CH₃CN (10 mL) at RT was added 5-fluoro-4-iodopyridin-3-amine (0.55 g, 2.3 mmol) in one portion followed by Et₃N (6.5 mL, 47 mmol).

N₂ was bubbled thru this solution for 15 min whereupon CuI (53 mg, 0.28 mmol) and PdCl₂(dppf) (0.11 g, 0.16 mmol) were added to the solution. The mixture was affixed with a reflux condenser and was heated to 70° C. under nitrogen for 5 h. The entire reaction mixture was carefully quenched with sat. aq. NaHCO₃ (2 mL) and was diluted with EtOAc (15 mL). The layers were separated and the aqueous layer was extracted with EtOAc (3×15 mL). The organic layer was dried (Na₂SO₄), filtered, and concentrated under reduced pressure. The crude material was dissolved in 5 mL CH₂Cl₂ and loaded on RS ISCO Gold 40 g column. A gradient of CH₂Cl₂/MeOH (0-10%) was run over 45 min to afford the title compound. MS: m/z=425.2 (M+H)⁺.

Step 2. (6R,9S)-tert-butyl 9-((3-fluoro-5-(2,2,2-trifluoroacetamido)pyridin-4-yl)ethynyl)-2-thia-1,7-diazabicyclo[4.3.1]decane-7-carboxylate 2,2-dioxide

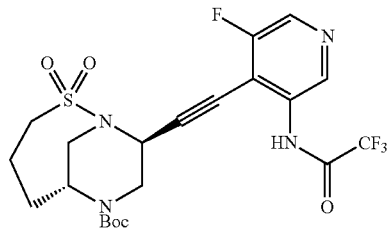 [SMILES: CC(C)(C)OC(=O)N1C[C@H](C#Cc2c(F)cncc2NC(=O)C(F)(F)F)N2C[C@H]1CCCS2(=O)=O]

To a mixture of (6R,9S)-tert-butyl 9-((3-amino-5-fluoropyridin-4-yl)ethynyl)-2-thia-1,7-diazabicyclo[4.3.1]decane-7-carboxylate 2,2-dioxide (0.53 g, 1.25 mmol) in CH₂Cl₂ (6 mL) at 0° C. under N₂ was added Et₃N (0.26 mL, 1.9 mmol) followed by TFAA (0.21 mL, 1.50 mmol). The mixture was warmed to RT and stirred under N₂ for 12 h. The reaction mixture was diluted with CH₂Cl₂ (15 mL) and sat. aq. NaHCO₃ (1.5 mL) was added. The layers were separated. The aqueous layer was extracted with CH₂Cl₂ (2×5 mL) and the organic layers were combined. The organic layer was washed with brine (3×1 mL), dried (Na₂SO₄), filtered, and was concentrated under reduced pressure. The crude material was dissolved in CH₂Cl₂ (5 mL) and was loaded onto RS ISCO Gold 24 g column. The column was eluted using a gradient of CH₂Cl₂/MeOH (0-10%) over 50 min to afford the title compound. MS: m/z=521.3 (M+H)⁺.

Step 3. (6R,9S)-tert-butyl 9-(2-(3-fluoro-5-(2,2,2-trifluoroacetamido)pyridin-4-yl)ethyl)-2-thia-1,7-diazabicyclo[4.3.1]decane-7-carboxylate 2,2-dioxide and (6R,9S)-tert-butyl 9-(2-(3-amino-5-fluoropyridin-4-yl)ethyl)-2-thia-1,7-diazabicyclo[4.3.1]decane-7-carboxylate 2,2-dioxide

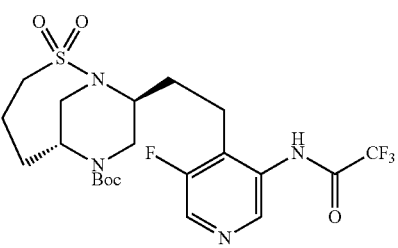

115
-continued

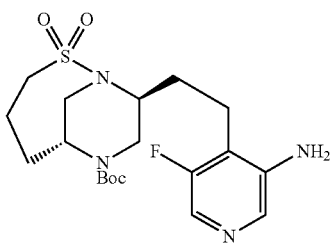

To a solution of (6R,9S)-tert-butyl 9-((3-fluoro-5-(2,2,2-trifluoroacetamido)pyridin-4-yl)ethynyl)-2-thia-1,7-diazabicyclo[4.3.1]decane-7-carboxylate 2,2-dioxide (0.55 g, 1.04 mmol) in EtOH (30 mL) in a pressure bottle was added PtO$_2$ (0.12 g) and 10% Pd/C (0.12 g). The bottle was shaken under 50 psi of H$_2$ for 12 h and was purged to N$_2$. The reaction mixture was filtered through a pad of CELITE® and the pad was washed with EtOH (100 mL). The resultant filtrate was concentrated under reduced pressure to afford a 2:1 mixture of the title compounds (0.50 g). MS: m/z=525.3 (M+H)$^+$ and 429.3 (M+H)$^+$. The crude material was used for the next Step without purification.

Step 4. (6R,9S)-tert-butyl 9-(2-(3-amino-5-fluoropyridin-4-yl)ethyl)-2-thia-1,7-diazabicyclo[4.3.1]decane-7-carboxylate 2,2-dioxide To a mixture of (6R,9S)-tert-butyl 9-(2-(3-fluoro-5-(2,2,2-trifluoroacetamido)pyridin-4-yl)ethyl)-2-thia-1,7-diazabicyclo[4.3.1]decane-7-carboxylate 2,2-dioxide and (6R,9S)-tert-butyl 9-(2-(3-amino-5-fluoropyridin-4-yl)ethyl)-2-thia-1,7-diazabicyclo[4.3.1]decane-7-carboxylate 2,2-dioxide (0.50 g) in EtOH (5 mL) was added 1M NaOH (4.5 mL, 4.5 mmol). The resulting mixture was affixed with a reflux condenser and was heated to 65° C. under N$_2$ for 12 h. The reaction mixture was cooled to RT, concentrated to dryness under vacuum, and suspended in EtOAc (20 mL). The organic layer was washed with water (2×3 mL) and brine (2×3 mL). The organic layer was dried (Na$_2$SO$_4$), filtered, and concentrated under reduced pressure to afford the title compound. MS: m/z=429.3 (M+H)$^+$.

Intermediate G (6R,9S)-tert-Butyl 9-(2-((1R,2S)-2-aminocyclohexyl)ethyl)-2-thia-1,7-diazabicyclo[4.3.1]decane-7-carboxylate 2,2-dioxide

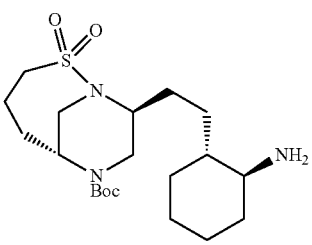 [SMILES: CC(C)(C)OC(=O)N1C[C@H](CC[C@H]2CCCC[C@@H]2N)N2C[C@H]1CCCS2(=O)=O]

116
Step 1. (1S,2S)-Methyl 2-aminocyclohexanecarboxylate hydrochloride

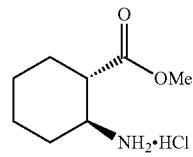

To a solution of (1S,2S)-2-aminocyclohexane carboxylic acid (2.0 g, 14 mmol) in MeOH (93 mL) at 0° C. was added thionyl chloride (5.1 mL, 70 mmol) dropwise over ~30 min to afford a homogenous solution. The mixture was affixed with a reflux condenser and was heated to 65° C. The mixture was stirred for 12 h at 65° C., cooled to RT, and was concentrated under reduced pressure. The crude material was taken up in CH$_2$Cl$_2$ (10 mL) and was concentrated under reduced pressure and this protocol was repeated 3 times. The resulting material was suspended in Et$_2$O (10 mL) and the organic layer was decanted. This procedure was repeated two additional times whereupon the resultant material was concentrated under reduced pressure and placed under high vacuum to afford the title compound. This material was carried onto the next Step without purification.

Step 2. (1S,2S)-Methyl 2-((tert-butoxycarbonyl)amino)cyclohexanecarboxylate

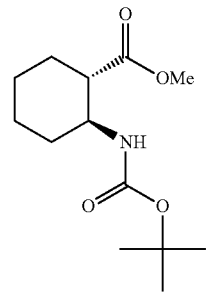 [SMILES: COC(=O)[C@H]1CCCC[C@@H]1NC(=O)OC(C)(C)C]

To a solution of (1S,2S)-methyl 2-aminocyclohexanecarboxylate hydrochloride (2.7 g, 14 mmol) from in CH$_2$Cl$_2$ (90 mL) at 0° C. was added Et$_3$N (4.9 mL, 35 mmol) followed by addition of Boc$_2$O (3.7 g, 16.8 mmol) in a single portion. The resulting mixture was allowed to gradually warm to RT and stir for a total reaction time of 1 h. TLC analysis revealed consumption of starting material and formation of a higher rf material. The mixture was treated with sat. aq. NaHCO$_3$ (10 mL) and diluted with CH$_2$Cl$_2$ (50 mL) and transferred to a separatory funnel. The layers were separated and the aqueous layer was extracted with CH$_2$Cl$_2$ (2×50 mL) and the organic layers were combined. The organic layer was washed with brine (1×5 mL), dried (Na$_2$SO$_4$), filtered, and concentrated under reduced pressure. The crude material was taken up in 2 mL of CH$_2$Cl$_2$ and loaded onto a 120 g silica gel column coupled to an ISCO purification system. A gradient of 100% hexanes to 100% EtOAc was run over 40 min whereupon fractions containing the compound were combined and concentrated in vacuo to provide the title compound. MS: m/z=258.2 (M+H)$^+$.

Step 3. tert-Butyl ((1S,2S)-2-(hydroxymethyl)cyclohexyl)carbamate

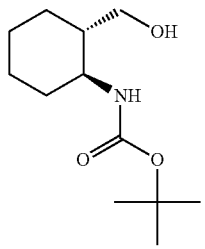 [SMILES: CC(C)(C)OC(=O)N[C@H]1CCCC[C@@H]1CO]

To a mixture of (1S,2S)-methyl 2-((tert-butoxycarbonyl)amino)cyclohexanecarboxylate (2.8 g, 11 mmol) from in THF (54 mL) at 0° C. was added 2M LiBH$_4$ in THF (11 mL, 22 mmol) dropwise to afford a solution. The resulting mixture was allowed to gradually warm to RT and was stirred overnight (12 h) at RT. The mixture was cooled to 0° C. quenched by addition of sat. aq. NH$_4$Cl (3 mL) and diluted with CH$_2$Cl$_2$ (20 mL). The layers were transferred to a separatory funnel, separated, and the aqueous layer was extracted with CH$_2$Cl$_2$ (2×20 mL). The organic layers were combined and were washed with brine (1×5 mL). The organic layer was dried (Na$_2$SO$_4$), filtered, and concentrated under reduced pressure to afford a the crude product. The crude product was dissolved in CH$_2$Cl$_2$ (3 mL) and was loaded onto an 80 g silica gel column. A gradient of 100% hexanes to 20% hexanes/80% EtOAc was run over 45 min and fractions containing product were combined and concentrated under reduced pressure to afford the title compound. MS: m/z=230.2 (M+H)$^+$.

Step 4. tert-butyl ((1S,2S)-2-formylcyclohexyl)carbamate

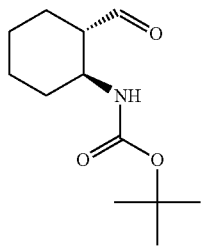 [SMILES: CC(C)(C)OC(=O)N[C@H]1CCCC[C@@H]1C=O]

To a mixture of tert-butyl ((1S,2S)-2-(hydroxymethyl)cyclohexyl)carbamate (1.2 g, 5.2 mmol) in CH$_2$Cl$_2$ (35 mL) under N$_2$ at 0° C. was added Dess-Martin Periodinane (2.7 g, 6.3 mmol) in one portion. The resulting heterogenous mixture was stirred for 3 h at 0° C. whereupon solid Ca(OH)$_2$ (~4 g) was added in a single portion. The mixture was stirred vigorously for 1 h at 0° C. whereupon the heterogenous reaction mixture was filtered thru a pad of CELITE®. The pad was washed with CH$_2$Cl$_2$ (3×20 mL) and the resulting filtrate was concentrated under reduced pressure to afford the title compound. The title compound was was carried on crude without purification to the next transformation.

Step 5. tert-butyl ((1S,2R)-2-vinylcyclohexyl)carbamate

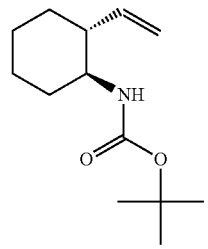 [SMILES: C=C[C@H]1CCCC[C@@H]1NC(=O)OC(C)(C)C]

To a solution of methyltriphenylphosphonium bromide (2.9 g, 8.4 mmol) in THF (25 mL) at RT was added a 0.5 M solution of KHMDS in toluene (17 mL, 8.4 mmol) dropwise to afford a solution. The mixture was stirred for 1 h at RT and was cooled to −78° C. whereupon a solution of tert-butyl ((1S,2S)-2-formylcyclohexyl)carbamate (1.2 g, 5.2 mmol) in THF (25 mL) was added dropwise over ~20 min. The resulting solution was allowed to gradually warm to RT and stir for 12 h. Sat. aq. Rochelle's salt (30 mL) was added followed by Et$_2$O (100 mL) and the mixture was transferred to a separatory funnel. The layers were separated and the aqueous layer was extracted with Et$_2$O (3×75 mL) and the organic layers were combined. The organic layer was washed with brine (1×30 mL), dried (MgSO$_4$), filtered, and concentrated under reduced pressure. The crude material was taken up in CH$_2$Cl$_2$ (5 mL) and was loaded onto a 120 g silica gel column attached to an ISCO purification system. A gradient of 100% hexanes to 50% hexanes/50% EtOAc was run over 35 min whereupon fractions containing product were combined and concentrated under reduced pressure to afford the title compound.

Step 6. (1S,2R)-2-vinylcyclohexanamine trifluoroacetate

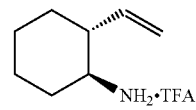

To a solution of tert-butyl ((1S,2R)-2-vinylcyclohexyl)carbamate (0.70 g, 3.1 mmol) in CH$_2$Cl$_2$ (14 mL) under N$_2$ at RT was added TFA (3.6 mL, 47 mmol) in one portion to afford a homogenous mixture. The mixture was stirred at RT for 3 h whereupon the mixture was concentrated under reduced pressure. The resultant residue was azeotroped with CH$_2$Cl$_2$ (3×3 mL) multiple times and was placed under high vacuum to afford the title compound. MS: m/z=126.2 (M+H)$^+$.

Step 7. benzyl ((1S,2R)-2-vinylcyclohexyl)carbamate

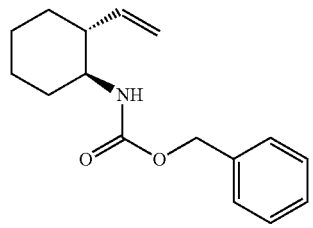 [SMILES: C=C[C@H]1CCCC[C@@H]1NC(=O)OCc1ccccc1]

To a mixture of (1S,2R)-2-vinylcyclohexanamine trifluoroacetate (0.73 g, 3.1 mmol) in CH$_2$Cl$_2$ (20 mL) under N$_2$ at 0° C. was added Et$_3$N (1.1 mL, 7.7 mmol) followed by benzyl chloroformate (0.53 mL, 3.7 mmol). The resulting mixture was allowed to warm to RT and was stirred for 3 h at RT. The mixture was quenched with sat. aq. NaHCO$_3$ (3 mL) and the mixture was transferred to a separatory funnel. The layers were separated and the aqueous layer was extracted with CH$_2$Cl$_2$ (3×15 mL) combining organic layers. The organic layer was washed with brine (1×10 mL), dried (Na$_2$SO$_4$), filtered, and concentrated under reduced pressure to afford the crude product. The crude material was taken up in CH$_2$Cl$_2$ (3 mL) and was loaded onto a 120 g silica gel column attached to an ISCO purification system. A gradient of 100% hexanes to 50% hexanes/50% EtOAc was run over 45 min whereupon fractions containing product were combined and concentrated under reduced pressure to afford the title compound. MS: m/z=260.2 (M+H)$^+$.

Step 8. (6R,9R)-tert-butyl 9-formyl-2-thia-1,7-diazabicyclo[4.3.1]decane-7-carboxylate 2,2-dioxide

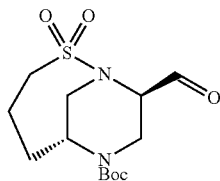 [SMILES: CC(C)(C)OC(=O)N1C[C@H](C=O)N2C[C@H]1CCCS2(=O)=O]

To a mixture of (6R,9R)-tert-butyl 9-(hydroxymethyl)-2-thia-1,7-diazabicyclo[4.3.1]decane-7-carboxylate 2,2-dioxide (2.2 g, 6.9 mmol) in CH$_2$Cl$_2$ (69 mL) under N$_2$ at 0° C. was added Dess-Martin Periodinane (3.5 g, 8.2 mmol) in one portion. The resulting heterogenous mixture was stirred for 2.5 h at 0° C. whereupon TLC analysis revealed consumption of starting material. Solid Ca(OH)$_2$ (~8 g) was added in a single portion and the mixture was stirred vigorously for 1 h at 0° C. The heterogenous reaction mixture was filtered thru a pad of CELITE® and the pad was washed with CH$_2$Cl$_2$ (3×30 mL). The resulting filtrate was concentrated under reduced pressure to afford the title compound. This material was taken on crude to to the next transformation directly.

Step 9. (6R,9S)-tert-butyl 9-vinyl-2-thia-1,7-diazabicyclo[4.3.1]decane-7-carboxylate 2,2-dioxide

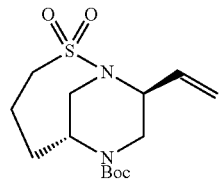 [SMILES: C=C[C@H]1CN(C(=O)OC(C)(C)C)[C@@H]2CCCS(=O)(=O)N1C2]

To a solution of methyltriphenylphosphonium bromide (3.9 g, 11 mmol) in THF (25 mL) at RT was added a 0.5 M solution of KHMDS in toluene (22 mL, 11 mmol) dropwise to afford a solution. The mixture was stirred for 1 h at RT and was cooled to −78° C. whereupon a solution of (6R,9R)-tert-butyl 9-formyl-2-thia-1,7-diazabicyclo[4.3.1]decane-7-carboxylate 2,2-dioxide (2.1 g, 6.9 mmol) from 0334436-0146-01 in THF (25 mL) was added dropwise over 20 min. The resulting orange solution was allowed to gradually warm to RT and stir for 12 h. The mixture was treated with sat. aq. Rochelle's salt (30 mL) was added followed by EtOAc (100 mL) and the mixture was transferred to a separatory funnel. The layers were separated and the aqueous layer was extracted with EtOAc (3×75 mL) and the organic layers were combined. The organic layer was washed with brine (1×25 mL), dried (MgSO$_4$), filtered, and concentrated under reduced pressure to afford the crude product. The crude material was taken up in CH$_2$Cl$_2$ (5 mL) and was loaded onto a 120 g silica gel column attached to an ISCO purification system. A gradient of 100% hexanes to 100% EtOAc was run over 45 min whereupon fractions containing product were combined and concentrated under reduced pressure to afford the title compound. MS: m/z=317.1 (M+H)$^+$.

Step 10. (6R,9S)-tert-butyl 9-((E)-2-((1R,2S)-2-(((benzyloxy)carbonyl)amino)cyclohexyl)vinyl)-2-thia-1,7-diazabicyclo[4.3.1]decane-7-carboxylate 2,2-dioxide

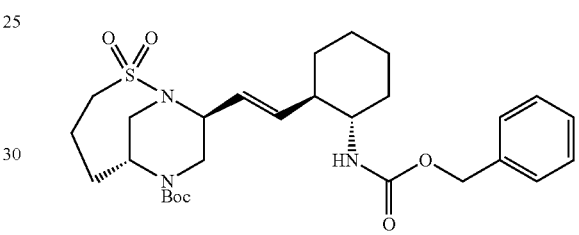

To a round bottom charged with a stir bar was added (6R,9S)-tert-butyl 9-vinyl-2-thia-1,7-diazabicyclo[4.3.1]decane-7-carboxylate 2,2-dioxide (0.77 g, 2.2 mmol) in CH$_2$Cl$_2$ (31 mL) at RT. Benzyl ((1S,2R)-2-vinylcyclohexyl)carbamate (0.41 g, 1.6 mmol) was added in one portion to afford a slightly heterogenous mixture which was subjected to N$_2$ bubbling via a needle for 20 min. Zhan 1a catalyst ([1,3-Bis(2,4,6-trimethylphenyl)-2-imidazolidinylidene]dichloro[[5-chloro-2-(1-methylethoxy-κO)phenyl]methylene-κC]-ruthenium[CAS 918870-68-5]) (208 mg, 0.31 mmol) was added to the mixture and the homogenous mixture was affixed with a reflux condenser and was heated to 50° C. The mixture was stirred vigorously for 12 h at 50° C. and the mixture was cooled to RT. The reaction mixture was filtered thru a pad of CELITE® which was generously washed with CH$_2$Cl$_2$ (3×7 mL). The resulting filtrate was concentrated under reduced pressure and placed under high vacuum. The crude material was dissolved in CH$_2$Cl$_2$ (3 mL) and was loaded onto an 80 g silica gel column attached to an ISCO purification system. A gradient of 100% hexanes to 80% EtOAc was run over 40 min whereupon fractions containing product were combined and concentrated under reduced pressure to afford the title compound. MS: m/z=548.4 (M+H)$^+$.

Step 11. (6R,9S)-tert-butyl 9-(2-((1R,2S)-2-aminocyclohexyl)ethyl)-2-thia-1,7-diazabicyclo[4.3.1]decane-7-carboxylate 2,2-dioxide To a mixture of (6R,9S)-tert-butyl 9-((E)-2-((1R,2S)-2-(((benzyloxy)carbonyl)amino)cyclohexyl)vinyl)-2-thia-1,7-diazabicyclo[4.3.1]decane-7-carboxylate 2,2-dioxide (0.40 g, 0.73 mmol) from in MeOH (8 mL) at RT was added 10%

Pd/C (78 mg) to afford a heterogenous mixture. The mixture was degassed under house vacuum and was filled with $N_2$ and this protocol was repeated four times total. The mixture was then degassed under house vacuum and was filled with $H_2$ and this protocol was repeated four times. The mixture was stirred under a balloon of $H_2$ for 3 h whereupon the mixture was purged to $N_2$. The resulting mixture was filtered thru a pad of Celite and the pad was washed generously with MeOH (3×5 mL) and the resulting filtrate was concentrated under reduced pressure and placed under high vacuum to afford the title compound. MS: m/z=317.1 (M+H)$^+$.

Intermediate H (6R,9S)-tert-Butyl 9-(2-((1R,2S)-2-aminocyclopentyl)ethyl)-2-thia-1,7-diazabicyclo[4.3.1]decane-7-carboxylate 2,2-dioxide

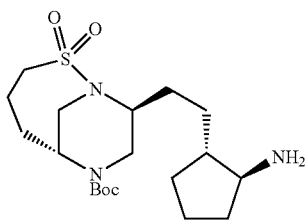 [SMILES: CC(C)(C)OC(=O)N1C[C@H](CC[C@H]2CCC[C@@H]2N)N2C[C@H]1CCCS2(=O)=O]

Intermediate H was prepared from (1S,2S)-2-aminocyclopentane carboxylic acid using the procedures described for Intermediate G. LCMS m/z=402.2 (M+H)$^+$.

Intermediate J (6S,10R)-tert-butyl 10-(hydroxymethyl)-2-thia-1,8-diazabicyclo[4.4.1]undecane-8-carboxylate 2,2-dioxide

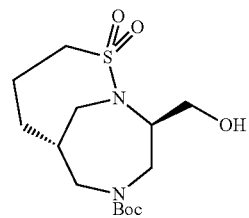 [SMILES: CC(C)(C)OC(=O)N1C[C@@H]2CCCS(=O)(=O)N(C2)[C@@H](CO)C1]

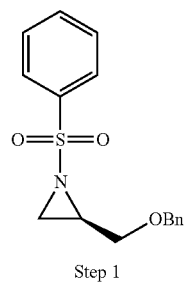

Step 1

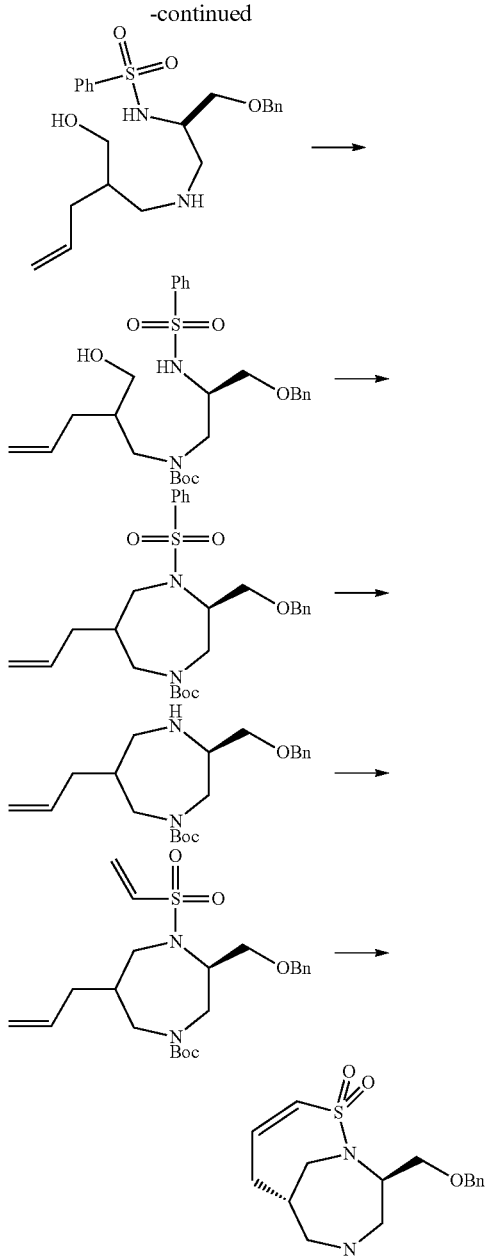

Step 7

Step 1: (R)-2-((Benzyloxy)methyl)-1-(phenylsulfonyl)aziridine

A solution of (R)-2-amino-3-(benzyloxy)propan-1-ol (3 g, 16.5 mmol), DIEA (7.23 mL, 41.4 mmol) and DMAP (0.20 g, 1.65 mmol) in DCM (220 mL) is cooled to −25° C. Then, benzenesulfonyl chloride (2.32 mL, 18.2 mmol) dissolved in DCM (10 mL) is added dropwise. The mixture is allowed to gradually warm up to 25° C. (this takes approx. 1-2 h). Then, further DIEA (7.23 mL, 41.4 mmol) is added followed by a solution of methanesulfonyl chloride (1.42 mL, 18.2 mmol) in dry DCM (10 mL) with stirring. The mixture was stirred for a further 4 h at 25° C. The mixture is then diluted with DCM and poured into sat. NaHCO$_3$. The organic phase is separated washed with brine, dried over MgSO$_4$ and the solvent removed in vacuo. The residue was purified on silica (25 g) eluting with EtOAc/DCM to give the title compound as a waxy white solid. LCMS m/z=304.1 (M+H)$^+$.

Step 2: N-((2R)-1-(Benzyloxy)-3-((2-(hydroxymethyl)pent-4-en-1-yl)amino)propan-2-yl)benzenesulfonamide (R)-2-((Benzyloxy)methyl)-1-(phenylsulfonyl)aziridine (650 mg, 2.143 mmol) and 2-(aminomethyl)pent-4-en-1-ol (370 mg, 3.2 mmol) were heated at 45° C. in tetrahydrofuran (11 mL) overnight. The reaction was quenched with brine and the mixture was extracted with ethyl acetate (3×). The combined organic fractions were dried (MgSO$_4$), filtered and the solvent was evaporated under reduced pressure. The crude material was dissolved in MeOH and loaded onto a 5 g Isolute Flash SCX-2 cartridge (preconditioned with MeOH). The cartridge was washed with 2 column volumes of MeOH, then the desired compound eluted with 2 column volumes of 2 M NH$_3$ in MeOH. The eluent was concentrated in vacuo to afford the title compound as a clear oil. LCMS m/z=419.4 (M+H)$^+$.

Step 3: tert-Butyl ((R)-3-(benzyloxy)-2-(phenylsulfonamido)propyl)(2-(hydroxymethyl)-pent-4-en-1-yl)carbamate Boc-anhydride (0.73 mL, 3.1 mmol) was added to a solution of N-((2R)-1-(benzyloxy)-3-((2-(hydroxymethyl)pent-4-en-1-yl)amino)propan-2-yl)benzenesulfonamide (819 mg, 1.96 mmol) and TEA (0.54 mL, 3.9 mmol) in acetonitrile (12 mL) at RT and the reaction was stirred for 2 hours. The reaction was quenched with water and the mixture was extracted with ethyl acetate (3×). The combined organic fractions were dried (MgSO$_4$), filtered and the solvent was evaporated under reduced pressure to afford the title compound. LCMS m/z=519.5 (M+H)$^+$.

Step 4: (3R)-tert-Butyl 6-allyl-3-((benzyloxy)methyl)-4-(phenylsulfonyl)-1,4-diazepane-1-carboxylate Tri-n-butylphosphine (0.73 mL, 2.95 mmol) was added to a solution of DIAD (0.57 mL, 2.95 mmol) and tert-butyl ((R)-3-(benzyloxy)-2-(phenylsulfonamido)propyl)(2-(hydroxymethyl)pent-4-en-1-yl)carbamate (1.02 g, 1.97 mmol) in THF (10 mL) at 0° C. and the reaction warmed immediately to RT and stirred for 20 min. The reaction was quenched with water and the mixture was extracted with ethyl acetate (3×). The combined organic fractions were dried (MgSO$_4$), filtered and the solvent was evaporated under reduced pressure. Purification on silica (80 g), eluting with a gradient of 0-100% EtOAc/hexanes over 15 column volumes, afforded the title compound as a colorless oil. LCMS m/z=501.4 (M+H)$^+$.

Step 5: (3R)-tert-Butyl 6-allyl-3-((benzyloxy)methyl)-1,4-diazepane-1-carboxylate (3R)-tert-Butyl 6-allyl-3-((benzyloxy)methyl)-4-(phenylsulfonyl)-1,4-diazepane-1-carboxylate (837 mg, 1.67 mmol) and magnesium (813 mg, 33.4 mmol) in MeOH (17 mL) were sonicated for 1 h at rt, after which time the magnesium was consumed. The solvent was removed in vacuo and the reaction was quenched with aqueous ammonium chloride (saturated) and the mixture was extracted with ethyl acetate (3×). The combined organic fractions were dried (MgSO$_4$), filtered and the solvent was evaporated under reduced pressure. Purification on silica (80 g), eluting with a gradient of 0-100% CHCl$_3$ to 70:20:10 CHCl$_3$/EtOAc/MeOH over 15 column volumes, afforded the title compound as a clear gum. LCMS m/z=361.3 (M+H)$^+$.

Step 6: (3R)-tert-Butyl 6-allyl-3-((benzyloxy)methyl)-4-(vinylsulfonyl)-1,4-diazepane-1-carboxylate (3R)-tert-Butyl 6-allyl-3-((benzyloxy)methyl)-1,4-diazepane-1-carboxylate (544 mg, 1.51 mmol) and TEA (1.05 mL, 7.55 mmol) in DCM were added dropwise to a solution of 2-chloroethanesulfonylchloride (0.32 mL, 3.02 mmol) in DCM, total DCM (15 mL) at 0° C. The reaction was warmed directly to RT and stirred for 30 min. The reaction was quenched with aqueous potassium phosphate monobasic (saturated) and the mixture was extracted with ethyl acetate (3×). The combined organic fractions were dried (MgSO$_4$), filtered and the solvent was evaporated under reduced pressure. Purification on silica (80 g), eluting with a gradient of 0-100% EtOAc/hexanes over 15 column volumes, afforded the title compound as a colorless oil. LCMS m/z=451.4 (M+H)$^+$.

Step 7: (6S,10R)-tert-Butyl 10-((benzyloxy)methyl)-2-thia-1,8-diazabicyclo[4.4.1]undec-3-ene-8-carboxylate 2,2-dioxide A solution of (3R)-tert-butyl 6-allyl-3-((benzyloxy)methyl)-4-(vinylsulfonyl)-1,4-diazepane-1-carboxylate (294 mg, 0.65 mmol) in DCE (6 mL) was degassed with nitrogen. 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (96 mg, 0.130 mmol) was added and the reaction heated at 50° C. for 2 h. The reaction was filtered through a plug of florisil, eluting with EtOAc, and the solvent was removed in vacuo. Purification on silica (24 g), eluting with a gradient of 0-100% EtOAc/hexanes over 15 column volumes, afforded the title compound as a foam. A single stereoisomer was isolated from this reaction. LCMS m/z=423.4 (M+H)$^+$.

Step 8: (6S,10R)-tert-Butyl 10-(hydroxymethyl)-2-thia-1,8-diazabicyclo[4.4.1]undecane-8-carboxylate 2,2-dioxide A solution of (6S,10R)-tert-butyl 10-((benzyloxy)methyl)-2-thia-1,8-diazabicyclo[4.4.1]undec-3-ene-8-carboxylate 2,2-dioxide (141 mg, 0.33 mmol) and Pearlman's catalyst (46.9 mg, 0.067 mmol) were stirred overnight under a balloon of hydrogen. The reaction was purged with nitrogen then filtered through a pad of celite and concentrated in vacuo. Purification on silica (12 g), eluting with a gradient of 0-100% EtOAc/hexanes over 15 column volumes, afforded the title compound as a white foam. LCMS m/z=335.3 (M+H)$^+$.

Intermediate K (5R,8R)-tert-Butyl 8-(hydroxymethyl)-2-thia-1,6-diazabicyclo[3.3.1]nonane-6-carboxylate 2,2-dioxide

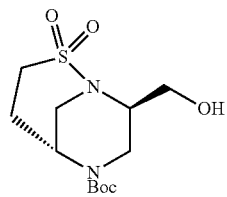 [SMILES: CC(C)(C)OC(=O)N1C[C@H](CO)N2C[C@H]1CCS2(=O)=O]

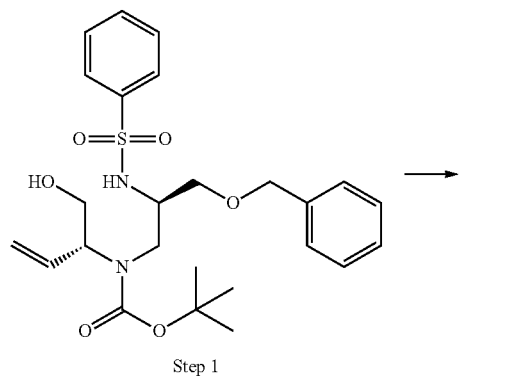

Step 1

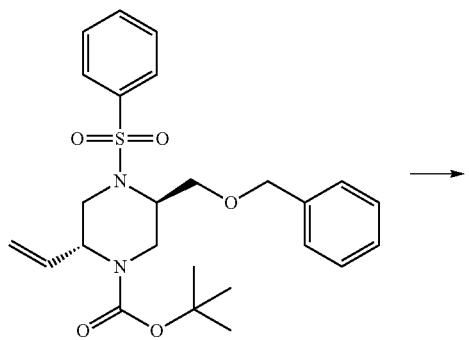

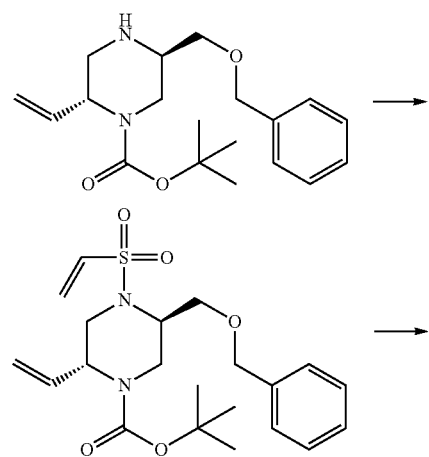

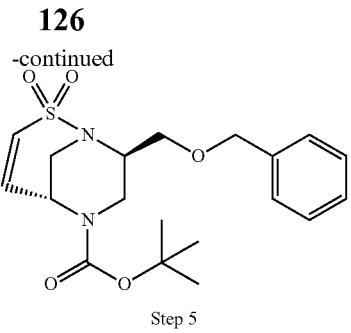

Step 5

Step 1: tert-Butyl ((R)-3-(benzyloxy)-2-(phenylsulfonamido)propyl)((R)-1-hydroxybut-3-en-2-yl)carbamate To a solution of (R)-2-((benzyloxy)methyl)-1-(phenylsulfonyl)aziridine (Intermediate J, step 1) (2.2 g, 7.25 mmol) in dry DCE (30 mL) is added (R)-2-aminobut-3-en-1-ol (948 mg, 10.9 mmol) and the mixture is heated at 50° C. overnight. The solvent was removed in vacuo and the residue redissolved in acetonitrile (30 mL). DIEA (5.07 mL, 29.0 mmol) is added followed by Boc-anhydride (5.05 mL, 21.7 mmol) with stirring at 25° C. After approx. 5 h the mixture is diluted with DCM, silica gel is added and the volatiles were removed in vacuo. The residue was purified on silica (20 g) eluting with EtOAc/DCM to afford the title compound as a viscous gum. LCMS m/z=491.2 (M+H)$^+$.

Step 2: (2R,5R)-tert-Butyl 5-((benzyloxy)methyl)-4-(phenylsulfonyl)-2-vinylpiperazine-1-carboxylate A solution of tert-butyl ((R)-3-(benzyloxy)-2-(phenylsulfonamido)propyl)((R)-1-hydroxybut-3-en-2-yl)carbamate (3.0 g, 6.11 mmol) and DIAD (2.38 mL, 12.2 mmol) in dry THF (60 mL) is set under N$_2$. Then, a solution of triphenylphosphine (3.2 g, 12.2 mmol) in dry THF (5 mL) is added dropwise with stirring at RT. After 50 min stirring at RT the mixture is diluted with DCM, then silica gel is added and the volatiles removed in vacuo. The residual yellow powder is purified on silica (20 g) eluting with EtOAc/DCM to afford the title compound as a viscous gum. LCMS m/z=473.2 (M+H)$^+$.

Step 3: (2R,5R)-tert-Butyl 5-((benzyloxy)methyl)-2-vinylpiperazine-1-carboxylate A mixture of (2R,5R)-tert-butyl 5-((benzyloxy)methyl)-4-(phenylsulfonyl)-2-vinylpiperazine-1-carboxylate (1.5 g, 3.17 mmol) and magnesium turnings (1.5 g, 63.5 mmol) in dry methanol (45 mL) is sonicated at RT for 1 h. The solvent was removed in vacuo and the reaction was quenched with aqueous ammonium chloride (saturated) and the mixture was extracted with ethyl acetate (3×). The combined organic fractions were dried (MgSO$_4$), filtered and the solvent was evaporated under reduced pressure. Purification on silica (10 g) eluting with 0-100% EtOAc/DCM afforded the title compound as a viscous gum. LCMS m/z=333.1 (M+H)$^+$.

Step 4: (2R,5R)-tert-Butyl 5-((benzyloxy)methyl)-2-vinyl-4-(vinylsulfonyl)piperazine-1-carboxylate A solution of 2-chloroethanesulfonyl chloride (834 mg, 5.11 mmol) in dry DCE (12 mL) was cooled to 0° C. A solution of (2R,5R)-tert-butyl 5-((benzyloxy)methyl)-2-vinylpiperazine-1-carboxylate (680 mg, 2.04 mmol) and DIEA (1.07 mL, 6.14 mmol) in DCE (12 mL) was added dropwise. The reaction was warmed directly to RT and stirred for an additional 30 min. The reaction was quenched with aqueous potassium phosphate monobasic (saturated) and the mixture was extracted with ethyl acetate (3×). The combined organic fractions were dried (MgSO$_4$), filtered and the solvent was evaporated under reduced pressure. Purification on silica (10 g) eluting with DCM/EtOAc=50/1 afforded the title compound as a viscous gum. LCMS m/z=423.2 (M+H)$^+$.

Step 5: (5R,8R)-tert-Butyl 8-((benzyloxy)methyl)-2-thia-1,6-diazabicyclo[3.3.1]non-3-ene-6-carboxylate 2,2-dioxide A solution of (2R,5R)-tert-butyl 5-((benzyloxy)methyl)-2-vinyl-4-(vinylsulfonyl)piperazine-1-carboxylate (480 mg, 1.13 mmol) in DCE (150 mL) was sonicated in an ultrasonic bath to degas the solution. Then, the mixture was set under an atmosphere of N$_2$ (2 cycles). Zhan-1b catalyst (41.7 mg, 0.057 mmol) was added and the mixture was set under an atmosphere of N$_2$ (3 cycles). The mixture was placed in an oil bath and heated at 50° C. for 3 h during which the colour of the reaction changed from green to a pale reddish-brown. The reaction was quenched by adding silica gel, then the volatiles removed in vacuo and the residual coloured powder is purified on a on silica (25 g) 0-100% eluting with hexane/EtOAc (3/1) to afford the title compound as a colorless gum which was taken directly to the next step.

Step 6: (5R,8R)-tert-Butyl 8-(hydroxymethyl)-2-thia-1,6-diazabicyclo[3.3.1]nonane-6-carboxylate A solution of (5R,8R)-tert-butyl 8-((benzyloxy)methyl)-2-thia-1,6-diazabicyclo[3.3.1]non-3-ene-6-carboxylate 2,2-dioxide (430 mg, 1.09 mmol) in ethyl acetate (40 mL) was evacuated and backfilled with nitrogen. Pearlman's catalyst (153 mg of 20% Pd(OH)$_2$/C) was added and the reaction vessel was evacuated and backfilled with hydrogen, then stirred under a balloon of hydrogen at RT overnight. The mixture was purged with nitrogen, then diluted with ethyl acetate and filtered through a pad of Celite. The filtrate was concentrated in vacuo and the residual material was purified on silica (5 g) 0-100% EtOAc/DCM to afford the title compound as a white solid. LCMS m/z=307.1 (M+H)$^+$.

Intermediate L (6R,9R)-tert-Butyl 9-(hydroxymethyl)-2-thia-1,7-diazabicyclo[4.3.2]undecane-7-carboxylate 2,2-dioxide

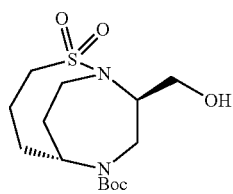 [SMILES: CC(C)(C)OC(=O)N1C[C@H](CO)N2CC[C@H]1CCCS2(=O)=O]

Step 1: N—((R)-1-(benzyloxy)-3-(((R)-1-hydroxy-hex-5-en-3-yl)amino)propan-2-yl)benzenesulfonamide

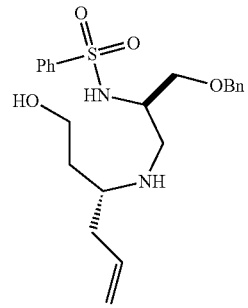 [SMILES: C=CC[C@H](CCO)NC[C@H](COCc1ccccc1)NS(=O)(=O)c1ccccc1]

The title compound was prepared from (R)-2-((benzyloxy)methyl)-1-(phenylsulfonyl)aziridine (Intermediate J, step 1) and (R)-3-aminohex-5-en-1-ol using the procedure described for Intermediate J, step 1. LCMS m/z=419.4 (M+H)$^+$.

Step 2

(6R,9R)-tert-Butyl 9-(hydroxymethyl)-2-thia-1,7-diazabicyclo[4.3.2]undecane-7-carboxylate 2,2-dioxide: The title compound was prepared from N—((R)-1-(benzyloxy)-3-(((R)-1-hydroxyhex-5-en-3-yl)amino)propan-2-yl)benzenesulfonamide using the procedures described for Intermediate J, steps 2-8.

Intermediate M (7R,10R)-tert-Butyl 10-(hydroxymethyl)-2-thia-1,8-diazabicyclo[5.3.1]undecane-8-carboxylate 2,2-dioxide

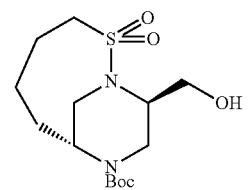 [SMILES: CC(C)(C)OC(=O)N1C[C@H](CO)N2C[C@H]1CCCCS2(=O)=O]

Step 1: (2R,5R)-2-allyl-4-(allylsulfonyl)-1-benzyl-5-((benzyloxy)methyl)piperazine

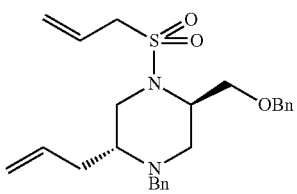 [SMILES: C=CC[C@@H]1CN(S(=O)(=O)CC=C)[C@@H](COCc2ccccc2)CN1Cc1ccccc1]

The title compound was prepared from (2R,5R)-2-allyl-1-benzyl-5-((benzyloxy)methyl)piperazine (Intermediate A, step 4) and prop-2-ene-1-sulfonyl chloride using the procedure described for Intermediate K, step 4. LCMS m/z=441.4 (M+H)⁺.

Step 2

(7R,10R)-tert-Butyl 10-(hydroxymethyl)-2-thia-1,8-diazabicyclo[5.3.1]undecane-8-carboxylate 2,2-dioxide: The title compound was prepared from (2R,5R)-2-allyl-4-(allylsulfonyl)-1-benzyl5-((benzyloxy)methyl)piperazine using the procedures described for Intermediate K, steps 5 and 6. LCMS m/z=335.2 (M+H)⁺.

Example 1

(βS)—N-{2-[2-(2,2-Dioxido-2-thia-1,7-diazabicyclo[4.3.1]dec-9-yl)ethyl]-3-fluorophenyl}-3,5-difluoro-β-(4-fluorophenyl)-L-phenylalaninamide

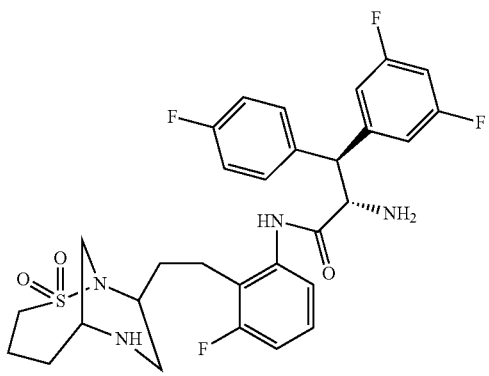 [SMILES: N[C@H](C(=O)Nc1cccc(F)c1CCC1CNC2CCCS(=O)(=O)N1C2)[C@@H](c1ccc(F)cc1)c1cc(F)cc(F)c1]

Step 1: (1S,6R,9S)-tert-butyl 9-(2-((2S,3S)-2-azido-3-(3,5-difluorophenyl)-3-(4-fluorophenyl)propanamido)-6-fluorophenethyl)-2-thia-1,7-diazabicyclo[4.3.1]decane-7-carboxylate 2,2-dioxide

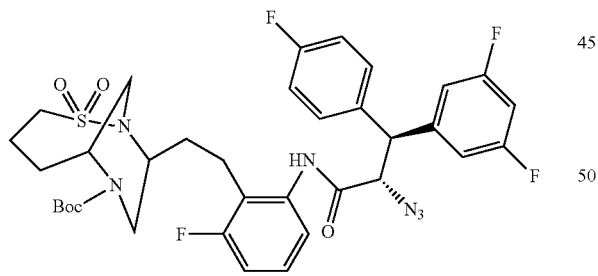

To a solution of (6R,9S)-tert-butyl 9-(2-amino-6-fluorophenethyl)-2-thia-1,7-diazabicyclo[4.3.1]decane-7-carboxylate 2,2-dioxide (Intermediate B) (85 mg, 0.2 mmol) and (2S,3S)-2-azido-3-(3,5-difluorophenyl)-3-(4-fluorophenyl)propanoic acid (Intermediate 2) (77 mg, 0.24 mmol) in DMF (0.2 mL) at RT was added HATU (113 mg, 0.3 mmol) and 2,6-lutidine (46 μL, 0.4 mmol). The mixture was stirred at RT for 16 h, then diluted with EtOAc and washed with 10% citric acid, water, saturated aqueous NaHCO₃ and brine. The organic layer was dried over MgSO₄, filtered, concentrated and purified by silica gel chromatography (gradient elution 0-50% EtOAc in hexanes) to afford the title compound. MS (ESI) m/z (M+H)⁺: 731.5.

Step 2: (1S,6R,9S)-tert-butyl 9-(2-((2S,3S)-2-amino-3-(3,5-difluorophenyl)-3-(4-fluorophenyl)propanamido)-6-fluorophenethyl)-2-thia-1,7-diazabicyclo[4.3.1]decane-7-carboxylate 2,2-dioxide

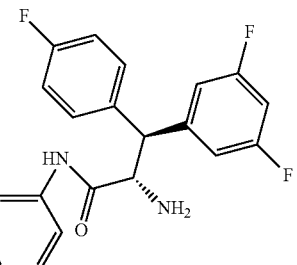

To a solution of (1S,6R,9S)-tert-butyl 9-(2-((2S,3S)-2-azido-3-(3,5-difluorophenyl)-3-(4-fluorophenyl)propanamido)-6-fluorophenethyl)-2-thia-1,7-diazabicyclo[4.3.1]decane-7-carboxylate 2,2-dioxide (67 mg, 0.09 mmol) in EtOH (1 mL) was added 10% Pd/C (10 mg) and the mixture was stirred at RT under H₂ (1 atm) for 16 h. The mixture was filtered, concentrated and purified by silica gel chromatography (gradient elution 0-80% EtOAc in hexanes) to afford the title compound. MS (ESI) m/z (M+H)⁺: 705.4.

Step 3: ((3S)—N-{2-[2-(2,2-Dioxido-2-thia-1,7-diazabicyclo[4.3.1]dec-9-yl)ethyl]-3-fluorophenyl}-3,5-difluoro-β-(4-fluorophenyl)-L-phenylalaninamide To a solution of (1S,6R,9S)-tert-butyl 9-(2-((2S,3S)-2-amino-3-(3,5-difluorophenyl)-3-(4-fluorophenyl)propanamido)-6-fluorophenethyl)-2-thia-1,7-diazabicyclo[4.3.1]decane-7-carboxylate 2,2-dioxide (17 mg, 0.02 mmol) in dioxane (0.5 mL) was added 4 M HCl in dioxane (0.5 mL). The mixture was stirred at RT for 60 min. The solvents were removed in vacuo to give the title compound. HRMS (ESI) m/z (M+H)⁺: 605.2194, calcd. for $C_{30}H_{34}F_4N_4O_3S$=605.2204.

Example 2

(βS)—N-{2-[2-(2,2-Dioxido-2-thia-1,7-diazabicyclo[4.3.1]dec-9-yl)ethyl]-3-fluorophenyl}-β-(4-fluorophenyl)-3-(trifluoromethyl)-L-phenylalaninamide

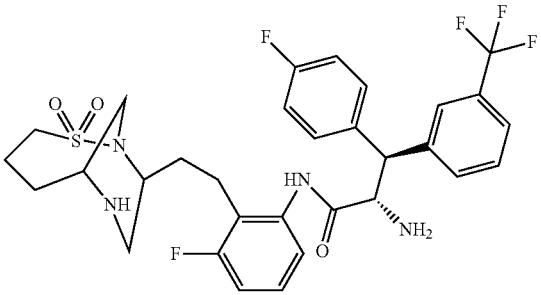 [SMILES: N[C@H](C(=O)Nc1cccc(F)c1CCC1CNC2CCCS(=O)(=O)N1C2)[C@@H](c1ccc(F)cc1)c1cccc(C(F)(F)F)c1]

The title compound was prepared from Intermediate B and Intermediate 16 using the procedure described for Example 1. HRMS (ESI) m/z (M+H)⁺: 637.2257, calcd. for $C_{31}H_{35}F_5N_4O_3S$=637.2266.

Example 3

Methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-3-methylbutyl]carbamate

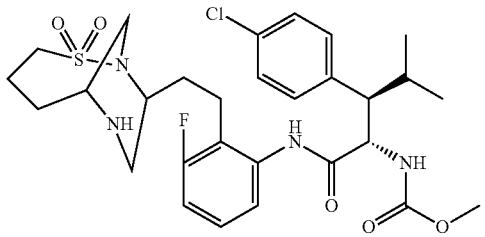 [SMILES: COC(=O)N[C@H](C(=O)Nc1cccc(F)c1CCC1CNC2CCCS(=O)(=O)N1C2)[C@@H](c1ccc(Cl)cc1)C(C)C]

Step 1: (1S,6R,9S)-tert-butyl 9-(2-((2S,3R)-2-azido-3-(4-chlorophenyl)-4-methylpentanamido)-6-fluorophenethyl)-2-thia-1,7-diazabicyclo[4.3.1]decane-7-carboxylate 2,2-dioxide

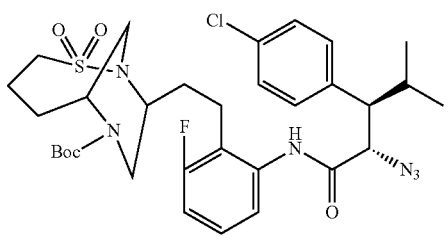 [SMILES: CC(C)[C@H](c1ccc(Cl)cc1)[C@H](N=[N+]=[N-])C(=O)Nc1cccc(F)c1CCC1CN(C(=O)OC(C)(C)C)C2CCCS(=O)(=O)N1C2]

To a solution of (6R,9S)-tert-butyl 9-(2-amino-6-fluorophenethyl)-2-thia-1,7-diazabicyclo[4.3.1]decane-7-carboxylate 2,2-dioxide (Intermediate B) (110 mg, 0.26 mmol) and (2S,3R)-2-azido-3-(4-chlorophenyl)-4-methylpentanoic acid (Intermediate 4) (103 mg, 0.38 mmol) in DMF (0.2 mL) at RT was added HATU (196 mg, 0.51 mmol) and 2,6-lutidine (90 µL, 0.77 mmol). The mixture was stirred at RT for 16 h, then diluted with EtOAc and washed with 10% citric acid, water, saturated aqueous NaHCO$_3$ and brine. The organic layer was dried over Na$_2$SO$_4$, filtered, concentrated and purified by silica gel chromatography (gradient elution 0-80% EtOAc in hexanes) to afford the title compound. MS (ESI) m/z (M+H)$^+$: 677.4.

Step 2: (1S,6R,9S)-tert-butyl 9-(2-((2S,3R)-2-amino-3-(4-chlorophenyl)-4-methylpentanamido)-6-fluorophenethyl)-2-thia-1,7-diazabicyclo[4.3.1]decane-7-carboxylate 2,2-dioxide

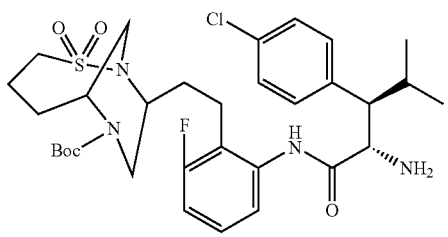 [SMILES: CC(C)[C@H](c1ccc(Cl)cc1)[C@H](N)C(=O)Nc1cccc(F)c1CCC1CN(C(=O)OC(C)(C)C)C2CCCS(=O)(=O)N1C2]

To a solution of (1S,6R,9S)-tert-butyl 9-(2-((2S,3R)-2-azido-3-(4-chlorophenyl)-4-methylpentanamido)-6-fluorophenethyl)-2-thia-1,7-diazabicyclo[4.3.1]decane-7-carboxylate 2,2-dioxide (158 mg, 0.23 mmol) in THF (2 mL) and water (0.4 mL) was added triphenylphosphine (61 mg, 0.23 mmol) and the mixture was heated to reflux and stirred for 16 h. The mixture was cooled, concentrated and purified by silica gel chromatography (gradient elution 0-50% EtOAc in hexanes) to afford the title compound. MS (ESI) m/z (M+H)$^+$: 651.4.

Step 3: (1S,6R,9S)-tert-butyl 9-(2-((2S,3R)-3-(4-chlorophenyl)-2-((methoxycarbonyl)amino)-4-methylpentanamido)-6-fluorophenethyl)-2-thia-1,7-diazabicyclo[4.3.1]decane-7-carboxylate 2,2-dioxide

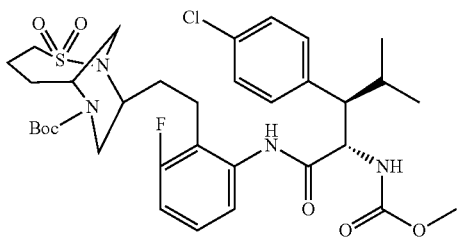 [SMILES: COC(=O)N[C@H](C(=O)Nc1cccc(F)c1CCC1CN(C(=O)OC(C)(C)C)C2CCCS(=O)(=O)N1C2)[C@@H](c1ccc(Cl)cc1)C(C)C]

To a solution of (1S,6R,9S)-tert-butyl 9-(2-((2S,3R)-2-amino-3-(4-chlorophenyl)-4-methylpentanamido)-6-fluorophenethyl)-2-thia-1,7-diazabicyclo[4.3.1]decane-7-carboxylate 2,2-dioxide (100 mg, 0.15 mmol) in CH$_2$Cl$_2$ (1 mL) was added 2,5-dioxopyrrolidin-1-yl methyl carbonate (32 mg, 0.18 mmol) and the mixture was stirred at RT for 16 h. The mixture was diluted with CH$_2$Cl$_2$ and washed with water and brine. The organic layer was dried over Na$_2$SO$_4$, filtered, concentrated and purified by silica gel chromatography (gradient elution 0-80% EtOAc in hexanes) to afford the title compound. MS (ESI) m/z (M+H)$^+$: 709.4.

Step 4: Methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-3-methylbutyl]carbamate (1S,6R,9S)-tert-Butyl 9-(2-((2S,3R)-3-(4-chlorophenyl)-2-((methoxycarbonyl)amino)-4-methylpentanamido)-6-fluorophenethyl)-2-thia-1,7-diazabicyclo[4.3.1]decane-7-carboxylate 2,2-dioxide (73 mg, 0.10 mmol) in dioxane (0.5 mL) was stirred in 4 M HCl in dioxane (0.3 mL) for 1 h at RT for 60 min. The solvents were removed in vacuo and the resulting material was concentrated twice from methanol to give the title compound. LCMS m/z=609.3 (M+H)$^+$.

Example 4

Methyl [(1S,2R)-2-(4-chlorophenyl)-2-(3,3-difluorocyclobutyl)-1-({2-[2-(2,2-dioxido-2-thia-1,7-diazabicyclo[4.3.1]dec-9-yl)ethyl]-3-fluorophenyl}carbamoyl)ethyl]carbamate

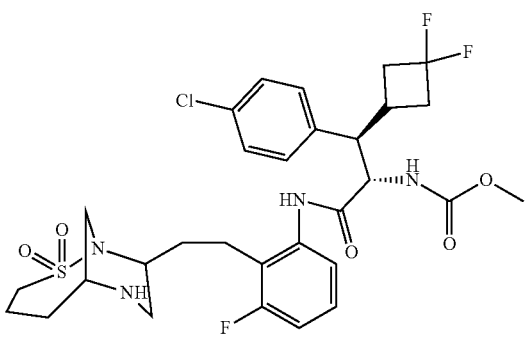 [SMILES: COC(=O)N[C@H](C(=O)Nc1cccc(F)c1CCC1CNC2CCCS(=O)(=O)N1C2)[C@@H](c1ccc(Cl)cc1)C1CC(F)(F)C1]

The title compound was prepared from Intermediate B and Intermediate 18 using the procedure described for Example 3. HRMS (ESI) m/z (M+H)$^+$: 657.2100, calcd. for $C_{30}H_{38}ClF_3N_4O_5S$=657.2120.

Example 5

Methyl [(1S,2R)-2-(4-chlorophenyl)-2-(4,4-difluorocyclohexyl)-1-({2-[2-(2,2-dioxido-2-thia-1,7-diazabicyclo[4.3.1]dec-9-yl)ethyl]-3-fluorophenyl}carbamoyl)ethyl]carbamate

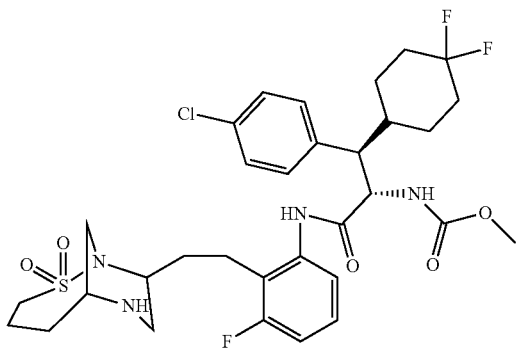 [SMILES: COC(=O)N[C@H](C(=O)Nc1cccc(F)c1CCC1CNC2CCCS(=O)(=O)N1C2)[C@@H](c1ccc(Cl)cc1)C1CCC(F)(F)CC1]

The title compound was prepared from Intermediate B and Intermediate 19 using the procedure described for Example 3. HRMS (ESI) m/z (M+H)$^+$: 685.2428, calcd. for $C_{32}H_{42}ClF_3N_4O_5S$=685.2433.

Example 6

(2S,3R)-2-amino-3-(4-chlorophenyl)-N-(2-(2-((6R,9S)-2,2-dioxido-2-thia-1,7-diazabicyclo[4.3.1]decan-9-yl)ethyl)-3-fluorophenyl)-3-((1r,4R)-4-ethoxycyclohexyl)propanamide

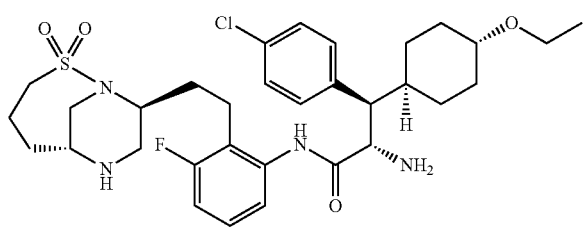 [SMILES: CCO[C@H]1CC[C@H]([C@H](c2ccc(Cl)cc2)[C@H](N)C(=O)Nc2cccc(F)c2CC[C@H]2CN[C@@H]3CCCS(=O)(=O)N2C3)CC1]

Step 1: (6R,9S)-tert-butyl 9-(2-((2S,3R)-2-azido-3-(4-chlorophenyl)-3-((1r,4R)-4-ethoxycyclohexyl)propanamido)-6-fluorophenethyl)-2-thia-1,7-diazabicyclo[4.3.1]decane-7-carboxylate 2,2-dioxide

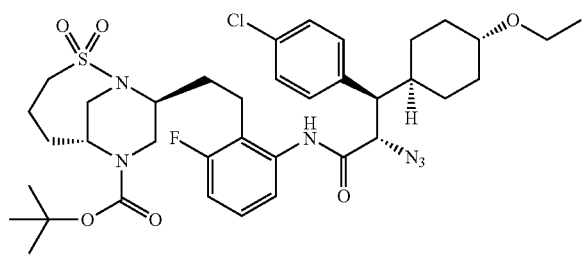 [SMILES: CCO[C@H]1CC[C@H]([C@H](c2ccc(Cl)cc2)[C@H](N=[N+]=[N-])C(=O)Nc2cccc(F)c2CC[C@H]2CN(C(=O)OC(C)(C)C)[C@@H]3CCCS(=O)(=O)N2C3)CC1]

To a solution of (6R,9S)-tert-butyl 9-(2-amino-6-fluorophenethyl)-2-thia-1,7-diazabicyclo[4.3.1]decane-7-carboxylate 2,2-dioxide (Intermediate B) (0.905 g, 2.57 mmol) and (2S,3R)-2-azido-3-(4-chlorophenyl)-3-((1r,4R)-4-ethoxycyclohexyl)propanoic acid (Intermediate 35) (1.1 g, 2.57 mmol) in pyridine (8 mL) at −15° C. was added POCl$_3$ (0.620 mL, 6.65 mmol) dropwise over 5 min. The mixture was stirred at −15° C. for 30 min, then quenched with saturated aqueous KH$_2$PO$_4$. The mixture was extracted with ethyl acetate (3×10 mL). The combined EtOAc extracts were dried over Na$_2$SO$_4$, filtered, and the solvent was evaporated under reduced pressure. The residue was purified by column chromatography on silica gel eluted with 33% EtOAc in petroleum ether to give the title compound. MS (ESI) m/z (M+H)$^+$: 761.2.

Step 2: (6R,9S)-tert-butyl 9-(2-((2S,3R)-2-amino-3-(4-chlorophenyl)-3-((1r,4R)-4-ethoxycyclohexyl)propanamido)-6-fluorophenethyl)-2-thia-1,7-diazabicyclo[4.3.1]decane-7-carboxylate 2,2-dioxide

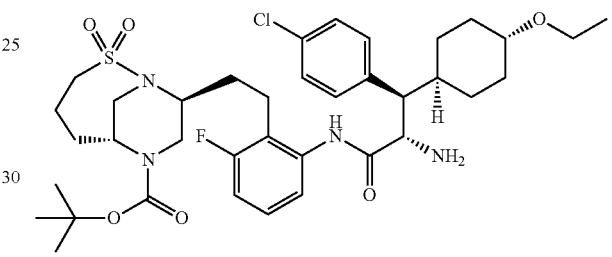

A solution of (6R,9S)-tert-butyl 9-(2-((2S,3R)-2-azido-3-(4-chlorophenyl)-3-((1r,4R)-4-ethoxycyclohexyl)propanamido)-6-fluorophenethyl)-2-thia-1,7-diazabicyclo[4.3.1]decane-7-carboxylate 2,2-dioxide (1.2 g, 1.57 mmol) in THF (5 mL) and water (1 mL), trimethylphosphine (0.180 g, 2.36 mmol) was stirred at RT for 30 min. The solvents were removed in vacuo to give the title compound. MS (ESI) m/z (M+H)$^+$: 735.2.

Step 3: (2S,3R)-2-amino-3-(4-chlorophenyl)-N-(2-(2-((6R,9S)-2,2-dioxido-2-thia-1,7-diazabicyclo[4.3.1]decan-9-yl)ethyl)-3-fluorophenyl)-3-((1r,4R)-4-ethoxy-cyclohexyl)propanamide To a solution of (6R,9S)-tert-butyl 9-(2-((2S,3R)-2-amino-3-(4-chloro-phenyl)-3-((1r,4R)-4-ethoxycyclohexyl)propanamido)-6-fluorophenethyl)-2-thia-1,7-diazabicyclo[4.3.1]decane-7-carboxylate 2,2-dioxide (1.0 g, 1.36 mmol) in DCM (5 mL) was added TFA (0.16 mL, 2.0 mmol). The mixture was stirred at RT for 30 min. The solvents were removed in vacuo and the residue was purified by peparative reverse phase HPLC and the free base was converted to the mono-HCl salt of the title compound. $^1$H NMR (Methanol-d4, 400 MHz) δ 7.43-7.29 (m, 4H), 7.16-7.06 (m, 1H), 6.97 (t, J=8.8 Hz, 1H), 6.46 (d, J=7.8 Hz, 1H), 4.43 (d, J=9.4 Hz, 1H), 4.11 (br. s., 1H), 3.90 (d, J=16.0 Hz, 1H), 3.71 (d, J=9.0 Hz, 1H), 3.65-3.48 (m, 6H), 3.17-3.07 (m, 2H), 3.01 (d, J=13.7 Hz, 1H), 2.62 (d, J=9.4 Hz, 1H), 2.56-2.39 (m, 2H), 2.23-2.04 (m, 5H), 2.00-1.74 (m, 5H), 1.36-1.27 (m, 3H), 1.17 (t, J=6.8 Hz, 3H), 0.91 (d, J=11.3 Hz, 1H) ppm. MS (ESI) m/z (M+H)$^+$: 635.3.

Example 7

(βR)-4-Chloro-N-(2-{2-[(6R,9S)-2,2-dioxido-2-thia-1,7-diazabicyclo[4.3.1]dec-9-yl]ethyl}-3-fluorophenyl)-β-[(1r,4R)-4-methoxycyclohexyl]-L-phenylalaninamide

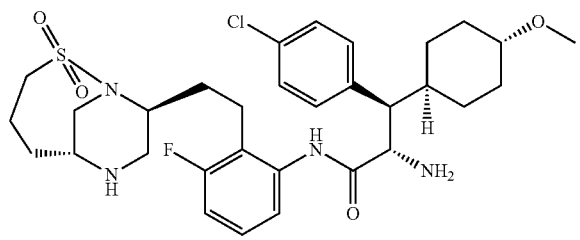 [SMILES: CO[C@H]1CC[C@H]([C@H](c2ccc(Cl)cc2)[C@H](N)C(=O)Nc2cccc(F)c2CC[C@H]2CN[C@@H]3CCCS(=O)(=O)N2C3)CC1]

The title compound was prepared from Intermediate B and Intermediate 9 using the procedure described for Example 6. LCMS m/z=621.3 (M+H)+.

Example 8

Methyl ((1R,2S)-1-(4-chlorophenyl)-3-((2-(2-((6R,9S)-2,2-dioxido-2-thia-1,7-diazabicyclo[4.3.1]decan-9-yl)ethyl)-3-fluorophenyl)amino)-3-oxo-1-((2R,4S)-2-(2,2,2-trifluoroethyl)tetrahydro-2H-pyran-4-yl)propan-2-yl)carbamate

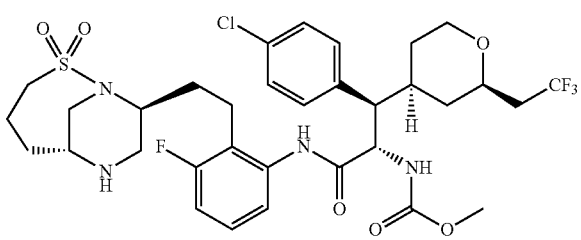 [SMILES: COC(=O)N[C@H](C(=O)Nc1cccc(F)c1CC[C@H]1CN[C@@H]2CCCS(=O)(=O)N1C2)[C@@H](c1ccc(Cl)cc1)[C@H]1CCO[C@@H](CC(F)(F)F)C1]

Step 1. (6R,9S)-tert-butyl 9-(2-((2S,3R)-2-azido-3-(4-chlorophenyl)-3-((2R,4S)-2-(2,2,2-trifluoroethyl)tetrahydro-2H-pyran-4-yl)propanamido)-6-fluorophenethyl)-2-thia-1,7-diazabicyclo[4.3.1]decane-7-carboxylate 2,2-dioxide

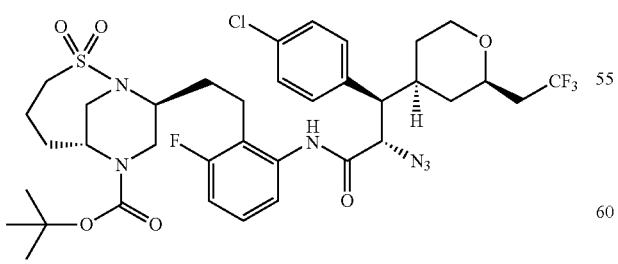

(2S,3R)-2-Azido-3-(4-chlorophenyl)-3-((2R,4S)-2-(2,2,2-trifluoroethyl)tetrahydro-2H-pyran-4-yl)propanoic acid (Intermediate 23) (101 mg, 0.26 mmol), (1S,6R,9S)-tert-butyl 9-(2-amino-6-fluorophenethyl)-2-thia-1,7-diazabicyclo[4.3.1]decane-7-carboxylate 2,2-dioxide (Intermediate B) (100 mg, 0.23 mmol), HATU (133 mg, 0.35 mmol), and 2,6-lutidine (0.041 mL, 0.35 mmol) were combined in 1 mL of DMF. The mixture was stirred at RT for 24 h. The mixture was diluted with EtOAc and the solution was washed with aqueous NaHCO3, water, 1 M citric acid solution, and brine, then dried over MgSO4, filtered, and the solvents were removed in vacuo. The crude product was chromatographed on a 12 g SiO2 column using 0-80% EtOAc:hexane over 15 min at 30 mL/min to give the title compound as a foam. LCMS m/z (M+H)+=801.6.

Step 2. (6R,9S)-tert-butyl 9-(2-((2S,3R)-2-amino-3-(4-chlorophenyl)-3-((2R,4S)-2-(2,2,2-trifluoroethyl)tetrahydro-2H-pyran-4-yl)propanamido)-6-fluorophenethyl)-2-thia-1,7-diazabicyclo[4.3.1]decane-7-carboxylate 2,2-dioxide

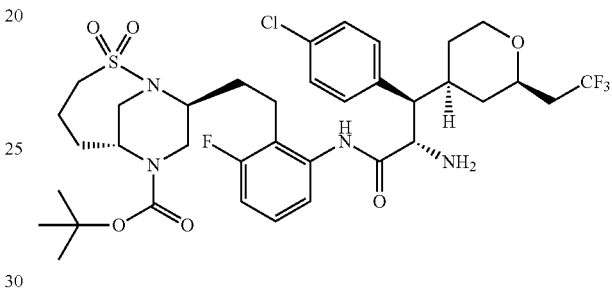

(6R,9S)-tert-butyl 9-(2-((2S,3R)-2-azido-3-(4-chlorophenyl)-3-((2R,4S)-2-(2,2,2-trifluoroethyl)tetrahydro-2H-pyran-4-yl)propanamido)-6-fluorophenethyl)-2-thia-1,7-diazabicyclo[4.3.1]decane-7-carboxylate 2,2-dioxide (102 mg, 0.13 mmol) was dissolved in 2 mL THF and 0.4 mL water. A solution of Me3P (0.13 mL of a 1.0 M solution in THF, 0.13 mmol) was added and the mixture was stirred at RT for 30 min. The mixture was diluted with EtOAc, washed with aqueous NaHCO3 and brine, dried over MgSO4, filtered, and the solvents were removed in vacuo to give the title compound as a foam. LCMS m/z (M+H)+=775.6.

Step 3. (6R,9S)-tert-butyl 9-(2-((2S,3R)-3-(4-chlorophenyl)-2-((methoxycarbonyl)amino)-3-((2R,4S)-2-(2,2,2-trifluoroethyl)tetrahydro-2H-pyran-4-yl)propanamido)-6-fluorophenethyl)-2-thia-1,7-diazabicyclo[4.3.1]decane-7-carboxylate 2,2-dioxide

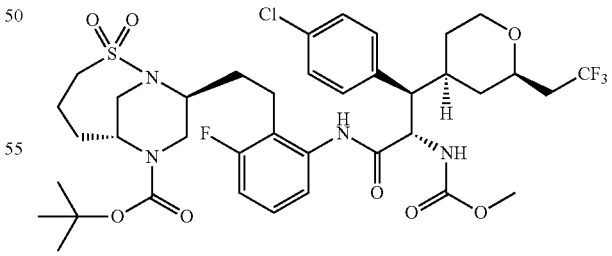

(6R,9S)-tert-Butyl 9-(2-((2S,3R)-2-amino-3-(4-chlorophenyl)-3-((2R,4S)-2-(2,2,2-trifluoroethyl)tetrahydro-2H-pyran-4-yl)propanamido)-6-fluorophenethyl)-2-thia-1,7-diazabicyclo[4.3.1]decane-7-carboxylate 2,2-dioxide (27 mg, 0.035 mmol) and 2,5-dioxopyrrolidin-1-yl methyl carbonate (6.0 mg, 0.035 mmol) were combined in 1 mL of DCM. The mixture was stirred at RT for 18 h. The mixture was diluted with DCM, washed with water and brine, dried (MgSO$_4$), filtered, and the solvent was removed in vacuo. The crude product was chromatographed on a 12 g SiO$_2$ column using 0-80% EtOAc:hexane over 15 min at 30 mL/min to give the title compound as a gum. LCMS m/z (M+H)$^+$=833.6.

Step 4. methyl ((1R,2S)-1-(4-chlorophenyl)-3-((2-(2-((6R,9S)-2,2-dioxido-2-thia-1,7-diazabicyclo[4.3.1]decan-9-yl)ethyl)-3-fluorophenyl)amino)-3-oxo-1-((2R,4S)-2-(2,2,2-trifluoroethyl)tetrahydro-2H-pyran-4-yl)propan-2-yl)carbamate (6R,9S)-tert-Butyl 9-(2-((2S,3R)-3-(4-chlorophenyl)-2-((methoxycarbonyl)amino)-3-((2R,4S)-2-(2,2,2-trifluoroethyl)tetrahydro-2H-pyran-4-yl)propanamido)-6-fluorophenethyl)-2-thia-1,7-diazabicyclo[4.3.1]decane-7-carboxylate 2,2-dioxide (19 mg, 0.023 mmol) was dissolved in 0.5 mL of a 4 M solution of HCl in dioxane (2 mmol). The mixture was stirred at RT for 30 min. The solvent was removed in vacuo to give the title compound. HRMS (ESI) m/z (M+H)$^+$: 733.2428, calcd. for C$_{33}$H$_{43}$ClF$_4$N$_4$O$_6$S=733.2444.

Example 9

Methyl [(1S,2R)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-4-(tetrahydro-2H-pyran-4-yl)butyl]carbamate

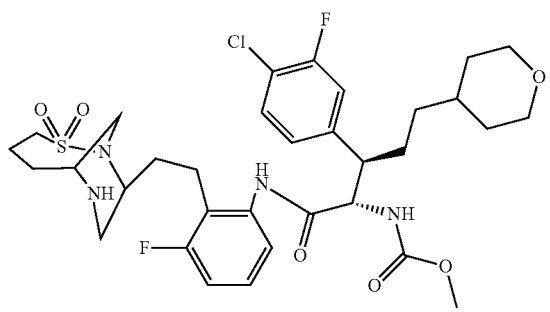 [SMILES: COC(=O)N[C@H](C(=O)Nc1cccc(F)c1CCC1CNC2CCCS(=O)(=O)N1C2)[C@H](CCC1CCOCC1)c1ccc(Cl)c(F)c1]

The title compound was prepared from Intermediate B and Intermediate 14 using the procedure described for Example 8. HRMS (ESI) m/z (M+H)$^+$: 697.2659, calcd. for C$_{33}$H$_{45}$ClF$_2$N$_4$O$_6$S=697.2633.

Example 10

(2S,3R)-2-amino-3-(4-chlorophenyl)-3-((S)-2,2-dimethyltetrahydro-2H-pyran-4-yl)-N-(2-(2-((6R,9S)-2,2-dioxido-2-thia-1,7-diazabicyclo[4.3.1]decan-9-yl)ethyl)-3-fluorophenyl)propanamide

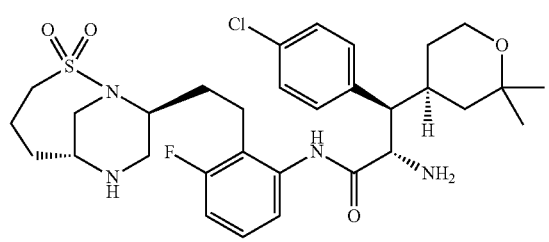 [SMILES: CC1(C)C[C@@H]([C@H](c2ccc(Cl)cc2)[C@H](N)C(=O)Nc2cccc(F)c2CC[C@H]2CN[C@@H]3CCCS(=O)(=O)N2C3)CCO1]

Step 1. (6R,9S)-tert-butyl 9-(2-((2S,3R)-2-azido-3-(4-chlorophenyl)-3-((S)-2,2-dimethyltetrahydro-2H-pyran-4-yl)propanamido)-6-fluorophenethyl)-2-thia-1,7-diazabicyclo[4.3.1]decane-7-carboxylate 2,2-dioxide

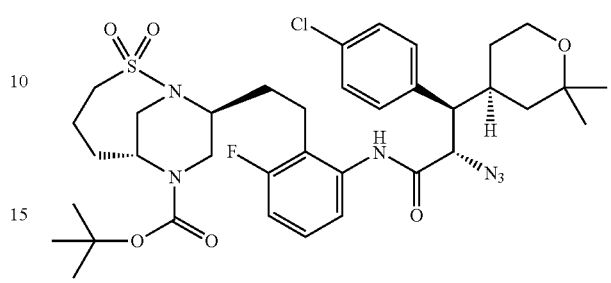

A stirred solution of (6R,9S)-tert-butyl 9-(2-amino-6-fluorophenethyl)-2-thia-1,7-diazabicyclo[4.3.1]decane-7-carboxylate 2,2-dioxide (Intermediate B) (200 mg, 0.47 mmol) and (2S,3R)-2-azido-3-(4-chlorophenyl)-3-((S)-2,2-dimethyltetrahydro-2H-pyran-4-yl)propanoic acid (Intermediate 7) (174 mg, 0.52 mmol) in 4 mL pyridine under N$_2$ atmosphere was cooled to −5° C. in an ice-acetone bath. To the stirred solution was added POCl$_3$ (0.048 mL, 0.52 mmol) dropwise over 5 min. The mixture was stirred at −5° C. for 30 min then quenched with the addition of aqueous NaHCO$_3$ (10 mL). The stirred mixture was diluted with water and EtOAc and transferred to a separatory funnel. The aqueous phase was collected and the organic phase was washed with aqueous NaHCO$_3$ and brine. The aqueous phases were combined and extracted with EtOAc. The organic phases were combined, dried over MgSO$_4$, filtered, diluted with an equal volume of toluene, and concentrated in vacuo. The crude product was chromatographed on a 40 g SiO$_2$ column eluting with a gradient of 0-90% EtOAc-hexanes. The peak eluting at 55% EtOAc was collected to give the title compound. LCMS m/z=747.6 (M+H)$^+$.

Step 2. (6R,9S)-tert-butyl 9-(2-((2S,3R)-2-amino-3-(4-chlorophenyl)-3-((S)-2,2-dimethyltetrahydro-2H-pyran-4-yl)propanamido)-6-fluorophenethyl)-2-thia-1,7-diazabicyclo[4.3.1]decane-7-carboxylate 2,2-dioxide

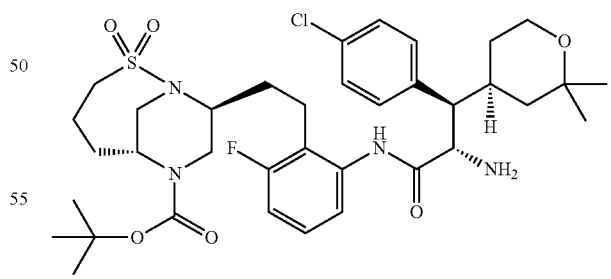

To a stirred solution of (6R,9S)-tert-butyl 9-(2-((2S,3R)-2-azido-3-(4-chlorophenyl)-3-((S)-2,2-dimethyltetrahydro-2H-pyran-4-yl)propanamido)-6-fluorophenethyl)-2-thia-1,7-diazabicyclo[4.3.1]decane-7-carboxylate 2,2-dioxide (323 mg, 432 mmol) in 3.4 mL of THF containing 0.86 mL water was added a solution of trimethylphosphine (0.45 mL of a 1.0 M solution in THF, 0.45 mmol). The mixture was stirred at RT for 30 min. The mixture was partitioned between aqueous NaHCO₃ and ethyl acetate. The layers were separated and the aqueous layer was extracted with two more portions of ethyl acetate. The combined organic extracts were washed with brine, dried over Na₂SO₄, filtered, and the solvents were removed in vacuo to give the title compound. LCMS m/z=721.4 (M+H)⁺.

Step 3. (2S,3R)-2-amino-3-(4-chlorophenyl)-3-((S)-2,2-dimethyltetrahydro-2H-pyran-4-yl)-N-(2-(2-((6R,9S)-2,2-dioxido-2-thia-1,7-diazabicyclo[4.3.1]decan-9-yl)ethyl)-3-fluorophenyl)propanamide A solution of (6R,9S)-tert-butyl 9-(2-(((2S,3R)-2-amino-3-(4-chlorophenyl)-3-((S)-2,2-dimethyltetrahydro-2H-pyran-4-yl)propanamido)-6-fluorophenethyl)-2-thia-1,7-diazabicyclo[4.3.1]decane-7-carboxylate 2,2-dioxide (312 mg, 0.433 mmol) in dioxane containing HCl (1.0 mL of a 4 M solution, 4.0 mmol) was stirred at RT for 18 h. The solvent was removed in vacuo and the crude product was purified by preparative HPLC on a C18 column eluting with a gradient of 10-60% acetonitrile in water containing 0.1% TFA. Fractions containing product were combined and the solvents were removed in vacuo and the residue was partitioned between aqueous NaHCO₃ and ethyl acetate. The layers were separated and the aqueous layer was extracted twice more with ethyl acetate. The combined organic extracts were washed with brine, dried over Na₂SO₄, filtered, and the solvent was removed in vacuo to give the free base of the title compound. The free base was dissolved in methanol (2 mL) containing 1.0 N aqueous HCl (0.26 mL, 0.26 mmol). The solvent was removed in vacuo to obtain the mono HCl salt of the title compound. HRMS (ESI) m/z (M+H)⁺: 621.2659, calcd. for C₃₁H₄₃ClFN₄O₄S=621.2672.

Example 11

(βS)-4-Chloro-N-{2-[2-(2,2-dioxido-2-thia-1,7-diazabicyclo[4.3.1]dec-9-yl)ethyl]-3-fluorophenyl}-β-[6-(1-methylethoxy)pyridin-3-yl]-L-phenylalaninamide

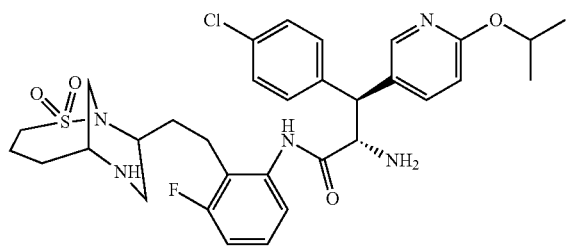 [SMILES: CC(C)Oc1ccc([C@H](c2ccc(Cl)cc2)[C@H](N)C(=O)Nc2cccc(F)c2CCC2CNC3CCCS(=O)(=O)N2C3)cn1]

Step 1. (6R,9S)-tert-butyl 9-(2-((2S,3S)-2-azido-3-(4-chlorophenyl)-3-(6-isopropoxypyridin-3-yl)propanamido)-6-fluorophenethyl)-2-thia-1,7-diazabicyclo[4.3.1]decane-7-carboxylate 2,2-dioxide

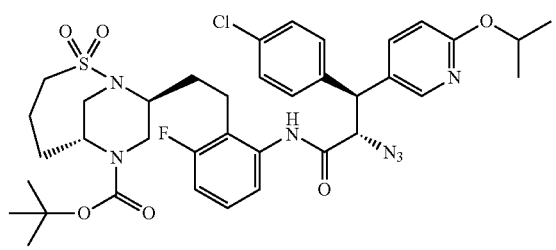 [SMILES: CC(C)Oc1ccc([C@H](c2ccc(Cl)cc2)[C@H](N=[N+]=[N-])C(=O)Nc2cccc(F)c2CC[C@H]2CN(C(=O)OC(C)(C)C)[C@@H]3CCCS(=O)(=O)N2C3)cn1]

A stirred solution of (6R,9S)-tert-butyl 9-(2-amino-6-fluorophenethyl)-2-thia-1,7-diazabicyclo[4.3.1]decane-7-carboxylate 2,2-dioxide (Intermediate B) (125 mg, 0.29 mmol) and (2S,3S)-2-azido-3-(4-chlorophenyl)-3-(6-isopropoxypyridin-3-yl)propanoic acid (Intermediate 6) (209 mg, 0.58 mmol) in 3 mL pyridine under N₂ atmosphere was cooled to −5° C. in an ice-acetone bath. To the stirred solution was added POCl₃ (0.060 mL, 0.64 mmol) dropwise over 3 min. The mixture was stirred at −5° C. for 30 min. The reaction was quenched with the addition of aqueous NaHCO₃ (5 mL). The cooling bath was removed and the mixture was diluted with water and EtOAc and transferred to a separatory funnel. The aqueous phase was collected and the organic phase was washed with aqueous NaHCO₃ and brine. The aqueous phases were combined and extracted with EtOAc. The organic phases were combined, dried over MgSO₄, filtered, diluted with an equal volume of toluene, and the solvents were removed in vacuo. The crude product was chromatographed on a 40 g SiO₂ column using a 0-100% EtOAc:hexanes gradient over 20 min at 40 mL/min. The peak eluting at 60% EtOAc was collected to give the title compound as a pale red gum. LCMS m/z=770.6 (M+H)⁺.

Step 2. (6R,9S)-tert-butyl 9-(2-((2S,3S)-2-amino-3-(4-chlorophenyl)-3-(6-isopropoxypyridin-3-yl)propanamido)-6-fluorophenethyl)-2-thia-1,7-diazabicyclo[4.3.1]decane-7-carboxylate 2,2-dioxide

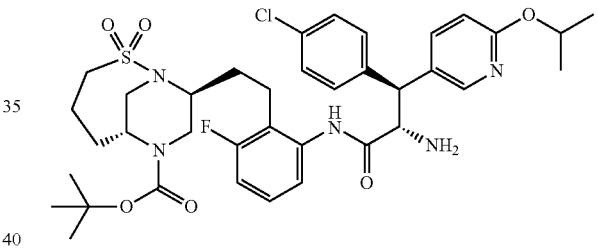

To a stirred solution of (6R,9S)-tert-butyl 9-(2-((2S,3S)-2-azido-3-(4-chlorophenyl)-3-(6-isopropoxypyridin-3-yl)propanamido)-6-fluorophenethyl)-2-thia-1,7-diazabicyclo[4.3.1]decane-7-carboxylate 2,2-dioxide (280 mg, 0.363 mmol) in 5 mL of THF containing 1 mL of water was added a solution of trimethylphosphine (0.99 mL of a 1.0 M solution in THF, 0.99 mmol) and three drops of TFA. The mixture was stirred at RT for 18 h. The solvents were removed in vacuo and the residue was partitioned between EtOAc and aqueous NaHCO₃. The aqueous phase was extracted with a second portion of EtOAc. The EtOAc layers were combined, dried over MgSO₄, filtered, and the solvent was removed in vacuo. The crude product was chromatographed on a 40 g SiO₂ column using a gradient elution of 0-90% A in B where A=5% MeOH in EtOAc, and B=1:1 CH₂Cl₂:hexanes. The broad peak eluting at 80% A was collected and the solvents were removed in vacuo to give the title compound. LCMS m/z=744.6 (M+H)⁺.

Step 3. (2S,3S)-2-amino-3-(4-chlorophenyl)-N-(2-(2-((6R,9S)-2,2-dioxido-2-thia-1,7-diazabicyclo[4.3.1]decan-9-yl)ethyl)-3-fluorophenyl)-3-(6-isopropoxypyridin-3-yl)propanamide A solution of (6R,9S)-tert-butyl 9-(2-((2S,3S)-2-amino-3-(4-chlorophenyl)-3-(6-isopropoxypyridin-3-yl)propanamido)-6-fluorophenethyl)-2-thia-1,7-diazabicyclo[4.3.1]decane-7-carboxylate 2,2-dioxide (290 mg, 0.39 mmol) in 25 mL of EtOAc was stirred and cooled to 0° C. under $N_2$ atmosphere. HCl gas was bubbled through the solution for 5 min. The solution was stirred at 0° C. for 30 min and then at ambient temperature for 1 h. The solvent was removed in vacuo and the resulting solid was stirred vigorously in ether. The solid was collected by filtration and dried in vacuo to give a hydrochloride salt of the title compound. HRMS (ESI) m/z (M+H)+: 644.2450, calcd. for $C_{32}H_{41}ClFN_5O_4S$=644.2468.

Example 12

(2S,3S)-2-amino-3-(4-chlorophenyl)-3-(6-(1,1-difluoroethyl)pyridin-3-yl)-N-(2-(2-((6R,9S)-2,2-dioxido-2-thia-1,7-diazabicyclo[4.3.1]decan-9-yl)ethyl)-3-fluorophenyl)propanamide

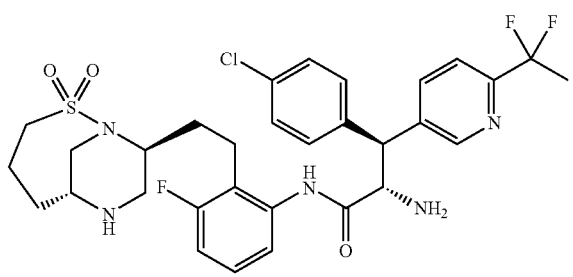 [SMILES: CC(F)(F)c1ccc([C@H](c2ccc(Cl)cc2)[C@H](N)C(=O)Nc2cccc(F)c2CC[C@H]2CN[C@@H]3CCCS(=O)(=O)N2C3)cn1]

Step 1. (6R,9S)-tert-butyl 9-(2-((2S,3S)-2-azido-3-(4-chlorophenyl)-3-(6-(1,1-difluoroethyl)pyridin-3-yl)propanamido)-6-fluorophenethyl)-2-thia-1,7-diazabicyclo[4.3.1]decane-7-carboxylate 2,2-dioxide

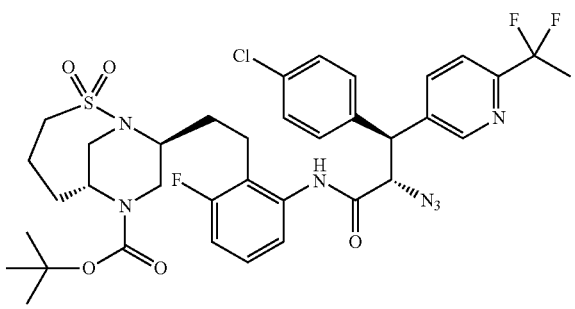 [SMILES: CC(C)(C)OC(=O)N1C[C@H](CCc2c(F)cccc2NC(=O)[C@@H](N=[N+]=[N-])[C@@H](c2ccc(Cl)cc2)c2ccc(C(C)(F)F)nc2)N2C[C@H]1CCCS2(=O)=O]

To a stirred solution of (6R,9S)-tert-butyl 9-(2-amino-6-fluorophenethyl)-2-thia-1,7-diazabicyclo[4.3.1]decane-7-carboxylate 2,2-dioxide (Intermediate B) (210 mg, 0.49 mmol) and (2S,3S)-2-azido-3-(4-chlorophenyl)-3-(6-(1,1-difluoroethyl)pyridin-3-yl)propanoic acid (200 mg, 0.55 mmol) in 5 mL of pyridine cooled in an ice-acetone bath was added $POCl_3$ (0.051 mL, 0.55 mmol) dropwise over a period of 2 min. The mixture was stirred for 15 min then diluted with 20 mL EtOAc, washed with aqueous $NaHCO_3$ and brine, dried ($MgSO_4$), filtered, and the solvents were removed in vacuo. The crude product was chromatograph on a 24 g $SiO_2$ column using 0-80% EtOAc:hexane over 16 min at 35 mL/min. Fractions containing product were combined and the solvents were removed in vacuo. The residue was purified on a C18 column using 20-100% $CH_3CN:H_2O$ with 0.1% TFA over 30 min at 50 mL/min. Fractions containing product were combined and the solvents were removed in vacuo to give the title compound as a foam. LCMS m/z=776.6 (M+H)+.

Step 2. (6R,9S)-tert-butyl 9-(2-((2S,3S)-2-amino-3-(4-chlorophenyl)-3-(6-(1,1-difluoroethyl)pyridin-3-yl)propanamido)-6-fluorophenethyl)-2-thia-1,7-diazabicyclo[4.3.1]decane-7-carboxylate 2,2-dioxide

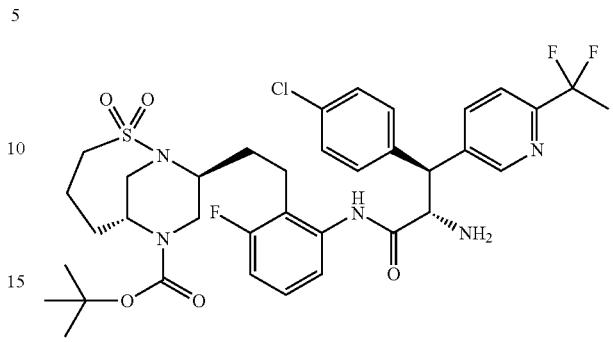

To a stirred solution of (6R,9S)-tert-butyl 9-(2-((2S,3S)-2-azido-3-(4-chlorophenyl)-3-(6-(1,1-difluoroethyl)pyridin-3-yl)propanamido)-6-fluorophenethyl)-2-thia-1,7-diazabicyclo[4.3.1]decane-7-carboxylate 2,2-dioxide (140 mg, 0.18 mmol) in 1 mL of THF was added water (0.2 mL) and $PMe_3$ (0.18 mL of a 1.0 M solution in THF, 0.18 mL). The mixture was stirred at RT for 1 h, then diluted with EtOAc and aqueous $NaHCO_3$. The organic phase was collected and washed with brine, dried ($MgSO_4$), filtered, and the solvent was removed in vacuo. The crude product was chromatographed on a 12 g $SiO_2$ column using 0-100% A:B (A=5% MeOH:EtOAc and B=1:1 hexane:DCM) over 15 min at 30 mL/min to give the title compound as a foam. LCMS m/z=750.6 (M+H)+.

Step 3: (2S,3S)-2-amino-3-(4-chlorophenyl)-3-(6-(1,1-difluoroethyl)pyridin-3-yl)-N-(2-(2-((6R,9S)-2,2-dioxido-2-thia-1,7-diazabicyclo[4.3.1]decan-9-yl)ethyl)-3-fluorophenyl)propanamide Into a stirred solution of (6R,9S)-tert-butyl 9-(2-((2S,3S)-2-amino-3-(4-chlorophenyl)-3-(6-(1,1-difluoroethyl)pyridin-3-yl)propanamido)-6-fluorophenethyl)-2-thia-1,7-diazabicyclo[4.3.1]decane-7-carboxylate 2,2-dioxide (120 mg, 0.16 mmol) in 2 mL of EtOAc at 0° C. was bubbled HCl gas for 2 min. The cooling bath was removed and the mixture was stirred for 30 min. The solvents were removed in vacuo to give the HCl salt of the title compound. HRMS (ESI) m/z (M+H)+: 650.2173, calcd. for $C_{31}H_{37}ClF_3N_5O_3S$=650.2174.

Example 13

Methyl {(1S)-1-[trans-1-(4-chlorophenyl)-4-methoxycyclohexyl]-2-[(2-{2-[(6R,9S)-2,2-dioxido-2-thia-1,7-diazabicyclo[4.3.1]dec-9-yl]ethyl}-3-fluorophenyl)amino]-2-oxoethyl}carbamate

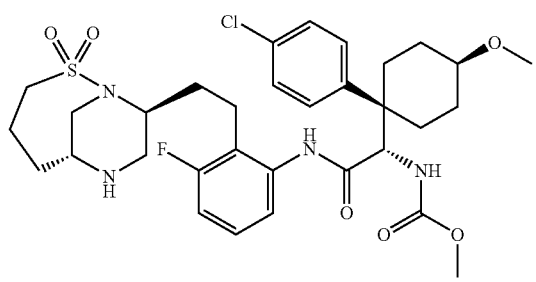 [SMILES: COC(=O)N[C@H](C(=O)Nc1cccc(F)c1CC[C@H]1CN[C@@H]2CCCS(=O)(=O)N1C2)[C@]1(c2ccc(Cl)cc2)CC[C@@H](OC)CC1]

143

Step 1. (6R,9S)-tert-butyl 9-(2-((S)-2-azido-2-((1r,4S)-1-(4-chlorophenyl)-4-methoxycyclohexyl)acetamido)-6-fluorophenethyl)-2-thia-1,7-diazabicyclo[4.3.1]decane-7-carboxylate 2,2-dioxide

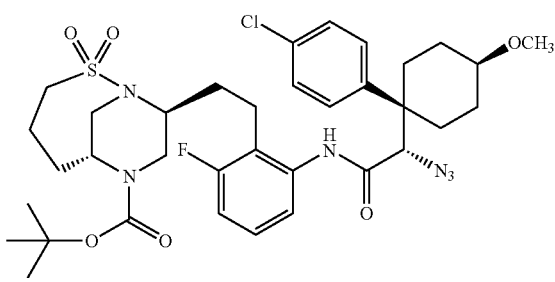 [SMILES: CO[C@H]1CC[C@](c2ccc(Cl)cc2)([C@H](N=[N+]=[N-])C(=O)Nc2cccc(F)c2CC[C@H]2CN(C(=O)OC(C)(C)C)[C@@H]3CCCS(=O)(=O)N2C3)CC1]

POCl₃ (31.26 mg, 0.204 mmol) was added to a solution of (S)-2-azido-2-((1r,4S)-1-(4-chlorophenyl)-4-methoxycyclohexyl)acetic acid (Intermediate 29) (60 mg, 0.186 mmol) and (6R,9S)-tert-butyl 9-(2-amino-6-fluorophenethyl)-2-thia-1,7-diaza-bicyclo[4.3.1]decane-7-carboxylate 2,2-dioxide (Intermediate B) (88.6 mg, 0.186 mmol) in pyridine (2 mL) at −15° C. The reaction was stirred for 30 min then warmed to 0° C. and stirred for 10 min. The reaction was quenched with aqueous KH₂PO₄ and warmed to RT. The mixture was extracted with two portions of EtOAc. The EtOAc extracts were combined, dried (Na₂SO₄), filtered, and the solvent was removed in vacuo to give the title compound. MS (M+H)⁺: 733

Step 2. (6R,9S)-tert-butyl 9-(2-((S)-2-amino-2-((1r,4S)-1-(4-chlorophenyl)-4-methoxycyclohexyl)acetamido)-6-fluorophenethyl)-2-thia-1,7-diaza-bicyclo[4.3.1]decane-7-carboxylate 2,2-dioxide

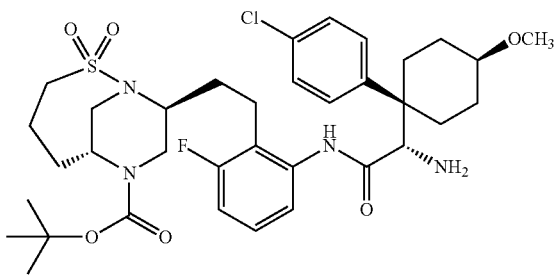

To a solution of (6R,9S)-tert-butyl 9-(2-((S)-2-azido-2-((1r,4S)-1-(4-chlorophenyl)-4-methoxycyclohexyl)acetamido)-6-fluorophenethyl)-2-thia-1,7-diazabicyclo[4.3.1]decane-7-carboxylate 2,2-dioxide (45 mg, 0.061 mmol) in 2:1 THF:H₂O (1 mL) was added MeP₃ (11.6 mg, 0.153 mmol). The solution was stirred for 30 min at RT. The solvent was removed in vacuo to give the title compound. MS (M+H)⁺: 707.

144

Step 3: (6R,9S)-tert-butyl 9-(2-((S)-2-((1r,4S)-1-(4-chlorophenyl)-4-methoxycyclo-hexyl)-2-((methoxycarbonyl)amino)acetamido)-6-fluorophenethyl)-2-thia-1,7-diaza-bicyclo[4.3.1]decane-7-carboxylate 2,2-dioxide

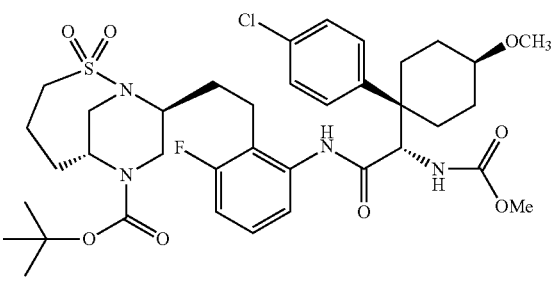 [SMILES: COC(=O)N[C@H](C(=O)Nc1cccc(F)c1CC[C@H]1CN(C(=O)OC(C)(C)C)[C@@H]2CCCS(=O)(=O)N1C2)[C@]1(c2ccc(Cl)cc2)CC[C@@H](OC)CC1]

To a solution of (6R,9S)-tert-butyl 9-(2-((S)-2-amino-2-((1r,4S)-1-(4-chlorophenyl)-4-methoxycyclohexyl)acetamido)-6-fluorophenethyl)-2-thia-1,7-diazabicyclo-[4.3.1]decane-7-carboxylate 2,2-dioxide (40 mg, 0.057 mmol) in DCM (3 mL) was added TEA (13 mg, 0.13 mmol) and 2,5-dioxopyrrolidin-1-yl methyl carbonate (23 mg, 0.132 mmol). The mixture was stirred at RT for 20 min. The solvent was removed in vacuo to give the title compound as a gum. MS (M+H)⁺: 765.

Step 4: Methyl ((1S)-1-((1r,4S)-1-(4-chlorophenyl)-4-methoxycyclohexyl)-2-((2-(2-((6R,9S)-2,2-dioxido-2-thia-1,7-diazabicyclo[4.3.1]decan-9-yl)ethyl)-3-fluorophenyl)amino)-2-oxoethyl)carbamate To a solution of (6R,9S)-tert-butyl 9-(2-((S)-2-((1r,4S)-1-(4-chlorophenyl)-4-methoxycyclohexyl)-2-((methoxycarbonyl)amino)acetamido)-6-fluorophenethyl)-2-thia-1,7-diazabicyclo[4.3.1]decane-7-carboxylate 2,2-dioxide (40 mg, 0.052 mmol) in DCM (1 mL) was added TFA (1 mL). The mixture was stirred at RT for 20 min. The solvents were removed in vacuo and the residue was purified by preparative reverse phase HPLC to give the TFA salt of the title compound. ¹H NMR (Methanol-d4 400 MHz): δ 7.41-7.50 (m, 4H), 7.20-7.22 (m, 1H), 6.99-7.03 (m, 1H), 6.76-6.78 (m, 1H), 4.73 (s, 1H), 4.35 (s, 1H), 3.32-3.70 (m, 9H), 3.28 (s, 3H), 3.11-3.14 (m, 1H), 2.44-2.62 (m, 5H), 1.77-2.16 (m, 9H), 1.06-1.17 (m, 2H) ppm. MS (M+H)⁺: 665.

Example 14

Methyl 4-{(1S)-1-amino-2-[(2-{2-[(6R,9S)-2,2-dioxido-2-thia-1,7-diazabicyclo[4.3.1]dec-9-yl]ethyl}-3-fluorophenyl)amino]-2-oxoethyl}-4-(4-chlorophenyl)piperidine-1-carboxylate

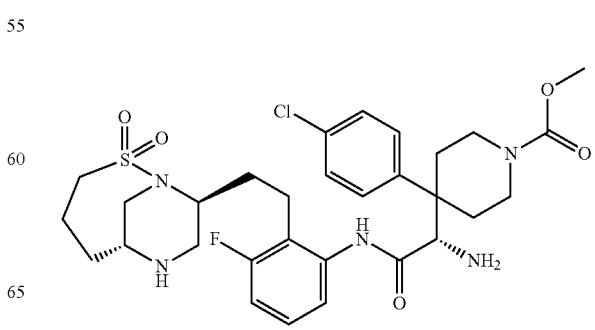

Step 1. (6R,9S)-tert-butyl 9-(2-((S)-2-azido-2-(4-(4-chlorophenyl)-1-(methoxy-carbonyl)piperidin-4-yl)acetamido)-6-fluorophenethyl)-2-thia-1,7-diazabicyclo[4.3.1]decane-7-carboxylate 2,2-dioxide

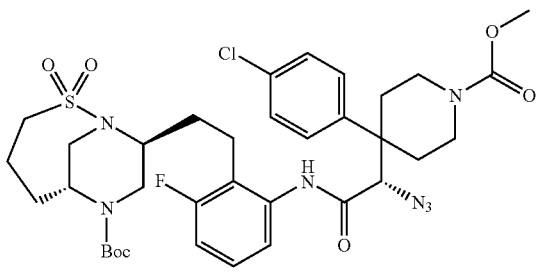 [SMILES: COC(=O)N1CCC(c2ccc(Cl)cc2)([C@H](N=[N+]=[N-])C(=O)Nc2cccc(F)c2CC[C@H]2CN(C(=O)OC(C)(C)C)[C@@H]3CCCS(=O)(=O)N2C3)CC1]

(6R,9S)-tert-butyl 9-(2-amino-6-fluorophenethyl)-2-thia-1,7-diazabicyclo[4.3.1]-decane-7-carboxylate 2,2-dioxide (Intermediate B) (79 mg, 0.18 mmol) and (S)-2-azido-2-(4-(4-chlorophenyl)-1-(methoxycarbonyl)piperidin-4-yl)acetic acid (Intermediate 30) (65 mg, 0.18 mmol) were dissolved in pyridine (3 mL), the stirred solution was cooled to 0° C., and POCl$_3$ (0.13 mL, 13.7 mmol) was added. The reaction was stirred for 30 min. The reaction was quenched with aqueous KH$_2$PO$_4$ and the mixture was extracted with ethyl acetate (3×10 mL). The combined EtOAc extracts were dried over Na$_2$SO$_4$, filtered, and the solvent was evaporated under reduced pressure to give the title compound as a gum. MS (ESI) m/z (M+23)$^+$: 784.4.

Step 2. methyl 4-((1S)-1-azido-2-((2-(2-((6R,9S)-2,2-dioxido-2-thia-1,7-diazabicyclo[4.3.1]decan-9-yl)ethyl)-3-fluorophenyl)amino)-2-oxoethyl)-4-(4-chlorophenyl)piperidine-1-carboxylate

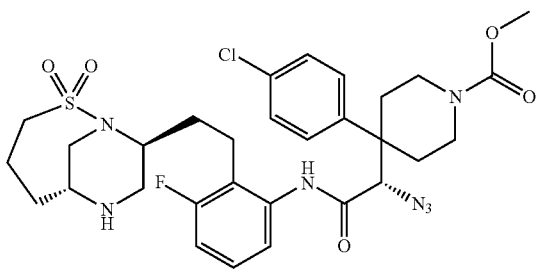 [SMILES: COC(=O)N1CCC(c2ccc(Cl)cc2)([C@H](N=[N+]=[N-])C(=O)Nc2cccc(F)c2CC[C@H]2CN[C@@H]3CCCS(=O)(=O)N2C3)CC1]

To a stirred solution of (6R,9S)-tert-butyl 9-(2-((S)-2-azido-2-(4-(4-chlorophenyl)-1-(methoxycarbonyl)piperidin-4-yl)acetamido)-6-fluorophenethyl)-2-thia-1,7-diazabicyclo[4.3.1]decane-7-carboxylate 2,2-dioxide (50 mg, 0.066 mmol) in DCM (2 mL) was added TFA (1 mL). The mixture was stirred at RT for 30 min. The solvents were removed in vacuo to give the TFA salt of the title compound as a gum. MS (ESI) m/z (M+H)$^+$: 662.2.

Step 3. methyl 4-((1S)-1-amino-2-((2-(2-((6R,9S)-2,2-dioxido-2-thia-1,7-diazabicyclo[4.3.1]decan-9-yl)ethyl)-3-fluorophenyl)amino)-2-oxoethyl)-4-(4-chloro-phenyl)piperidine-1-carboxylate To a solution of methyl 4-((1S)-1-azido-2-((2-(2-((6R,9S)-2,2-dioxido-2-thia-1,7-diazabicyclo[4.3.1]decan-9-yl)ethyl)-3-fluorophenyl)amino)-2-oxoethyl)-4-(4-chlorophenyl)piperidine-1-carboxylate (31 mg, 0.047 mmol) in THF (5 mL) and H$_2$O (1 mL), trimethylphosphine (7 mg, 0.094 mmol) was added. The mixture was stirred at RT for 30 min. The solvents were removed in vacuo and the residue was purified by preparative reverse phase HPLC to give the TFA salt of the title compound. $^1$H NMR (Methanol-d4, 400 MHz) δ: 7.53 (s, 4H), 7.32-7.24 (m, 1H), 7.16-7.02 (m, 2H), 4.26-4.01 (m, 5H), 3.90-3.83 (m, 1H), 3.76-3.71 (m, 1H), 3.69 (s, 3H), 3.67-3.59 (m, 2H), 3.58-3.48 (m, 1H), 3.22-3.15 (m, 1H), 2.72 (d, J=13.1 Hz, 4H), 2.55 (d, J=14.6 Hz, 3H), 2.42-2.30 (m, 1H), 2.27-2.12 (m, 2H), 2.11-1.89 (m, 3H), 1.77 (br. s., 1H) ppm. MS (ESI) m/z (M+H)$^+$: 636.2.

Example 15

β-[(2R,4r,6S)-2,6-Dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-4-fluoro-L-phenylalaninamide

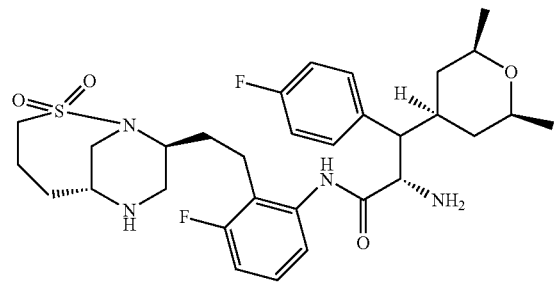 [SMILES: C[C@@H]1C[C@H](C(c2ccc(F)cc2)[C@H](N)C(=O)Nc2cccc(F)c2CC[C@H]2CN[C@@H]3CCCS(=O)(=O)N2C3)C[C@H](C)O1]

The title compound was prepared from Intermediate B and Intermediate 21 using the procedure described for Example 10. LCMS m/z=605.3 (M+H)$^+$.

Example 16

Methyl {(1S,2R)-2-(4-chloro-3-fluorophenyl)-2-[(2R,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate

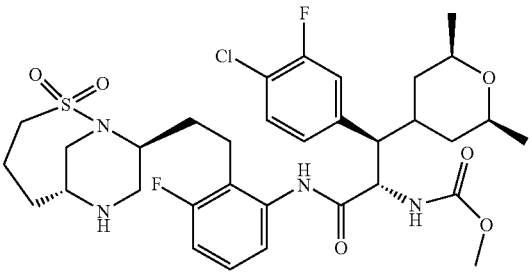 [SMILES: COC(=O)N[C@H](C(=O)Nc1cccc(F)c1CC[C@H]1CN[C@@H]2CCCS(=O)(=O)N1C2)[C@@H](c1ccc(Cl)c(F)c1)C1C[C@@H](C)O[C@@H](C)C1]

The title compound was prepared from Intermediate B and Intermediate 22 using the procedure described for Example 13. LCMS m/z=697.2 (M+H)$^+$.

Example 17

(βS)-4-Chloro-N-{2-[2-(2,2-dioxido-2-thia-1,7-diaz-abicyclo[4.3.1]dec-9-yl)ethyl]-3-fluorophenyl}-β-[2-(1-methylethoxy)pyridin-4-yl]-L-phenylalaninamide

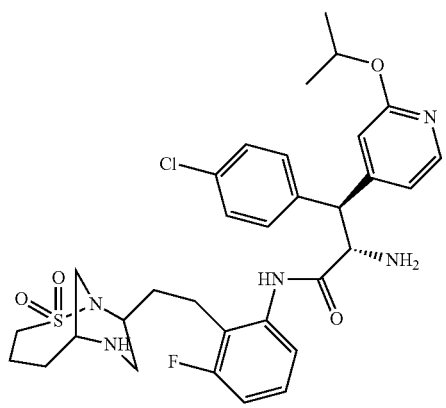 [SMILES: CC(C)Oc1cc([C@H](c2ccc(Cl)cc2)[C@H](N)C(=O)Nc2cccc(F)c2CCC2CNC3CCCS(=O)(=O)N2C3)ccn1]

The title compound was prepared from Intermediate B and Intermediate 26 using the procedure described for Example 11. HRMS (ESI) m/z (M+H)$^+$: 644.2466, calcd. for $C_{32}H_{41}ClFN_5O_4S$=644.2468.

Example 18

Methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(trifluoromethyl)pyridin-4-yl]ethyl}carbamate

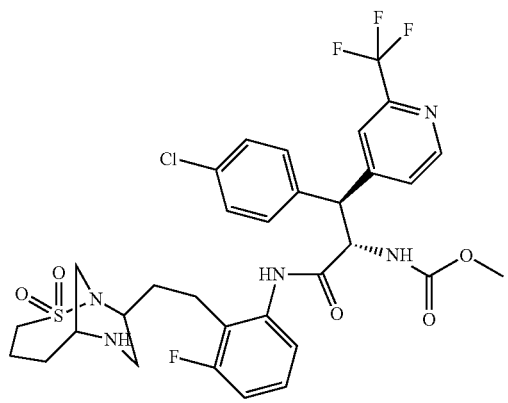 [SMILES: COC(=O)N[C@H](C(=O)Nc1cccc(F)c1CCC1CNC2CCCS(=O)(=O)N1C2)[C@@H](c1ccc(Cl)cc1)c1ccnc(C(F)(F)F)c1]

The title compound was prepared from Intermediate B and Intermediate 24 using the procedure described for Example 8. HRMS (ESI) m/z (M+H)$^+$: 712.2003, calcd. for $C_{32}H_{36}ClF_4N_5O_5S$=712.1978.

Example 19

Methyl {(1S,2S)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-2-[5-(trifluoromethyl)pyridin-3-yl]ethyl}carbamate

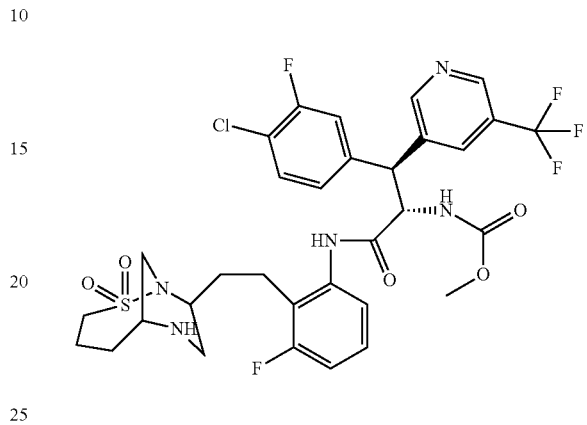

The title compound was prepared from Intermediate B and Intermediate 25 using the procedure described for Example 8. HRMS (ESI) m/z (M+H)$^+$: 730.1859, calcd. for $C_{32}H_{35}ClF_5N_5O_5S$=730.1884.

Example 20

(βS)-4-Chloro-β-[5-(1,1-difluoroethyl)pyridin-3-yl]-N-{2-[2-(2,2-dioxido-2-thia-1,7-diazabicyclo[4.3.1]dec-9-yl)ethyl]-3-fluorophenyl}-L-phenylalaninamide

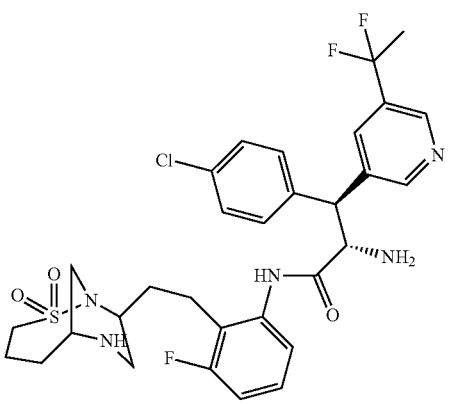 [SMILES: CC(F)(F)c1cncc([C@H](c2ccc(Cl)cc2)[C@H](N)C(=O)Nc2cccc(F)c2CCC2CNC3CCCS(=O)(=O)N2C3)c1]

The title compound was prepared from Intermediate B and Intermediate 32 using the procedure described for Example 12. HRMS (ESI) m/z (M+H)$^+$: 650.2172, calcd. for $C_{31}H_{37}ClF_3N_5O_3S$=650.2174.

Example 21

Methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[6-(trifluoromethyl)pyridin-3-yl]ethyl}carbamate

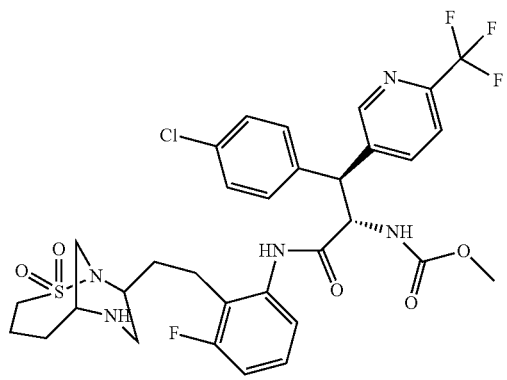 [SMILES: COC(=O)N[C@H](C(=O)Nc1cccc(F)c1CCC1CNC2CCCS(=O)(=O)N1C2)[C@@H](c1ccc(Cl)cc1)c1ccc(C(F)(F)F)nc1]

The title compound was prepared from Intermediate B and Intermediate 33 using the procedure described for Example 8. LCMS m/z=712.2 (M+H)⁺.

Example 22

Methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(S)-(4-fluorophenyl)[2-(trifluoromethyl)pyrimidin-5-yl]methyl}-2-oxoethyl]carbamate

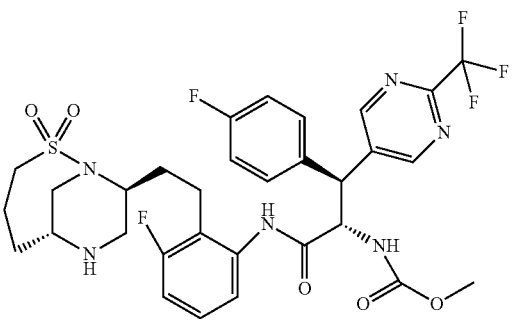 [SMILES: COC(=O)N[C@H](C(=O)Nc1cccc(F)c1CC[C@H]1CN[C@@H]2CCCS(=O)(=O)N1C2)[C@@H](c1ccc(F)cc1)c1cnc(C(F)(F)F)nc1]

The title compound was prepared from Intermediate B and Intermediate 27 using the procedure described for Example 13. LCMS m/z=697.2 (M+H)⁺.

Example 23

(βS)—N-(2-{2-[(6R,9S)-2,2-Dioxido-2-thia-1,7-diazabicyclo[4.3.1]dec-9-yl]ethyl}-3-fluorophenyl)-4-fluoro-β-[2-(1-methylethoxy)pyrimidin-5-yf]-L-phenylalaninamide

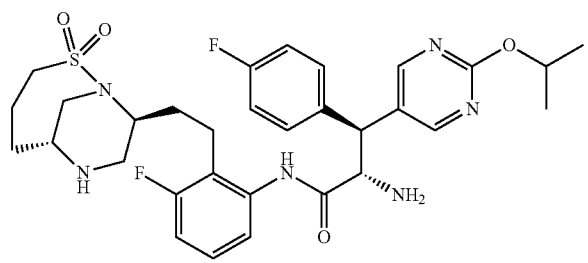 [SMILES: CC(C)Oc1ncc([C@H](c2ccc(F)cc2)[C@H](N)C(=O)Nc2cccc(F)c2CC[C@H]2CN[C@@H]3CCCS(=O)(=O)N2C3)cn1]

The title compound was prepared from Intermediate B and Intermediate 28 using the procedure described for Example 13. LCMS m/z=629.2 (M+H)⁺.

Example 24

(βR)-4-Chloro-N-[(1S,2R)-2-{2-[(6R,9S)-2,2-dioxido-2-thia-1,7-diazabicyclo[4.3.1]dec-9-yl]ethyl}cyclohexyl]-β-(tetrahydro-2H-pyran-4-yl)-L-phenylalaninamide

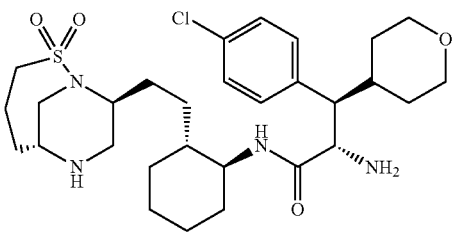 [SMILES: N[C@H](C(=O)N[C@H]1CCCC[C@@H]1CC[C@H]1CN[C@@H]2CCCS(=O)(=O)N1C2)[C@@H](c1ccc(Cl)cc1)C1CCOCC1]

Step 1. (6R,9S)-tert-butyl 9-(2-((1R,2S)-2-((2S,3R)-2-azido-3-(4-chlorophenyl)-3-(tetrahydro-2H-pyran-4-yl)propanamido)cyclohexyl)ethyl)-2-thia-1,7-diazabicyclo[4.3.1]decane-7-carboxylate 2,2-dioxide

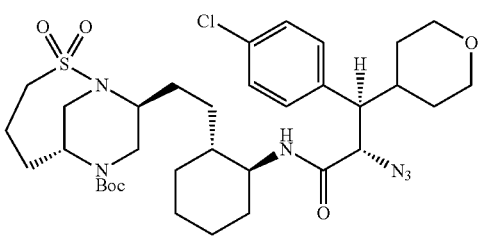

To a solution of (6R,9S)-tert-butyl 9-(2-((1R,2S)-2-aminocyclohexyl)ethyl)-2-thia-1,7-diazabicyclo[4.3.1]decane-7-carboxylate 2,2-dioxide (Intermediate G) (95 mg, 0.23 mmol) in CH₂Cl₂ (1 mL) under N₂ at 0° C. was added (2S,3R)-2-azido-3-(4-chlorophenyl)-3-(tetrahydro-2H-pyran-4-yl)propanoic acid (Intermediate 13) (85 mg, 0.27 mmol) followed by dropwise addition of DIPEA (60 uL, 0.34 mmol). HATU (0.10 g, 0.27 mmol) was added in one portion and the resulting mixture was stirred for 4 h at 0° C. The mixture was diluted with sat. aq. NaHCO₃ (4 mL) and EtOAc (10 mL) and the layers were separated. The aqueous layer was extracted with EtOAc (3×10 mL) and the organic layers were combined. The organic layer was washed with brine (1×5 mL), dried (Na₂SO₄), filtered, and concentrated under reduced pressure. The crude material was taken up in CH₂Cl₂ (3 mL) and loaded onto 3×1000 uM silica gel preparative TLC plates. The plates were run in an eluent of hexanes/EtOAc (1:1) to afford the title compound. MS: m/z=707.6 (M+H)⁺.

Step 2. (6R,9S)-tert-butyl 9-(2-((1R,2S)-2-((2S,3R)-2-amino-3-(4-chlorophenyl)-3-(tetrahydro-2H-pyran-4-yl)propanamido)cyclohexyl)ethyl)-2-thia-1,7-diazabicyclo[4.3.1]decane-7-carboxylate 2,2-dioxide

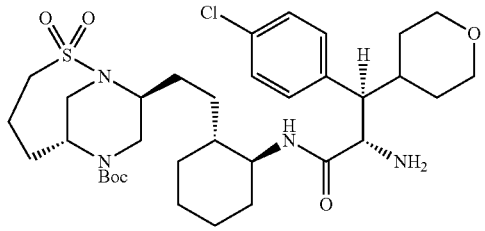 [SMILES: CC(C)(C)OC(=O)N1C[C@H](CC[C@H]2CCCC[C@@H]2NC(=O)[C@@H](N=[N+]=[N-])[C@@H](c2ccc(Cl)cc2)C2CCOCC2)N2C[C@H]1CCCS2(=O)=O]

To a round bottom flask charged with (6R,9S)-tert-butyl 9-(2-((1R,2S)-2-((2S,3R)-2-azido-3-(4-chlorophenyl)-3-(tetrahydro-2H-pyran-4-yl)propanamido)cyclohexyl)ethyl)-2-thia-1,7-diazabicyclo[4.3.1]decane-7-carboxylate 2,2-dioxide (0.13 g, 0.18 mmol) was added THF/water (1.5 mL/0.37 mL) to afford a homogenous mixture. Triphenylphosphine resin (0.14 g, 0.28 mmol) was added to the flask which was affixed with a reflux condenser. The mixture was heated to 70° C., stirred for 12 h at this temperature, and was cooled to RT. The reaction mixture was filtered thru a disposable filter to remove the resin. The resin was washed with EtOAc (3×10 mL) and the resulting filtrate was concentrated under reduced pressure to afford the title compound. MS: m/z=681.6 (M+H)$^+$. This material was taken on crude without purification to the next transformation.

Step 3: (βR)-4-Chloro-N-[(1S,2R)-2-{2-[(6R,9S)-2,2-dioxido-2-thia-1,7-diazabicyclo[4.3.1]dec-9-yl]ethyl}cyclohexyl]-β-(tetrahydro-2H-pyran-4-yl)-L-phenylalaninamide To a solution of (6R,9S)-tert-butyl 9-(2-((1R,2S)-2-((2S,3R)-2-amino-3-(4-chlorophenyl)-3-(tetrahydro-2H-pyran-4-yl)propanamido)cyclohexyl)ethyl)-2-thia-1,7-diazabicyclo[4.3.1]decane-7-carboxylate 2,2-dioxide (40 mg, 0.059 mmol) in CH$_2$Cl$_2$ (0.6 mL) at RT was added TFA (90 µL, 1.2 mmol) in one portion to afford a homogenous mixture. The mixture was stirred at RT for 2 h whereupon. The mixture was concentrated under reduced pressure and the resultant residue was azeotroped with CH$_2$Cl$_2$ (3×3 mL) multiple times and was concentrated to dryness. The crude product was purified by reverse phase HPLC (Gilson, C18 column: gradient 10-100% acetonitrile in water with 0.05% TFA as buffer, 12 min method, detection=254 nM) to afford the product after lyophilization as the di TFA salt form. MS: m/z=581.5 (M+H)$^+$.

Example 25

Methyl [(1S,2R)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-(tetrahydro-2H-pyran-4-yl)ethyl]carbamate

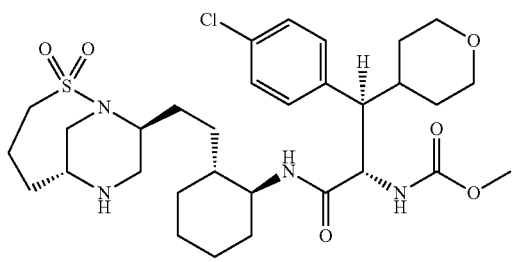 [SMILES: COC(=O)N[C@H](C(=O)N[C@H]1CCCC[C@@H]1CC[C@H]1CN[C@@H]2CCCS(=O)(=O)N1C2)[C@@H](c1ccc(Cl)cc1)C1CCOCC1]

Step 1. (6R,9S)-tert-butyl 9-(2-((1R,2S)-2-((2S,3R)-3-(4-chlorophenyl)-2-((methoxycarbonyl)amino)-3-(tetrahydro-2H-pyran-4-yl)propanamido)cyclohexyl)ethyl)-2-thia-1,7-diazabicyclo[4.3.1]decane-7-carboxylate 2,2-dioxide

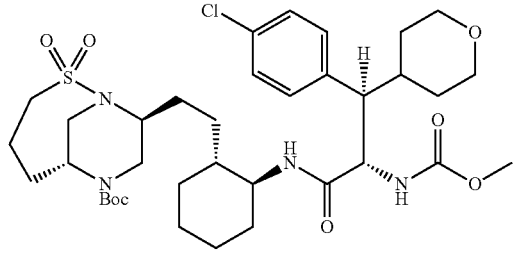 [SMILES: COC(=O)N[C@H](C(=O)N[C@H]1CCCC[C@@H]1CC[C@H]1CN(C(=O)OC(C)(C)C)[C@@H]2CCCS(=O)(=O)N1C2)[C@@H](c1ccc(Cl)cc1)C1CCOCC1]

To a solution of (6R,9S)-tert-butyl 9-(2-((1R,2S)-2-((2S,3R)-2-amino-3-(4-chlorophenyl)-3-(tetrahydro-2H-pyran-4-yl)propanamido)cyclohexyl)ethyl)-2-thia-1,7-diazabicyclo[4.3.1]decane-7-carboxylate 2,2-dioxide (Example 24, Step 2) (80 mg, 0.12 mmol) in CH$_2$Cl$_2$ (1 mL) under N$_2$ at RT was added 2,5-dioxopyrrolidin-1-yl methyl carbonate (24 mg, 0.14 mmol) to afford a homogenous solution. The resulting mixture was stirred at RT for 12 h whereupon the reaction was complete. The reaction mixture was directly loaded onto 3×1000 uM preparative TLC plates chromatography plates. The plates were eluted with a 20:1 mixture of CH$_2$Cl$_2$/MeOH to afford the product. MS: m/z=739.5 (M+H)$^+$.

Step 2: Methyl [(1S,2R)-2-(4-chlorophenyl)-1-{[(1S,2R)-2-{2-[(6R, 9S)-2,2-dioxido-2-thia-1,7-diazabicyclo[4.3.1]dec-9-yl]ethyl}cyclohexyl]carbamoyl}-2-(tetrahydro-2H-pyran-4-yl)ethyl]carbamate To a solution of (6R,9S)-tert-butyl 9-(2-((1R,2S)-2-((2S,3R)-3-(4-chlorophenyl)-2-((methoxycarbonyl)amino)-3-(tetrahydro-2H-pyran-4-yl)propanamido)cyclohexyl)ethyl)-2-thia-1,7-diazabicyclo[4.3.1]decane-7-carboxylate 2,2-dioxide (60 mg, 0.081 mmol) in CH$_2$Cl$_2$ (1 mL) at RT was added TFA (0.19 mL, 2.4 mmol) in one portion to afford a homogenous mixture. The mixture was stirred at RT for 2 h whereupon the mixture was concentrated under reduced pressure. The resultant residue was azeotroped with CH$_2$Cl$_2$ (3×3 mL) multiple times and was concentrated to dryness. The crude product was purified by reverse phase HPLC (Gilson, C18 column: gradient 10-100% acetonitrile in water with 0.05% TFA as buffer, 12 min method, detection=220 nM). The product was isolated after lyophilization as the TFA salt. MS: m/z=639.5 (M+H)$^+$.

Example 26

Methyl ((2S,3R)-1-((2-(2-((6R,9S)-2,2-dioxido-2-thia-1,7-diazabicyclo[4.3.1]decan-9-yl)ethyl)-3,4-difluorophenyl)amino)-3-(4-fluorophenyl)-3-((1r,4R)-4-methoxycyclohexyl)-1-oxopropan-2-yl)carbamate

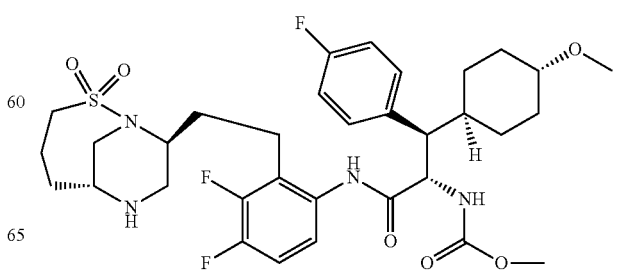

The title compound was prepared from Intermediate D and Intermediate 8 using the procedure described for Example 13. LCMS m/z=681 (M+H)⁺.

Example 27

(2S,3R)-2-Amino-N-(4-(2-((6R,9S)-2,2-dioxido-2-thia-1,7-diazabicyclo[4.3.1]decan-9-yl)ethyl)-5-fluoropyridin-3-yl)-3-(4-fluorophenyl)-3-((1r,4R)-4-methoxycyclohexyl)propanamide

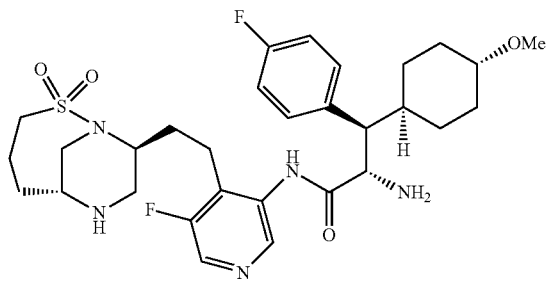 [SMILES: CO[C@H]1CC[C@H]([C@H](c2ccc(F)cc2)[C@H](N)C(=O)Nc2cncc(F)c2CC[C@H]2CN[C@@H]3CCCS(=O)(=O)N2C3)CC1]

The title compound was prepared from Intermediate F and Intermediate 8 using the procedure described for Example 6. LCMS m/z=606.5 (M+H)⁺.

Example 28

Methyl [(1S,2R)-2-(2,2-dimethyltetrahydro-2H-pyran-4-yl)-1-[(2-{2-[(6R,9S)-2,2-dioxido-2-thia-1,7-diazabicyclo[4.3.1]dec-9-yl]ethyl}-3,4-difluorophenyl)carbamoyl]-2-(4-fluorophenyl)ethyl] carbamate

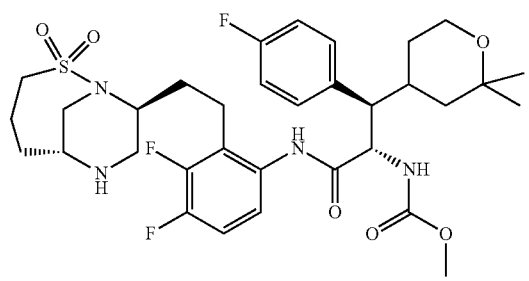 [SMILES: COC(=O)N[C@H](C(=O)Nc1ccc(F)c(F)c1CC[C@H]1CN[C@@H]2CCCS(=O)(=O)N1C2)[C@@H](c1ccc(F)cc1)C1CCOC(C)(C)C1]

The title compound was prepared from Intermediate D and Intermediate 31 using the procedure described for Example 13. LCMS m/z=681 (M+H)⁺.

Example 29

Methyl [(1S,2R)-2-(4-chlorophenyl)-2-(2,2-dimethyltetrahydro-2H-pyran-4-yl)-1-{[(1S,2R)-2-{2-[(6R,9S)-2,2-dioxido-2-thia-1,7-diazabicyclo[4.3.1]dec-9-yl]ethyl}cyclopentyl]carbamoyl}ethyl]carbamate

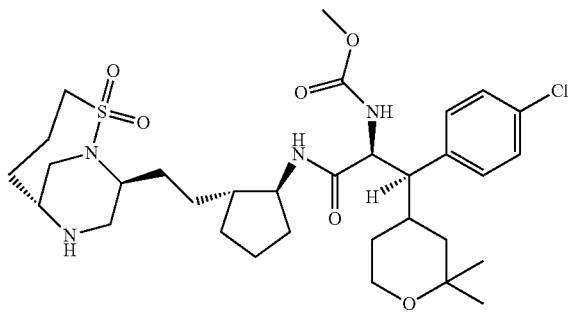 [SMILES: COC(=O)N[C@H](C(=O)N[C@H]1CCC[C@@H]1CC[C@H]1CN[C@@H]2CCCS(=O)(=O)N1C2)[C@@H](c1ccc(Cl)cc1)C1CCOC(C)(C)C1]

The title compound was prepared from Intermediate H and Intermediate 7 using the procedure described for Example 8. LCMS m/z=653.5 (M+H)⁺.

Example 30

Methyl [(1S,2R)-2-[(2R,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-5-fluorophenyl)carbamoyl]-2-(4-fluorophenyl)ethyl] carbamate

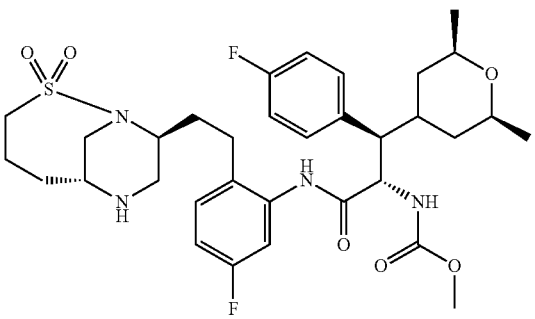 [SMILES: COC(=O)N[C@H](C(=O)Nc1cc(F)ccc1CC[C@H]1CN[C@@H]2CCCS(=O)(=O)N1C2)[C@@H](c1ccc(F)cc1)C1C[C@@H](C)O[C@@H](C)C1]

The title compound was prepared from Intermediate C and Intermediate 21 using the procedure described for Example 13. LCMS m/z=663.3 (M+H)⁺.

Example 31

(2S,3R)-2-Amino-3-(4-chlorophenyl)-3-((2R,4r,6S)-2,6-dimethyltetrahydro-2H-pyran-4-yl)-N-(4-(2-((6R,9S)-2,2-dioxido-2-thia-1,7-diazabicyclo[4.3.1]decan-9-yl)ethyl)-5-fluoropyridin-3-yl)propanamide

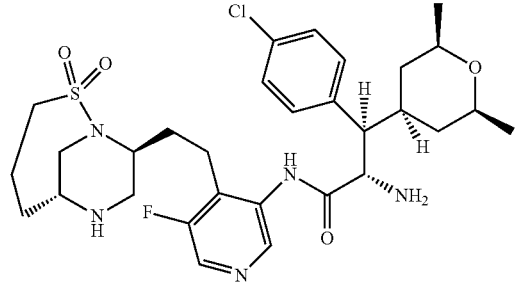 [SMILES: C[C@@H]1C[C@H]([C@H](c2ccc(Cl)cc2)[C@H](N)C(=O)Nc2cncc(F)c2CC[C@H]2CN[C@@H]3CCCS(=O)(=O)N2C3)C[C@H](C)O1]

Step 1. (6R,9S)-tert-butyl 9-(2-(3-((2S,3R)-2-azido-3-(4-chlorophenyl)-3-((2R,6S)-2,6-dimethyltetrahydro-2H-pyran-4-yl)propanamido)-5-fluoropyridin-4-yl)ethyl)-2-thia-1,7-diazabicyclo[4.3.1]decane-7-carboxylate 2,2-dioxide

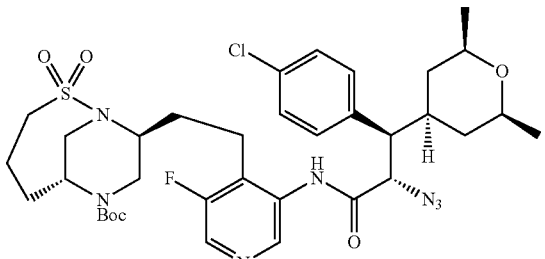

To a round bottom flask charged with a stir bar at RT was added (6R,9S)-tert-butyl 9-(2-(3-amino-5-fluoropyridin-4-yl)ethyl)-2-thia-1,7-diazabicyclo[4.3.1]decane-7-carboxylate 2,2-dioxide (Intermediate F) (44 mg, 0.10 mmol) and (2S,3R)-2-azido-3-(4-chlorophenyl)-3-((2R,6S)-2,6-dimethyltetrahydro-2H-pyran-4-yl)propanoic acid (Intermediate 20) (45 mg, 0.13 mmol). Dry pyridine (1.5 mL) was added to the mixture which was cooled to −15° C. (ice/acetone mix) whereupon POCl₃ (12 μL, 0.13 mmol) was added dropwise to the mixture. The reaction mixture was stirred at −15° C. for 1.5 h whereupon sat. aq. NaHCO₃ (1 mL) was added followed by EtOAc (10 mL). The layers were separated and the aqueous layer was extracted with EtOAc (3×15 mL). The organic layers were combined and were washed with brine (1×7 mL). The organic layer was dried (Na₂SO₄), filtered, and concentrated under reduced pressure. The crude material was dissolved in CH₂Cl₂ (2 mL) and was loaded onto 2×1000 µM preparative chromatography plates. The plates were eluted with a mixture of CH₂Cl₂/MeOH (95:5) to afford the title compound. MS: m/z=748.7 (M+H)⁺.

Step 2. (6R,9S)-tert-butyl 9-(2-(3-((2S,3R)-2-amino-3-(4-chlorophenyl)-3-((2R,4R,6S)-2,6-dimethyltetrahydro-2H-pyran-4-yl)propanamido)-5-fluoropyridin-4-yl)ethyl)-2-thia-1,7-diazabicyclo[4.3.1]decane-7-carboxylate 2,2-dioxide

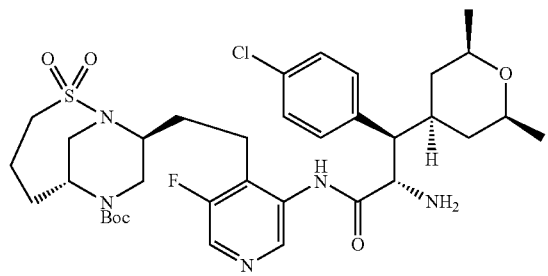 [SMILES: C[C@@H]1C[C@H]([C@H](c2ccc(Cl)cc2)[C@H](N)C(=O)Nc2cncc(F)c2CC[C@H]2CN(C(=O)OC(C)(C)C)[C@@H]3CCCS(=O)(=O)N2C3)C[C@H](C)O1]

To a round bottom flask charged with (6R,9S)-tert-butyl 9-(2-(3-((2S,3R)-2-azido-3-(4-chlorophenyl)-3-((2R,6S)-2,6-dimethyltetrahydro-2H-pyran-4-yl)propanamido)-5-fluoropyridin-4-yl)ethyl)-2-thia-1,7-diazabicyclo[4.3.1]decane-7-carboxylate 2,2-dioxide. (44 mg, 0.06 mmol) was added THF/water (2 mL/0.5 mL) to afford a homogenous mixture. Triphenylphosphine resin (24 mg, 0.09 mmol) was added to the flask which was affixed with a reflux condenser and heated at 70° C. under N₂ for 12 h. The reaction mixture was cooled to RT and was filtered through a disposable filter to remove the resin. The resin was washed with EtOAc (3×5 mL) and the resulting filtrate was concentrated under reduced pressure to afford the title compound. MS: m/z=722.7 (M+H)⁺. This material was taken on to the next transformation without purification.

Step 3. (2S,3R)-2-Amino-3-(4-chlorophenyl)-3-((2R,4R,6S)-2,6-dimethyltetrahydro-2H-pyran-4-yl)-N-(4-(2-((6R,9S)-2,2-dioxido-2-thia-1,7-diazabicyclo[4.3.1]decan-9-yl)ethyl)-5-fluoropyridin-3-yl)propanamide To a solution of (6R,9S)-tert-butyl 9-(2-(3-((2S,3R)-2-amino-3-(4-chlorophenyl)-3-((2R,4R,6S)-2,6-dimethyltetrahydro-2H-pyran-4-yl)propanamido)-5-fluoropyridin-4-yl)ethyl)-2-thia-1,7-diazabicyclo[4.3.1]decane-7-carboxylate 2,2-dioxide (39 mg, 0.05 mmol) in CH₂Cl₂ (2 mL) under N₂ at RT was added TFA (0.20 mL, 2.6 mmol) dropwise. The mixture was stirred for 1.5 h at RT whereupon the mixture concentrated to dryness. The resulting material was azeotroped with CH₂Cl₂ (4×5 mL) and placed under high vacuum. The crude product was purified by reverse phase HPLC (Gilson, C18 column: gradient 10-100% acetonitrile in water with 0.05% TFA as buffer, 12 min method, detection=254 nM) to afford the title product after lyophilization as the tri TFA salt form. MS: m/z=622.6 (M+H)⁺.

Example 32

Methyl [(1S,2R)-2-(4-chlorophenyl)-1-[(2-{2-[(6R,9S)-2,2-dioxido-2-thia-1,7-diazabicyclo[4.3.1]dec-9-yl]ethyl}-3,6-difluorophenyl)carbamoyl]-2-(tetrahydro-2H-pyran-4-yl)ethyl]carbamate

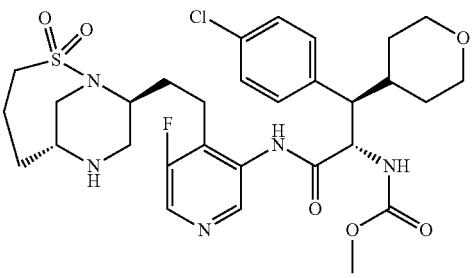 [SMILES: COC(=O)N[C@H](C(=O)Nc1cncc(F)c1CC[C@H]1CN[C@@H]2CCCS(=O)(=O)N1C2)[C@@H](c1ccc(Cl)cc1)C1CCOCC1]

The title compound was prepared from Intermediate E and Intermediate 13 using the procedure described for Example 13. LCMS m/z=669.4 (M+H)⁺.

Example 33

(βR)—N-{2-[2-(2,2-Dioxido-2-thia-1,7-diazabicyclo[4.3.1]dec-9-yl)ethyl]-3-fluorophenyl}-β-(4-fluorophenyl)-4-(trifluoromethyl)-L-phenylalaninamide

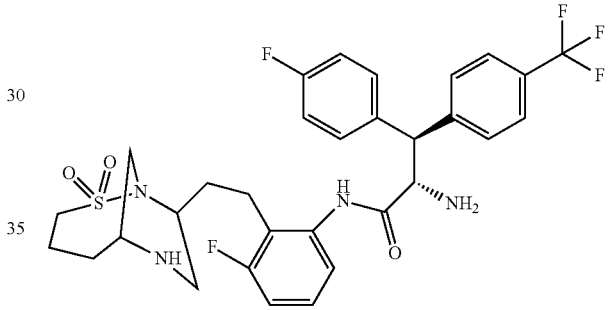

The title compound was prepared from Intermediate B and Intermediate 15 using the procedure described for Example 1. HRMS (ESI) m/z (M+H)⁺: 637.2238, calcd. for C₃₁H₃₅F₅N₄O₃S=637.2266.

Example 34

Methyl [(1S,2S)-2-(2,3-dihydro-1H-inden-5-yl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate

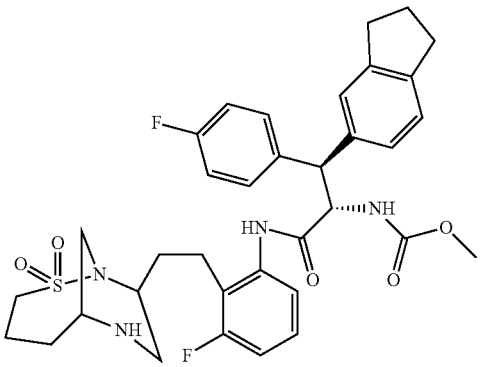 [SMILES: COC(=O)N[C@H](C(=O)Nc1cccc(F)c1CCC1CNC2CCCS(=O)(=O)N1C2)[C@@H](c1ccc(F)cc1)c1ccc2c(c1)CCC2]

The title compound was prepared from Intermediate B and Intermediate 17 using the procedure described for Example 3. HRMS (ESI) m/z (M+H)⁺: 667.2755, calcd. for C₃₅H₄₂F₂N₄O₅S=667.2760.

The compounds shown in Table 1 were made by following procedures analogous to Examples 1 to 34.

TABLE 1

| Example No. | Structure | IUPAC Name | Exact Mass [M + H]+ |
|---|---|---|---|
| 35 | 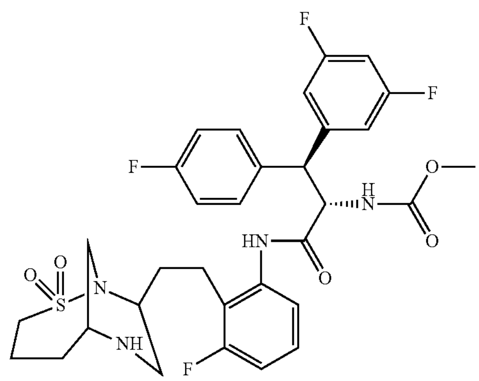 [SMILES: COC(=O)N[C@H](C(=O)Nc1cccc(F)c1CCC1CNC2CCCS(=O)(=O)N1C2)[C@@H](c1ccc(F)cc1)c1cc(F)cc(F)c1] | methyl [(1S,2S)-2-(3,5-difluorophenyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate | 663.2 |
| 36 | 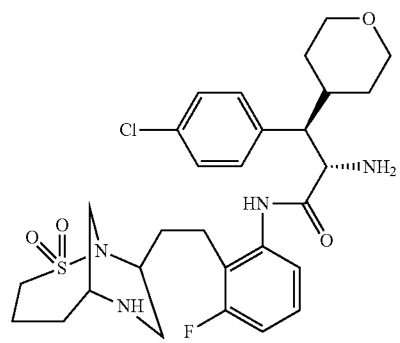 [SMILES: N[C@H](C(=O)Nc1cccc(F)c1CCC1CNC2CCCS(=O)(=O)N1C2)[C@@H](c1ccc(Cl)cc1)C1CCOCC1] | (βR)-4-chloro-N-{2-[2-(2,2-dioxido-2-thia-1,7-diazabicyclo[4.3.1]dec-9-yl)ethyl]-3-fluorophenyl}-β-(tetrahydro-2H-pyran-4-yl)-L-phenylalaninamide | 593.2 |
| 37 | 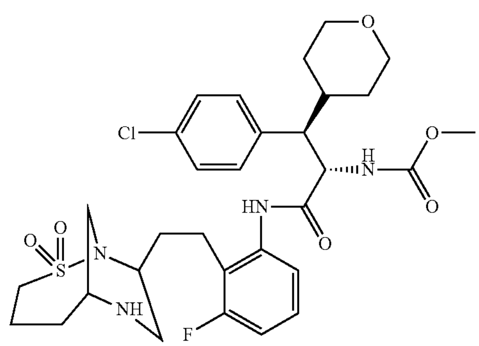 [SMILES: COC(=O)N[C@H](C(=O)Nc1cccc(F)c1CCC1CNC2CCCS(=O)(=O)N1C2)[C@@H](c1ccc(Cl)cc1)C1CCOCC1] | methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-(tetrahydro-2H-pyran-4-yl)ethyl]carbamate | 651.2 |
| 38 | 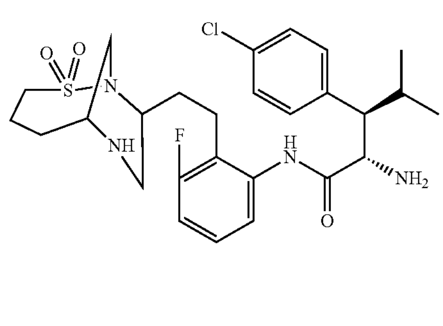 [SMILES: CC(C)[C@H](c1ccc(Cl)cc1)[C@H](N)C(=O)Nc1cccc(F)c1CCC1CNC2CCCS(=O)(=O)N1C2] | (βR)-4-chloro-N-{2-[2-(2,2-dioxido-2-thia-1,7-diazabicyclo[4.3.1]dec-9-yl)ethyl]-3-fluorophenyl}-β-(1-methylethyl)-L-phenylalaninamide | 551.2 |

TABLE 1-continued

| Example No. | Structure | IUPAC Name | Exact Mass [M + H]+ |
|---|---|---|---|
| 39 | 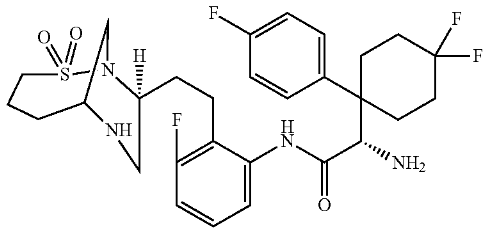 [SMILES: N[C@H](C(=O)Nc1cccc(F)c1CC[C@H]1CNC2CCCS(=O)(=O)N1C2)C1(c2ccc(F)cc2)CCC(F)(F)CC1] | (2S)-2-amino-2-[4,4-difluoro-1-(4-fluorophenyl)cyclohexyl]-N-(2-{2-[(9S)-2,2-dioxido-2-thia-1,7-diazabicyclo[4.3.1]dec-9-yl]ethyl}-3-fluorophenyl)ethanamide | 597.3 |
| 40 | 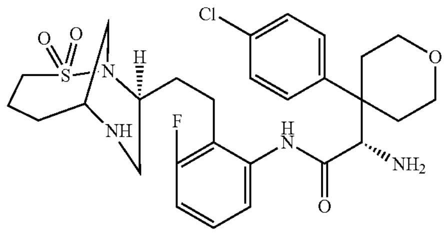 [SMILES: N[C@H](C(=O)Nc1cccc(F)c1CC[C@H]1CNC2CCCS(=O)(=O)N1C2)C1(c2ccc(Cl)cc2)CCOCC1] | (2S)-2-amino-2-[4-(4-chlorophenyl)tetrahydro-2H-pyran-4-yl]-N-(2-{2-[(9S)-2,2-dioxido-2-thia-1,7-diazabicyclo[4.3.1]dec-9-yl]ethyl}-3-fluorophenyl)ethanamide | 579.2 |
| 41 | 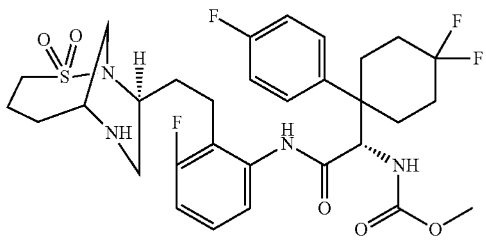 [SMILES: COC(=O)N[C@H](C(=O)Nc1cccc(F)c1CC[C@H]1CNC2CCCS(=O)(=O)N1C2)C1(c2ccc(F)cc2)CCC(F)(F)CC1] | methyl {(1S)-1-[4,4-difluoro-1-(4-fluorophenyl)cyclohexyl]-2-[(2-{2-[(9S)-2,2-dioxido-2-thia-1,7-diazabicyclo[4.3.1]dec-9-yl]ethyl}-3-fluorophenyl)amino]-2-oxoethyl}carbamate | 655.3 |
| 42 | 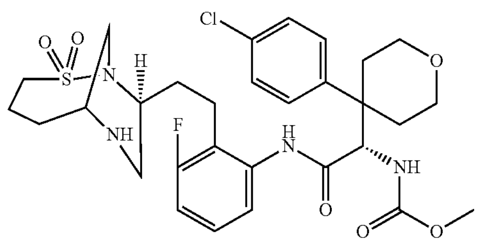 [SMILES: COC(=O)N[C@H](C(=O)Nc1cccc(F)c1CC[C@H]1CNC2CCCS(=O)(=O)N1C2)C1(c2ccc(Cl)cc2)CCOCC1] | methyl {(1S)-1-[4-(4-chlorophenyl)tetrahydro-2H-pyran-4-yl]-2-[(2-{2-[(9S)-2,2-dioxido-2-thia-1,7-diazabicyclo[4.3.1]dec-9-yl]ethyl}-3-fluorophenyl)amino]-2-oxoethyl}carbamate | 637.2 |
| 43 | 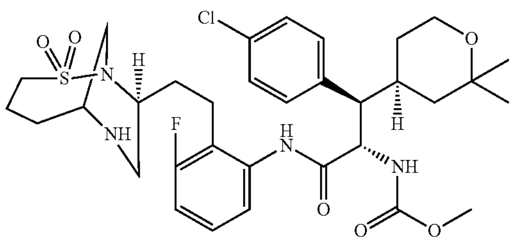 [SMILES: COC(=O)N[C@H](C(=O)Nc1cccc(F)c1CC[C@H]1CNC2CCCS(=O)(=O)N1C2)[C@@H](c1ccc(Cl)cc1)[C@H]1CCOC(C)(C)C1] | methyl {(1S,2R)-2-(4-chlorophenyl)-2-[(4S)-2,2-dimethyltetrahydro-2H-pyran-4-yl]-1-[(2-{2-[(9S)-2,2-dioxido-2-thia-1,7-diazabicyclo[4.3.1]dec-9-yl]ethyl}-3-fluorophenyl)carbamoyl]ethyl}carbamate | 679.3 |
| 44 | 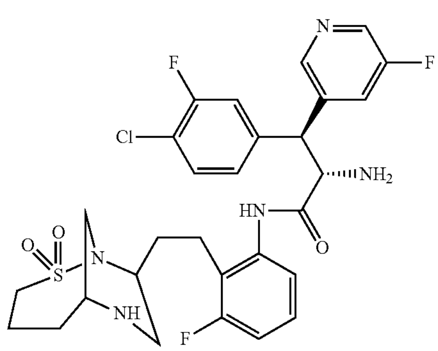 [SMILES: N[C@H](C(=O)Nc1cccc(F)c1CCC1CNC2CCCS(=O)(=O)N1C2)[C@H](c1cncc(F)c1)c1ccc(Cl)c(F)c1] | (βS)-4-chloro-N-{2-[2-(2,2-dioxido-2-thia-1,7-diazabicyclo[4.3.1]dec-9-yl)ethyl]-3-fluorophenyl}-3-fluoro-β-(5-fluoropyridin-3-yl)-L-phenylalaninamide | 622.2 |

TABLE 1-continued

| Example No. | Structure | IUPAC Name | Exact Mass [M + H]+ |
|---|---|---|---|
| 45 | 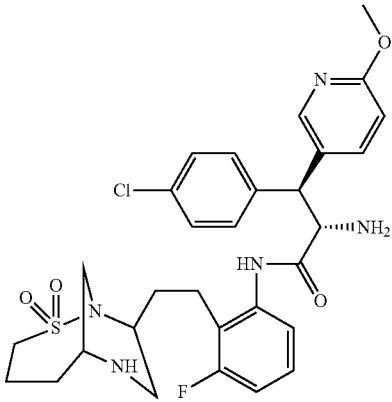 [SMILES: COc1ccc([C@H](c2ccc(Cl)cc2)[C@H](N)C(=O)Nc2cccc(F)c2CCC2CNC3CCCS(=O)(=O)N2C3)cn1] | (βS)-4-chloro-N-{2-[2-(2,2-dioxido-2-thia-1,7-diazabicyclo[4.3.1]dec-9-yl)ethyl]-3-fluorophenyl}-β-(6-methoxypyridin-3-yl)-L-phenylalaninamide | 616.2 |
| 46 | 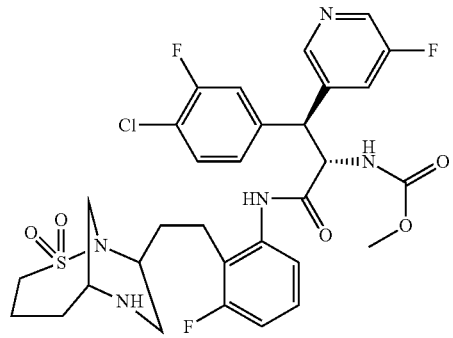 [SMILES: COC(=O)N[C@H](C(=O)Nc1cccc(F)c1CCC1CNC2CCCS(=O)(=O)N1C2)[C@H](c1cncc(F)c1)c1ccc(Cl)c(F)c1] | methyl [(1S,2S)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-2-(5-fluoropyridin-3-yl)ethyl]carbamate | 680.2 |
| 47 | 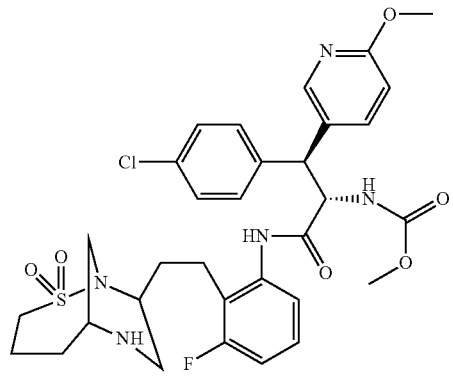 [SMILES: COC(=O)N[C@H](C(=O)Nc1cccc(F)c1CCC1CNC2CCCS(=O)(=O)N1C2)[C@@H](c1ccc(Cl)cc1)c1ccc(OC)nc1] | methyl [(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-(6-methoxypyridin-3-yl)ethyl]carbamate | 674.2 |
| 48 | 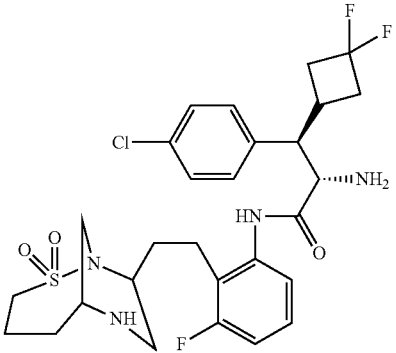 [SMILES: N[C@H](C(=O)Nc1cccc(F)c1CCC1CNC2CCCS(=O)(=O)N1C2)[C@@H](c1ccc(Cl)cc1)C1CC(F)(F)C1] | (βR)-4-chloro-β-(3,3-difluorocyclobutyl)-N-{2-[2-(2,2-dioxido-2-thia-1,7-diazabicyclo[4.3.1]dec-9-yl)ethyl]-3-fluorophenyl}-L-phenylalaninamide | 599.2 |

TABLE 1-continued

| Example No. | Structure | IUPAC Name | Exact Mass [M + H]+ |
|---|---|---|---|
| 49 | 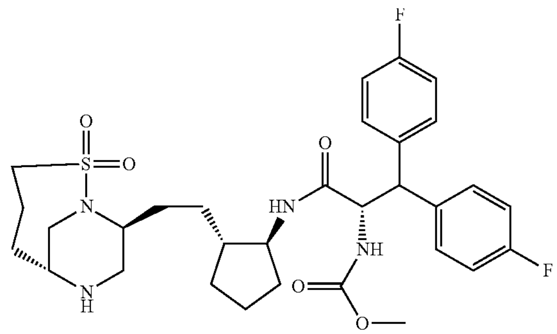 [SMILES: COC(=O)N[C@H](C(=O)N[C@H]1CCC[C@@H]1CC[C@H]1CN[C@@H]2CCCS(=O)(=O)N1C2)C(c1ccc(F)cc1)c1ccc(F)cc1] | methyl [(1S)-1-[bis(4-fluorophenyl)methyl]-2-{[(1S,2R)-2-{2-[(6R,9S)-2,2-dioxido-2-thia-1,7-diazabicyclo[4.3.1]dec-9-yl]ethyl}cyclopentyl]amino}-2-oxoethyl]carbamate | 619.3 |
| 50 | 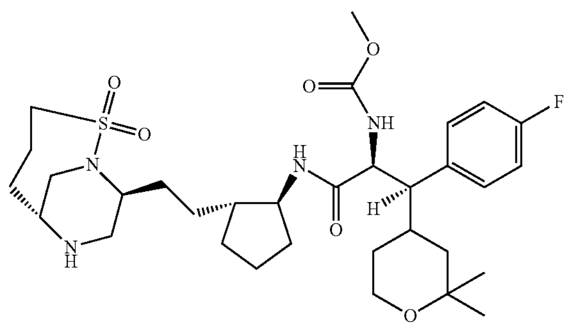 [SMILES: COC(=O)N[C@H](C(=O)N[C@H]1CCC[C@@H]1CC[C@H]1CN[C@@H]2CCCS(=O)(=O)N1C2)[C@@H](c1ccc(F)cc1)C1CCOC(C)(C)C1] | methyl [(1S,2R)-2-(2,2-dimethyltetrahydro-2H-pyran-4-yl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(4-fluorophenyl)ethyl]carbamate | 637.3 |
| 51 | 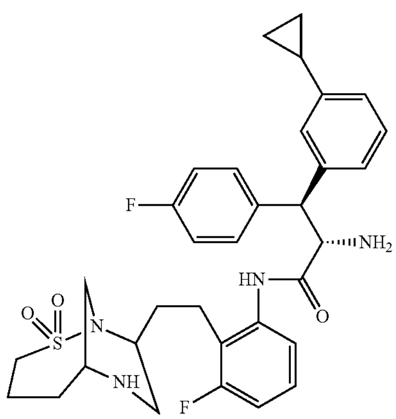 [SMILES: N[C@H](C(=O)Nc1cccc(F)c1CCC1CNC2CCCS(=O)(=O)N1C2)[C@@H](c1ccc(F)cc1)c1cccc(C2CC2)c1] | (βS)-3-cyclopropyl-N-{2-[2-(2,2-dioxido-2-thia-1,7-diazabicyclo[4.3.1]dec-9-yl)ethyl]-3-fluorophenyl}-β-(4-fluorophenyl)-L-phenylalaninamide | 609.3 |
| 52 | 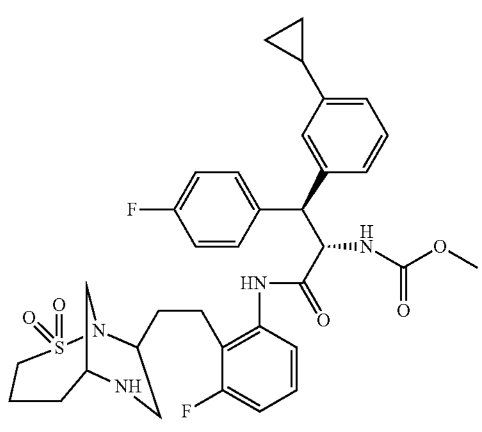 [SMILES: COC(=O)N[C@H](C(=O)Nc1cccc(F)c1CCC1CNC2CCCS(=O)(=O)N1C2)[C@@H](c1ccc(F)cc1)c1cccc(C2CC2)c1] | methyl [(1S,2S)-2-(3-cyclopropylphenyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate | 667.3 |

TABLE 1-continued

| Example No. | Structure | IUPAC Name | Exact Mass [M + H]+ |
|---|---|---|---|
| 53 | 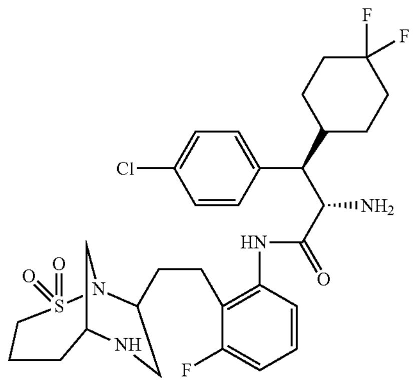 [SMILES: N[C@H](C(=O)Nc1cccc(F)c1CCC1CNC2CCCS(=O)(=O)N1C2)[C@@H](c1ccc(Cl)cc1)C1CCC(F)(F)CC1] | (βR)-4-chloro-β-(4,4-difluorocyclohexyl)-N-{2-[2-(2,2-dioxido-2-thia-1,7-diazabicyclo[4.3.1]dec-9-yl)ethyl]-3-fluorophenyl}-L-phenylalaninamide | 627.2 |
| 54 | 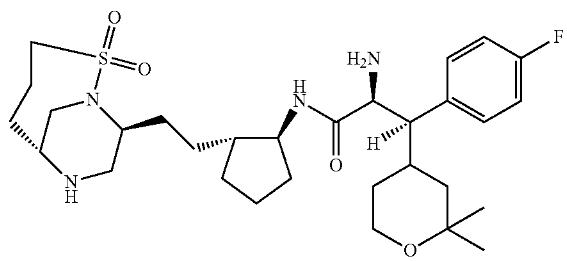 [SMILES: CC1(C)CC([C@H](c2ccc(F)cc2)[C@H](N)C(=O)N[C@H]2CCC[C@@H]2CC[C@H]2CN[C@@H]3CCCS(=O)(=O)N2C3)CCO1] | (βR)-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-4-fluoro-L-phenylalaninamide | 579.3 |
| 55 | 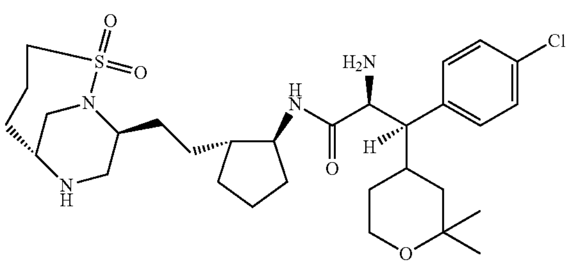 [SMILES: CC1(C)CC([C@H](c2ccc(Cl)cc2)[C@H](N)C(=O)N[C@H]2CCC[C@@H]2CC[C@H]2CN[C@@H]3CCCS(=O)(=O)N2C3)CCO1] | (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 595.3 |
| 56 | 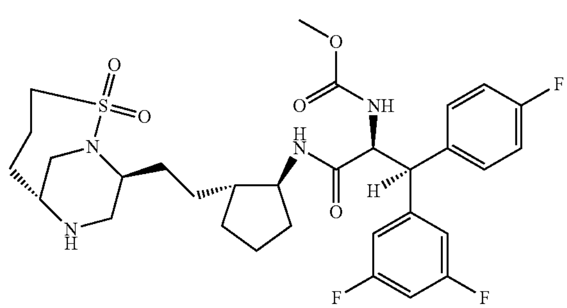 [SMILES: COC(=O)N[C@H](C(=O)N[C@H]1CCC[C@@H]1CC[C@H]1CN[C@@H]2CCCS(=O)(=O)N1C2)[C@@H](c1ccc(F)cc1)c1cc(F)cc(F)c1] | methyl [(1S,2S)-2-(3,5-difluorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(4-fluorophenyl)ethyl]carbamate | 637.3 |
| 57 | 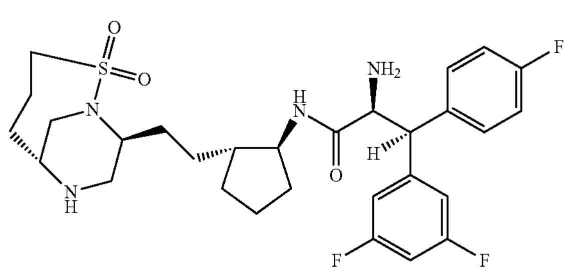 [SMILES: N[C@H](C(=O)N[C@H]1CCC[C@@H]1CC[C@H]1CN[C@@H]2CCCS(=O)(=O)N1C2)[C@@H](c1ccc(F)cc1)c1cc(F)cc(F)c1] | (βS)-β-(3,5-difluorophenyl)-N-[(1S,2R)-2-{2-[(6R,9S)-2,2-dioxido-2-thia-1,7-diazabicyclo[4.3.1]dec-9-yl]ethyl}cyclopentyl]-4-fluoro-L-phenylalaninamide | 579.3 |

TABLE 1-continued

| Example No. | Structure | IUPAC Name | Exact Mass [M + H]+ |
|---|---|---|---|
| 58 | 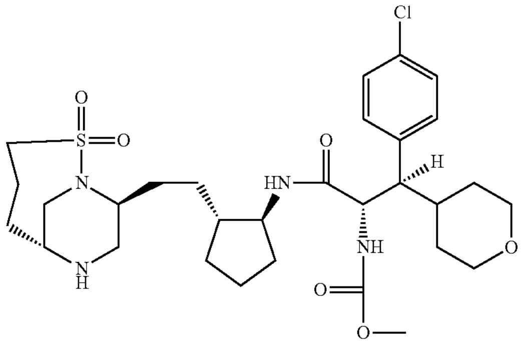 [SMILES: COC(=O)N[C@H](C(=O)N[C@H]1CCC[C@@H]1CC[C@H]1CN[C@@H]2CCCS(=O)(=O)N1C2)[C@@H](c1ccc(Cl)cc1)C1CCOCC1] | methyl [(1S,2R)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(tetrahydro-2H-pyran-4-yl)ethyl]carbamate | 625.3 |
| 59 | 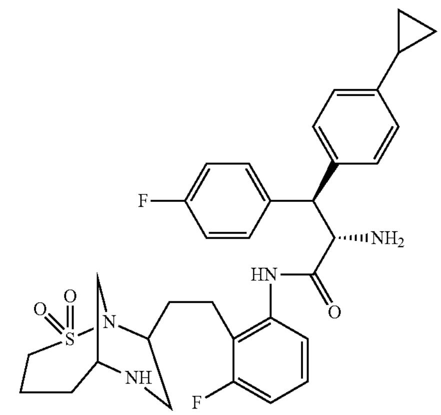 [SMILES: N[C@H](C(=O)Nc1cccc(F)c1CCC1CNC2CCCS(=O)(=O)N1C2)[C@@H](c1ccc(F)cc1)c1ccc(C2CC2)cc1] | (βR)-4-cyclopropyl-N-{2-[2-(2,2-dioxido-2-thia-1,7-diazabicyclo[4.3.1]dec-9-yl)ethyl]-3-fluorophenyl}-β-(4-fluorophenyl)-L-phenylalaninamide | 609.3 |
| 60 | 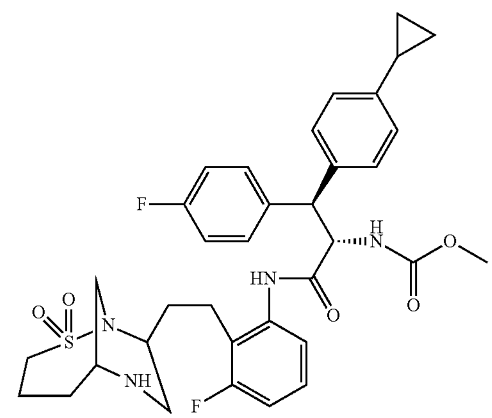 [SMILES: COC(=O)N[C@H](C(=O)Nc1cccc(F)c1CCC1CNC2CCCS(=O)(=O)N1C2)[C@@H](c1ccc(F)cc1)c1ccc(C2CC2)cc1] | methyl [(1S,2R)-2-(4-cyclopropylphenyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate | 667.3 |
| 61 | 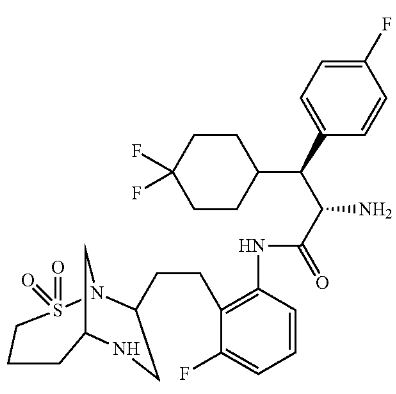 [SMILES: N[C@H](C(=O)Nc1cccc(F)c1CCC1CNC2CCCS(=O)(=O)N1C2)[C@H](c1ccc(F)cc1)C1CCC(F)(F)CC1] | (βS)-β-(4,4-difluorocyclohexyl)-N-{2-[2-(2,2-dioxido-2-thia-1,7-diazabicyclo[4.3.1]dec-9-yl)ethyl]-3-fluorophenyl}-4-fluoro-L-phenylalaninamide | 611.3 |

TABLE 1-continued

| Example No. | Structure | IUPAC Name | Exact Mass [M + H]+ |
|---|---|---|---|
| 62 | 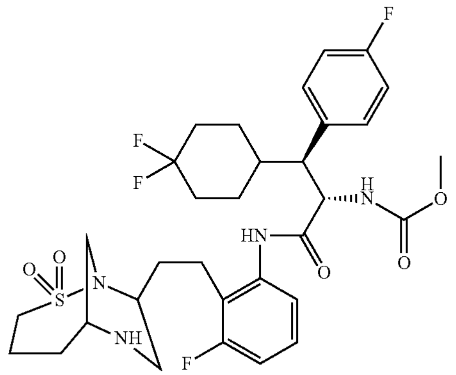 [SMILES: COC(=O)N[C@H](C(=O)Nc1cccc(F)c1CCC1CNC2CCCS(=O)(=O)N1C2)[C@H](c1ccc(F)cc1)C1CCC(F)(F)CC1] | methyl [(1S,2S)-2-(4,4-difluorocyclohexyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate | 669.3 |
| 63 | 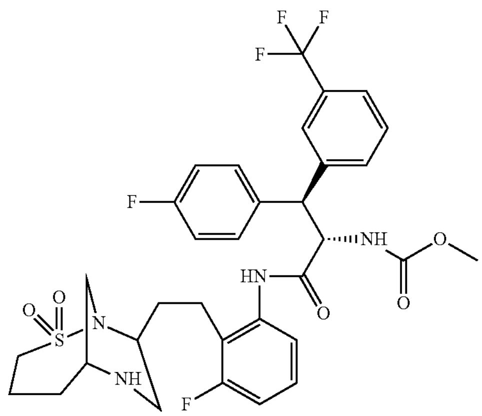 [SMILES: COC(=O)N[C@H](C(=O)Nc1cccc(F)c1CCC1CNC2CCCS(=O)(=O)N1C2)[C@@H](c1ccc(F)cc1)c1cccc(C(F)(F)F)c1] | methyl [(1S)-2-({2-[2-(2,2-dioxido-2-thia-1,7-diazabicyclo[4.3.1]dec-9-yl)ethyl]-3-fluorophenyl}amino)-1-{(S)-(4-fluorophenyl)[3-(trifluoromethyl)phenyl]methyl}-2-oxoethyl]carbamate | 695.2 |
| 64 | 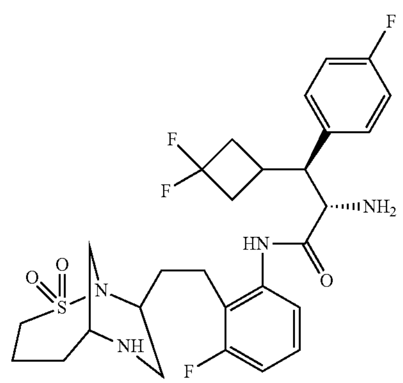 [SMILES: N[C@H](C(=O)Nc1cccc(F)c1CCC1CNC2CCCS(=O)(=O)N1C2)[C@H](c1ccc(F)cc1)C1CC(F)(F)C1] | (βS)-β-(3,3-difluorocyclobutyl)-N-{2-[2-(2,2-dioxido-2-thia-1,7-diazabicyclo[4.3.1]dec-9-yl)ethyl]-3-fluorophenyl}-4-fluoro-L-phenylalaninamide | 583.2 |
| 65 | 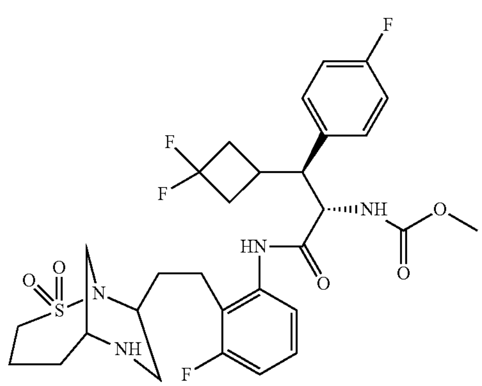 [SMILES: COC(=O)N[C@H](C(=O)Nc1cccc(F)c1CCC1CNC2CCCS(=O)(=O)N1C2)[C@H](c1ccc(F)cc1)C1CC(F)(F)C1] | methyl [(1S,2S)-2-(3,3-difluorocyclobutyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate | 641.2 |

TABLE 1-continued

| Example No. | Structure | IUPAC Name | Exact Mass [M + H]+ |
|---|---|---|---|
| 66 | 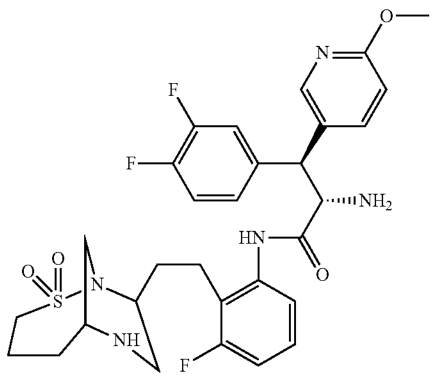 [SMILES: COc1ccc([C@H](c2ccc(F)c(F)c2)[C@H](N)C(=O)Nc2cccc(F)c2CCC2CNC3CCCS(=O)(=O)N2C3)cn1] | (βS)-N-{2-[2-(2,2-dioxido-2-thia-1,7-diazabicyclo[4.3.1]dec-9-yl)ethyl]-3-fluorophenyl}-3,4-difluoro-β-(6-methoxypyridin-3-yl)-L-phenylalaninamide | 618.2 |
| 67 | 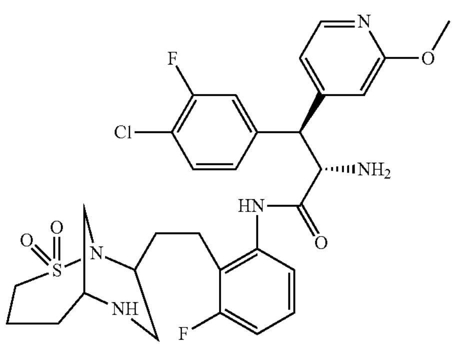 [SMILES: COc1cc([C@H](c2ccc(Cl)c(F)c2)[C@H](N)C(=O)Nc2cccc(F)c2CCC2CNC3CCCS(=O)(=O)N2C3)ccn1] | (βR)-4-chloro-N-{2-[2-(2,2-dioxido-2-thia-1,7-diazabicyclo[4.3.1]dec-9-yl)ethyl]-3-fluorophenyl}-3-fluoro-β-(2-methoxypyridin-4-yl)-L-phenylalaninamide | 634.2 |
| 68 | 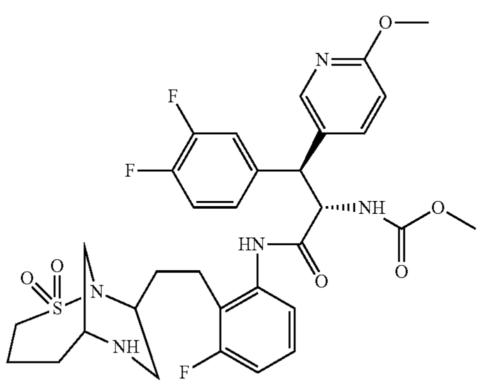 [SMILES: COC(=O)N[C@H](C(=O)Nc1cccc(F)c1CCC1CNC2CCCS(=O)(=O)N1C2)[C@H](c1ccc(OC)nc1)c1ccc(F)c(F)c1] | methyl [(1S,2R)-2-(3,4-difluorophenyl)-1-({2-[2-(2,2-dioxido-2-thia-1,7-diazabicyclo[4.3.1]dec-9-yl)ethyl]-3-fluorophenyl}carbamoyl)-2-(6-methoxypyridin-3-yl)ethyl]carbamate | 676.2 |
| 69 | 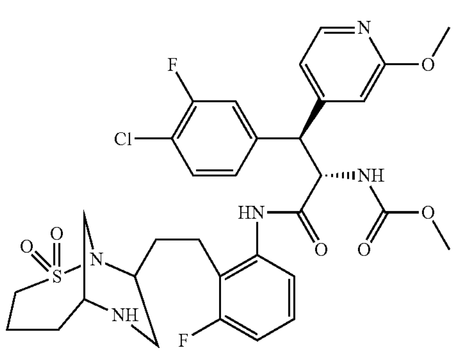 [SMILES: COC(=O)N[C@H](C(=O)Nc1cccc(F)c1CCC1CNC2CCCS(=O)(=O)N1C2)[C@H](c1ccnc(OC)c1)c1ccc(Cl)c(F)c1] | methyl [(1S,2R)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-2-(2-methoxypyridin-4-yl)ethyl]carbamate | 692.2 |

TABLE 1-continued

| Example No. | Structure | IUPAC Name | Exact Mass [M + H]+ |
|---|---|---|---|
| 70 | 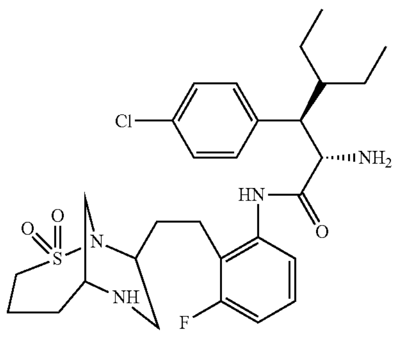 [SMILES: CCC(CC)[C@H](c1ccc(Cl)cc1)[C@H](N)C(=O)Nc1cccc(F)c1CCC1CNC2CCCS(=O)(=O)N1C2] | (βR)-4-chloro-N-{2-[2-(2,2-dioxido-2-thia-1,7-diazabicyclo[4.3.1]dec-9-yl)ethyl]-3-fluorophenyl}-β-(1-ethylpropyl)-L-phenylalaninamide | 579.3 |
| 71 | 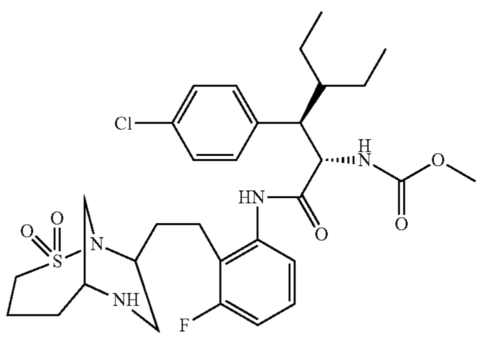 [SMILES: CCC(CC)[C@H](c1ccc(Cl)cc1)[C@H](NC(=O)OC)C(=O)Nc1cccc(F)c1CCC1CNC2CCCS(=O)(=O)N1C2] | methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-3-ethylpentyl]carbamate | 637.3 |
| 72 | 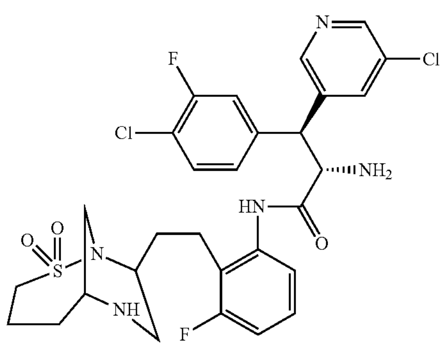 [SMILES: N[C@H](C(=O)Nc1cccc(F)c1CCC1CNC2CCCS(=O)(=O)N1C2)[C@H](c1cncc(Cl)c1)c1ccc(Cl)c(F)c1] | (βS)-4-chloro-β-(5-chloropyridin-3-yl)-N-{2-[2-(2,2-dioxido-2-thia-1,7-diazabicyclo[4.3.1]dec-9-yl)ethyl]-3-fluorophenyl}-3-fluoro-L-phenylalaninamide | 638.2 |
| 73 | 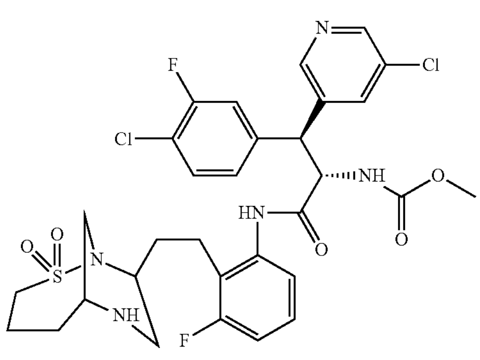 [SMILES: COC(=O)N[C@H](C(=O)Nc1cccc(F)c1CCC1CNC2CCCS(=O)(=O)N1C2)[C@H](c1cncc(Cl)c1)c1ccc(Cl)c(F)c1] | methyl [(1S,2S)-2-(4-chloro-3-fluorophenyl)-2-(5-chloropyridin-3-yl)-1-({2-[2-(2,2-dioxido-2-thia-1,7-diazabicyclo[4.3.1]dec-9-yl)ethyl]-3-fluorophenyl}carbamoyl)ethyl]carbamate | 696.2 |

TABLE 1-continued

| Example No. | Structure | IUPAC Name | Exact Mass [M + H]+ |
|---|---|---|---|
| 74 | 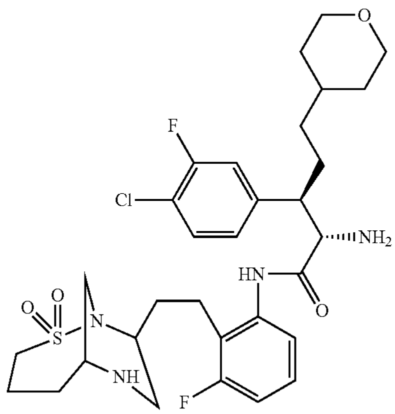 [SMILES: N[C@H](C(=O)Nc1cccc(F)c1CCC1CNC2CCCS(=O)(=O)N1C2)[C@H](CCC1CCOCC1)c1ccc(Cl)c(F)c1] | (βR)-4-chloro-N-{2-[2-(2,2-dioxido-2-thia-1,7-diazabicyclo[4.3.1]dec-9-yl)ethyl]-3-fluorophenyl}-3-fluoro-β-[2-(tetrahydro-2H-pyran-4-yl)ethyl]-L-phenylalaninamide | 639.3 |
| 75 | 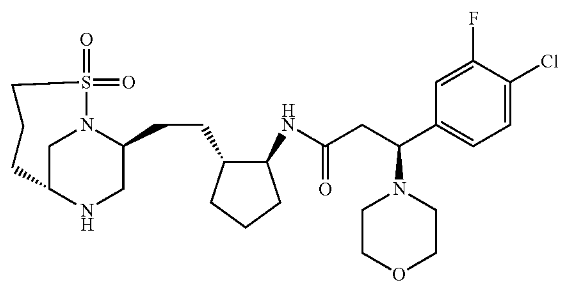 [SMILES: O=C(C[C@@H](c1ccc(Cl)c(F)c1)N1CCOCC1)N[C@H]1CCC[C@@H]1CC[C@H]1CN[C@@H]2CCCS(=O)(=O)N1C2] | (3S)-3-(4-chloro-3-fluorophenyl)-N-[(1S,2R)-2-{2-[(6R,9S)-2,2-dioxido-2-thia-1,7-diazabicyclo[4.3.1]dec-9-yl]ethyl}cyclopentyl]-3-morpholin-4-ylpropanamide | 571.3 |
| 76 | 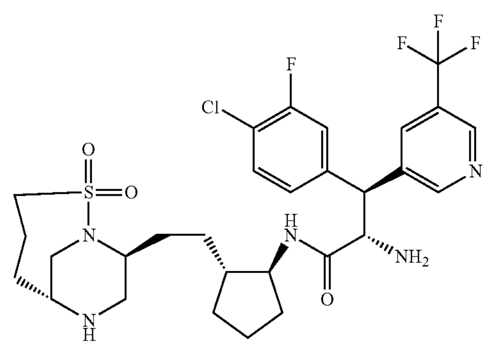 [SMILES: N[C@H](C(=O)N[C@H]1CCC[C@@H]1CC[C@H]1CN[C@@H]2CCCS(=O)(=O)N1C2)[C@H](c1cncc(C(F)(F)F)c1)c1ccc(Cl)c(F)c1] | (βS)-4-chloro-N-[(1S,2R)-2-{2-[(6R,9S)-2,2-dioxido-2-thia-1,7-diazabicyclo[4.3.1]dec-9-yl]ethyl}cyclopentyl]-3-fluoro-β-[5-(trifluoromethyl)pyridin-3-yl]-L-phenylalaninamide | 646.2 |
| 77 | 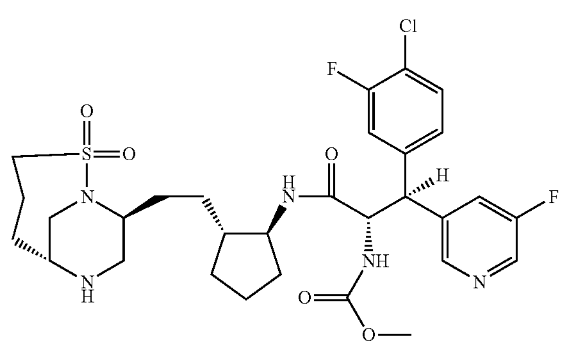 [SMILES: COC(=O)N[C@H](C(=O)N[C@H]1CCC[C@@H]1CC[C@H]1CN[C@@H]2CCCS(=O)(=O)N1C2)[C@H](c1cncc(F)c1)c1ccc(Cl)c(F)c1] | methyl [(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(5-fluoropyridin-3-yl)ethyl]carbamate | 654.2 |

TABLE 1-continued

| Example No. | Structure | IUPAC Name | Exact Mass [M + H]+ |
|---|---|---|---|
| 78 | 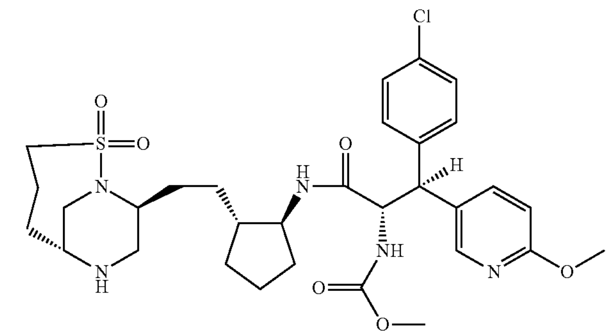 [SMILES: COC(=O)N[C@H](C(=O)N[C@H]1CCC[C@@H]1CC[C@H]1CN[C@@H]2CCCS(=O)(=O)N1C2)[C@@H](c1ccc(Cl)cc1)c1ccc(OC)nc1] | methyl [(1S,2S)-2-(4-chlorophenyl)-1-{[(1S,2R)-2-{2-[(1S,2S)-2,2-dioxido-2-thia-1,7-diazabicyclo[4.3.1]dec-9-yl]ethyl}cyclopentyl]carbamoyl}-2-(6-methoxypyridin-3-yl)ethyl]carbamate | 648.3 |
| 79 | 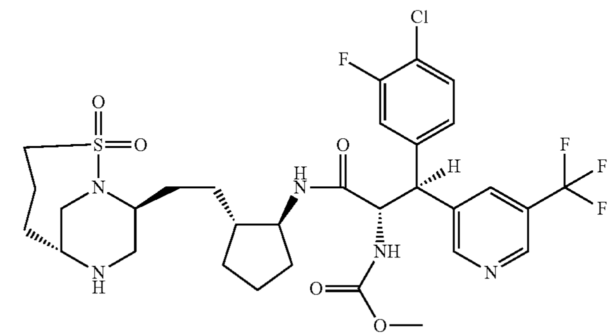 [SMILES: COC(=O)N[C@H](C(=O)N[C@H]1CCC[C@@H]1CC[C@H]1CN[C@@H]2CCCS(=O)(=O)N1C2)[C@H](c1cncc(C(F)(F)F)c1)c1ccc(Cl)c(F)c1] | methyl {(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-[5-(trifluoromethyl)pyridin-3-yl]ethyl}carbamate | 704.2 |
| 80 | 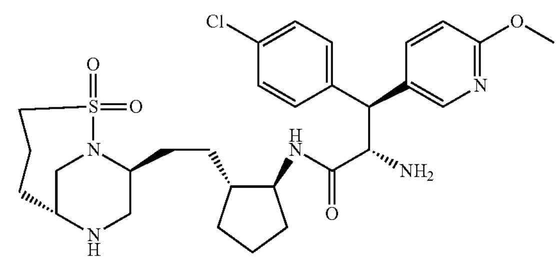 [SMILES: COc1ccc([C@H](c2ccc(Cl)cc2)[C@H](N)C(=O)N[C@H]2CCC[C@@H]2CC[C@H]2CN[C@@H]3CCCS(=O)(=O)N2C3)cn1] | (βS)-4-chloro-N-[(1S,2R)-2-{2-[(6R,9S)-2,2-dioxido-2-thia-1,7-diazabicyclo[4.3.1]dec-9-yl]ethyl}cyclopentyl]-β-(6-methoxypyridin-3-yl)-L-phenylalaninamide | 590.3 |
| 81 | 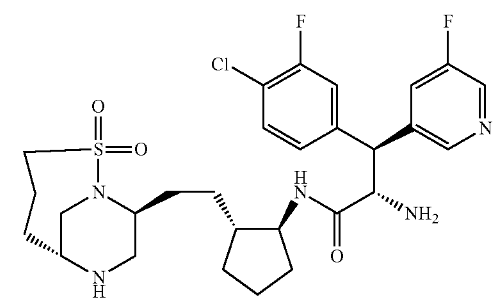 [SMILES: N[C@H](C(=O)N[C@H]1CCC[C@@H]1CC[C@H]1CN[C@@H]2CCCS(=O)(=O)N1C2)[C@H](c1cncc(F)c1)c1ccc(Cl)c(F)c1] | (βS)-4-chloro-N-[(1S,2R)-2-{2-[(6R,9S)-2,2-dioxido-2-thia-1,7-diazabicyclo[4.3.1]dec-9-yl]ethyl}cyclopentyl]-3-fluoro-β-(5-fluoropyridin-3-yl)-L-phenylalaninamide | 596.2 |
| 82 | 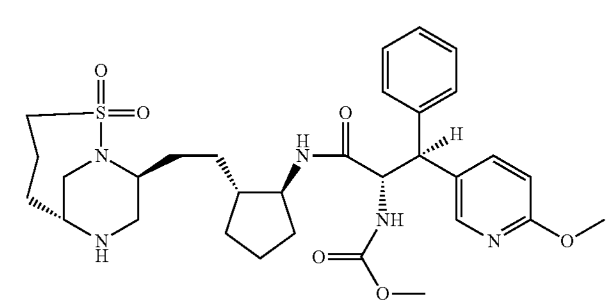 [SMILES: COC(=O)N[C@H](C(=O)N[C@H]1CCC[C@@H]1CC[C@H]1CN[C@@H]2CCCS(=O)(=O)N1C2)[C@@H](c1ccccc1)c1ccc(OC)nc1] | methyl {(1S)-2-{[(1S,2R)-2-{2-[(6R,9S)-2,2-dioxido-2-thia-1,7-diazabicyclo[4.3.1]dec-9-yl]ethyl}cyclopentyl]amino}-1-[(S)-(6-methoxypyridin-3-yl)(phenyl)methyl]-2-oxoethyl}carbamate | 614.3 |

TABLE 1-continued

| Example No. | Structure | IUPAC Name | Exact Mass [M + H]+ |
|---|---|---|---|
| 83 | 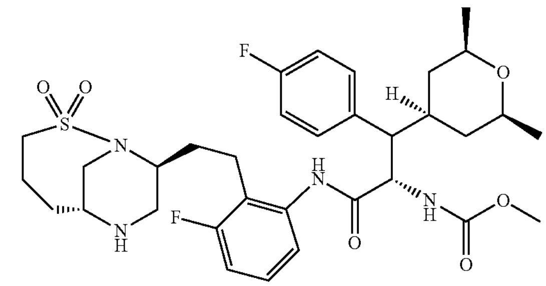 [SMILES: COC(=O)N[C@H](C(=O)Nc1cccc(F)c1CC[C@H]1CN[C@@H]2CCCS(=O)(=O)N1C2)C(c1ccc(F)cc1)[C@H]1C[C@@H](C)O[C@@H](C)C1] | methyl [(1S)-2-[(2R,4r,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]-2-(4-fluorophenyl)ethyl]carbamate | 663.3 |
| 84 | 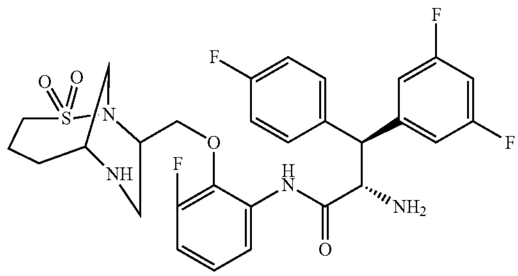 [SMILES: N[C@H](C(=O)Nc1cccc(F)c1OCC1CNC2CCCS(=O)(=O)N1C2)[C@@H](c1ccc(F)cc1)c1cc(F)cc(F)c1] | (βS)-β-(3,5-difluorophenyl)-N-{2-[(2,2-dioxido-2-thia-1,7-diazabicyclo[4.3.1]dec-9-yl)methoxy]-3-fluorophenyl}-4-fluoro-L-phenylalaninamide | 607.2 |
| 85 | 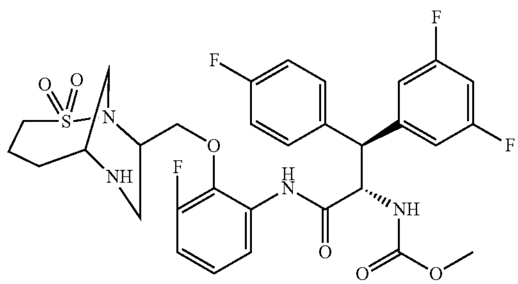 [SMILES: COC(=O)N[C@H](C(=O)Nc1cccc(F)c1OCC1CNC2CCCS(=O)(=O)N1C2)[C@@H](c1ccc(F)cc1)c1cc(F)cc(F)c1] | methyl [(1S,2S)-2-(3,5-difluorophenyl)-1-({2-[(2,2-dioxido-2-thia-1,7-diazabicyclo[4.3.1]dec-9-yl)methoxy]-3-fluorophenyl}carbamoyl)-2-(4-fluorophenyl)ethyl]carbamate | 665.2 |
| 86 | 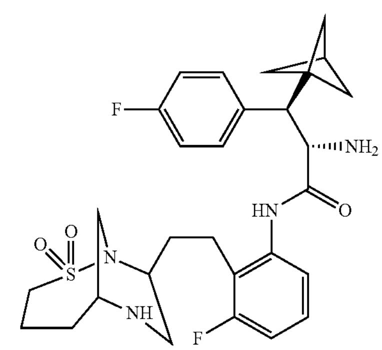 [SMILES: N[C@H](C(=O)Nc1cccc(F)c1CCC1CNC2CCCS(=O)(=O)N1C2)[C@@H](c1ccc(F)cc1)C12CC(C1)C2] | (βR)-β-bicyclo[1.1.1]pent-1-yl-N-{2-[2-(2,2-dioxido-2-thia-1,7-diazabicyclo[4.3.1]dec-9-yl)ethyl]-3-fluorophenyl}-4-fluoro-L-phenylalaninamide | 559.3 |
| 87 | 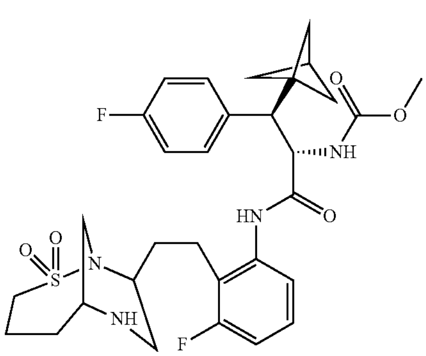 [SMILES: COC(=O)N[C@H](C(=O)Nc1cccc(F)c1CCC1CNC2CCCS(=O)(=O)N1C2)[C@@H](c1ccc(F)cc1)C12CC(C1)C2] | methyl [(1S,2R)-2-bicyclo[1.1.1]pent-1-yl-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate | 617.3 |

| Example No. | Structure | IUPAC Name | Exact Mass [M + H]+ |
|---|---|---|---|
| 88 | 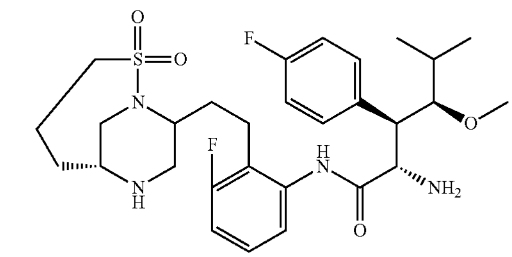 [SMILES: CO[C@H](C(C)C)[C@H](c1ccc(F)cc1)[C@H](N)C(=O)Nc1cccc(F)c1CCC1CN[C@@H]2CCCS(=O)(=O)N1C2] | (βR)-N-(2-{2-[(6R)-2,2-dioxido-2-thia-1,7-diazabicyclo[4.3.1]dec-9-yl]ethyl}-3-fluorophenyl)-4-fluoro-β-[(1R)-1-methoxy-2-methylpropyl]-L-phenylalaninamide | 579.3 |
| 89 | 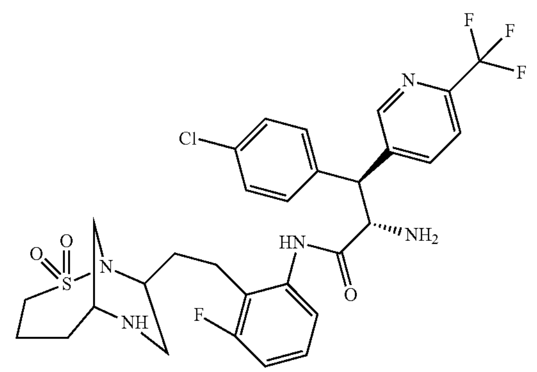 [SMILES: N[C@H](C(=O)Nc1cccc(F)c1CCC1CNC2CCCS(=O)(=O)N1C2)[C@@H](c1ccc(Cl)cc1)c1ccc(C(F)(F)F)nc1] | (βS)-4-chloro-N-{2-[2-(2,2-dioxido-2-thia-1,7-diazabicyclo[4.3.1]dec-9-yl]ethyl]-3-fluorophenyl}-β-[6-(trifluoromethyl)pyridin-3-yl]-L-phenylalaninamide | 654.2 |
| 90 | 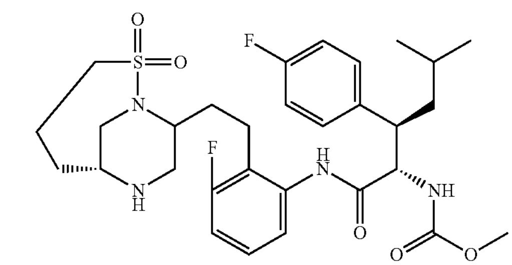 [SMILES: COC(=O)N[C@H](C(=O)Nc1cccc(F)c1CCC1CN[C@@H]2CCCS(=O)(=O)N1C2)[C@H](CC(C)C)c1ccc(F)cc1] | methyl [(1S,2R)-1-[(2-{2-[(6R)-2,2-dioxido-2-thia-1,7-diazabicyclo[4.3.1]dec-9-yl]ethyl}-3-fluorophenyl)carbamoyl]-2-(4-fluorophenyl)-4-methylpenlyl]carbamate | 607.3 |
| 91 | 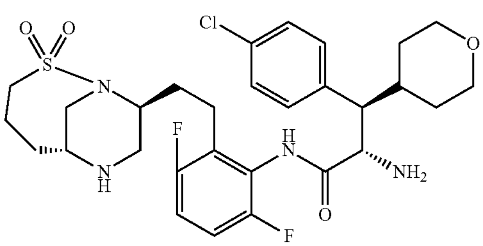 [SMILES: N[C@H](C(=O)Nc1c(F)ccc(F)c1CC[C@H]1CN[C@@H]2CCCS(=O)(=O)N1C2)[C@@H](c1ccc(Cl)cc1)C1CCOCC1] | (βR)-4-chloro-N-(2-{2-[(6R,9S)-2,2-dioxido-2-thia-1,7-diazabicyclo[4.3.1]dec-9-yl]ethyl}-3,6-difluorophenyl)-β-(tetrahydro-2H-pyran-4-yl)-L-phenylalaninamide | 611.2 |
| 92 | 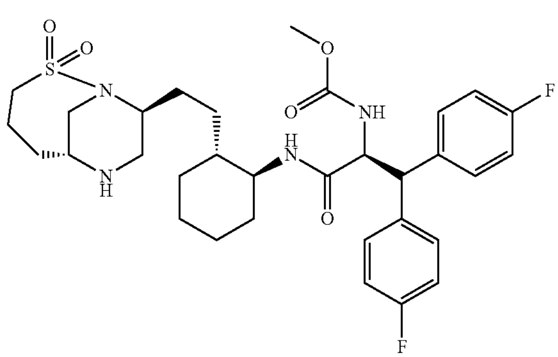 [SMILES: COC(=O)N[C@H](C(=O)N[C@H]1CCCC[C@@H]1CC[C@H]1CN[C@@H]2CCCS(=O)(=O)N1C2)C(c1ccc(F)cc1)c1ccc(F)cc1] | methyl [(1S)-1-[bis(4-fluorophenyl)methyl]-2-{[(1S,2R)-2-{2-[(6R,9S)-2,2-dioxido-2-thia-1,7-diazabicyclo[4.3.1]dec-9-yl]ethyl}cyclohexyl]amino}-2-oxoethyl]carbamate | 633.3 |

TABLE 1-continued

| Example No. | Structure | IUPAC Name | Exact Mass [M + H]+ |
|---|---|---|---|
| 93 | 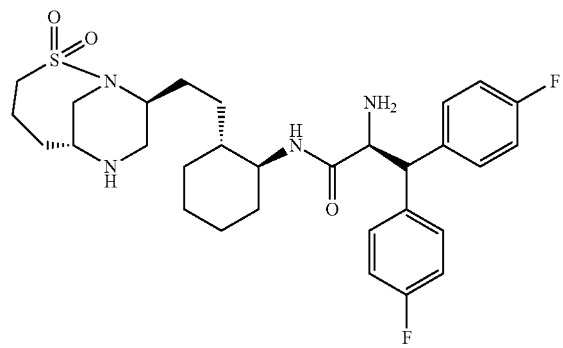 [SMILES: N[C@H](C(=O)N[C@H]1CCCC[C@@H]1CC[C@H]1CN[C@@H]2CCCS(=O)(=O)N1C2)C(c1ccc(F)cc1)c1ccc(F)cc1] | N-[(1S,2R)-2-{2-[(6R,9S)-2,2-dioxido-2-thia-1,7-diazabicyclo[4.3.1]dec-9-yl]ethyl}cyclohexyl]-4-fluoro-β-(4-fluorophenyl)-L-phenylalaninamide | 575.3 |
| 94 | 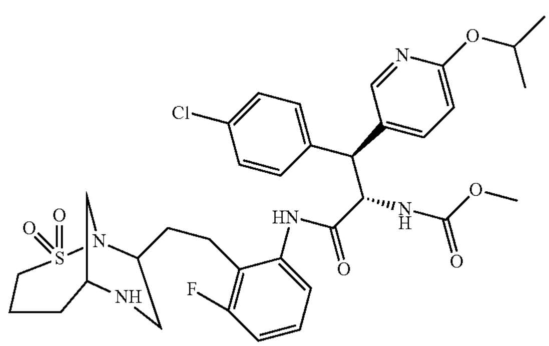 [SMILES: COC(=O)N[C@H](C(=O)Nc1cccc(F)c1CCC1CNC2CCCS(=O)(=O)N1C2)[C@@H](c1ccc(Cl)cc1)c1ccc(OC(C)C)nc1] | methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[6-(1-methylethoxy)pyridin-3-yl]ethyl}carbamate | 702.3 |
| 95 | 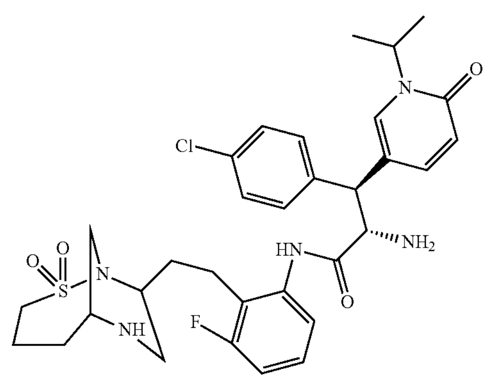 [SMILES: CC(C)n1cc([C@H](c2ccc(Cl)cc2)[C@H](N)C(=O)Nc2cccc(F)c2CCC2CNC3CCCS(=O)(=O)N2C3)ccc1=O] | (βS)-4-chloro-N-{2-[2-(2,2-dioxido-2-thia-1,7-diazabicyclo[4.3.1]dec-9-yl)ethyl]-3-fluorophenyl}-β-[1-(1-methylethyl)-6-oxo-1,6-dihydropyridin-3-yl]-L-phenylalaninamide | 644.2 |
| 96 | 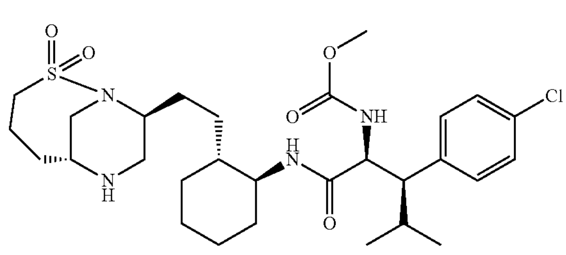 [SMILES: COC(=O)N[C@H](C(=O)N[C@H]1CCCC[C@@H]1CC[C@H]1CN[C@@H]2CCCS(=O)(=O)N1C2)[C@@H](c1ccc(Cl)cc1)C(C)C] | methyl [(1S,2S)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-3-methylbutyl]carbamate | 597.3 |

TABLE 1-continued

| Example No. | Structure | IUPAC Name | Exact Mass [M + H]+ |
|---|---|---|---|
| 97 | 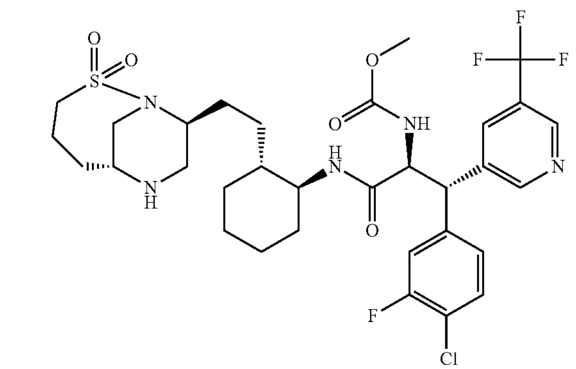 [SMILES: COC(=O)N[C@H](C(=O)N[C@H]1CCCC[C@@H]1CC[C@H]1CN[C@@H]2CCCS(=O)(=O)N1C2)[C@H](c1cncc(C(F)(F)F)c1)c1ccc(Cl)c(F)c1] | methyl {(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-[5-(trifluoromethyl)pyridin-3-yl]ethyl}carbamate | 718.2 |
| 98 | 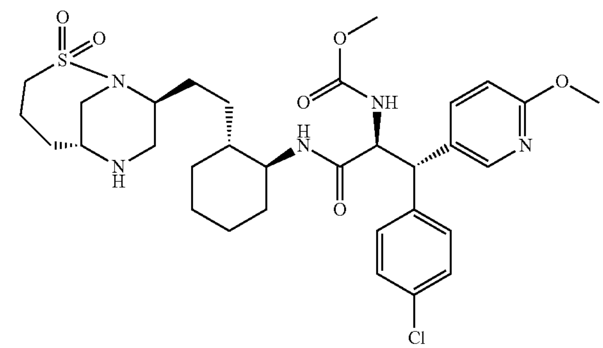 [SMILES: COC(=O)N[C@H](C(=O)N[C@H]1CCCC[C@@H]1CC[C@H]1CN[C@@H]2CCCS(=O)(=O)N1C2)[C@@H](c1ccc(Cl)cc1)c1ccc(OC)nc1] | methyl [(1S,2S)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-(6-methoxypyridin-3-yl)ethyl]carbamate | 662.3 |
| 99 | 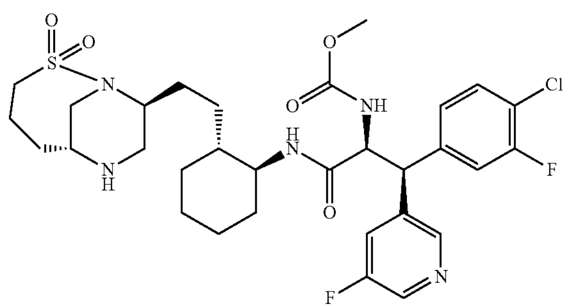 [SMILES: COC(=O)N[C@H](C(=O)N[C@H]1CCCC[C@@H]1CC[C@H]1CN[C@@H]2CCCS(=O)(=O)N1C2)[C@H](c1cncc(F)c1)c1ccc(Cl)c(F)c1] | methyl [(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-(5-fluoropyridin-3-yl)ethyl]carbamate | 668.2 |
| 100 | 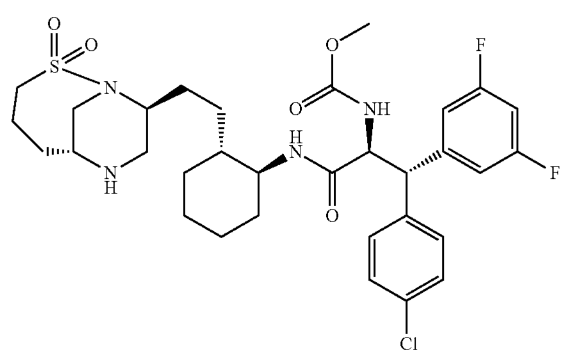 [SMILES: COC(=O)N[C@H](C(=O)N[C@H]1CCCC[C@@H]1CC[C@H]1CN[C@@H]2CCCS(=O)(=O)N1C2)[C@@H](c1ccc(Cl)cc1)c1cc(F)cc(F)c1] | methyl [(1S,2S)-2-(4-chlorophenyl)-2-(3,5-difluorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}ethyl]carbamate | 667.3 |

TABLE 1-continued

| Example No. | Structure | IUPAC Name | Exact Mass [M + H]+ |
|---|---|---|---|
| 101 | 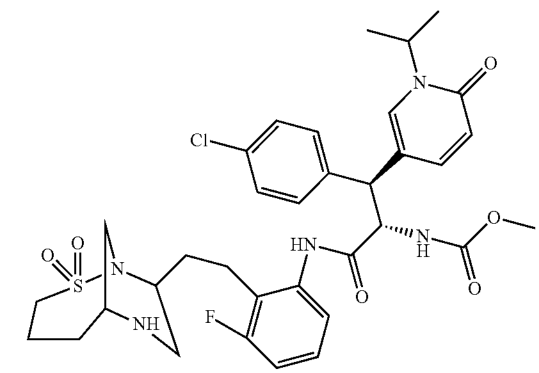 [SMILES: COC(=O)N[C@H](C(=O)Nc1cccc(F)c1CCC1CNC2CCCS(=O)(=O)N1C2)[C@@H](c1ccc(Cl)cc1)c1ccc(=O)n(C(C)C)c1] | methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[1-(1-methylethyl)-6-oxo-1,6-dihydropyridin-3-yl]ethyl}carbamate | 702.3 |
| 102 | 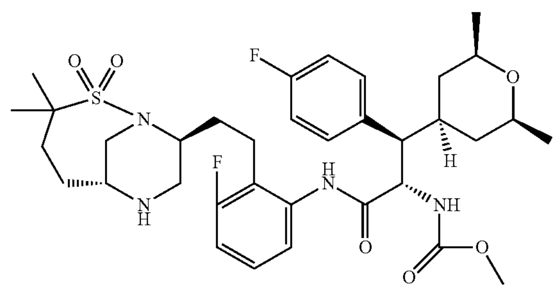 | methyl {(1S)-2-[(2-{2-[(6R,9S)-3,3-dimethyl-2,2-dioxido-2-thia-1,7-diazabicyclo[4.3.1]dec-9-yl]ethyl}-3-fluorophenyl)amino]-1-[(R)-[(2R,4r,6S)-2,6-dimethyltetrahydro-2H-pyran-4-yl](4-fluorophenyl)methyl]-2-oxoethyl}carbamate | 691.3 |
| 103 | 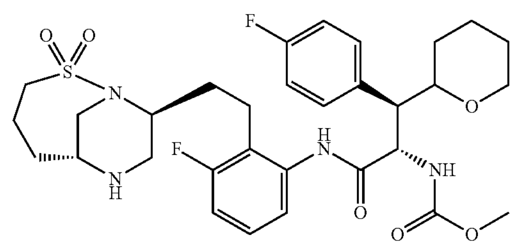 [SMILES: COC(=O)N[C@H](C(=O)Nc1cccc(F)c1CC[C@H]1CN[C@@H]2CCCS(=O)(=O)N1C2)[C@@H](c1ccc(F)cc1)C1CCCCO1] | methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-(4-fluorophenyl)(tetrahydro-2H-pyran-2-yl)methyl]-2-oxoethyl}carbamate | 635.3 |
| 104 | 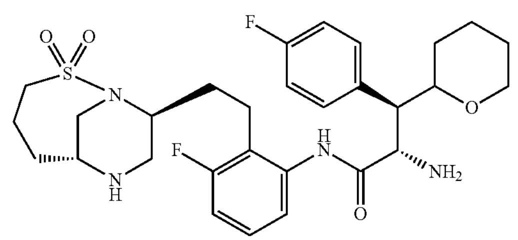 [SMILES: N[C@H](C(=O)Nc1cccc(F)c1CC[C@H]1CN[C@@H]2CCCS(=O)(=O)N1C2)[C@@H](c1ccc(F)cc1)C1CCCCO1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-(tetrahydro-2H-pyran-2-yl)-L-phenylalaninamide | 577.3 |
| 105 | 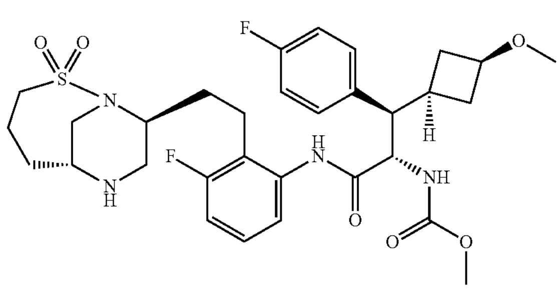 [SMILES: COC(=O)N[C@H](C(=O)Nc1cccc(F)c1CC[C@H]1CN[C@@H]2CCCS(=O)(=O)N1C2)[C@@H](c1ccc(F)cc1)[C@H]1C[C@@H](OC)C1] | methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(R)-(4-fluorophenyl)[(1s,3S)-3-methoxycyclobutyl]methyl}-2-oxoethyl]carbamate | 635.3 |

TABLE 1-continued

| Example No. | Structure | IUPAC Name | Exact Mass [M + H]+ |
|---|---|---|---|
| 106 | 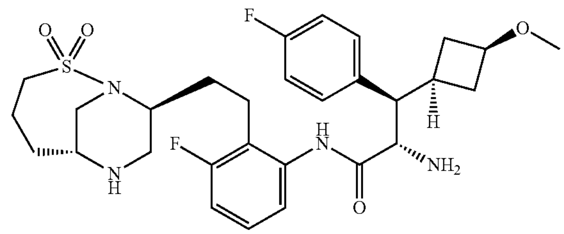 [SMILES: CO[C@H]1C[C@@H]([C@H](c2ccc(F)cc2)[C@H](N)C(=O)Nc2cccc(F)c2CC[C@H]2CN[C@@H]3CCCS(=O)(=O)N2C3)C1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-[(1s,3S)-3-methoxycyclobutyl]-L-phenylalaninamide | 577.3 |
| 107 | 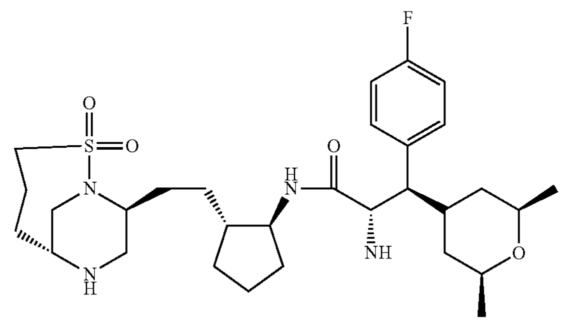 [SMILES: C[C@@H]1CC([C@H](c2ccc(F)cc2)[C@H](N)C(=O)N[C@H]2CCC[C@@H]2CC[C@H]2CN[C@@H]3CCCS(=O)(=O)N2C3)C[C@H](C)O1] | (βR)-β-[(2R,4s,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclopentyl]-4-fluoro-L-phenylalaninamide | 579.3 |
| 108 | 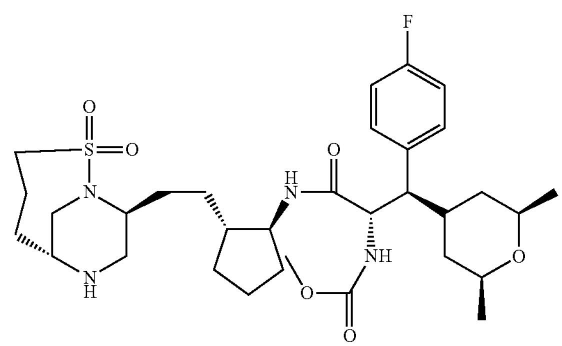 [SMILES: COC(=O)N[C@H](C(=O)N[C@H]1CCC[C@@H]1CC[C@H]1CN[C@@H]2CCCS(=O)(=O)N1C2)[C@@H](c1ccc(F)cc1)C1C[C@@H](C)O[C@@H](C)C1] | methyl [(1S,2R)-2-[(2R,4s,6S)-2,6-dimethyltetrahydro-2H-pyran-4-yl]-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(4-fluorophenyl)ethyl]carbamate | 637.3 |
| 109 | 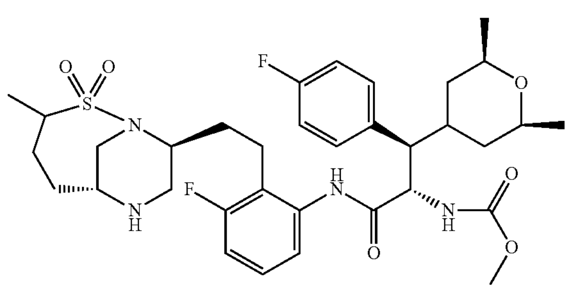 | methyl [(1S,2R)-2-[(2R,6S)-2,6-dimethyltetrahydro-2H-pyran-4-yl]-1-[(3-fluoro-2-{2-[(6R,9S)-3-methyl-2,2-dioxido-2-thia-1,7-diazabicyclo[4.3.1]dec-9-yl]ethyl}phenyl)carbamoyl]-2-(4-fluorophenyl)ethyl]carbamate | 677.3 |
| 110 | 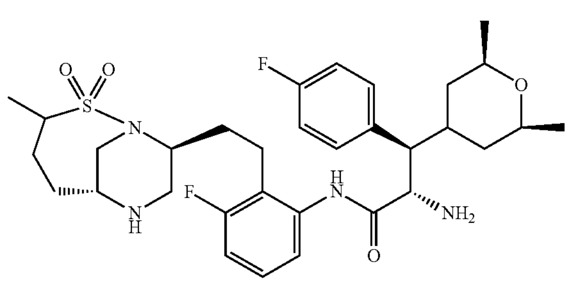 | (βR)-β-[(2R,6S)-2,6-dimethyltetrahydro-2H-pyran-4-yl]-4-fluoro-N-(3-fluoro-2-{2-[(6R,9S)-3-methyl-2,2-dioxido-2-thia-1,7-diazabicyclo[4.3.1]dec-9-yl]ethyl}phenyl)-L-phenylalaninamide | 619.3 |

TABLE 1-continued

| Example No. | Structure | IUPAC Name | Exact Mass [M + H]+ |
|---|---|---|---|
| 111 | 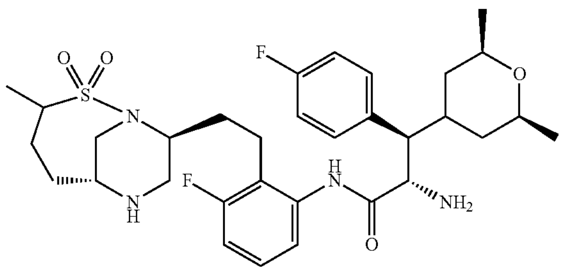 | (βR)-β-[(2R,6S)-2,6-dimethyltetrahydro-2H-pyran-4-yl]-4-fluoro-N-(3-fluoro-2-{2-[(6R,9S)-3-methyl-2,2-dioxido-2-thia-1,7-diazabicyclo[4.3.1]dec-9-yl]ethyl}phenyl)-L-phenylalaninamide | 619.3 |
| 112 | 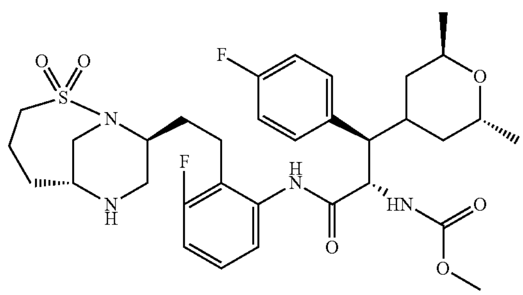 [SMILES: COC(=O)N[C@H](C(=O)Nc1cccc(F)c1CC[C@H]1CN[C@@H]2CCCS(=O)(=O)N1C2)[C@@H](c1ccc(F)cc1)C1C[C@@H](C)O[C@H](C)C1] | methyl [(1S,2R)-2-[(2R,6R)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]-2-(4-fluorophenyl)ethyl]carbamate | 663.3 |
| 113 | 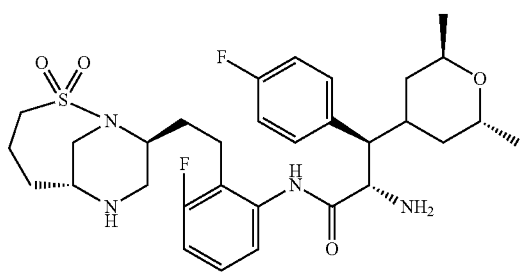 [SMILES: C[C@@H]1CC([C@H](c2ccc(F)cc2)[C@H](N)C(=O)Nc2cccc(F)c2CC[C@H]2CN[C@@H]3CCCS(=O)(=O)N2C3)C[C@@H](C)O1] | (βR)-β-[(2R,6R)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-4-fluoro-L-phenylalaninamide | 605.3 |
| 114 | 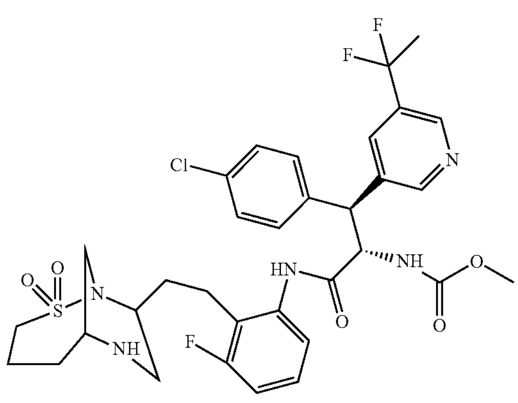 [SMILES: COC(=O)N[C@H](C(=O)Nc1cccc(F)c1CCC1CNC2CCCS(=O)(=O)N1C2)[C@@H](c1ccc(Cl)cc1)c1cncc(C(C)(F)F)c1] | methyl [(1S,2S)-2-(4-chlorophenyl)-2-[5-(1,1-difluoroethyl)pyridin-3-yl]-1-({2-[2-(2,2-dioxido-2-thia-1,7-diazabicyclo[4.3.1]dec-9-yl)ethyl]-3-fluorophenyl}carbamoyl)ethyl]carbamate | 708.2 |
| 115 | 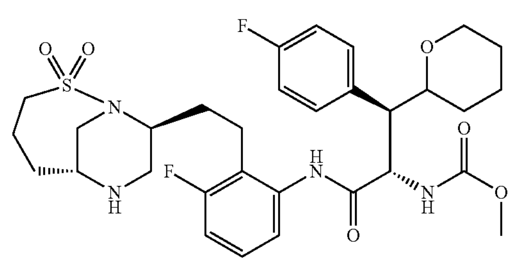 [SMILES: COC(=O)N[C@H](C(=O)Nc1cccc(F)c1CC[C@H]1CN[C@@H]2CCCS(=O)(=O)N1C2)[C@@H](c1ccc(F)cc1)C1CCCCO1] | methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-(4-fluorophenyl)(tetrahydro-2H-pyran-2-yl)methyl]-2-oxoethyl}carbamate | 635.3 |

TABLE 1-continued

| Example No. | Structure | IUPAC Name | Exact Mass [M + H]+ |
|---|---|---|---|
| 116 | 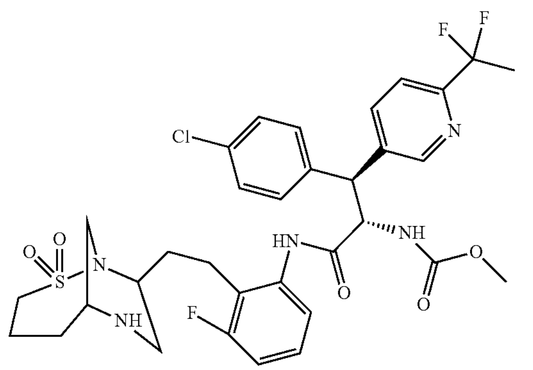 [SMILES: COC(=O)N[C@H](C(=O)Nc1cccc(F)c1CCC1CNC2CCCS(=O)(=O)N1C2)[C@@H](c1ccc(Cl)cc1)c1ccc(C(C)(F)F)nc1] | methyl [(1S,2S)-2-(4-chlorophenyl)-2-[6-(1,1-difluoroethyl)pyridin-3-yl]-1-({2-[2-(2,2-dioxido-2-thia-1,7-diazabicyclo[4.3.1]dec-9-yl)ethyl]-3-fluorophenyl}carbamoyl)ethyl]carbamate | 708.2 |
| 117 | 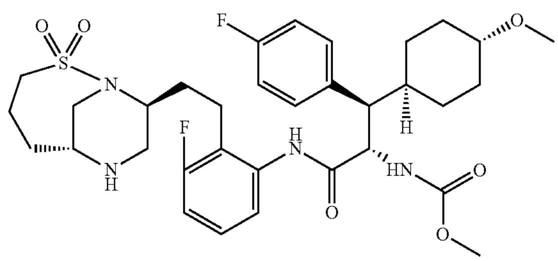 [SMILES: COC(=O)N[C@H](C(=O)Nc1cccc(F)c1CC[C@H]1CN[C@@H]2CCCS(=O)(=O)N1C2)[C@@H](c1ccc(F)cc1)[C@H]1CC[C@H](OC)CC1] | methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(R)-(4-fluorophenyl)[(1r,4R)-4-methoxycyclohexyl]methyl}-2-oxoethyl]carbamate | 663.3 |
| 118 | 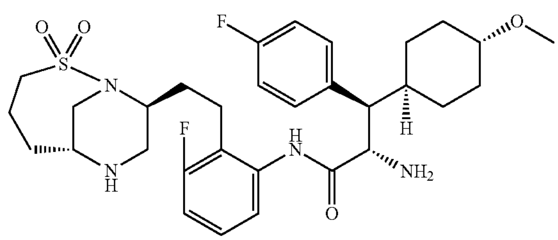 [SMILES: CO[C@H]1CC[C@H]([C@H](c2ccc(F)cc2)[C@H](N)C(=O)Nc2cccc(F)c2CC[C@H]2CN[C@@H]3CCCS(=O)(=O)N2C3)CC1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-[(1r,4R)-4-methoxycyclohexyl]-L-phenylalaninamide | 605.3 |
| 119 | 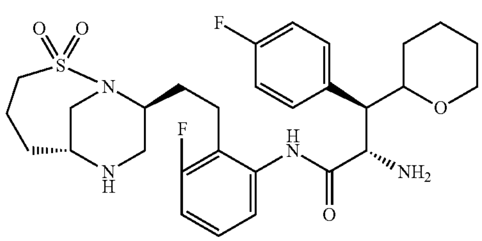 [SMILES: N[C@H](C(=O)Nc1cccc(F)c1CC[C@H]1CN[C@@H]2CCCS(=O)(=O)N1C2)[C@@H](c1ccc(F)cc1)C1CCCCO1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-(tetrahydro-2H-pyran-2-yl)-L-phenylalaninamide | 577.3 |
| 120 | 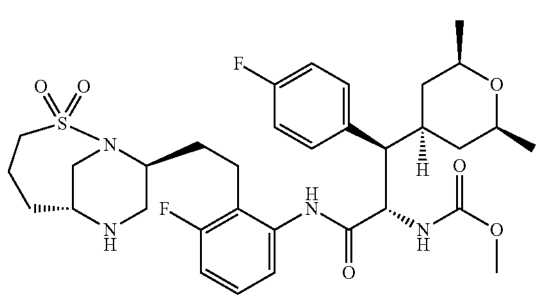 [SMILES: COC(=O)N[C@H](C(=O)Nc1cccc(F)c1CC[C@H]1CN[C@@H]2CCCS(=O)(=O)N1C2)[C@@H](c1ccc(F)cc1)[C@H]1C[C@@H](C)O[C@@H](C)C1] | methyl {(1S,2R)-2-(4-chlorophenyl)-2-[(2R,4r,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate | 679.3 |

TABLE 1-continued

| Example No. | Structure | IUPAC Name | Exact Mass [M + H]+ |
|---|---|---|---|
| 121 | 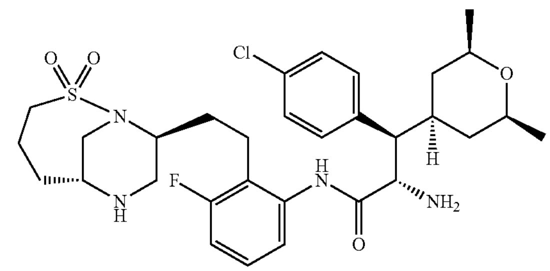 [SMILES: C[C@@H]1C[C@H]([C@H](c2ccc(Cl)cc2)[C@H](N)C(=O)Nc2cccc(F)c2CC[C@H]2CN[C@@H]3CCCS(=O)(=O)N2C3)C[C@H](C)O1] | (βR)-4-chloro-β-[(2R,4r,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-L-phenylalaninamide | 621.3 |
| 122 | 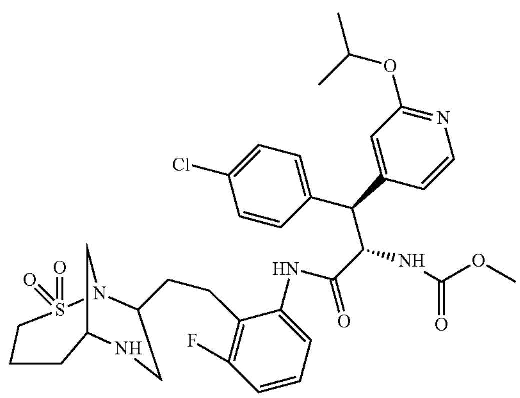 [SMILES: COC(=O)N[C@H](C(=O)Nc1cccc(F)c1CCC1CNC2CCCS(=O)(=O)N1C2)[C@@H](c1ccc(Cl)cc1)c1ccnc(OC(C)C)c1] | methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethoxy)pyridin-4-yl]ethyl}carbamate | 702.3 |
| 123 | 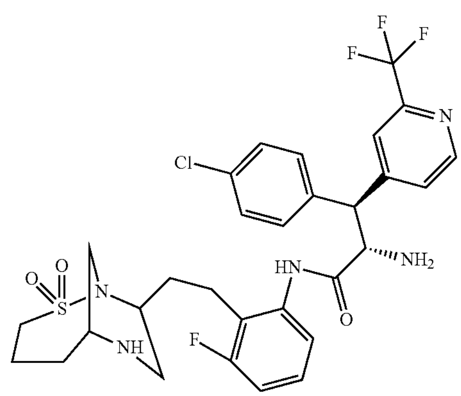 [SMILES: N[C@H](C(=O)Nc1cccc(F)c1CCC1CNC2CCCS(=O)(=O)N1C2)[C@@H](c1ccc(Cl)cc1)c1ccnc(C(F)(F)F)c1] | (βR)-4-chloro-N-{2-[2-(2,2-dioxido-2-thia-1,7-diazabicyclo[4.3.1]dec-9-yl)ethyl]-3-fluorophenyl}-β-[2-(trifluoromethyl)pyridin-4-yl]-L-phenylalaninamide | 654.2 |
| 124 | 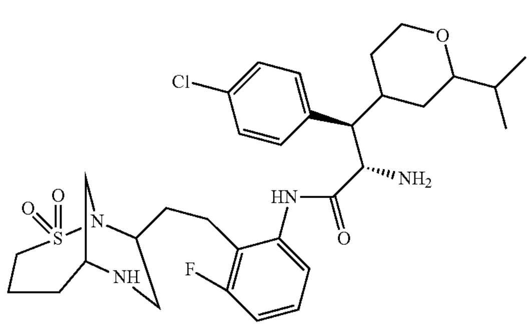 [SMILES: CC(C)C1CC([C@H](c2ccc(Cl)cc2)[C@H](N)C(=O)Nc2cccc(F)c2CCC2CNC3CCCS(=O)(=O)N2C3)CCO1] | (βR)-4-chloro-N-{2-[2-(2,2-dioxido-2-thia-1,7-diazabicyclo[4.3.1]dec-9-yl)ethyl]-3-fluorophenyl}-β-[2-(1-methylethyl)tetrahydro-2H-pyran-4-yl]-L-phenylalaninamide | 635.3 |

TABLE 1-continued

| Example No. | Structure | IUPAC Name | Exact Mass [M + H]+ |
|---|---|---|---|
| 125 | 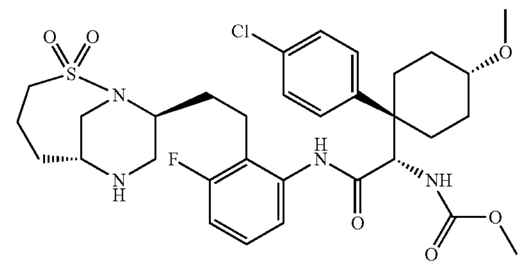 [SMILES: COC(=O)N[C@H](C(=O)Nc1cccc(F)c1CC[C@H]1CN[C@@H]2CCCS(=O)(=O)N1C2)[C@]1(c2ccc(Cl)cc2)CC[C@H](OC)CC1] | methyl {(1S)-1-[cis-1-(4-chlorophenyl)-4-methoxycyclohexyl]-2-[(2-{2-[(6R,9S)-2,2-dioxido-2-thia-1,7-diazabicyclo[4.3.1]dec-9-yl]ethyl}-3-fluorophenyl)amino]-2-oxoethyl}carbamate | 665.3 |
| 126 | 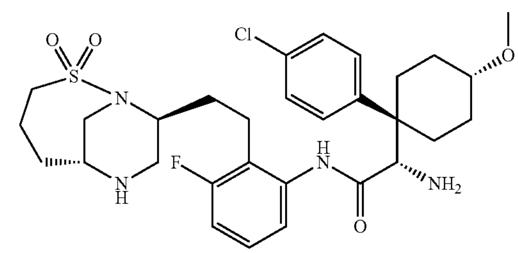 [SMILES: CO[C@H]1CC[C@@](c2ccc(Cl)cc2)([C@H](N)C(=O)Nc2cccc(F)c2CC[C@H]2CN[C@@H]3CCCS(=O)(=O)N2C3)CC1] | (2S)-2-amino-2-[cis-1-(4-chlorophenyl)-4-methoxycyclohexyl]-N-(2-{2-[(6R,9S)-2,2-dioxido-2-thia-1,7-diazabicyclo[4.3.1]dec-9-yl]ethyl}-3-fluorophenyl)ethanamide | 607.3 |
| 127 | 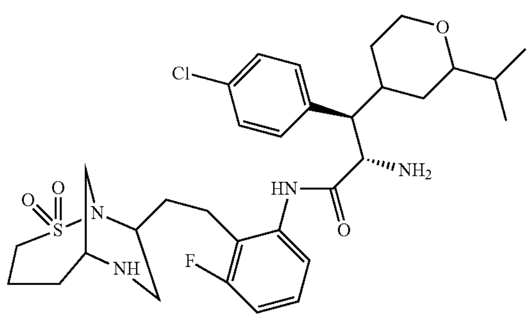 [SMILES: CC(C)C1CC([C@H](c2ccc(Cl)cc2)[C@H](N)C(=O)Nc2cccc(F)c2CCC2CNC3CCCS(=O)(=O)N2C3)CCO1] | (βR)-4-chloro-N-{2-[2-(2,2-dioxido-2-thia-1,7-diazabicyclo[4.3.1]dec-9-yl)ethyl]-3-fluorophenyl}-β-[2-(1-methylethyl)tetrahydro-2H-pyran-4-yl]-L-phenylalaninamide | 635.3 |
| 128 | 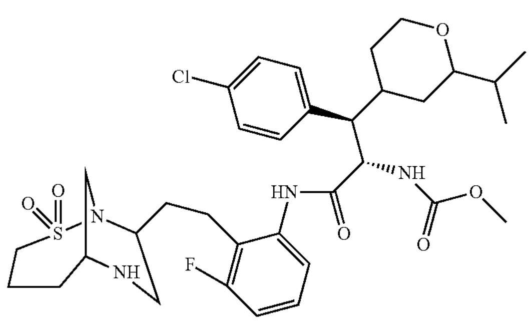 [SMILES: COC(=O)N[C@H](C(=O)Nc1cccc(F)c1CCC1CNC2CCCS(=O)(=O)N1C2)[C@@H](c1ccc(Cl)cc1)C1CCOC(C(C)C)C1] | methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethyl)tetrahydro-2H-pyran-4-yl]ethyl}carbamate | 693.3 |
| 129 | 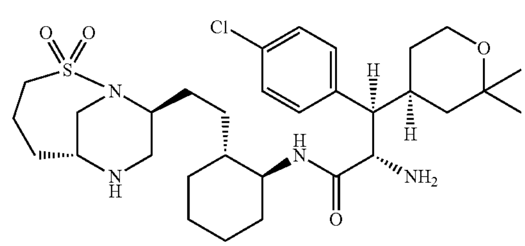 [SMILES: CC1(C)C[C@@H]([C@H](c2ccc(Cl)cc2)[C@H](N)C(=O)N[C@H]2CCCC[C@@H]2CC[C@H]2CN[C@@H]3CCCS(=O)(=O)N2C3)CCO1] | (βR)-4-chloro-β-[(4S)-2,2-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-L-phenylalaninamide | 609.3 |

TABLE 1-continued

| Example No. | Structure | IUPAC Name | Exact Mass [M + H]+ |
|---|---|---|---|
| 130 | 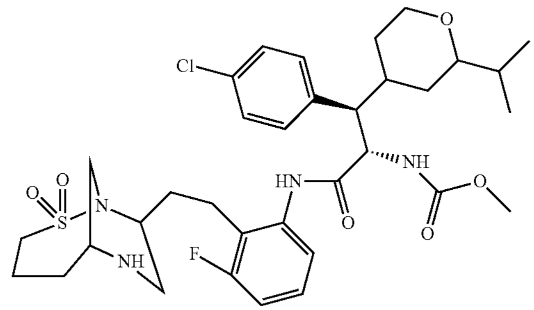 [SMILES: COC(=O)N[C@H](C(=O)Nc1cccc(F)c1CCC1CNC2CCCS(=O)(=O)N1C2)[C@@H](c1ccc(Cl)cc1)C1CCOC(C(C)C)C1] | methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethyl)tetrahydro-2H-pyran-4-yl]ethyl}carbamate | 693.3 |
| 131 | 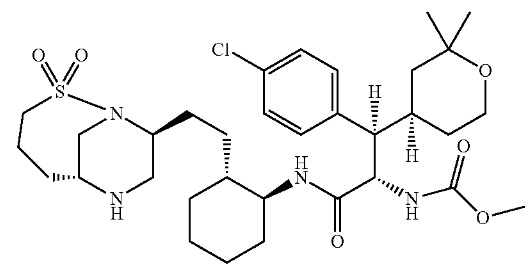 [SMILES: COC(=O)N[C@H](C(=O)N[C@H]1CCCC[C@@H]1CC[C@H]1CN[C@@H]2CCCS(=O)(=O)N1C2)[C@@H](c1ccc(Cl)cc1)[C@@H]1CCOC(C)(C)C1] | methyl [(1S,2R)-2-(4-chlorophenyl)-2-[(4R)-2,2-dimethyltetrahydro-2H-pyran-4-yl]-1-{[(1S,2R)-2-{2-[(6R,9S)-2,2-dioxido-2-thia-1,7-diazabicyclo[4.3.1]dec-9-yl]ethyl}cyclohexyl]carbamoyl}ethyl]carbamate | 667.3 |
| 132 | 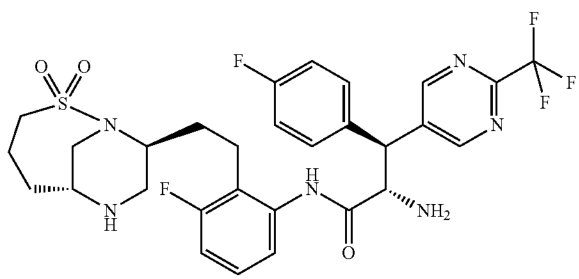 [SMILES: N[C@H](C(=O)Nc1cccc(F)c1CC[C@H]1CN[C@@H]2CCCS(=O)(=O)N1C2)[C@@H](c1ccc(F)cc1)c1cnc(C(F)(F)F)nc1] | (βS)-N-(2-{2-[(6R,9S)-2,2-dioxido-2-thia-1,7-diazabicyclo[4.3.1]dec-9-yl]ethyl})-3-fluorophenyl)-4-fluoro-β-[2-(trifluoromethyl)pyrimidin-5-yl]-L-phenylalaninamide | 639.2 |
| 133 | 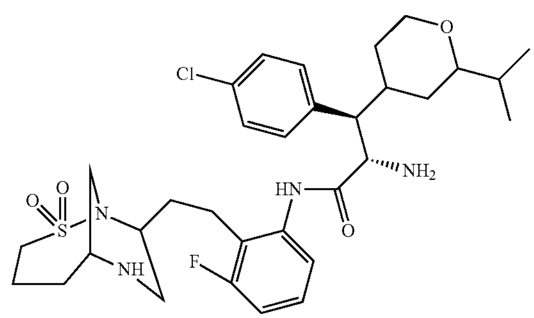 [SMILES: CC(C)C1CC([C@H](c2ccc(Cl)cc2)[C@H](N)C(=O)Nc2cccc(F)c2CCC2CNC3CCCS(=O)(=O)N2C3)CCO1] | (βR)-4-chloro-N-{2-[2-(2,2-dioxido-2-thia-1,7-diazabicyclo[4.3.1]dec-9-yl)ethyl]-3-fluorophenyl}-β-[2-(1-methylethyl)tetrahydro-2H-pyran-4-yl]-L-phenylalaninamide | 635.3 |
| 134 | 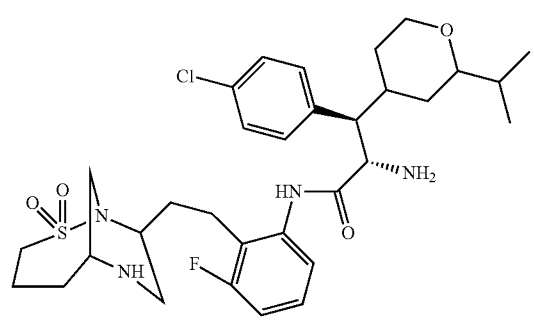 [SMILES: CC(C)C1CC([C@H](c2ccc(Cl)cc2)[C@H](N)C(=O)Nc2cccc(F)c2CCC2CNC3CCCS(=O)(=O)N2C3)CCO1] | (βR)-4-chloro-N-{2-[2-(2,2-dioxido-2-thia-1,7-diazabicyclo[4.3.1]dec-9-yl)ethyl]-3-fluorophenyl}-β-[2-(1-methylethyl)tetrahydro-2H-pyran-4-yl]-L-phenylalaninamide | 635.3 |

TABLE 1-continued

| Example No. | Structure | IUPAC Name | Exact Mass [M + H]+ |
|---|---|---|---|
| 135 | 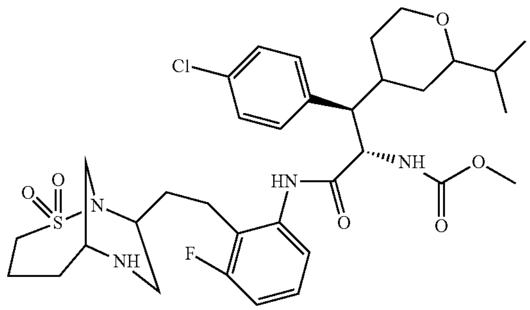 [SMILES: COC(=O)N[C@H](C(=O)Nc1cccc(F)c1CCC1CNC2CCCS(=O)(=O)N1C2)[C@@H](c1ccc(Cl)cc1)C1CCOC(C(C)C)C1] | methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethyl)tetrahydro-2H-pyran-4-yl]ethyl}carbamate | 693.3 |
| 136 | 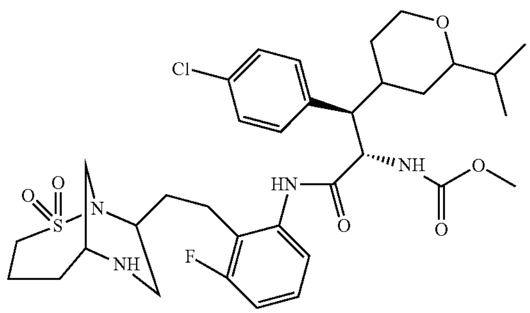 [SMILES: COC(=O)N[C@H](C(=O)Nc1cccc(F)c1CCC1CNC2CCCS(=O)(=O)N1C2)[C@@H](c1ccc(Cl)cc1)C1CCOC(C(C)C)C1] | methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethyl)tetrahydro-2H-pyran-4-yl]ethyl}carbamate | 693.3 |
| 137 | 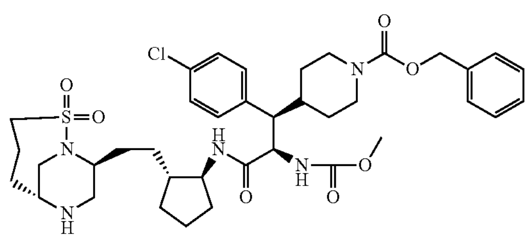 [SMILES: COC(=O)N[C@@H](C(=O)N[C@H]1CCC[C@@H]1CC[C@H]1CN[C@@H]2CCCS(=O)(=O)N1C2)[C@@H](c1ccc(Cl)cc1)C1CCN(C(=O)OCc2ccccc2)CC1] | benzyl 4-{(1R,2R)-1-(4-chlorophenyl)-3-{[(1S,2R)-2-{2-[(6R,9S)-2,2-dioxido-2-thia-1,7-diazabicyclo[4.3.1]dec-9-yl]ethyl}cyclopentyl]amino}-2-[(methoxycarbonyl)amino]-3-oxopropyl}piperidine-1-carboxylate | 758.3 |
| 138 | 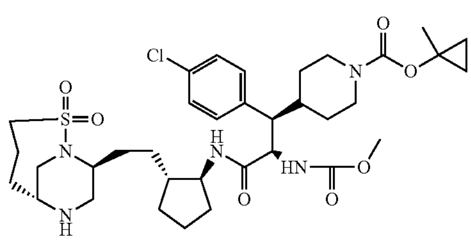 [SMILES: COC(=O)N[C@@H](C(=O)N[C@H]1CCC[C@@H]1CC[C@H]1CN[C@@H]2CCCS(=O)(=O)N1C2)[C@@H](c1ccc(Cl)cc1)C1CCN(C(=O)OC2(C)CC2)CC1] | 1-methylcyclopropyl 4-{(1R,2R)-1-(4-chlorophenyl)-3-{[(1S,2R)-2-{2-[(6R,9S)-2,2-dioxido-2-thia-1,7-diazabicyclo[4.3.1]dec-9-yl]ethyl}cyclopentyl]amino}-2-[(methoxycarbonyl)amino]-3-oxopropyl}piperidine-1-carboxylate | 722.3 |
| 139 | 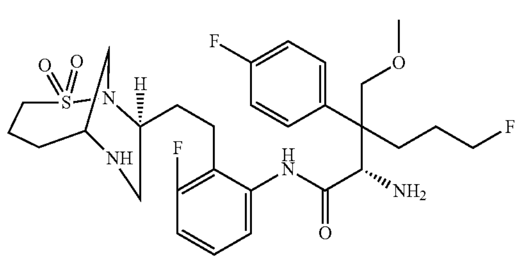 [SMILES: COCC(CCCF)(c1ccc(F)cc1)[C@H](N)C(=O)Nc1cccc(F)c1CC[C@H]1CNC2CCCS(=O)(=O)N1C2] | N-2-{2-[(9S)-2,2-dioxido-2-thia-1,7-diazabicyclo[4.3.1]dec-9-yl]ethyl}-3-fluorophenyl)-4-fluoro-β-(3-fluoropropyl)-β-(methoxymethyl)-L-phenylalaninamide | 597.3 |

TABLE 1-continued

| Example No. | Structure | IUPAC Name | Exact Mass [M + H]+ |
|---|---|---|---|
| 140 | 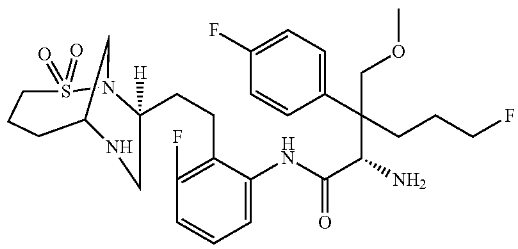 [SMILES: COCC(CCCF)(c1ccc(F)cc1)[C@H](N)C(=O)Nc1cccc(F)c1CC[C@H]1CNC2CCCS(=O)(=O)N1C2] | N-2-{2-[(9S)-2,2-dioxido-2-thia-1,7-diazabicyclo[4.3.1]dec-9-yl]ethyl}-3-fluorophenyl)-4-fluoro-β-(3-fluoropropyl)-β-(methoxymethyl)-L-phenylalaninamide | 597.3 |
| 141 | 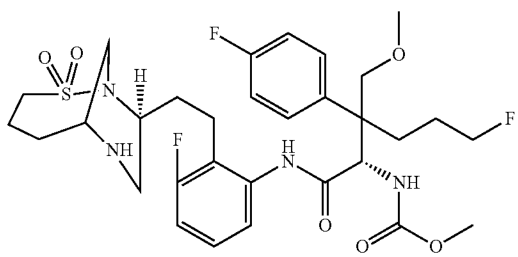 [SMILES: COCC(CCCF)(c1ccc(F)cc1)[C@H](NC(=O)OC)C(=O)Nc1cccc(F)c1CC[C@H]1CNC2CCCS(=O)(=O)N1C2] | methyl [(1S)-1-[(2-{2-[(9S)-2,2-dioxido-2-thia-1,7-diazabicyclo[4.3.1]dec-9-yl]ethyl}-3-fluorophenyl)carbamoyl]-5-fluoro-2-(4-fluorophenyl)-2-(methoxymethyl)pentyl]carbamate | 655.3 |
| 142 | 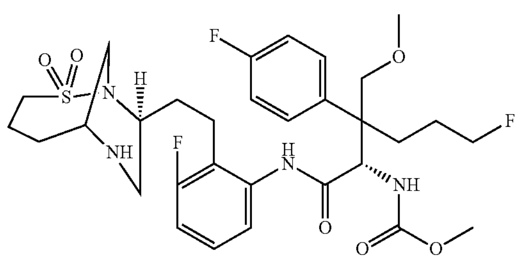 [SMILES: COCC(CCCF)(c1ccc(F)cc1)[C@H](NC(=O)OC)C(=O)Nc1cccc(F)c1CC[C@H]1CNC2CCCS(=O)(=O)N1C2] | methyl [(1S)-1-[(2-{2-[(9S)-2,2-dioxido-2-thia-1,7-diazabicyclo[4.3.1]dec-9-yl]ethyl}-3-fluorophenyl)carbamoyl]-5-fluoro-2-(4-fluorophenyl)-2-(methoxymethyl)pentyl]carbamate | 655.3 |
| 143 | 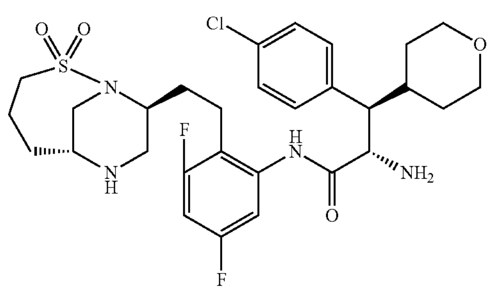 [SMILES: N[C@H](C(=O)Nc1cc(F)cc(F)c1CC[C@H]1CN[C@@H]2CCCS(=O)(=O)N1C2)[C@@H](c1ccc(Cl)cc1)C1CCOCC1] | (βR)-4-chloro-N-(2-{2-[(6R,9S)-2,2-dioxido-2-thia-1,7-diazabicyclo[4.3.1]dec-9-yl]ethyl}-3,5-difluorophenyl)-β-(tetrahydro-2H-pyran-4-yl)-L-phenylalaninamide | 611.2 |
| 144 | 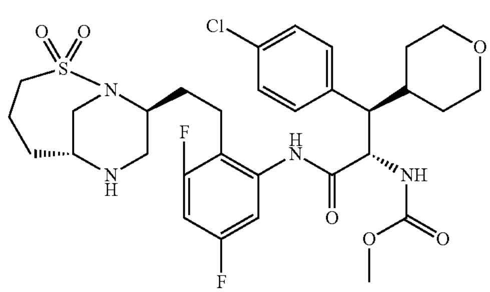 [SMILES: COC(=O)N[C@H](C(=O)Nc1cc(F)cc(F)c1CC[C@H]1CN[C@@H]2CCCS(=O)(=O)N1C2)[C@@H](c1ccc(Cl)cc1)C1CCOCC1] | methyl [(1S,2R)-2-(4-chlorophenyl)-1-[(2-{2-[(6R,9S)-2,2-dioxido-2-thia-1,7-diazabicyclo[4.3.1]dec-9-yl]ethyl}-3,5-difluorophenyl)carbamoyl]-2-(tetrahydro-2H-pyran-4-yl)ethyl]carbamate | 669.2 |

TABLE 1-continued

| Example No. | Structure | IUPAC Name | Exact Mass [M + H]+ |
|---|---|---|---|
| 145 | 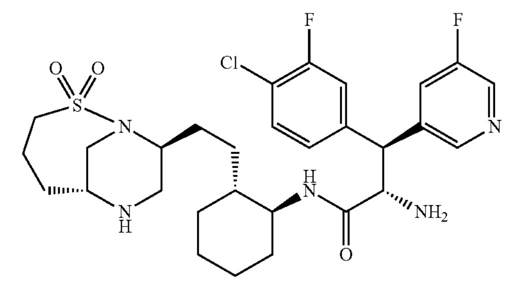 [SMILES: N[C@H](C(=O)N[C@H]1CCCC[C@@H]1CC[C@H]1CN[C@@H]2CCCS(=O)(=O)N1C2)[C@H](c1cncc(F)c1)c1ccc(Cl)c(F)c1] | (βS)-4-chloro-N-[(1S,2R)-2-{2-[(6R,9S)-2,2-dioxido-2-thia-1,7-diazabicyclo[4.3.1]dec-9-yl]ethyl}cyclohexyl]-3-fluoro-β-(5-fluoropyridin-3-yl)-L-phenylalaninamide | 610.2 |
| 146 | 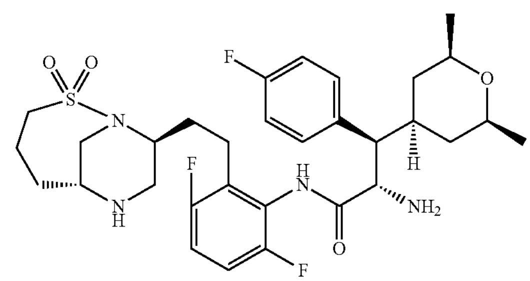 [SMILES: C[C@@H]1C[C@H]([C@H](c2ccc(F)cc2)[C@H](N)C(=O)Nc2c(F)ccc(F)c2CC[C@H]2CN[C@@H]3CCCS(=O)(=O)N2C3)C[C@H](C)O1] | (βR)-β-[(2R,4r,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3,6-difluorophenyl)-4-fluoro-L-phenylalaninamide | 623.3 |
| 147 | 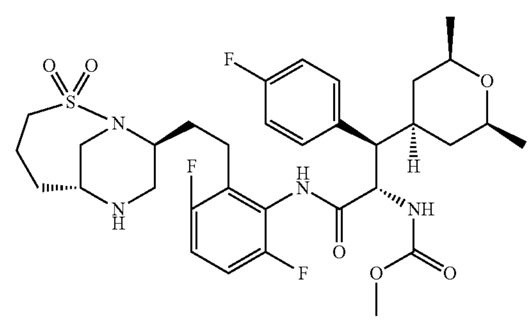 [SMILES: COC(=O)N[C@H](C(=O)Nc1c(F)ccc(F)c1CC[C@H]1CN[C@@H]2CCCS(=O)(=O)N1C2)[C@@H](c1ccc(F)cc1)[C@H]1C[C@@H](C)O[C@@H](C)C1] | methyl [(1S,2R)-2-[(2R,4r,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3,6-difluorophenyl)carbamoyl]-2-(4-fluorophenyl)ethyl]carbamate | 681.3 |
| 148 | 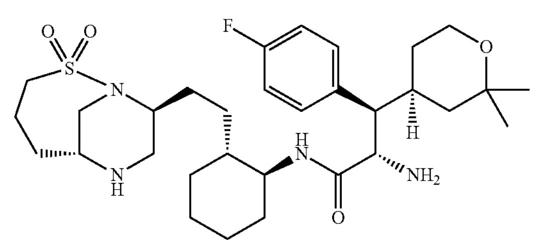 [SMILES: CC1(C)C[C@@H]([C@H](c2ccc(F)cc2)[C@H](N)C(=O)N[C@H]2CCCC[C@@H]2CC[C@H]2CN[C@@H]3CCCS(=O)(=O)N2C3)CCO1] | (βR)-β-[(4S)-2,2-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-4-fluoro-L-phenylalaninamide | 593.4 |
| 149 | 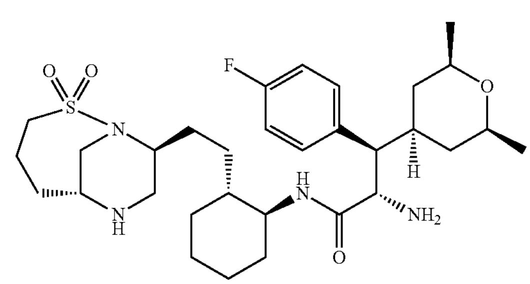 [SMILES: C[C@@H]1C[C@H]([C@H](c2ccc(F)cc2)[C@H](N)C(=O)N[C@H]2CCCC[C@@H]2CC[C@H]2CN[C@@H]3CCCS(=O)(=O)N2C3)C[C@H](C)O1] | (βR)-β-[(2R,4r,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-4-fluoro-L-phenylalaninamide | 593.4 |

TABLE 1-continued

| Example No. | Structure | IUPAC Name | Exact Mass [M + H]+ |
|---|---|---|---|
| 150 | 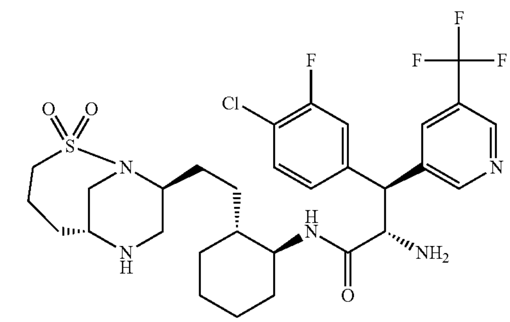 [SMILES: N[C@H](C(=O)N[C@H]1CCCC[C@@H]1CC[C@H]1CN[C@@H]2CCCS(=O)(=O)N1C2)[C@H](c1cncc(C(F)(F)F)c1)c1ccc(Cl)c(F)c1] | (βR)-4-chloro-N-[(1S,2R)-2-{2-[6R,9S)-2,2-dioxido-2-thia-1,7-diazabicyclo[4.3.1]dec-9-yl]ethyl}cyclohexyl]-3-fluoro-β-[5-(trifluoromethyl)pyridin-3-yl]-L-phenylalaninamide | 660.2 |
| 151 | 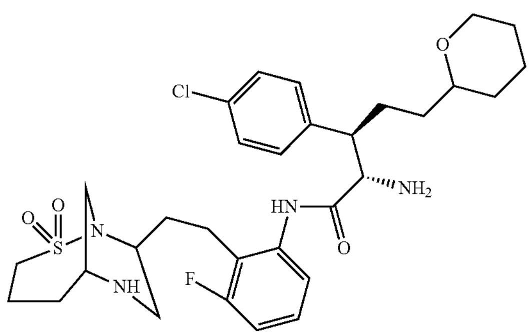 [SMILES: N[C@H](C(=O)Nc1cccc(F)c1CCC1CNC2CCCS(=O)(=O)N1C2)[C@H](CCC1CCCCO1)c1ccc(Cl)cc1] | (βR)-4-chloro-N-{2-[2-(2,2-dioxido-2-thia-1,7-diazabicyclo[4.3.1]dec-9-yl)ethyl]-3-fluorophenyl}-β-[2-(tetrahydro-2H-pyran-2-yl)ethyl]-L-phenylalaninamide | 621.3 |
| 152 | 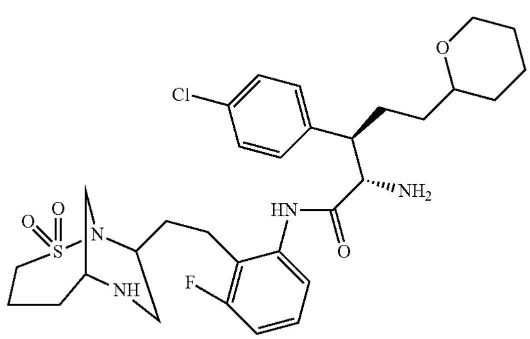 [SMILES: N[C@H](C(=O)Nc1cccc(F)c1CCC1CNC2CCCS(=O)(=O)N1C2)[C@H](CCC1CCCCO1)c1ccc(Cl)cc1] | (βR)-4-chloro-N-{2-[2-(2,2-dioxido-2-thia-1,7-diazabicyclo[4.3.1]dec-9-yl)ethyl]-3-fluorophenyl}-β-[2-(tetrahydro-2H-pyran-2-yl)ethyl]-L-phenylalaninamide | 621.3 |
| 153 | 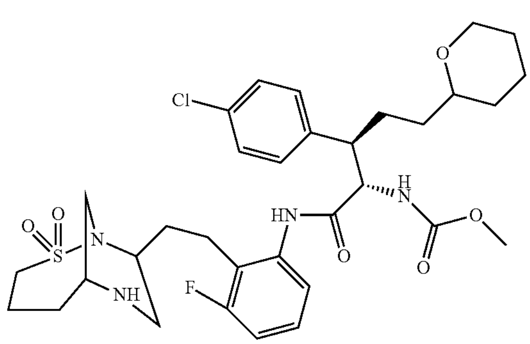 [SMILES: COC(=O)N[C@H](C(=O)Nc1cccc(F)c1CCC1CNC2CCCS(=O)(=O)N1C2)[C@H](CCC1CCCCO1)c1ccc(Cl)cc1] | methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-4-(tetrahydro-2H-pyran-2-yl)butyl]carbamate | 679.3 |

TABLE 1-continued

| Example No. | Structure | IUPAC Name | Exact Mass [M + H]+ |
|---|---|---|---|
| 154 | 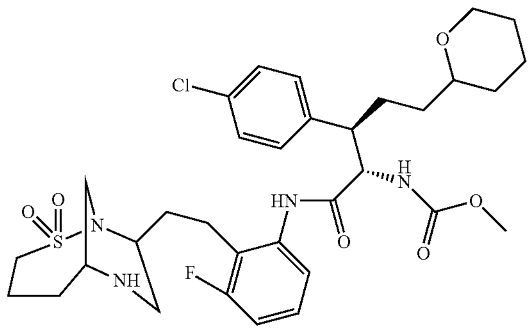 [SMILES: COC(=O)N[C@H](C(=O)Nc1cccc(F)c1CCC1CNC2CCCS(=O)(=O)N1C2)[C@H](CCC1CCCCO1)c1ccc(Cl)cc1] | methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-4-(tetrahydro-2H-pyran-2-yl)butyl]carbamate | 679.3 |
| 155 | 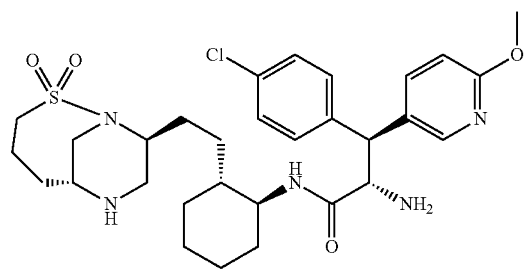 [SMILES: COc1ccc([C@H](c2ccc(Cl)cc2)[C@H](N)C(=O)N[C@H]2CCCC[C@@H]2CC[C@H]2CN[C@@H]3CCCS(=O)(=O)N2C3)cn1] | (βS)-4-chloro-N-[(1S,2R)-2-{2-[(6R,9S)-2,2-dioxido-2-thia-1,7-diazabicyclo[4.3.1]dec-9-yl]ethyl}cyclohexyl]-β-(6-methoxypyridin-3-yl)-L-phenylalaninamide | 604.3 |
| 156 | 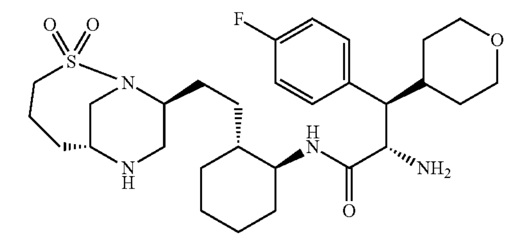 [SMILES: N[C@H](C(=O)N[C@H]1CCCC[C@@H]1CC[C@H]1CN[C@@H]2CCCS(=O)(=O)N1C2)[C@@H](c1ccc(F)cc1)C1CCOCC1] | (βR)-N-[(1S,2R)-2-{2-[(6R,9S)-2,2-dioxido-2-thia-1,7-diazabicyclo[4.3.1]dec-9-yl]ethyl}cyclohexyl]-4-fluoro-β-(tetrahydro-2H-pyran-4-yl)-L-phenylalaninamide | 565.3 |
| 157 | 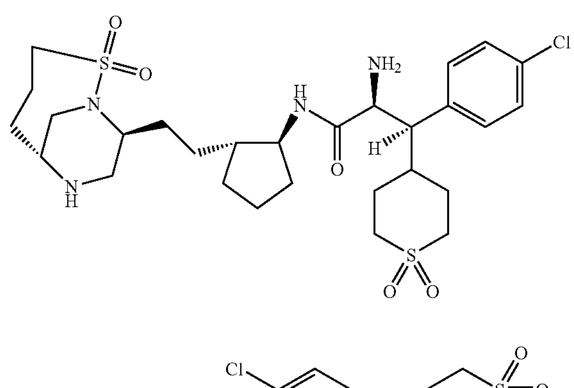 | (βR)-4-chloro-β-(1,1-dioxidotetrahydro-2H-thiopyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 615.2 |
| 158 | 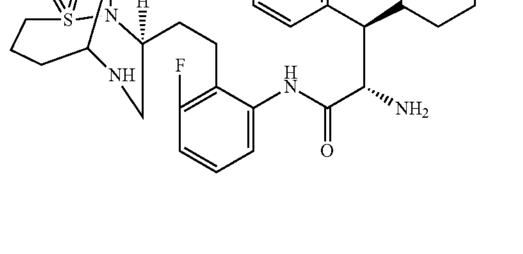 | (βR)-4-chloro-β-(1,1-dioxidotetrahydro-2H-thiopyran-4-yl)-N-(2-{2-[(9S)-2,2-dioxido-2-thia-1,7-diazabicyclo[4.3.1]dec-9-yl]ethyl}-3-fluorophenyl)-L-phenylalaninamide | 641.2 |

TABLE 1-continued

| Example No. | Structure | IUPAC Name | Exact Mass [M + H]+ |
|---|---|---|---|
| 159 | 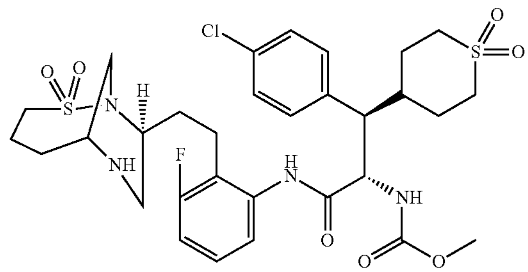 [SMILES: COC(=O)N[C@H](C(=O)Nc1cccc(F)c1CC[C@H]1CNC2CCCS(=O)(=O)N1C2)[C@@H](c1ccc(Cl)cc1)C1CCS(=O)(=O)CC1] | methyl {(1S,2R)-2-(4-chlorophenyl)-2-(1,1-dioxidotetrahydro-2H-thiopyran-4-yl)-1-[(2-{2-[(9S)-2,2-dioxido-2-thia-1,7-diazabicyclo[4.3.1]dec-9-yl]ethyl}-3-fluorophenyl)carbamoyl]ethyl}carbamate | 699.2 |
| 160 | 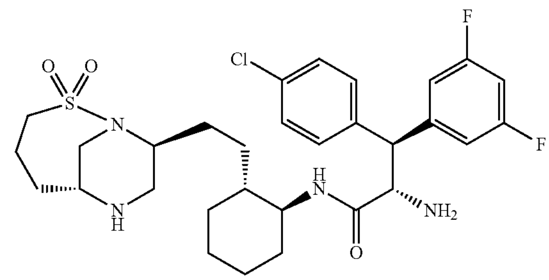 [SMILES: N[C@H](C(=O)N[C@H]1CCCC[C@@H]1CC[C@H]1CN[C@@H]2CCCS(=O)(=O)N1C2)[C@@H](c1ccc(Cl)cc1)c1cc(F)cc(F)c1] | (βS)-β-(4-chlorophenyl)-N-[(1S,2R)-2-{2-[(6R,9S)-2,2-dioxido-2-thia-1,7-diazabicyclo[4.3.1]dec-9-yl]ethyl}cyclohexyl]-3,5-difluoro-L-phenylalaninamide | 609.2 |
| 161 | 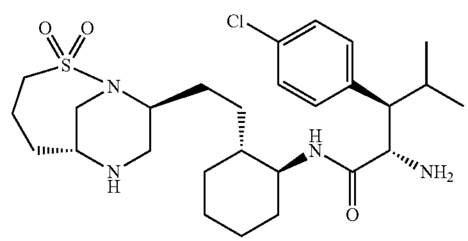 [SMILES: CC(C)[C@H](c1ccc(Cl)cc1)[C@H](N)C(=O)N[C@H]1CCCC[C@@H]1CC[C@H]1CN[C@@H]2CCCS(=O)(=O)N1C2] | (βR)-4-chloro-N-[(1S,2R)-2-{2-[(6R,9S)-2,2-dioxido-2-thia-1,7-diazabicyclo[4.3.1]dec-9-yl]ethyl}cyclohexyl]-β-(1-methylethyl)-L-phenylalaninamide | 539.3 |
| 162 | 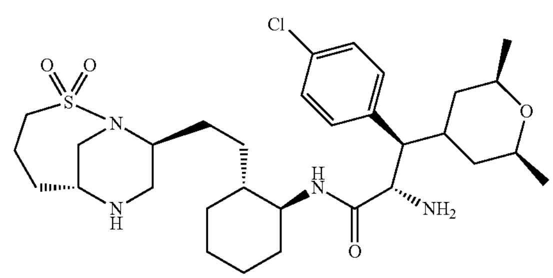 [SMILES: C[C@@H]1CC([C@H](c2ccc(Cl)cc2)[C@H](N)C(=O)N[C@H]2CCCC[C@@H]2CC[C@H]2CN[C@@H]3CCCS(=O)(=O)N2C3)C[C@H](C)O1] | (βR)-4-chloro-β-[(2R,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-L-phenylalaninamide | 609.3 |
| 163 | 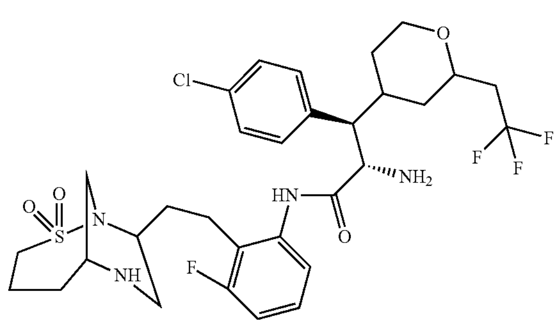 [SMILES: N[C@H](C(=O)Nc1cccc(F)c1CCC1CNC2CCCS(=O)(=O)N1C2)[C@@H](c1ccc(Cl)cc1)C1CCOC(CC(F)(F)F)C1] | (βR)-4-chloro-N-{2-[2-(2,2-dioxido-2-thia-1,7-diazabicyclo[4.3.1]dec-9-yl)ethyl]-3-fluorophenyl}-β-[2-(2,2,2-trifluoroethyl)tetrahydro-2H-pyran-4-yl]-L-phenylalaninamide | 675.2 |

TABLE 1-continued

| Example No. | Structure | IUPAC Name | Exact Mass [M + H]+ |
|---|---|---|---|
| 164 | 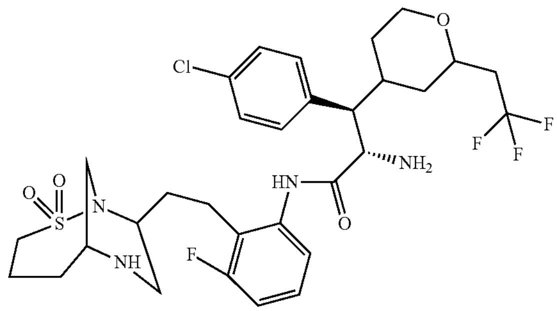 [SMILES: N[C@H](C(=O)Nc1cccc(F)c1CCC1CNC2CCCS(=O)(=O)N1C2)[C@@H](c1ccc(Cl)cc1)C1CCOC(CC(F)(F)F)C1] | (βR)-4-chloro-N-{2-[2-(2,2-dioxido-2-thia-1,7-diazabicyclo[4.3.1]dec-9-yl)ethyl]-3-fluorophenyl}-β-[2-(2,2,2-trifluoroethyl)tetrahydro-2H-pyran-4-yl]-L-phenylalaninamide | 675.2 |
| 165 | 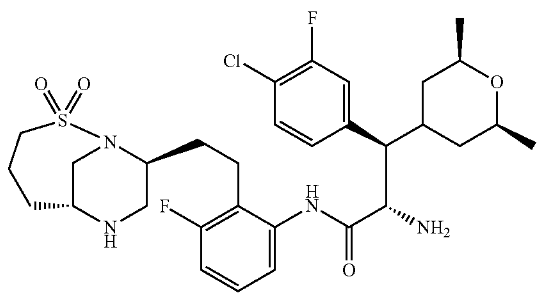 [SMILES: C[C@@H]1CC([C@H](c2ccc(Cl)c(F)c2)[C@H](N)C(=O)Nc2cccc(F)c2CC[C@H]2CN[C@@H]3CCCS(=O)(=O)N2C3)C[C@H](C)O1] | (βR)-4-chloro-β-[(2R,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-3-fluoro-L-phenylalaninamide | 639.3 |
| 166 | 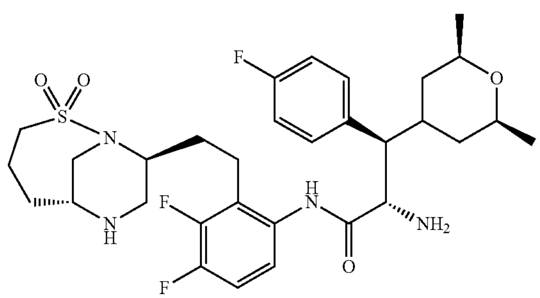 [SMILES: C[C@@H]1CC([C@H](c2ccc(F)cc2)[C@H](N)C(=O)Nc2ccc(F)c(F)c2CC[C@H]2CN[C@@H]3CCCS(=O)(=O)N2C3)C[C@H](C)O1] | (βR)-β-[(2R,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3,4-difluorophenyl)-4-fluoro-L-phenylalaninamide | 623.3 |
| 167 | 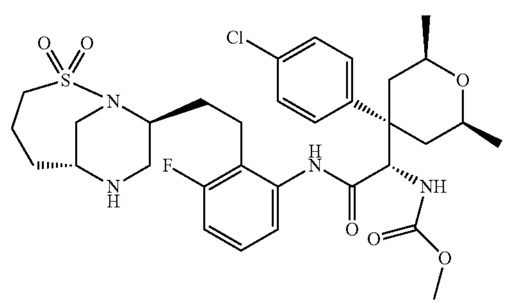 [SMILES: COC(=O)N[C@H](C(=O)Nc1cccc(F)c1CC[C@H]1CN[C@@H]2CCCS(=O)(=O)N1C2)[C@@]1(c2ccc(Cl)cc2)C[C@@H](C)O[C@@H](C)C1] | methyl {(1S)-1-[(2R,4r,6S)-4-(4-chlorophenyl)-2,6-dimethyltetrahydro-2H-pyran-4-yl]-2-[(2-{2-[(6R,9S)-2,2-dioxido-2-thia-1,7-diazabicyclo[4.3.1]dec-9-yl]ethyl}-3-fluorophenyl)amino]-2-oxoethyl}carbamate | 665.3 |
| 168 | 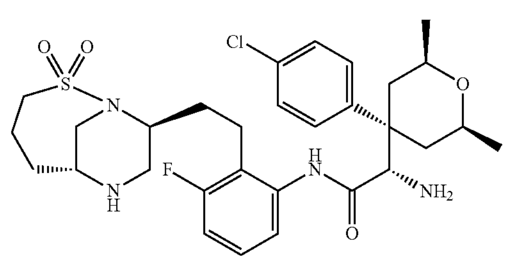 [SMILES: C[C@@H]1C[C@](c2ccc(Cl)cc2)([C@H](N)C(=O)Nc2cccc(F)c2CC[C@H]2CN[C@@H]3CCCS(=O)(=O)N2C3)C[C@H](C)O1] | (2S)-2-amino-2-[(2R,4r,6S)-4-(4-chlorophenyl)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)ethanamide | 607.3 |

TABLE 1-continued

| Example No. | Structure | IUPAC Name | Exact Mass [M + H]+ |
|---|---|---|---|
| 169 | 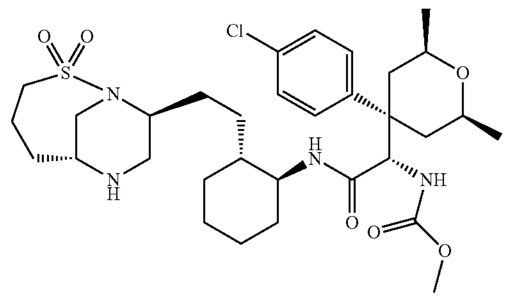 [SMILES: COC(=O)N[C@H](C(=O)N[C@H]1CCCC[C@@H]1CC[C@H]1CN[C@@H]2CCCS(=O)(=O)N1C2)[C@@]1(c2ccc(Cl)cc2)C[C@@H](C)O[C@@H](C)C1] | methyl [(1S)-1-[(2R,4r,6S)-4-(4-chlorophenyl)-2,6-dimethyltetrahydro-2H-pyran-4-yl]-2-{[(1S,2R)-2-{2-[(6R,9S)-2,2-dioxido-2-thia-1,7-diazabicyclo[4.3.1]dec-9-yl]ethyl}cyclohexyl]amino}-2-oxoethyl]carbamate | 653.3 |
| 170 | 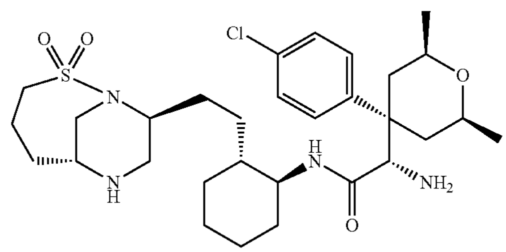 [SMILES: C[C@@H]1C[C@](c2ccc(Cl)cc2)([C@H](N)C(=O)N[C@H]2CCCC[C@@H]2CC[C@H]2CN[C@@H]3CCCS(=O)(=O)N2C3)C[C@H](C)O1] | (2S)-2-amino-2-[(2R,4r,6S)-4-(4-chlorophenyl)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]ethanamide | 595.3 |
| 171 | 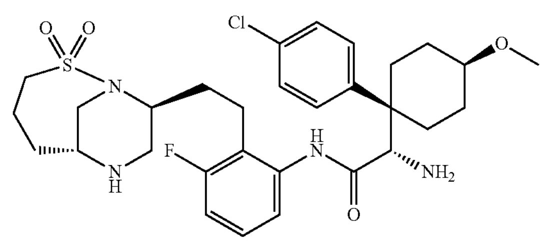 [SMILES: CO[C@H]1CC[C@](c2ccc(Cl)cc2)([C@H](N)C(=O)Nc2cccc(F)c2CC[C@H]2CN[C@@H]3CCCS(=O)(=O)N2C3)CC1] | (2S)-2-amino-2-[trans-1-(4-chlorophenyl)-4-methoxycyclohexyl]-N-(2-{2-[(6R,9S)-2,2-dioxido-2-thia-1,7-diazabicyclo[4.3.1]dec-9-yl]ethyl}-3-fluorophenyl)ethanamide | 607.3 |
| 172 | 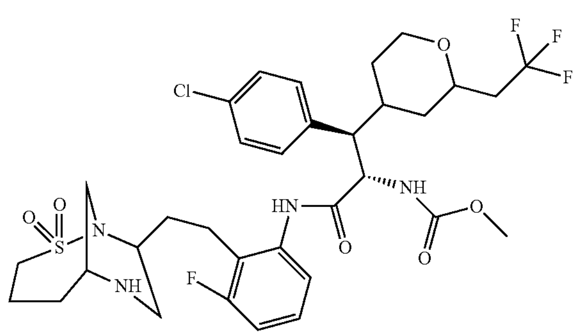 [SMILES: COC(=O)N[C@H](C(=O)Nc1cccc(F)c1CCC1CNC2CCCS(=O)(=O)N1C2)[C@@H](c1ccc(Cl)cc1)C1CCOC(CC(F)(F)F)C1] | methyl {(1S,2R)-2-(4-chlorophenyl)-1-({2-[2-(2,2-dioxido-2-thia-1,7-diazabicyclo[4.3.1]dec-9-yl]ethyl]-3-fluorophenyl}carbamoyl)-2-[2-(2,2,2-trifluoroethyl)tetrahydro-2H-pyran-4-yl]ethyl}carbamate | 733.2 |
| 173 | 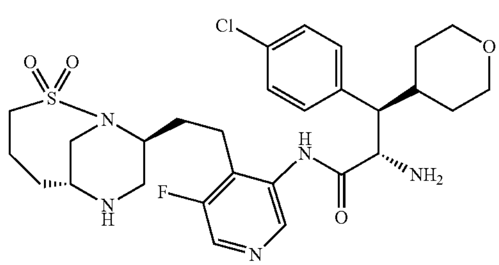 | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-(tetrahydro-2H-pyran-4-yl)-L-phenylalaninamide | 594.2 |

TABLE 1-continued

| Example No. | Structure | IUPAC Name | Exact Mass [M + H]+ |
|---|---|---|---|
| 174 | 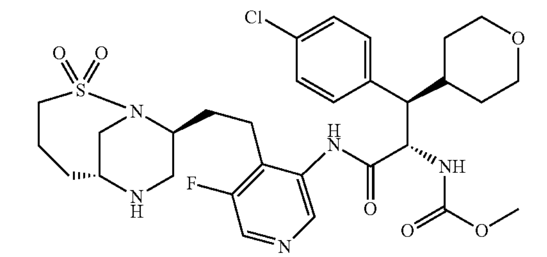 | methyl [(1S,2R)-2-(4-chlorophenyl)-1-[(4-{2-[(6R,9S)-2,2-dioxido-2-thia-1,7-diazabicyclo[4.3.1]dec-9-yl]ethyl}-5-fluoropyridin-3-yl)carbamoyl]-2-(tetrahydro-2H-pyran-4-yl)ethyl]carbamate | 652.2 |
| 175 | 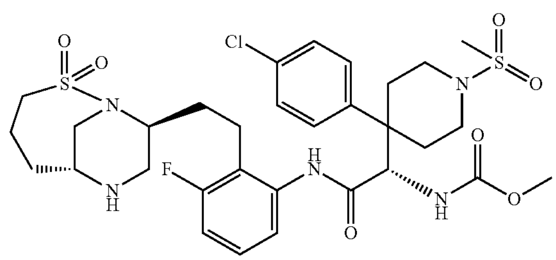 [SMILES: COC(=O)N[C@H](C(=O)Nc1cccc(F)c1CC[C@H]1CN[C@@H]2CCCS(=O)(=O)N1C2)C1(c2ccc(Cl)cc2)CCN(S(C)(=O)=O)CC1] | methyl {(1S)-1-[4-(4-chlorophenyl)-1-(methylsulfonyl)piperidin-4-yl]-2-[(2-{2-[(6R,9S)-2,2-dioxido-2-thia-1,7-diazabicyclo[4.3.1]dec-9-yl]ethyl}-3-fluorophenyl)amino]-2-oxoethyl}carbamate | 714.2 |
| 176 | 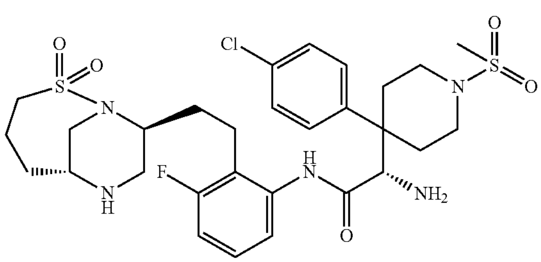 [SMILES: CS(=O)(=O)N1CCC(c2ccc(Cl)cc2)([C@H](N)C(=O)Nc2cccc(F)c2CC[C@H]2CN[C@@H]3CCCS(=O)(=O)N2C3)CC1] | (2S)-2-amino-2-[4-(4-chlorophenyl)-1-(methylsulfonyl)piperidin-4-yl]-N-(2-{2-[(6R,9S)-2,2-dioxido-2-thia-1,7-diazabicyclo[4.3.1]dec-9-yl]ethyl}-3-fluorophenyl)ethanamide | 656.2 |
| 177 | 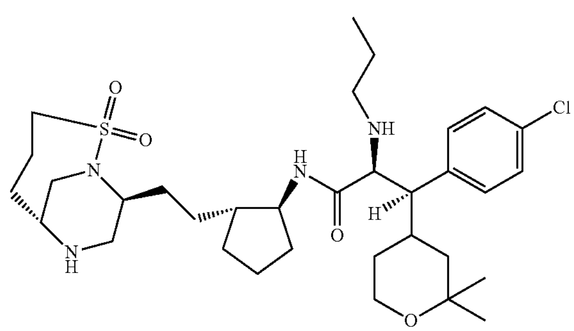 [SMILES: CCCN[C@H](C(=O)N[C@H]1CCC[C@@H]1CC[C@H]1CN[C@@H]2CCCS(=O)(=O)N1C2)[C@@H](c1ccc(Cl)cc1)C1CCOC(C)(C)C1] | (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-propyl-L-phenylalaninamide | 637.4 |
| 178 | 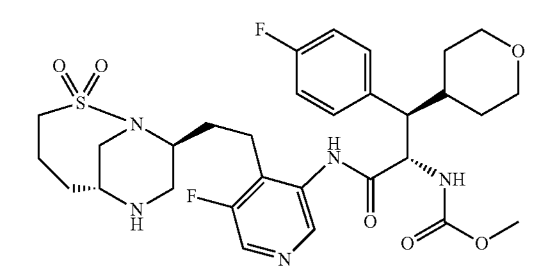 | methyl {(1S)-2-[(4-{2-[(6R,9S)-2,2-dioxido-2-thia-1,7-diazabicyclo[4.3.1]dec-9-yl]ethyl}-5-fluoropyridin-3-yl)amino]-1-[(R)-(4-fluorophenyl)(tetrahydro-2H-pyran-4-yl)methyl]-2-oxoethyl}carbamate | 636.3 |

TABLE 1-continued

| Example No. | Structure | IUPAC Name | Exact Mass [M + H]+ |
|---|---|---|---|
| 179 | 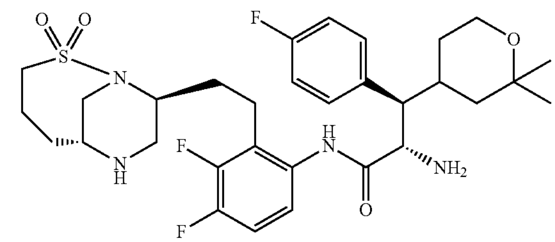 [SMILES: CC1(C)CC([C@H](c2ccc(F)cc2)[C@H](N)C(=O)Nc2ccc(F)c(F)c2CC[C@H]2CN[C@@H]3CCCS(=O)(=O)N2C3)CCO1] | (βR)-β-(2,2-dimethyltetrahydro-2H-pyran-4-yl)-N-(2-{2-[(6R,9S)-2,2-dioxido-2-thia-1,7-diazabicyclo[4.3.1]dec-9-yl]ethyl}-3,4-difluorophenyl)-4-fluoro-L-phenylalaninamide | 623.3 |
| 180 | 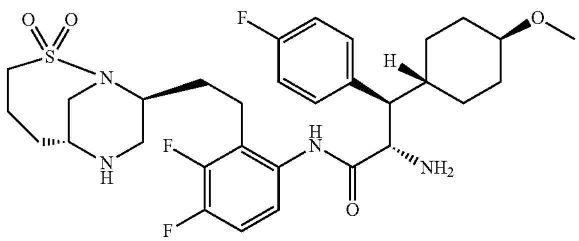 [SMILES: CO[C@H]1CC[C@H]([C@H](c2ccc(F)cc2)[C@H](N)C(=O)Nc2ccc(F)c(F)c2CC[C@H]2CN[C@@H]3CCCS(=O)(=O)N2C3)CC1] | (βR)-N-(2-{2-[(6R,9S)-2,2-dioxido-2-thia-1,7-diazabicyclo[4.3.1]dec-9-yl]ethyl}-3,4-difluorophenyl)-4-fluoro-β-[(1r,4R)-4-methoxycyclohexyl]-L-phenylalaninamide | 623.3 |
| 181 | 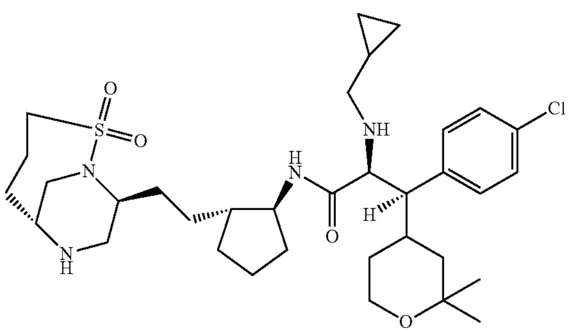 [SMILES: CC1(C)CC([C@H](c2ccc(Cl)cc2)[C@H](NCC2CC2)C(=O)N[C@H]2CCC[C@@H]2CC[C@H]2CN[C@@H]3CCCS(=O)(=O)N2C3)CCO1] | (βR)-4-chloro-Nα-(cyclopropylmethyl)-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 649.4 |
| 182 | 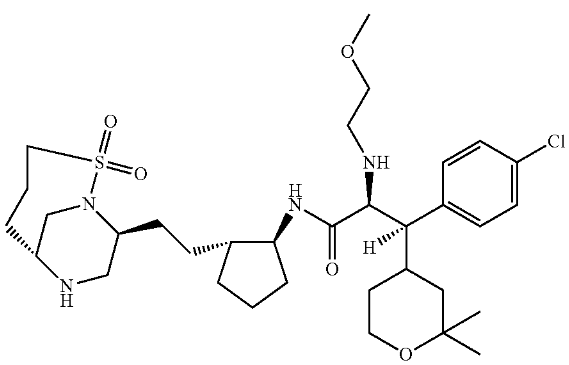 [SMILES: COCCN[C@H](C(=O)N[C@H]1CCC[C@@H]1CC[C@H]1CN[C@@H]2CCCS(=O)(=O)N1C2)[C@@H](c1ccc(Cl)cc1)C1CCOC(C)(C)C1] | (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-(2-methoxyethyl)-L-phenylalaninamide | 653.3 |
| 183 | 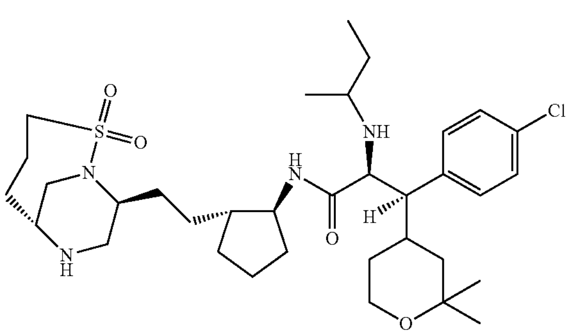 [SMILES: CCC(C)N[C@H](C(=O)N[C@H]1CCC[C@@H]1CC[C@H]1CN[C@@H]2CCCS(=O)(=O)N1C2)[C@@H](c1ccc(Cl)cc1)C1CCOC(C)(C)C1] | (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-[(1S)-1-methylpropyl]-L-phenylalaninamide | 651.4 |

TABLE 1-continued

| Example No. | Structure | IUPAC Name | Exact Mass [M + H]+ |
|---|---|---|---|
| 184 | 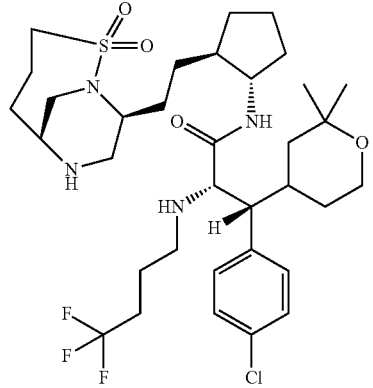 [SMILES: CC1(C)CC([C@H](c2ccc(Cl)cc2)[C@H](NCCCC(F)(F)F)C(=O)N[C@H]2CCC[C@@H]2CC[C@H]2CN[C@@H]3CCCS(=O)(=O)N2C3)CCO1] | (βR)-4-chloro-β-(2,2-dimethyltetrdhydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-(4,4,4-trifluorobutyl)-L-phenylalaninamide | 705.3 |
| 185 | 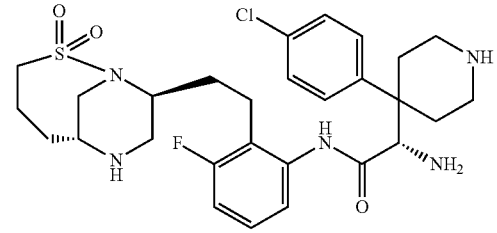 [SMILES: N[C@H](C(=O)Nc1cccc(F)c1CC[C@H]1CN[C@@H]2CCCS(=O)(=O)N1C2)C1(c2ccc(Cl)cc2)CCNCC1] | (2S)-2-amino-2-[4-(4-chlorophenyl)piperidin-4-yl]-N-(2-{2-[(6R,9S)-2,2-dioxido-2-thia-1,7-diazabicyclo[4.3.1]dec-9-yl]ethyl}-3-fluorophenyl)ethanamide | 578.2 |
| 186 | 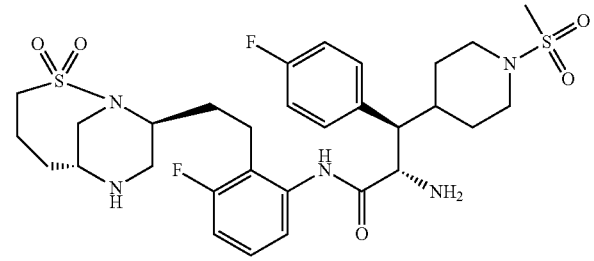 [SMILES: CS(=O)(=O)N1CCC([C@H](c2ccc(F)cc2)[C@H](N)C(=O)Nc2cccc(F)c2CC[C@H]2CN[C@@H]3CCCS(=O)(=O)N2C3)CC1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-[1-(methylsulfonyl)piperidin-4-yl]-L-phenylalaninamide | 654.3 |
| 187 | 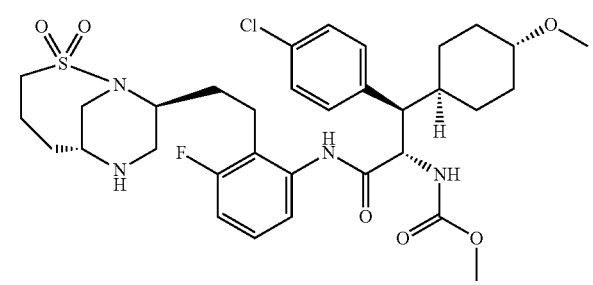 [SMILES: COC(=O)N[C@H](C(=O)Nc1cccc(F)c1CC[C@H]1CN[C@@H]2CCCS(=O)(=O)N1C2)[C@@H](c1ccc(Cl)cc1)[C@H]1CC[C@H](OC)CC1] | methyl {(1S,2R)-2-(4-chlorophenyl)-1-[(2-{2-[(6R,9S)-2,2-dioxido-2-thia-1,7-diazabicyclo[4.3.1]dec-9-yl]ethyl}-3-fluorophenyl)carbamoyl]-2-[(1r,4R)-4-methoxycyclohexyl]ethyl}carbamate | 679.3 |
| 188 | 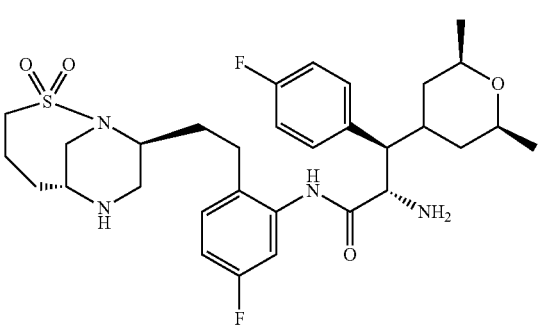 [SMILES: C[C@@H]1CC([C@H](c2ccc(F)cc2)[C@H](N)C(=O)Nc2cc(F)ccc2CC[C@H]2CN[C@@H]3CCCS(=O)(=O)N2C3)C[C@H](C)O1] | (βR)-β-[(2S,2R)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-5-fluorophenyl)-4-fluoro-L-phenylalaninamide | 605.3 |

TABLE 1-continued

| Example No. | Structure | IUPAC Name | Exact Mass [M + H]+ |
|---|---|---|---|
| 189 | 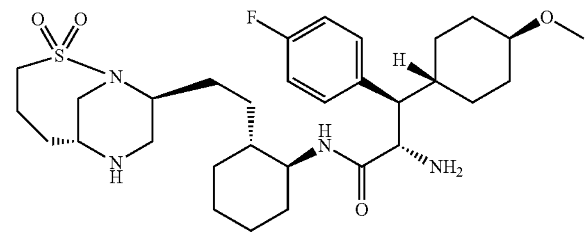 [SMILES: CO[C@H]1CC[C@H]([C@H](c2ccc(F)cc2)[C@H](N)C(=O)N[C@H]2CCCC[C@@H]2CC[C@H]2CN[C@@H]3CCCS(=O)(=O)N2C3)CC1] | (βR)-N-[(1S,2R)-2-{2-[(6R,9S)-2,2-dioxido-2-thia-1,7-diazabicyclo[4.3.1]dec-9-yl]ethyl}cyclohexyl]-4-fluoro-β-[(1r,4R)-4-methoxycyclohexyl]-L-phenylalaninamide | 593.4 |
| 190 | 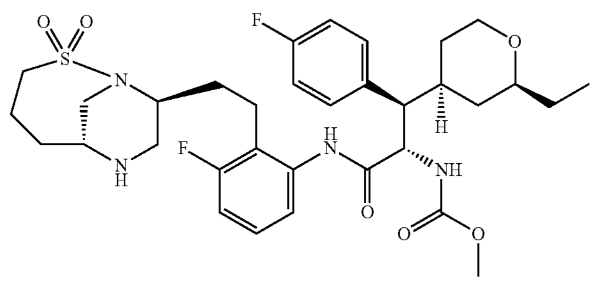 [SMILES: CC[C@H]1C[C@@H]([C@H](c2ccc(F)cc2)[C@H](NC(=O)OC)C(=O)Nc2cccc(F)c2CC[C@H]2CN[C@@H]3CCCS(=O)(=O)N2C3)CCO1] | methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-[(2S,4S)-2-ethyltetrahydro-2H-pyran-4-yl](4-fluorophenyl)methyl]-2-oxoethyl}carbamate | 663.3 |
| 191 | 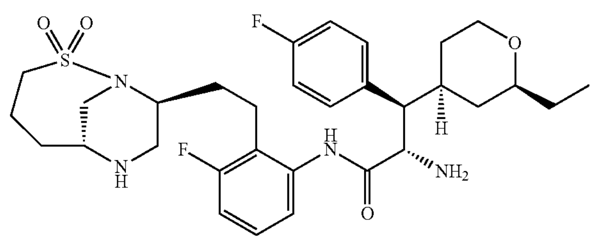 [SMILES: CC[C@H]1C[C@@H]([C@H](c2ccc(F)cc2)[C@H](N)C(=O)Nc2cccc(F)c2CC[C@H]2CN[C@@H]3CCCS(=O)(=O)N2C3)CCO1] | (βR)-N-(2-{2-[(6R,9S)-2,2-dioxido-2-thia-1,7-diazabicyclo[4.3.1]dec-9-yl]ethyl}-3-fluorophenyl)-β-[(2S,4S)-2-ethyltetrahydro-2H-pyran-4-yl]-4-fluoro-L-phenylalaninamide | 605.3 |
| 192 | 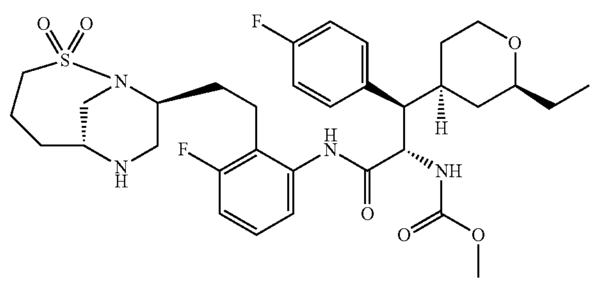 [SMILES: CC[C@H]1C[C@@H]([C@H](c2ccc(F)cc2)[C@H](NC(=O)OC)C(=O)Nc2cccc(F)c2CC[C@H]2CN[C@@H]3CCCS(=O)(=O)N2C3)CCO1] | methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-[(2S,4S)-2-ethyltetrahydro-2H-pyran-4-yl](4-fluorophenyl)methyl]-2-oxoethyl}carbamate | 663.3 |
| 193 | 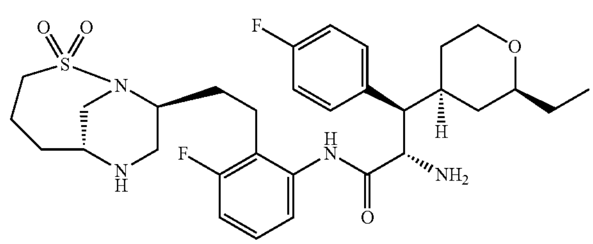 [SMILES: CC[C@H]1C[C@@H]([C@H](c2ccc(F)cc2)[C@H](N)C(=O)Nc2cccc(F)c2CC[C@H]2CN[C@@H]3CCCS(=O)(=O)N2C3)CCO1] | (βR)-N-(2-{2-[(6R,9S)-2,2-dioxido-2-thia-1,7-diazabicyclo[4.3.1]dec-9-yl]ethyl}-3-fluorophenyl)-β-[(2S,4S)-2-ethyltetrahydro-2H-pyran-4-yl]-4-fluoro-L-phenylalaninamide | 605.3 |
| 194 | 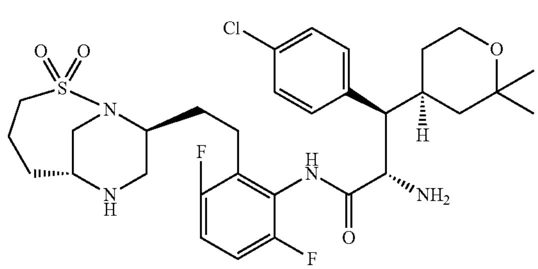 [SMILES: CC1(C)C[C@@H]([C@H](c2ccc(Cl)cc2)[C@H](N)C(=O)Nc2c(F)ccc(F)c2CC[C@H]2CN[C@@H]3CCCS(=O)(=O)N2C3)CCO1] | (βR)-4-chloro-β-[(4S)-2,2-dimethyltetrahydro-2H-pyran-4-yl]-N-(2-{2-[(6R,9S)-2,2-dioxido-2-thia-1,7-diazabicyclo[4.3.1]dec-9-yl]ethyl}-3,6-difluorophenyl)-L-phenylalaninamide | 639.3 |

TABLE 1-continued

| Example No. | Structure | IUPAC Name | Exact Mass [M + H]+ |
|---|---|---|---|
| 195 | 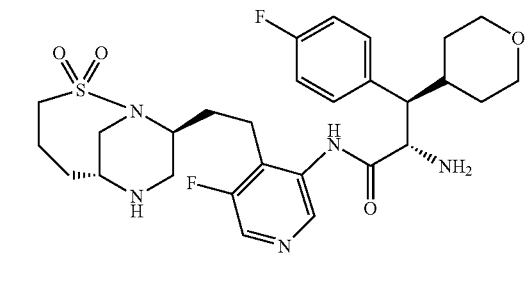 [SMILES: N[C@H](C(=O)Nc1cncc(F)c1CC[C@H]1CN[C@@H]2CCCS(=O)(=O)N1C2)[C@@H](c1ccc(F)cc1)C1CCOCC1] | (βR)-N-(4-{2-[(6R,9S)-2,2-dioxido-2-thia-1,7-diazabicyclo[4.3.1]dec-9-yl]ethyl}-5-fluoropyridin-3-yl)-4-fluoro-β-(tetrahydro-2H-pyran-4-yl)-L-phenylalaninamide | 578.3 |
| 196 | 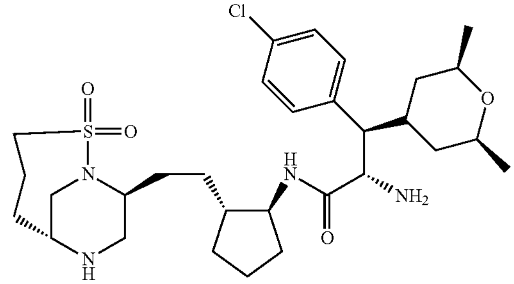 [SMILES: C[C@@H]1CC([C@H](c2ccc(Cl)cc2)[C@H](N)C(=O)N[C@H]2CCC[C@@H]2CC[C@H]2CN[C@@H]3CCCS(=O)(=O)N2C3)C[C@H](C)O1] | (βR)-4-chloro-β-[(2R,4s,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 595.3 |
| 197 | 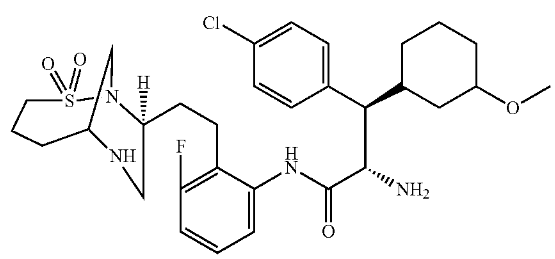 [SMILES: COC1CCCC([C@H](c2ccc(Cl)cc2)[C@H](N)C(=O)Nc2cccc(F)c2CC[C@H]2CNC3CCCS(=O)(=O)N2C3)C1] | (βR)-4-chloro-N-(2-{2-[(9S)-2,2-dioxido-2-thia-1,7-diazabicyclo[4.3.1]dec-9-yl]ethyl}-3-fluorophenyl)-β-(3-methoxycyclohexyl)-L-phenylalaninamide | 621.3 |
| 198 | 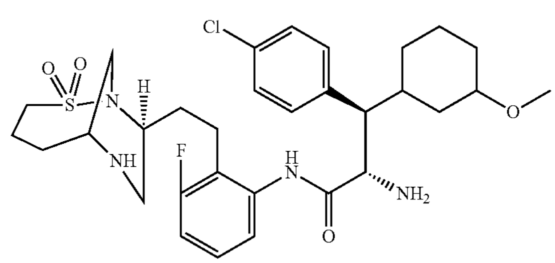 [SMILES: COC1CCCC([C@H](c2ccc(Cl)cc2)[C@H](N)C(=O)Nc2cccc(F)c2CC[C@H]2CNC3CCCS(=O)(=O)N2C3)C1] | (βR)-4-chloro-N-(2-{2-[(9S)-2,2-dioxido-2-thia-1,7-diazabicyclo[4.3.1]dec-9-yl]ethyl}-3-fluorophenyl)-β-(3-methoxycyclohexyl)-L-phenylalaninamide | 621.3 |
| 199 | 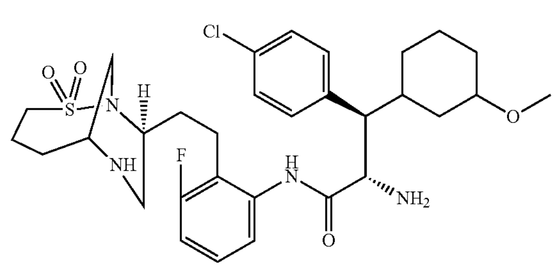 [SMILES: COC1CCCC([C@H](c2ccc(Cl)cc2)[C@H](N)C(=O)Nc2cccc(F)c2CC[C@H]2CNC3CCCS(=O)(=O)N2C3)C1] | (βR)-4-chloro-N-(2-{2-[(9S)-2,2-dioxido-2-thia-1,7-diazabicyclo[4.3.1]dec-9-yl]ethyl}-3-fluorophenyl)-β-(3-methoxycyclohexyl)-L-phenylalaninamide | 621.3 |

TABLE 1-continued

| Example No. | Structure | IUPAC Name | Exact Mass [M + H]+ |
|---|---|---|---|
| 200 | 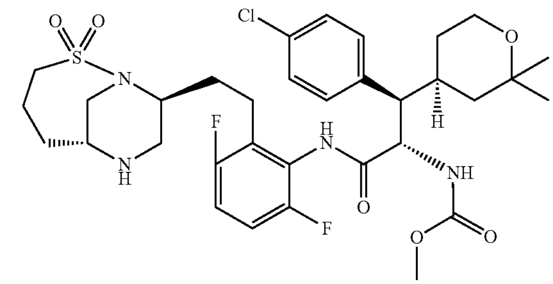 [SMILES: COC(=O)N[C@H](C(=O)Nc1c(F)ccc(F)c1CC[C@H]1CN[C@@H]2CCCS(=O)(=O)N1C2)[C@@H](c1ccc(Cl)cc1)[C@H]1CCOC(C)(C)C1] | methyl {(1S,2R)-2-(4-chlorophenyl)-2-[(4S)-2,2-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3,6-difluorophenyl)carbamoyl]ethyl}carbamate | 697.3 |
| 201 | 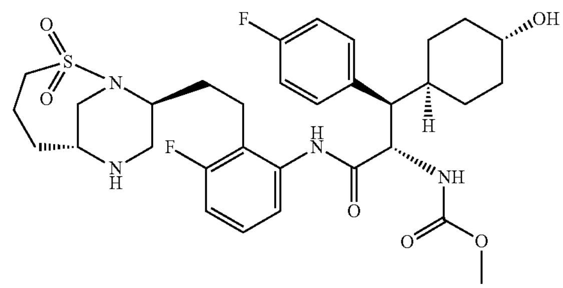 [SMILES: COC(=O)N[C@H](C(=O)Nc1cccc(F)c1CC[C@H]1CN[C@@H]2CCCS(=O)(=O)N1C2)[C@@H](c1ccc(F)cc1)[C@H]1CC[C@H](O)CC1] | methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(R)-(4-fluorophenyl)[(1r,4R)-4-hydroxycyclohexyl]methyl}-2-oxoethyl]carbamate | 649.3 |
| 202 | 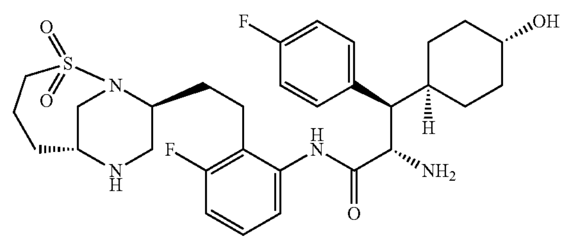 [SMILES: N[C@H](C(=O)Nc1cccc(F)c1CC[C@H]1CN[C@@H]2CCCS(=O)(=O)N1C2)[C@@H](c1ccc(F)cc1)[C@H]1CC[C@H](O)CC1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-[(1r,4R)-4-hydroxycyclohexyl]-L-phenylalaninamide | 591.3 |
| 203 | 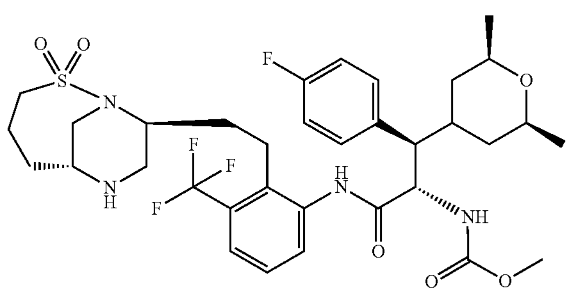 [SMILES: COC(=O)N[C@H](C(=O)Nc1cccc(C(F)(F)F)c1CC[C@H]1CN[C@@H]2CCCS(=O)(=O)N1C2)[C@@H](c1ccc(F)cc1)C1C[C@@H](C)O[C@@H](C)C1] | methyl [(1S,2R)-2-[(2R,6S)-2,6-dimethyltetrahydro-2H-pyran-4-yl]-1-{[2-{2-[(6R,9S)-2,2-dioxido-2-thia-1,7-diazabicyclo[4.3.1]dec-9-yl]ethyl}-3-(trifluoromethyl)phenyl]carbamoyl}-2-(4-fluorophenyl)ethyl]carbamate | 713.3 |
| 204 | 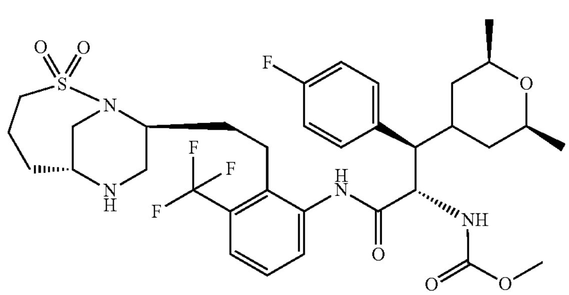 [SMILES: COC(=O)N[C@H](C(=O)Nc1cccc(C(F)(F)F)c1CC[C@H]1CN[C@@H]2CCCS(=O)(=O)N1C2)[C@@H](c1ccc(F)cc1)C1C[C@@H](C)O[C@@H](C)C1] | (βR)-β-[(2R,6S)-2,6-dimethyltetrahydro-2H-pyran-4-yl]-N-[2-{2-[(6R,9S)-2,2-dioxido-2-thia-1,7-diazabicyclo[4.3.1]dec-9-yl]ethyl}-3-(trifluoromethyl)phenyl]-4-fluoro-L-phenylalaninamide | 655.3 |

TABLE 1-continued

| Example No. | Structure | IUPAC Name | Exact Mass [M + H]+ |
|---|---|---|---|
| 205 | 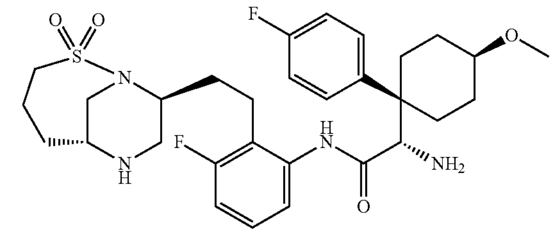 [SMILES: CO[C@H]1CC[C@](c2ccc(F)cc2)([C@H](N)C(=O)Nc2cccc(F)c2CC[C@H]2CN[C@@H]3CCCS(=O)(=O)N2C3)CC1] | (2S)-2-amino-N-(2-{2-[(6R,9S)-2,2-dioxido-2-thia-1,7-diazabicyclo[4.3.1]dec-9-yl]ethyl}-3-fluorophenyl)-2-[trans-1-(4-fluorophenyl)-4-methoxycyclohexyl]ethanamide | 591.3 |
| 206 | 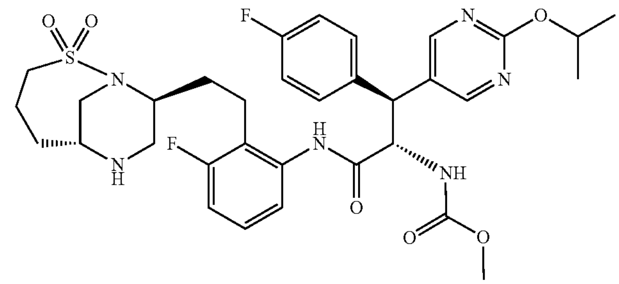 [SMILES: COC(=O)N[C@H](C(=O)Nc1cccc(F)c1CC[C@H]1CN[C@@H]2CCCS(=O)(=O)N1C2)[C@@H](c1ccc(F)cc1)c1cnc(OC(C)C)nc1] | methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(S)-(4-fluorophenyl)[2-(1-methylethoxy)pyrimidin-5-yl]methyl}-2-oxoethyl]carbamate | 687.3 |
| 207 | 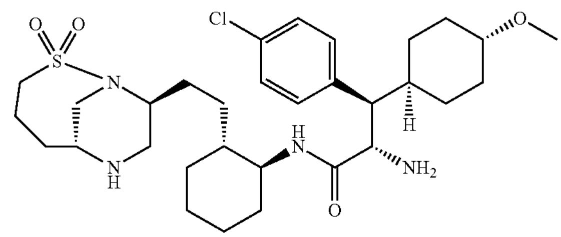 [SMILES: CO[C@H]1CC[C@H]([C@H](c2ccc(Cl)cc2)[C@H](N)C(=O)N[C@H]2CCCC[C@@H]2CC[C@H]2CN[C@@H]3CCCS(=O)(=O)N2C3)CC1] | (βR)-4-chloro-N-[(1S,2R)-2-{2-[(6R,9S)-2,2-dioxido-2-thia-1,7-diazabicyclo[4.3.1]dec-9-yl]ethyl}cyclohexyl]-β-[(1r,4R)-4-methoxycyclohexyl]-L-phenylalaninamide | 609.3 |
| 208 | 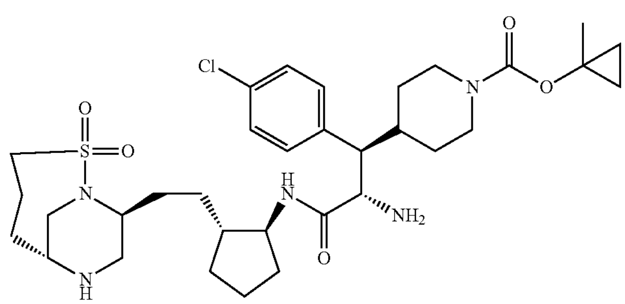 [SMILES: CC1(OC(=O)N2CCC([C@H](c3ccc(Cl)cc3)[C@H](N)C(=O)N[C@H]3CCC[C@@H]3CC[C@H]3CN[C@@H]4CCCS(=O)(=O)N3C4)CC2)CC1] | 1-methylcyclopropyl 4-[(1R,2S)-2-amino-1-(4-chlorophenyl)-3-{[(1S,2R)-2-{2-[(6R,9S)-2,2-dioxido-2-thia-1,7-diazabicyclo[4.3.1]dec-9-yl]ethyl}cyclopentyl]amino}-3-oxopropyl]piperidine-1-carboxylate | 664.3 |
| 209 | 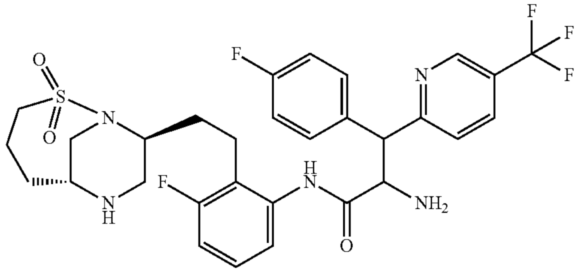 [SMILES: NC(C(=O)Nc1cccc(F)c1CC[C@H]1CN[C@@H]2CCCS(=O)(=O)N1C2)C(c1ccc(F)cc1)c1ccc(C(F)(F)F)cn1] | N-(2-{2-[(6R,9S)-2,2-dioxido-2-thia-1,7-diazabicyclo[4.3.1]dec-9-yl]ethyl}-3-fluorophenyl)-4-fluoro-β-[5-(trifluoromethyl)pyridin-2-yl]phenylalaninamide | 638.2 |

TABLE 1-continued

| Example No. | Structure | IUPAC Name | Exact Mass [M + H]+ |
|---|---|---|---|
| 210 | 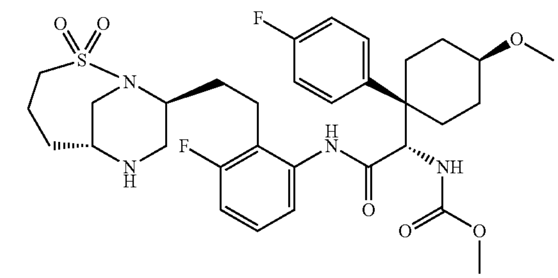 [SMILES: COC(=O)N[C@H](C(=O)Nc1cccc(F)c1CC[C@H]1CN[C@@H]2CCCS(=O)(=O)N1C2)[C@]1(c2ccc(F)cc2)CC[C@@H](OC)CC1] | methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[trans-1-(4-fluorophenyl)-4-methoxycyclohexyl]-2-oxoethyl}carbamate | 649.3 |
| 211 | 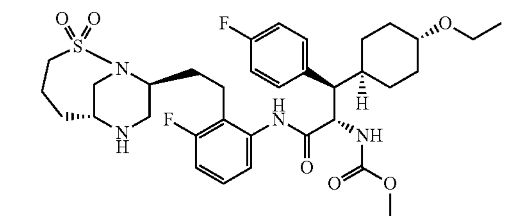 [SMILES: CCO[C@H]1CC[C@H]([C@H](c2ccc(F)cc2)[C@H](NC(=O)OC)C(=O)Nc2cccc(F)c2CC[C@H]2CN[C@@H]3CCCS(=O)(=O)N2C3)CC1] | methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-[(1r,4R)-4-ethoxycyclohexyl](4-fluorophenyl)methyl]-2-oxoethyl}carbamate | 677.3 |
| 212 | 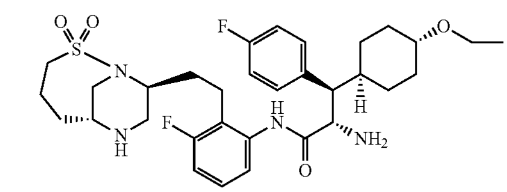 [SMILES: CCO[C@H]1CC[C@H]([C@H](c2ccc(F)cc2)[C@H](N)C(=O)Nc2cccc(F)c2CC[C@H]2CN[C@@H]3CCCS(=O)(=O)N2C3)CC1] | (βR)-N-(2-{2-[(6R,9S)-2,2-dioxido-2-thia-1,7-diazabicyclo[4.3.1]dec-9-yl]ethyl}-3-fluorophenyl)-β-[(1r,4R)-4-ethoxycyclohexyl]-4-fluoro-L-phenylalaninamide | 619.3 |
| 213 | 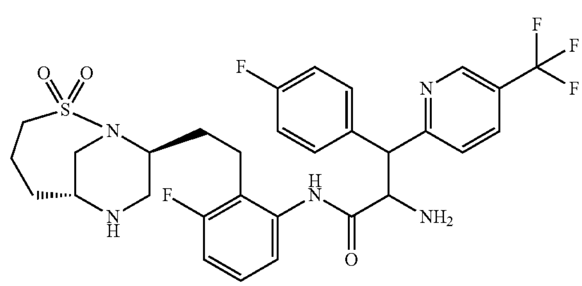 [SMILES: NC(C(=O)Nc1cccc(F)c1CC[C@H]1CN[C@@H]2CCCS(=O)(=O)N1C2)C(c1ccc(F)cc1)c1ccc(C(F)(F)F)cn1] | N-(2-{2-[(6R,9S)-2,2-dioxido-2-thia-1,7-diazabicyclo[4.3.1]dec-9-yl]ethyl}-3-fluorophenyl)-4-fluoro-β-[5-(trifluoromethyl)pyridin-2-yl]phenylalaninamide | 638.2 |
| 214 | 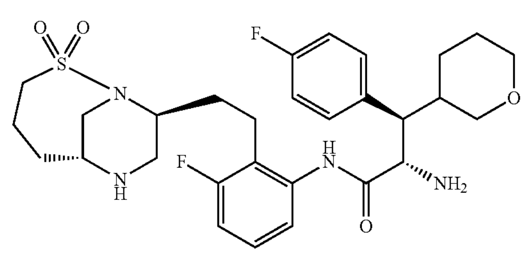 [SMILES: N[C@H](C(=O)Nc1cccc(F)c1CC[C@H]1CN[C@@H]2CCCS(=O)(=O)N1C2)[C@@H](c1ccc(F)cc1)C1CCCOC1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-(tetrahydro-2H-pyran-3-yl)-L-phenylalaninamide | 577.3 |
| 215 | 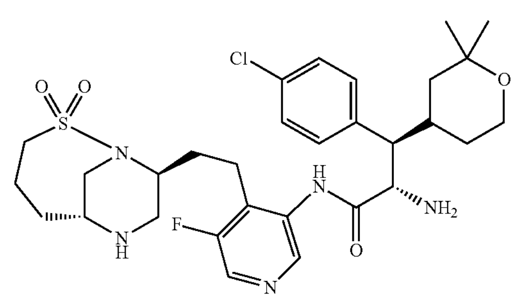 [SMILES: CC1(C)CC([C@H](c2ccc(Cl)cc2)[C@H](N)C(=O)Nc2cncc(F)c2CC[C@H]2CN[C@@H]3CCCS(=O)(=O)N2C3)CCO1] | (βR)-4-chloro-β-[(4S)-2,2-dimethyltetrahydro-2H-pyran-4-yl]-N-(4-{2-[(6R,9S)-2,2-dioxido-2-thia-1,7-diazabicyclo[4.3.1]dec-9-yl]ethyl}-5-fluoropyridin-3-yl)-L-phenylalaninamide | 622.3 |

TABLE 1-continued

| Example No. | Structure | IUPAC Name | Exact Mass [M + H]+ |
|---|---|---|---|
| 216 | 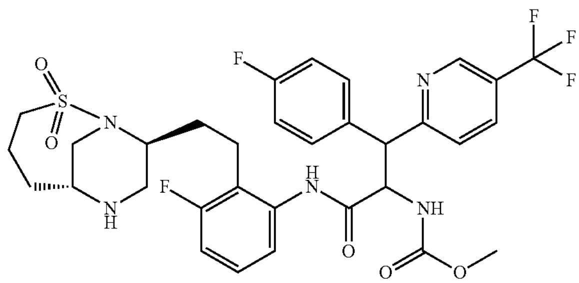 [SMILES: COC(=O)NC(C(=O)Nc1cccc(F)c1CC[C@H]1CN[C@@H]2CCCS(=O)(=O)N1C2)C(c1ccc(F)cc1)c1ccc(C(F)(F)F)cn1] | methyl (2-[(2-{2-[(6R,9S)-2,2-dioxido-2-thia-1,7-diazabicyclo[4.3.1]dec-9-yl]ethyl}-3-fluorophenyl)amino]-1-{(4-fluorophenyl)[5-(trifluoromethyl)pyridin-2-yl]methyl}-2-oxoethyl)carbamate | 696.2 |
| 217 | 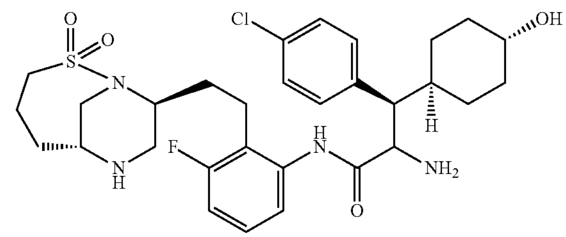 [SMILES: NC(C(=O)Nc1cccc(F)c1CC[C@H]1CN[C@@H]2CCCS(=O)(=O)N1C2)[C@@H](c1ccc(Cl)cc1)[C@H]1CC[C@H](O)CC1] | (βR)-4-chloro-N-(2-{2-[(6R,9S)-2,2-dioxido-2-thia-1,7-diazabicyclo[4.3.1]dec-9-yl]ethyl}-3-fluorophenyl)-β-[(1r,4R)-4-hydroxycyclohexyl]-L-phenylalaninamide | 607.3 |
| 218 | 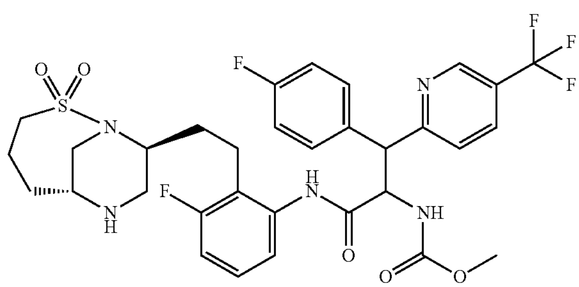 [SMILES: COC(=O)NC(C(=O)Nc1cccc(F)c1CC[C@H]1CN[C@@H]2CCCS(=O)(=O)N1C2)C(c1ccc(F)cc1)c1ccc(C(F)(F)F)cn1] | methyl (2-[(2-{2-[(6R,9S)-2,2-dioxido-2-thia-1,7-diazabicyclo[4.3.1]dec-9-yl]ethyl}-3-fluorophenyl)amino]-1-{(4-fluorophenyl)[5-(trifluoromethyl)pyridin-2-yl]methyl}-2-oxoethyl)carbamate | 696.2 |
| 219 | 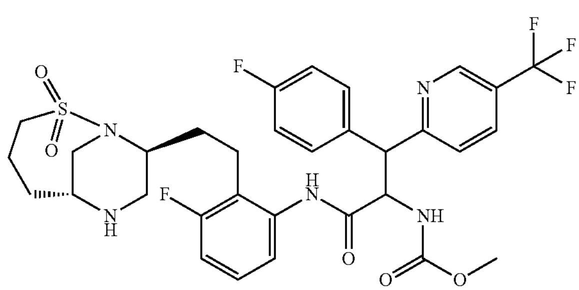 [SMILES: COC(=O)NC(C(=O)Nc1cccc(F)c1CC[C@H]1CN[C@@H]2CCCS(=O)(=O)N1C2)C(c1ccc(F)cc1)c1ccc(C(F)(F)F)cn1] | methyl (2-[(2-{2-[(6R,9S)-2,2-dioxido-2-thia-1,7-diazabicyclo[4.3.1]dec-9-yl]ethyl}-3-fluorophenyl)amino]-1-{(4-fluorophenyl)[5-(trifluoromethyl)pyridin-2-yl]methyl}-2-oxoethylcarbamate | 696.2 |
| 220 | 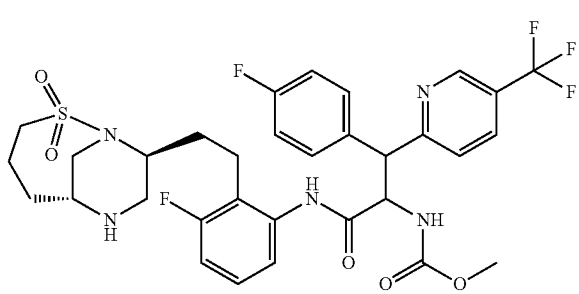 [SMILES: COC(=O)NC(C(=O)Nc1cccc(F)c1CC[C@H]1CN[C@@H]2CCCS(=O)(=O)N1C2)C(c1ccc(F)cc1)c1ccc(C(F)(F)F)cn1] | methyl (2-[(2-{2-[(6R,9S)-2,2-dioxido-2-thia-1,7-diazabicyclo[4.3.1]dec-9-yl]ethyl}-3-fluorophenyl)amino]-1-{(4-fluorophenyl)[5-(trifluoromethyl)pyridin-2-yl]methyl}-2-oxoethyl)carbamate | 696.2 |

TABLE 1-continued

| Example No. | Structure | IUPAC Name | Exact Mass [M + H]+ |
|---|---|---|---|
| 221 | 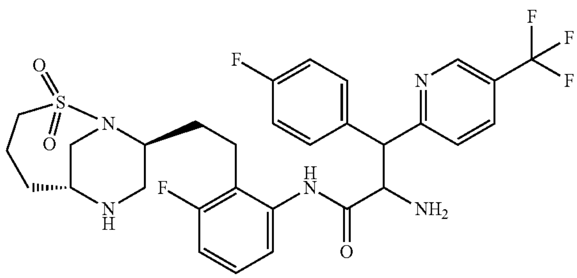 [SMILES: NC(C(=O)Nc1cccc(F)c1CC[C@H]1CN[C@@H]2CCCS(=O)(=O)N1C2)C(c1ccc(F)cc1)c1ccc(C(F)(F)F)cn1] | N-(2-{2-[(6R,9S)-2,2-dioxido-2-thia-1,7-diazabicyclo[4.3.1]dec-9-yl]ethyl}-3-fluorophenyl)-4-fluoro-β-[5-(trifluoromethyl)pyridin-2-yl]phenylalaninamide | 638.2 |
| 222 | 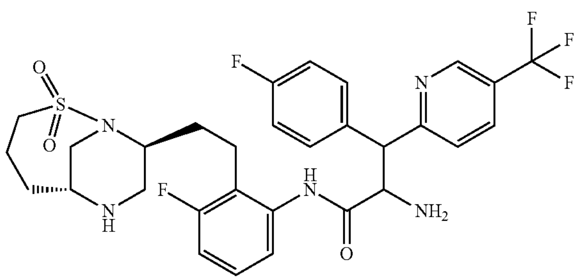 [SMILES: NC(C(=O)Nc1cccc(F)c1CC[C@H]1CN[C@@H]2CCCS(=O)(=O)N1C2)C(c1ccc(F)cc1)c1ccc(C(F)(F)F)cn1] | N-(2-{2-[(6R,9S)-2,2-dioxido-2-thia-1,7-diazabicyclo[4.3.1]dec-9-yl]ethyl}-3-fluorophenyl)-4-fluoro-β-[5-(trifluoromethyl)pyridin-2-yl]phenylalaninamide | 638.2 |
| 223 | 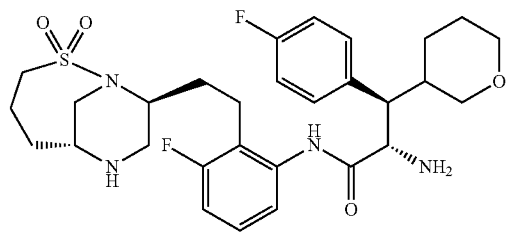 [SMILES: N[C@H](C(=O)Nc1cccc(F)c1CC[C@H]1CN[C@@H]2CCCS(=O)(=O)N1C2)[C@@H](c1ccc(F)cc1)C1CCCOC1] | (βR)-N-(2-{2-[(6R,9S)-2,2-dioxido-2-thia-1,7-diazabicyclo[4.3.1]dec-9-yl]ethyl}-3-fluorophenyl)-4-fluoro-β-(tetrahydro-2H-pyran-3-yl)-L-phenylalaninamide | 577.3 |
| 224 | 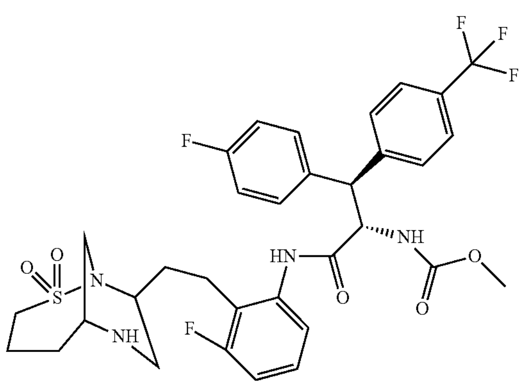 [SMILES: COC(=O)N[C@H](C(=O)Nc1cccc(F)c1CCC1CNC2CCCS(=O)(=O)N1C2)[C@@H](c1ccc(F)cc1)c1ccc(C(F)(F)F)cc1] | Methyl [(1S)-2-({2-[2-(2,2-dioxido-2-thia-1,7-diazabicyclo[4.3.1]dec-9-yl)ethyl]-3-fluorophenyl}amino)-1-{(R)-(4-fluorophenyl)[4-(trifluoromethyl)phenyl]methyl}-2-oxoethyl]carbamate | 695.2 |
| 225 | 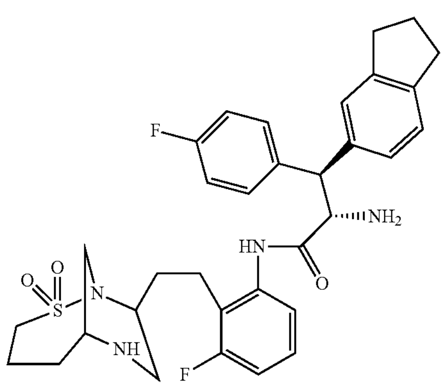 [SMILES: N[C@H](C(=O)Nc1cccc(F)c1CCC1CNC2CCCS(=O)(=O)N1C2)[C@@H](c1ccc(F)cc1)c1ccc2c(c1)CCC2] | (2S,3S)-2-Amino-3-(2,3-dihydro-1H-inden-5-yl)-N-{2-[2-(2,2-dioxido-2-thia-1,7-diazabicyclo[4.3.1]dec-9-yl)ethyl]-3-fluorophenyl}-3-(4-fluorophenyl)propanamide | 609.3 |

TABLE 1-continued

| Example No. | Structure | IUPAC Name | Exact Mass [M + H]+ |
|---|---|---|---|
| 226 | 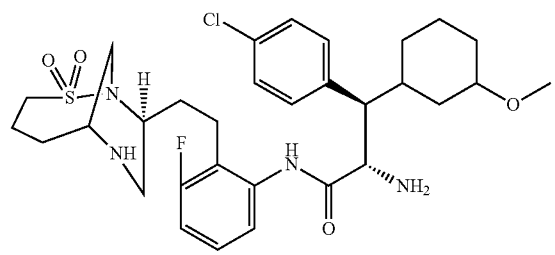 [SMILES: COC1CCCC([C@H](c2ccc(Cl)cc2)[C@H](N)C(=O)Nc2cccc(F)c2CC[C@H]2CNC3CCCS(=O)(=O)N2C3)C1] | (βR)-4-Chloro-N-(2-{2-[(9S)-2,2-dioxido-2-thia-1,7-diazabicyclo[4.3.1]dec-9-yl]ethyl}-3-fluorophenyl)-β-(3-methoxycyclohexyl)-L-phenylalaninamide | 621.3 |
| 227 | 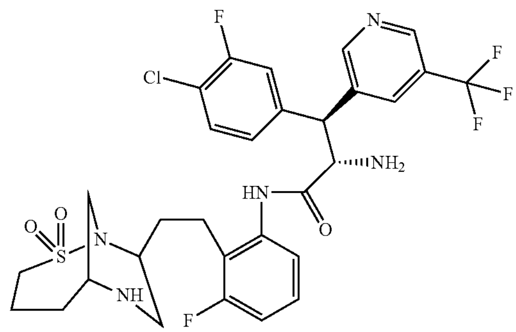 [SMILES: N[C@H](C(=O)Nc1cccc(F)c1CCC1CNC2CCCS(=O)(=O)N1C2)[C@H](c1cncc(C(F)(F)F)c1)c1ccc(Cl)c(F)c1] | (βS)-4-Chloro-N-{2-[2-(2,2-dioxido-2-thia-1,7-diazabicyclo[4.3.1]dec-9-yl)ethyl]-3-fluorophenyl}-3-fluoro-β-[5-(trifluoromethyl)pyridin-3-yl]-L-phenylalaninamide | 672.2 |
| 228 | 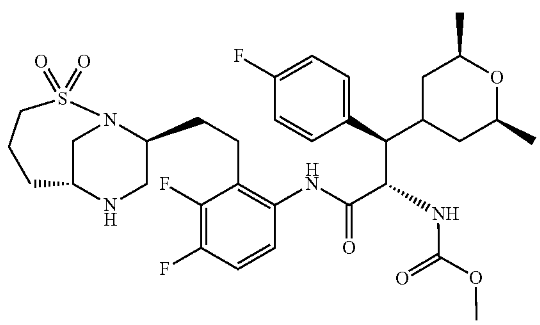 [SMILES: COC(=O)N[C@H](C(=O)Nc1ccc(F)c(F)c1CC[C@H]1CN[C@@H]2CCCS(=O)(=O)N1C2)[C@@H](c1ccc(F)cc1)C1C[C@@H](C)O[C@@H](C)C1] | Methyl [(1S,2R)-2-[(2R,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3,4-difluorophenyl)carbamoyl]-2-(4-fluorophenyl)ethyl]carbamate | 681.3 |
| 229 | 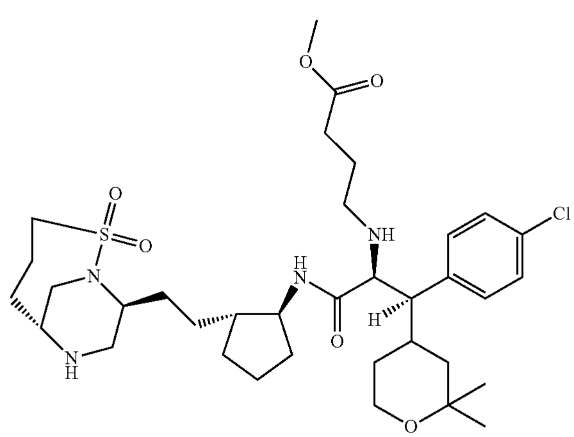 [SMILES: COC(=O)CCCN[C@H](C(=O)N[C@H]1CCC[C@@H]1CC[C@H]1CN[C@@H]2CCCS(=O)(=O)N1C2)[C@@H](c1ccc(Cl)cc1)C1CCOC(C)(C)C1] | methyl 4-{[(1S,2R)-2-(4-chlorophenyl)-2-(2,2-dimethyltetrahydro-2H-pyran-4-yl)-1-{[(1S,2R)-2-{2-[(6R,9S)-2,2-dioxido-2-thia-1,7-diazabicyclo[4.3.1]dec-9-yl]ethyl}cyclopentyl]carbamoyl}ethyl]amino}butanoate | 695.4 |

TABLE 1-continued

| Example No. | Structure | IUPAC Name | Exact Mass [M + H]+ |
|---|---|---|---|
| 230 | 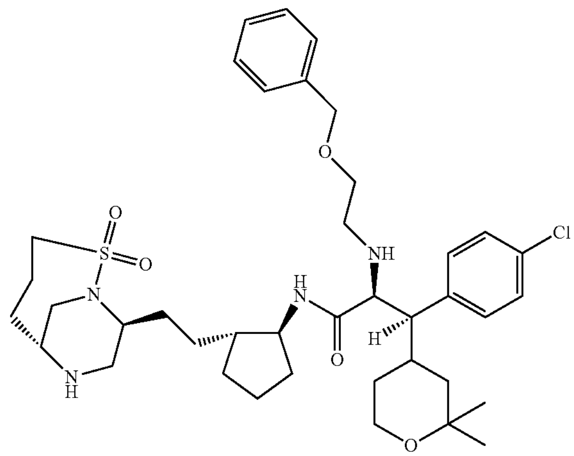 [SMILES: CC1(C)CC([C@H](c2ccc(Cl)cc2)[C@H](NCCOCc2ccccc2)C(=O)N[C@H]2CCC[C@@H]2CC[C@H]2CN[C@@H]3CCCS(=O)(=O)N2C3)CCO1] | (βR)-Nα-[2-(benzyloxy)ethyl]-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 729.4 |
| 231 | 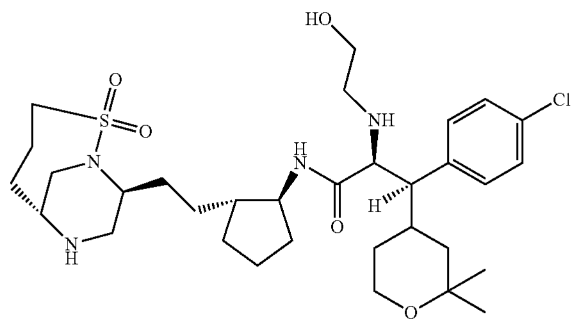 [SMILES: CC1(C)CC([C@H](c2ccc(Cl)cc2)[C@H](NCCO)C(=O)N[C@H]2CCC[C@@H]2CC[C@H]2CN[C@@H]3CCCS(=O)(=O)N2C3)CCO1] | (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-(2-hydroxyethyl)-L-phenylalaninamide | 639.3 |
| 232 | 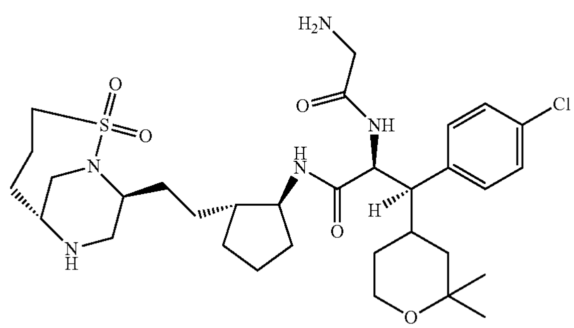 [SMILES: CC1(C)CC([C@H](c2ccc(Cl)cc2)[C@H](NC(=O)CN)C(=O)N[C@H]2CCC[C@@H]2CC[C@H]2CN[C@@H]3CCCS(=O)(=O)N2C3)CCO1] | glycyl-(βR)-4-chloro-β-(2,2-dimelhyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 652.3 |
| 233 | 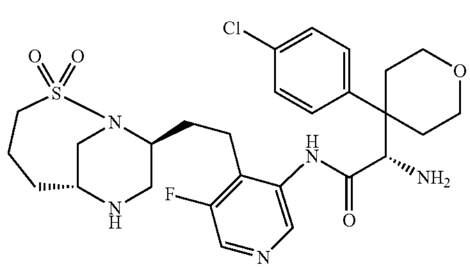 [SMILES: N[C@H](C(=O)Nc1cncc(F)c1CC[C@H]1CN[C@@H]2CCCS(=O)(=O)N1C2)C1(c2ccc(Cl)cc2)CCOCC1] | (2S)-2-amino-2-[4-(4-chlorophenyl)tetrahydro-2H-pyran-4-yl]-N-(4-{2-[(6R,9S)-2,2-dioxido-2-thia-1,7-diazabicyclo[4.3.1]dec-9-yl]ethyl}-5-fluoropyridin-3-yl)ethanamide | 580.2 |

TABLE 1-continued

| Example No. | Structure | IUPAC Name | Exact Mass [M + H]+ |
|---|---|---|---|
| 234 | 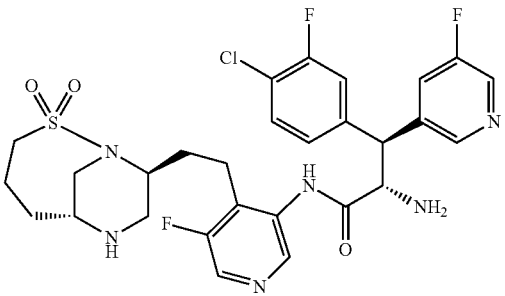 [SMILES: N[C@H](C(=O)Nc1cncc(F)c1CC[C@H]1CN[C@@H]2CCCS(=O)(=O)N1C2)[C@H](c1cncc(F)c1)c1ccc(Cl)c(F)c1] | (βS)-4-chloro-N-(4-{2-[(6R,9S)-2,2-dioxido-2-thia-1,7-diazabicyclo[4.3.1]dec-9-yl]ethyl}-5-fluoropyridin-3-yl)-3-fluoro-β-(5-fluoropyridin-3-yl)-L-phenylalaninamide | 623.2 |
| 235 | 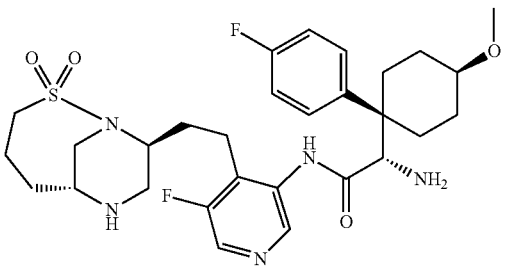 [SMILES: CO[C@H]1CC[C@](c2ccc(F)cc2)([C@H](N)C(=O)Nc2cncc(F)c2CC[C@H]2CN[C@@H]3CCCS(=O)(=O)N2C3)CC1] | (2S)-2-amino-N-(4-{2-[(6R,9S)-2,2-dioxido-2-thia-1,7-diazabicyclo[4.3.1]dec-9-yl]ethyl}-5-fluoropyridin-3-yl)-2-[trans-1-(4-fluorophenyl)-4-methoxycyclohexyl]ethanamide | 592.3 |
| 236 | 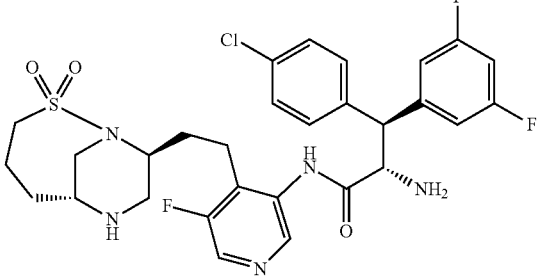 | (βS)-β-(4-chlorophenyl)-N-(4-{2-[(6R,9S)-2,2-dioxido-2-thia-1,7-diazabicyclo[4.3.1]dec-9-yl]ethyl}-5-fluoropyridin-3-yl)-3,5-difluoro-L-phenylalaninamide | 622.2 |
| 237 | 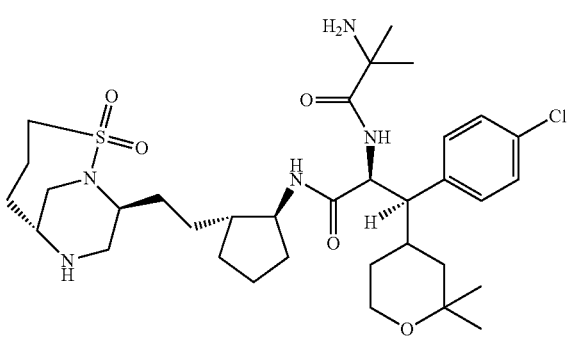 [SMILES: CC1(C)CC([C@H](c2ccc(Cl)cc2)[C@H](NC(=O)C(C)(C)N)C(=O)N[C@H]2CCC[C@@H]2CC[C@H]2CN[C@@H]3CCCS(=O)(=O)N2C3)CCO1] | 2-methylalanyl-(βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide | 680.4 |
| 238 | 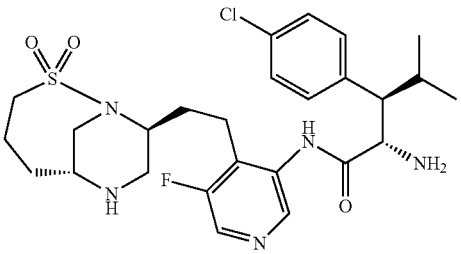 [SMILES: CC(C)[C@H](c1ccc(Cl)cc1)[C@H](N)C(=O)Nc1cncc(F)c1CC[C@H]1CN[C@@H]2CCCS(=O)(=O)N1C2] | (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-4-methylpentanamide | 552.4 |

TABLE 1-continued

| Example No. | Structure | IUPAC Name | Exact Mass [M + H]+ |
|---|---|---|---|
| 239 | 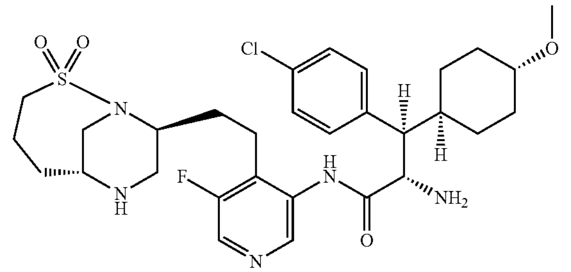 [SMILES: CO[C@H]1CC[C@H]([C@H](c2ccc(Cl)cc2)[C@H](N)C(=O)Nc2cncc(F)c2CC[C@H]2CN[C@@H]3CCCS(=O)(=O)N2C3)CC1] | (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-3-((1r,4R)-4-methoxycyclohexyl)propanamide | 622.5 |
| 240 | 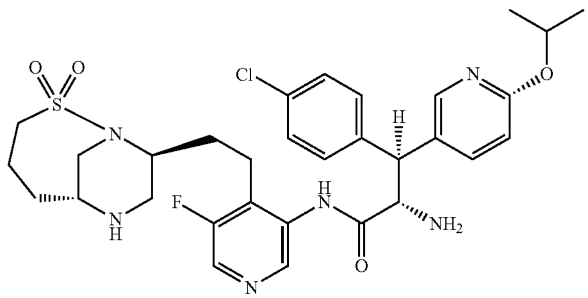 | (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-3-(6-isopropoxypyridin-3-yl)propanamide | 645.5 |
| 241 | 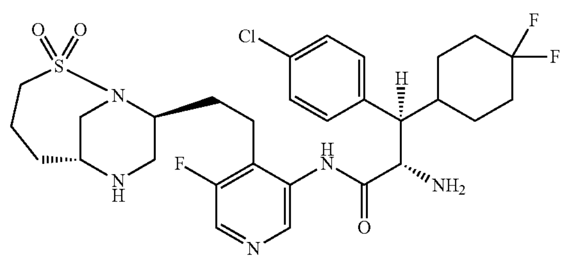 [SMILES: N[C@H](C(=O)Nc1cncc(F)c1CC[C@H]1CN[C@@H]2CCCS(=O)(=O)N1C2)[C@@H](c1ccc(Cl)cc1)C1CCC(F)(F)CC1] | (2S,3R)-2-amino-3-(4-chlorophenyl)-3-(4,4-difluorocyclohexyl)-N-(4-(2-((6R,9S)-2,2-dioxido-2-thia-1,7-diazabicyclo[4.3.1]decan-9-yl)ethyl)-5-fluoropyridin-3-yl)propanamide | 628.6 |
| 242 | 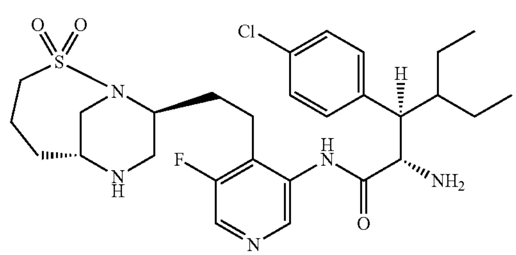 [SMILES: CCC(CC)[C@H](c1ccc(Cl)cc1)[C@H](N)C(=O)Nc1cncc(F)c1CC[C@H]1CN[C@@H]2CCCS(=O)(=O)N1C2] | (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-4-ethylhexanamide | 580.5 |
| 243 | 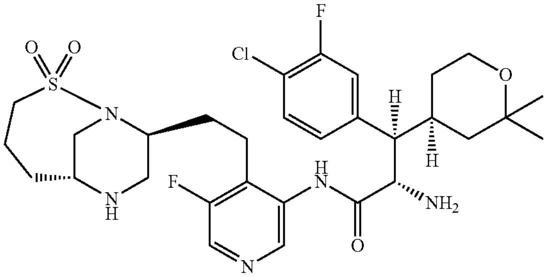 [SMILES: CC1(C)C[C@@H]([C@H](c2ccc(Cl)c(F)c2)[C@H](N)C(=O)Nc2cncc(F)c2CC[C@H]2CN[C@@H]3CCCS(=O)(=O)N2C3)CCO1] | (2S,3R)-2-amino-3-(4-chloro-3-fluorophenyl)-3-((S)-2,2-dimethyltetrahydro-2H-pyran-4-yl)-N-(4-(2-((6R,9S)-2,2-dioxido-2-thia-1,7-diazabicyclo[4.3.1]decan-9-yl)ethyl)-5-fluoropyridin-3-yl)propanamide | 640.6 |

TABLE 1-continued

| Example No. | Structure | IUPAC Name | Exact Mass [M + H]+ |
|---|---|---|---|
| 244 | 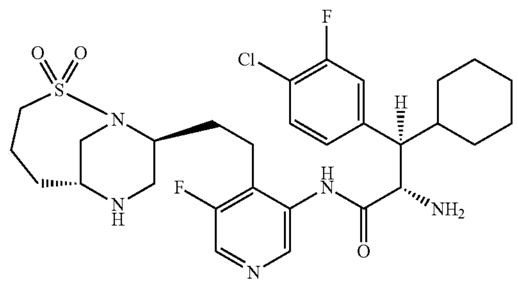 [SMILES: N[C@H](C(=O)Nc1cncc(F)c1CC[C@H]1CN[C@@H]2CCCS(=O)(=O)N1C2)[C@@H](c1ccc(Cl)c(F)c1)C1CCCCC1] | (2S,3R)-2-amino-3-(4-chloro-3-fluorophenyl)-3-cyclohexyl-N-(4-(2-((6R,9S)-2,2-dioxido-2-thia-1,7-diazabicyclo[4.3.1]decan-9-yl)ethyl)-5-fluoropyridin-3-yl)propanamide | 610.5 |
| 245 | 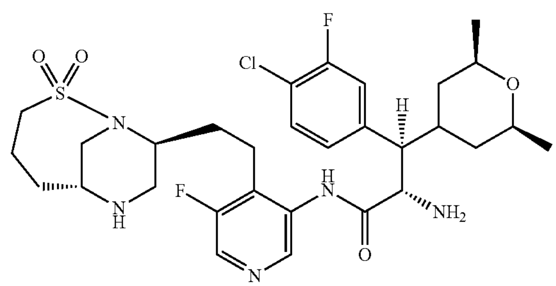 [SMILES: C[C@@H]1CC([C@H](c2ccc(Cl)c(F)c2)[C@H](N)C(=O)Nc2cncc(F)c2CC[C@H]2CN[C@@H]3CCCS(=O)(=O)N2C3)C[C@H](C)O1] | (2S,3R)-2-amino-3-(4-chloro-3-fluorophenyl)-3-((2R,6S)-2,6-dimethyltetrahydro-2H-pyran-4-yl)-N-(4-(2-((6R,9S)-2,2-dioxido-2-thia-1,7-diazabicyclo[4.3.1]decan-9-yl)ethyl)-5-fluoropyridin-3-yl)propanamide | 640.6 |
| 246 | 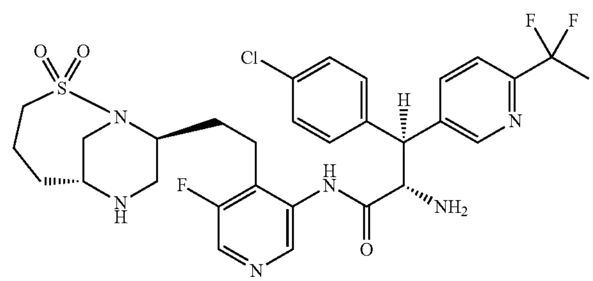 [SMILES: CC(F)(F)c1ccc([C@H](c2ccc(Cl)cc2)[C@H](N)C(=O)Nc2cncc(F)c2CC[C@H]2CN[C@@H]3CCCS(=O)(=O)N2C3)cn1] | (2S,3R)-2-amino-3-(4-chlorophenyl)-3-(6-(1,1-difluoroethyl)pyridin-3-yl)-9-(4-(2-((6R,9S)-2,2-dioxido-2-thia-1,7-diazabicyclo[4.3.1]decan-9-yl)ethyl)-5-fluoropyridin-3-yl)propanamide | 651.6 |
| 247 | 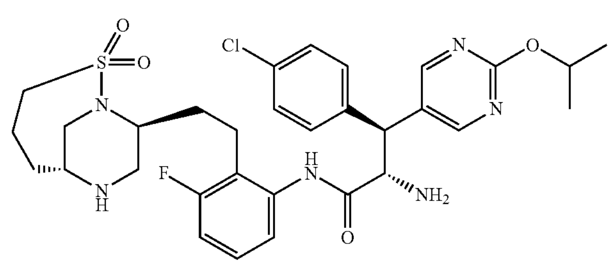 [SMILES: CC(C)Oc1ncc([C@H](c2ccc(Cl)cc2)[C@H](N)C(=O)Nc2cccc(F)c2CC[C@H]2CN[C@@H]3CCCS(=O)(=O)N2C3)cn1] | (βS)-4-chloro-N-(2-{2-[(6R,9S)-2,2-dioxido-2-thia-1,7-diazabicyclo[4.3.1]dec-9-yl]ethyl}-3-fluorophenyl)-β-[2-(1-methylethoxy)pyrimidin-5-yl]-L-phenylalaninamide | 645.2 |
| 248 | 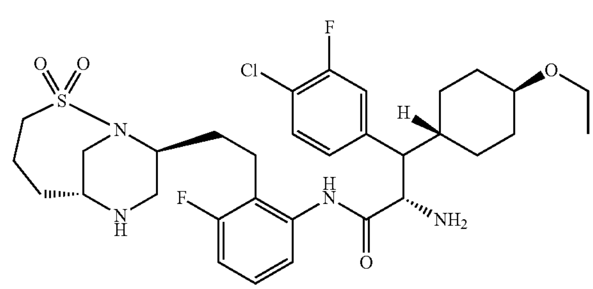 [SMILES: CCO[C@H]1CC[C@H](C(c2ccc(Cl)c(F)c2)[C@H](N)C(=O)Nc2cccc(F)c2CC[C@H]2CN[C@@H]3CCCS(=O)(=O)N2C3)CC1] | (βR).4-chloro-N-(2-{2-[(6R,9S)-2,2-dioxido-2-thia-1,7-diazabicyclo[4.3.1]dec-9-yl]ethyl}-3-fluorophenyl)-β-[(1r,4R)-4-ethoxycyclohexyl]-3-fluoro-L-phenylalaninamide | 653.3 |

TABLE 1-continued

| Example No. | Structure | IUPAC Name | Exact Mass [M + H]+ |
|---|---|---|---|
| 249 | 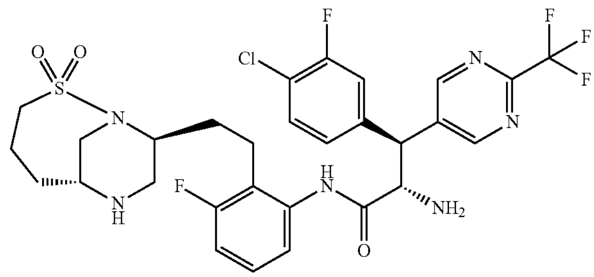 [SMILES: N[C@H](C(=O)Nc1cccc(F)c1CC[C@H]1CN[C@@H]2CCCS(=O)(=O)N1C2)[C@H](c1cnc(C(F)(F)F)nc1)c1ccc(Cl)c(F)c1] | (βS)-4-chloro-N-(2-{2-[(6R,9S)-2,2-dioxido-2-thia-1,7-diazabicyclo[4.3.1]dec-9-yl]ethyl}-3-fluorophenyl)-3-fluoro-β-[2-(trifluoromethyl)pyrimidin-5-yl]-L-phenylalaninamide | 673.2 |
| 250 | 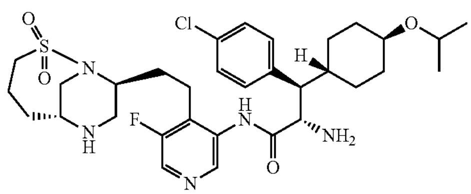 [SMILES: CC(C)O[C@H]1CC[C@H]([C@H](c2ccc(Cl)cc2)[C@H](N)C(=O)Nc2cncc(F)c2CC[C@H]2CN[C@@H]3CCCS(=O)(=O)N2C3)CC1] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-(1-methylethoxy)cyclohexyl]-L-phenylalaninamide | 650.3 |
| 251 | 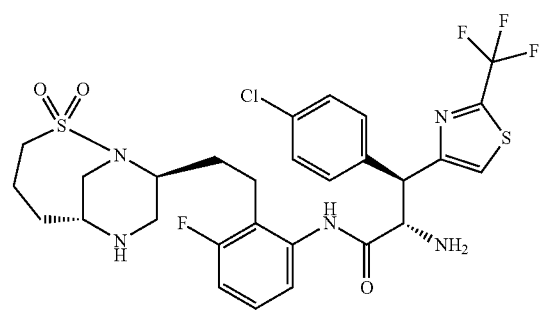 [SMILES: N[C@H](C(=O)Nc1cccc(F)c1CC[C@H]1CN[C@@H]2CCCS(=O)(=O)N1C2)[C@@H](c1ccc(Cl)cc1)c1csc(C(F)(F)F)n1] | (βR)-4-chloro-N-(2-{2-[(6R,9S)-2,2-dioxido-2-thia-1,7-diazabicyclo[4.3.1]dec-9-yl]ethyl}-3-fluorophenyl)-β-[2-(trifluoromethyl)-1,3-thiazol-4-yl]-L-phenylalaninamide | 660.1 |
| 252 | 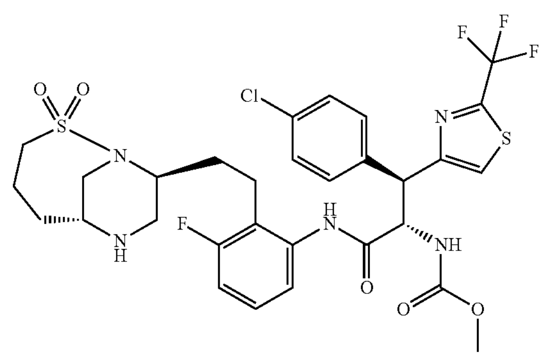 [SMILES: COC(=O)N[C@H](C(=O)Nc1cccc(F)c1CC[C@H]1CN[C@@H]2CCCS(=O)(=O)N1C2)[C@@H](c1ccc(Cl)cc1)c1csc(C(F)(F)F)n1] | methyl {(1S,2R)-2-(4-chlorophenyl)-1-[(2-{2-[(6R,9S)-2,2-dioxido-2-thia-1,7-diazabicyclo[4.3.1]dec-9-yl]ethyl}-3-fluorophenyl)carbamoyl]-2-[2-(trifluoromethyl)-1,3-thiazol-4-yl]ethyl}carbamate | 718.2 |
| 253 | 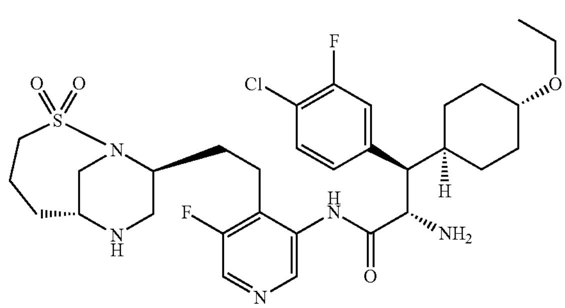 [SMILES: CCO[C@H]1CC[C@H]([C@H](c2ccc(Cl)c(F)c2)[C@H](N)C(=O)Nc2cncc(F)c2CC[C@H]2CN[C@@H]3CCCS(=O)(=O)N2C3)CC1] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-ethoxycyclohexyl]-3-fluoro-L-phenylalaninamide | 654.3 |

TABLE 1-continued

| Example No. | Structure | IUPAC Name | Exact Mass [M + H]+ |
|---|---|---|---|
| 254 | 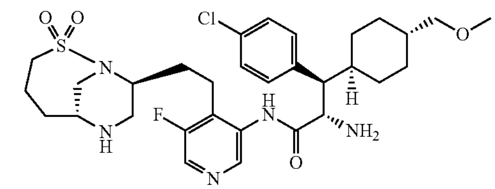 [SMILES: COC[C@H]1CC[C@H]([C@H](c2ccc(Cl)cc2)[C@H](N)C(=O)Nc2cncc(F)c2CC[C@H]2CN[C@@H]3CCCS(=O)(=O)N2C3)CC1] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-(methoxymethyl)cyclohexyl]-L-phenylalaninamide | 636.3 |
| 255 | 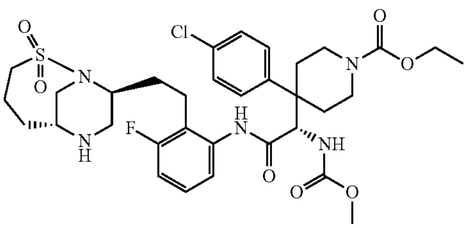 [SMILES: CCOC(=O)N1CCC(c2ccc(Cl)cc2)([C@H](NC(=O)OC)C(=O)Nc2cccc(F)c2CC[C@H]2CN[C@@H]3CCCS(=O)(=O)N2C3)CC1] | ethyl 4-(4-chlorophenyl)-4-{(1S)-2-[(2-{2-[(6R,9S)-2,2-dioxido-2-thia-1,7-diazabicyclo[4.3.1]dec-9-yl]ethyl}-3-fluorophenyl)amino]-1-[(methoxycarbonyl)amino]-2-oxoethyl}piperidine-1-carboxylate | 708.3 |
| 256 | 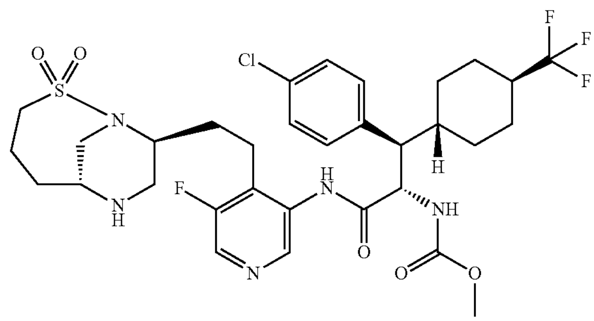 [SMILES: COC(=O)N[C@H](C(=O)Nc1cncc(F)c1CC[C@H]1CN[C@@H]2CCCS(=O)(=O)N1C2)[C@@H](c1ccc(Cl)cc1)[C@H]1CC[C@H](C(F)(F)F)CC1] | methyl {(1S,2R)-2-(4-chlorophenyl)-1-[(4-{2-[(6R,9S)-2,2-dioxido-2-thia-1,7-diazabicyclo[4.3.1]dec-9-yl]ethyl}-5-fluoropyridin-3-yl)carbamoyl]-2-[(1r,4R)-4-(trifluoromethyl)cyclohexyl]ethyl}carbamate | 718.2 |
| 257 | 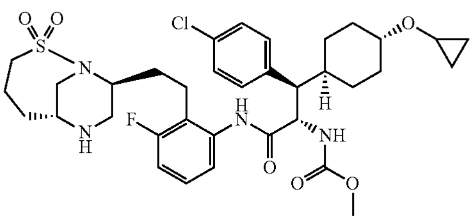 [SMILES: COC(=O)N[C@H](C(=O)Nc1cccc(F)c1CC[C@H]1CN[C@@H]2CCCS(=O)(=O)N1C2)[C@@H](c1ccc(Cl)cc1)[C@H]1CC[C@H](OC2CC2)CC1] | methyl {(1S,2R)-2-(4-chlorophenyl)-2-[(1r,4R)-4-(cyclopropyloxy)cyclohexyl]-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate | 705.3 |
| 258 | 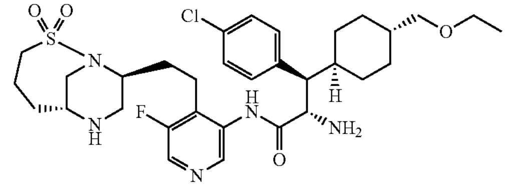 [SMILES: CCOC[C@H]1CC[C@H]([C@H](c2ccc(Cl)cc2)[C@H](N)C(=O)Nc2cncc(F)c2CC[C@H]2CN[C@@H]3CCCS(=O)(=O)N2C3)CC1] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-(ethoxymethyl)cyclohexyl]-L-phenylalaninamide | 650.3 |
| 259 | 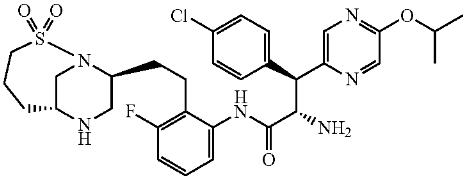 [SMILES: CC(C)Oc1cnc([C@H](c2ccc(Cl)cc2)[C@H](N)C(=O)Nc2cccc(F)c2CC[C@H]2CN[C@@H]3CCCS(=O)(=O)N2C3)cn1] | (βR)-4-chloro-N-(2-{2-[(6R,9S)-2,2-dioxido-2-thia-1,7-diazabicyclo[4.3.1]dec-9-yl]ethyl}-3-fluorophenyl)-β-[5-(1-methylethoxy)pyrazin-2-yl]-L-phenylalaninamide | 645.2 |

TABLE 1-continued

| Example No. | Structure | IUPAC Name | Exact Mass [M + H]+ |
|---|---|---|---|
| 260 | 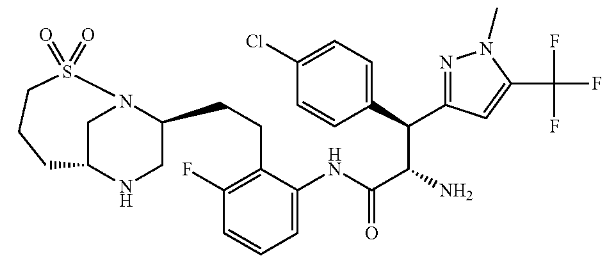 [SMILES: Cn1nc([C@H](c2ccc(Cl)cc2)[C@H](N)C(=O)Nc2cccc(F)c2CC[C@H]2CN[C@@H]3CCCS(=O)(=O)N2C3)cc1C(F)(F)F] | (βR)-4-chloro-N-(2-{2-[(6R,9S)-2,2-dioxido-2-thia-1,7-diazabicyclo[4.3.1]dec-9-yl]ethyl}-3-fluorophenyl)-β-[1-methyl-5-(trifluoromethyl)-1H-pyrazol-3-yl]-L-phenylalaninamide | 657.2 |
| 261 | 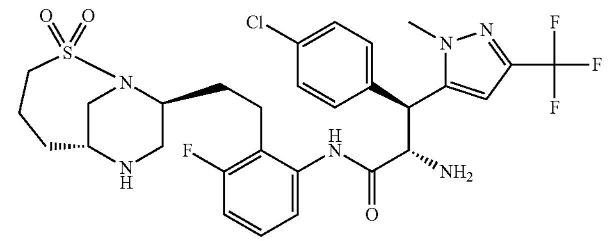 [SMILES: Cn1nc(C(F)(F)F)cc1[C@H](c1ccc(Cl)cc1)[C@H](N)C(=O)Nc1cccc(F)c1CC[C@H]1CN[C@@H]2CCCS(=O)(=O)N1C2] | (βR)-4-chloro-N-(2-{2-[(6R,9S)-2,2-dioxido-2-thia-1,7-diazabicyclo[4.3.1]dec-9-yl]ethyl}-3-fluorophenyl)-β-[1-methyl-3-(trifluoromethyl)-1H-pyrazol-5-yl]-L-phenylalaninamide | 657.2 |
| 262 | 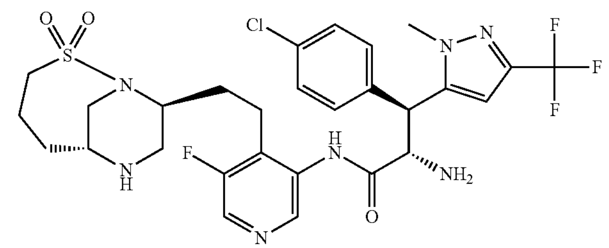 [SMILES: Cn1nc(C(F)(F)F)cc1[C@H](c1ccc(Cl)cc1)[C@H](N)C(=O)Nc1cncc(F)c1CC[C@H]1CN[C@@H]2CCCS(=O)(=O)N1C2] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[1-methyl-3-(trifluoromethyl)-1H-pyrazol-5-yl]-L-phenylalaninamide | 658.2 |
| 263 | 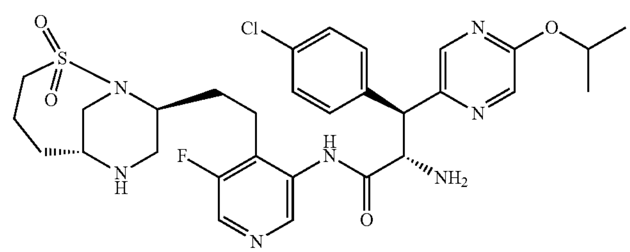 [SMILES: CC(C)Oc1cnc([C@H](c2ccc(Cl)cc2)[C@H](N)C(=O)Nc2cncc(F)c2CC[C@H]2CN[C@@H]3CCCS(=O)(=O)N2C3)cn1] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[5-(1-methylethoxy)pyrazin-2-yl]-L-phenylalaninamide | 646.2 |
| 264 | 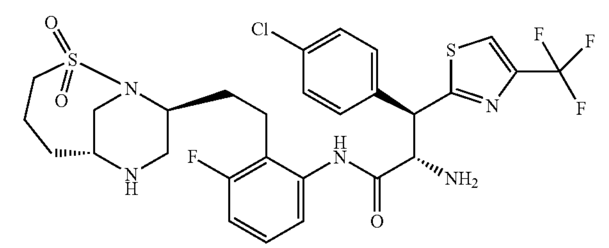 [SMILES: N[C@H](C(=O)Nc1cccc(F)c1CC[C@H]1CN[C@@H]2CCCS(=O)(=O)N1C2)[C@@H](c1ccc(Cl)cc1)c1nc(C(F)(F)F)cs1] | (βR)-4-chloro-N-(2-{2-[(6R,9S)-2,2-dioxido-2-thia-1,7-diazabicyclo[4.3.1]dec-9-yl]ethyl}-3-fluorophenyl)-β-[4-(trifluoromethyl)-1,3-thiazol-2-yl]-L-phenylalaninamide | 660.1 |
| 265 | 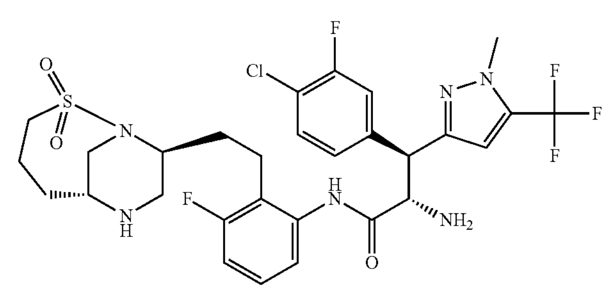 [SMILES: Cn1nc([C@H](c2ccc(Cl)c(F)c2)[C@H](N)C(=O)Nc2cccc(F)c2CC[C@H]2CN[C@@H]3CCCS(=O)(=O)N2C3)cc1C(F)(F)F] | (βR)-4-chloro-N-(2-{2-[(6R,9S)-2,2-dioxido-2-thia-1,7-diazabicyclo[4.3.1]dec-9-yl]ethyl}-3-fluorophenyl)-3-fluoro-β-[1-methyl-5-(trifluoromethyl)-1H-pyrazol-3-yl]-L-phenylalaninamide | 675.2 |

TABLE 1-continued

| Example No. | Structure | IUPAC Name | Exact Mass [M + H]+ |
|---|---|---|---|
| 266 | 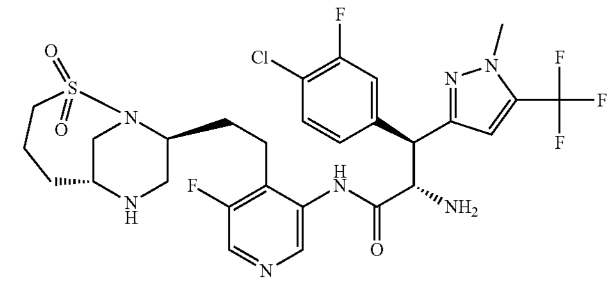 [SMILES: Cn1nc([C@H](c2ccc(Cl)c(F)c2)[C@H](N)C(=O)Nc2cncc(F)c2CC[C@H]2CN[C@@H]3CCCS(=O)(=O)N2C3)cc1C(F)(F)F] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-3-fluoro-β-[1-methyl-5-(trifluoromethyl)-1H-pyrazol-3-yl]-L-phenylalaninamide | 676.2 |
| 267 | 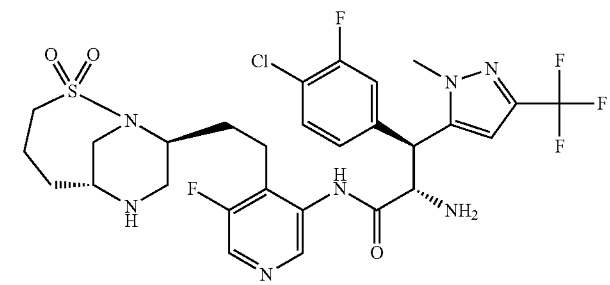 [SMILES: Cn1nc(C(F)(F)F)cc1[C@H](c1ccc(Cl)c(F)c1)[C@H](N)C(=O)Nc1cncc(F)c1CC[C@H]1CN[C@@H]2CCCS(=O)(=O)N1C2] | (βR)-4-chloro-N-(2-{2-[(6R,9S)-2,2-dioxido-2-thia-1,7-diazabicyclo[4.3.1]dec-9-yl]ethyl}-3-fluorophenyl)-3-fluoro-β-[1-methyl-3-(trifluoromethyl)-1H-pyrazol-5-yl]-L-phenylalaninamide | 675.2 |
| 268 | 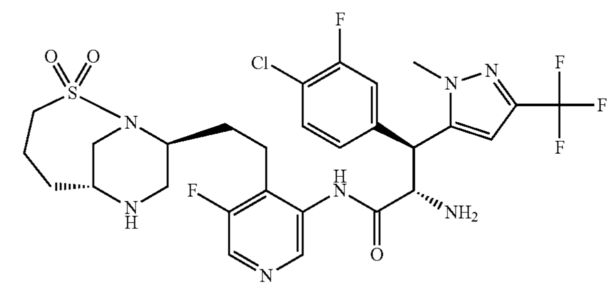 [SMILES: Cn1nc(C(F)(F)F)cc1[C@H](c1ccc(Cl)c(F)c1)[C@H](N)C(=O)Nc1cncc(F)c1CC[C@H]1CN[C@@H]2CCCS(=O)(=O)N1C2] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-3-fluoro-β-[1-methyl-3-(trifluoromethyl)-1H-pyrazol-5-yl]-L-phenylalaninamide | 676.2 |
| 269 | 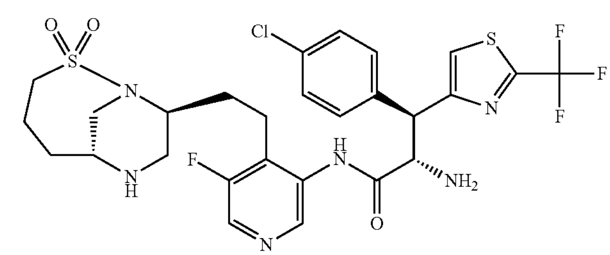 [SMILES: N[C@H](C(=O)Nc1cncc(F)c1CC[C@H]1CN[C@@H]2CCCS(=O)(=O)N1C2)[C@@H](c1ccc(Cl)cc1)c1csc(C(F)(F)F)n1] | (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[2-(trifluoromethyl)-1,3-thiazol-4-yl]-L-phenylalaninamide | 661.1 |
| 270 | 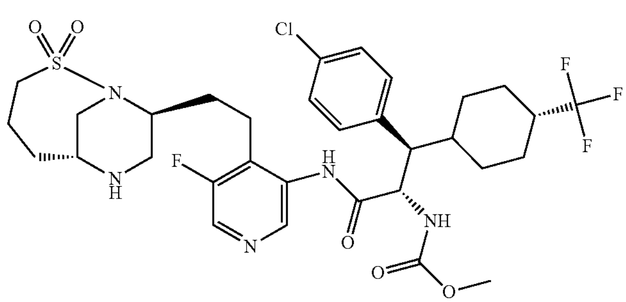 | methyl {(1S)-1-[cis-1-(4-chlorophenyl)-4-(trifluoromethyl)cyclohexyl]-2-[(4-{2-[(6R,9S)-2,2-dioxido-2-thia-1,7-diazabicyclo[4.3.1]dec-9-yl]ethyl}-5-fluoropyridin-3-yl)amino]-2-oxoethyl}carbamate | 704.2 |

TABLE 1-continued

| Example No. | Structure | IUPAC Name | Exact Mass [M + H]+ |
|---|---|---|---|
| 271 | 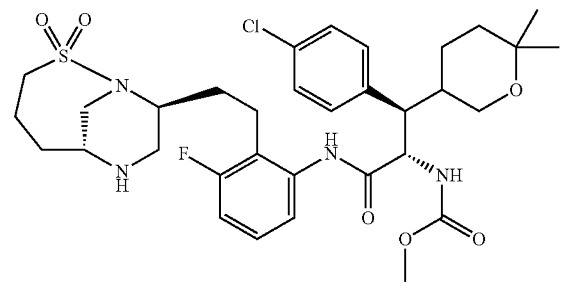 [SMILES: COC(=O)N[C@H](C(=O)Nc1cccc(F)c1CC[C@H]1CN[C@@H]2CCCS(=O)(=O)N1C2)[C@@H](c1ccc(Cl)cc1)C1CCC(C)(C)OC1] | methyl {(1S,2R)-2-(4-chlorophenyl)-2-(6,6-dimethyltetrahydro-2H-pyran-3-yl)-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate | 679.3 |
| 272 | 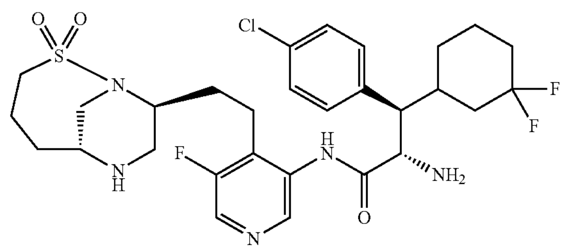 [SMILES: N[C@H](C(=O)Nc1cncc(F)c1CC[C@H]1CN[C@@H]2CCCS(=O)(=O)N1C2)[C@@H](c1ccc(Cl)cc1)C1CCCC(F)(F)C1] | (βR)-4-chloro-β-(3,3-difluorocyclohexyl)-N-(4-{2-[(6R,9S)-2,2-dioxido-2-thia-1,7-diazabicyclo[4.3.1]dec-9-yl]ethyl}-5-fluoropyridin-3-yl)-L-phenylalaninamide | 628.2 |
| 273 | 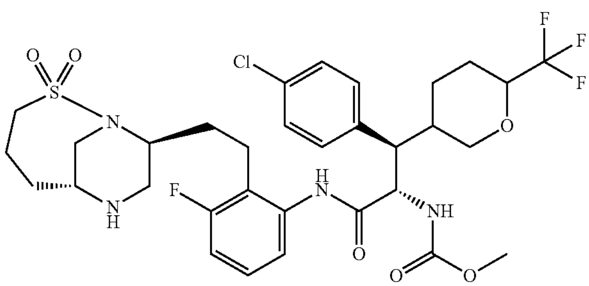 [SMILES: COC(=O)N[C@H](C(=O)Nc1cccc(F)c1CC[C@H]1CN[C@@H]2CCCS(=O)(=O)N1C2)[C@@H](c1ccc(Cl)cc1)C1CCC(C(F)(F)F)OC1] | methyl {(1S,2R)-2-(4-chlorophenyl)-1-[(2-{2-[(6R,9S)-2,2-dioxido-2-thia-1,7-diazabicyclo[4.3.1]dec-9-yl]ethyl}-3-fluorophenyl)carbamoyl]-2-[6-(trifluoromethyl)tetrahydro-2H-pyran-3-yl]ethyl}carbamate | 719.2 |

Example 274

(2S,3R)-2-Amino-3-(4-chlorophenyl)-N-(2-(2-((6S,10S)-2,2-dioxido-2-thia-1,8-diazabicyclo[4.4.1]undecan-10-yl)ethyl)-3-fluorophenyl)-3-(tetrahydro-2H-pyran-4-yl)propanamide

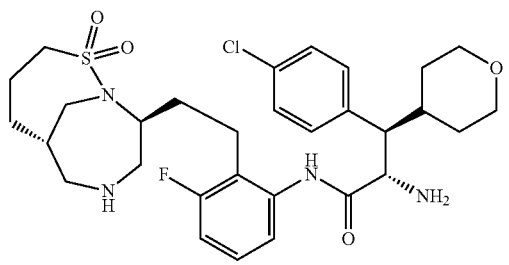 [SMILES: N[C@H](C(=O)Nc1cccc(F)c1CC[C@H]1CNC[C@@H]2CCCS(=O)(=O)N1C2)[C@@H](c1ccc(Cl)cc1)C1CCOCC1]

The title compound was prepared from Intermediate J and Intermediate 13 using the procedures described for Intermediate B and Example 1. LCMS m/z=607.3 (M+H)⁺.

Example 275

(2S,3R)-2-amino-3-(4-chlorophenyl)-3-((R)-2,2-dimethyltetrahydro-2H-pyran-4-yl)-N-(2-(2-((5R,8S)-2,2-dioxido-2-thia-1,6-diazabicyclo[3.3.1]nonan-8-yl)ethyl)-3-fluorophenyl)propanamide

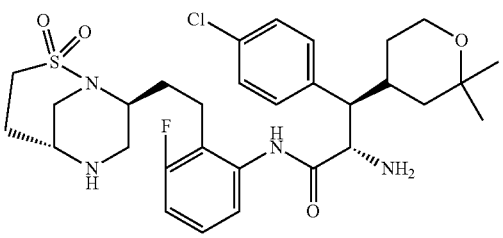 [SMILES: CC1(C)CC([C@H](c2ccc(Cl)cc2)[C@H](N)C(=O)Nc2cccc(F)c2CC[C@H]2CN[C@@H]3CCS(=O)(=O)N2C3)CCO1]

The title compound was prepared from Intermediate K and Intermediate 7 using the procedures described for Intermediate B and Example 1. LCMS m/z=608.0 (M+H)⁺.

Example 276

(2S,3S)-2-Amino-3-(3,5-difluorophenyl)-N-(2-(2-((6R,9S)-2,2-dioxido-2-thia-1,7-diazabicyclo[4.3.2]undecan-9-yl)ethyl)-3-fluorophenyl)-3-(4-fluorophenyl)propanamide

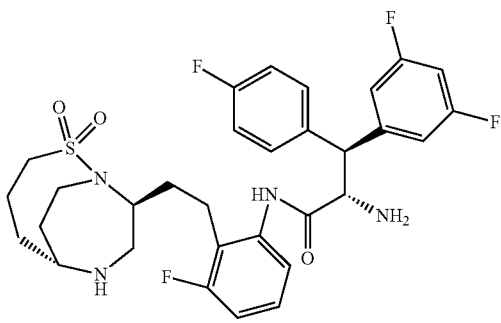 [SMILES: N[C@H](C(=O)Nc1cccc(F)c1CC[C@H]1CN[C@@H]2CCCS(=O)(=O)N1CC2)[C@@H](c1ccc(F)cc1)c1cc(F)cc(F)c1]

The title compound was prepared from Intermediate L and Intermediate 2 using the procedures described for Intermediate B and for Example 1. LCMS m/z=619.4 (M+H)$^+$.

Example 277

Methyl ((1S,2S)-1-(3,5-difluorophenyl)-3-((2-(2-((7R,10S)-2,2-dioxido-2-thia-1,8-diazabicyclo[5.3.1]undecan-10-yl)ethyl)-3-fluorophenyl)amino)-1-(4-fluorophenyl)-3-oxopropan-2-yl)carbamate

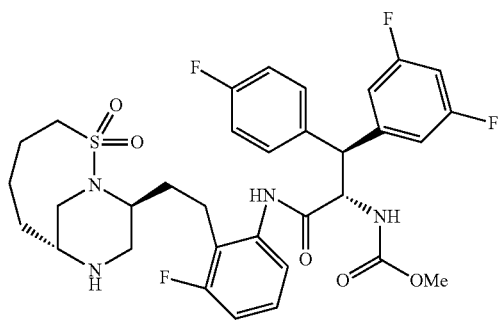 [SMILES: COC(=O)N[C@H](C(=O)Nc1cccc(F)c1CC[C@H]1CN[C@@H]2CCCCS(=O)(=O)N1C2)[C@@H](c1ccc(F)cc1)c1cc(F)cc(F)c1]

The title compound was prepared from Intermediate M and Intermediate 2 using the procedures described for Intermediate B and Example 2. LCMS m/z=677.3 (M+H)$^+$.

Cell-Based HIV Infection Assay Using a Reporter ("Cell-Based"):

MT4-GFP cells contain a stably integrated HIV long terminal repeat promoter directing the transcription of green fluorescent protein (GFP). When HIV infects the cell, GFP is produced and the cell becomes green. MT4-GFP cells (250,000 cells/mL) were bulk-infected with HIV-1 (H9IIIB strain) at low multiplicity of infection (MOI) in RPM 1640 media, supplemented with 10% FBS for 24 h. Cells were then washed once in RPMI 1640 plus 10% FBS and resuspended in RPMI plus 50% normal human serum (NHS). Test compounds were serial-diluted in DMSO using an ECHO liquid dispenser. A control well included a combination of three HIV drugs (an inhibitor of HIV protease, integrase strand transfer and a non-nucleoside reverse transcriptase inhibitor; triple drug). The infected MT4-GFP cells were added to a 384-well poly-D-lysine coated black plate with clear bottom in which the diluted test compounds were placed. The cells were seeded in the plate at 8,000 cells per well and the final DMSO concentration was 0.4%. Infected cells were quantified at both 24 and 48 h post incubation using an Acumen eX3 plate reader. Viral reproductive ratio ($R_0$) was determined using the number of infected cells at 48 h divided by the number of infected cells at 24 h. Percent viral growth inhibition was calculated by $[1-(R-R_{tripledrug})/(R_{DMSO}-R_{tripledrug})]*100$. Compound potency inflection point (IP) was determined with use of a 4-parameter dose response curve analysis.

Table 2 shows data obtained from the above described assays for the Examples herein. Data shown in the table reflects the mean of at least two independent experiments.

TABLE 2

| Example Number | Cell Based IP (50% NHS) (nM) |
| --- | --- |
| 1 | 2.9 |
| 2 | 6.7 |
| 3 | 14 |
| 4 | 13 |
| 5 | 9.4 |
| 6 | 6.2 |
| 7 | 3.1 |
| 8 | 8.7 |
| 9 | 7.1 |
| 10 | 6.7 |
| 11 | 4.0 |
| 12 | 5.9 |
| 13 | 7.6 |
| 14 | 14 |
| 15 | 8.8 |
| 16 | 4.9 |
| 17 | 8.9 |
| 18 | 8.7 |
| 19 | 5.2 |
| 20 | 11 |
| 21 | 5.0 |
| 22 | 15 |
| 23 | 9.3 |
| 24 | 13 |
| 25 | 41 |
| 26 | 11 |
| 27 | 7.5 |
| 28 | 13 |
| 29 | 23 |
| 30 | 10 |
| 31 | 6.3 |
| 32 | 20 |
| 33 | 8.5 |
| 34 | 23 |
| 35 | 3.8 |
| 36 | 22 |
| 37 | 13 |
| 38 | 28 |
| 39 | 200 |
| 40 | 99 |
| 41 | 43 |
| 42 | 31 |
| 43 | 8.5 |
| 44 | 4.5 |
| 45 | 3.8 |
| 46 | 9.1 |
| 47 | 18 |
| 48 | 33 |
| 49 | 18 |
| 50 | 28 |
| 51 | 20 |
| 52 | 72 |
| 53 | 24 |
| 54 | 180 |
| 55 | 80 |
| 56 | 24 |

TABLE 2-continued

| Example Number | Cell Based IP (50% NHS) (nM) |
|---|---|
| 57 | 27 |
| 58 | 59 |
| 59 | 16 |
| 60 | 9.9 |
| 61 | 160 |
| 62 | 190 |
| 63 | 14 |
| 64 | 260 |
| 65 | 47 |
| 66 | 8.2 |
| 67 | 4.5 |
| 68 | 12 |
| 69 | 13 |
| 70 | 49 |
| 71 | 41 |
| 72 | 5.1 |
| 73 | 18 |
| 74 | 151 |
| 75 | 110 |
| 76 | 30 |
| 77 | 57 |
| 78 | 38 |
| 79 | 31 |
| 80 | 71 |
| 81 | 68 |
| 82 | 160 |
| 83 | 8.2 |
| 84 | 210 |
| 85 | 150 |
| 86 | 340 |
| 87 | 130 |
| 88 | 91 |
| 89 | 5.1 |
| 90 | 23 |
| 91 | 22 |
| 92 | 56 |
| 93 | 56 |
| 94 | 6.4 |
| 95 | 63 |
| 96 | 180 |
| 97 | 19 |
| 98 | 47 |
| 99 | 55 |
| 100 | 24 |
| 101 | 59 |
| 102 | 32 |
| 103 | 68 |
| 104 | 24 |
| 105 | 33 |
| 106 | 110 |
| 107 | 84 |
| 108 | 50 |
| 109 | 38 |
| 110 | 55 |
| 111 | 28 |
| 112 | 42 |
| 113 | 22 |
| 114 | 22 |
| 115 | 190 |
| 116 | 18 |
| 117 | 5.0 |
| 118 | 7.5 |
| 119 | 180 |
| 120 | 6.2 |
| 121 | 5.7 |
| 122 | 6.7 |
| 123 | 6.8 |
| 124 | 41 |
| 125 | 71 |
| 126 | 610 |
| 127 | 27 |
| 128 | 80 |
| 129 | 56 |
| 130 | 8.2 |
| 131 | 24 |
| 132 | 15 |
| 133 | 83 |
| 134 | 77 |
| 135 | 100 |
| 136 | 5.8 |
| 137 | 1300 |
| 138 | 490 |
| 139 | 460 |
| 140 | 1200 |
| 141 | 690 |
| 142 | 270 |
| 143 | 77 |
| 144 | 21 |
| 145 | 76 |
| 146 | 25 |
| 147 | 22 |
| 148 | 160 |
| 149 | 97 |
| 150 | 22 |
| 151 | 23 |
| 152 | 27 |
| 153 | 9.7 |
| 154 | 8.8 |
| 155 | 600 |
| 156 | 200 |
| 157 | 3400 |
| 158 | 110 |
| 159 | 720 |
| 160 | 22 |
| 161 | 78 |
| 162 | 37 |
| 163 | 19 |
| 164 | 12 |
| 165 | 7.5 |
| 166 | 25 |
| 167 | 27 |
| 168 | 170 |
| 169 | 89 |
| 170 | 230 |
| 171 | 34 |
| 172 | 38 |
| 173 | 23 |
| 174 | 89 |
| 175 | 120 |
| 176 | 150 |
| 177 | 400 |
| 178 | 160 |
| 179 | 31 |
| 180 | 11 |
| 181 | 640 |
| 182 | 70 |
| 183 | 1300 |
| 184 | 330 |
| 185 | 3300 |
| 186 | 33 |
| 187 | 3.2 |
| 188 | 25 |
| 189 | 45 |
| 190 | 41 |
| 191 | 7.1 |
| 192 | 15 |
| 193 | 20 |
| 194 | 19 |
| 195 | 67 |
| 196 | 120 |
| 197 | 10 |
| 198 | 48 |
| 199 | 8.0 |
| 200 | 35 |
| 201 | 220 |
| 202 | 89 |
| 203 | 150 |
| 204 | 230 |
| 205 | 130 |
| 206 | 16 |
| 207 | 40 |
| 208 | 100 |
| 209 | 48 |
| 210 | 16 |

TABLE 2-continued

| Example Number | Cell Based IP (50% NHS) (nM) |
|---|---|
| 211 | 6.4 |
| 212 | 7.0 |
| 213 | 200 |
| 214 | 18 |
| 215 | 8.0 |
| 216 | 24 |
| 217 | 13 |
| 218 | 560 |
| 219 | 12 |
| 220 | 300 |
| 221 | 6.4 |
| 222 | 87 |
| 223 | 13 |
| 224 | 5.7 |
| 225 | 45 |
| 226 | 6.1 |
| 227 | 7.1 |
| 228 | 10 |
| 229 | 210 |
| 230 | 310 |
| 231 | 310 |
| 232 | 2500 |
| 233 | 67 |
| 234 | 50 |
| 235 | 67 |
| 236 | 2.8 |
| 237 | 150 |
| 238 | 13 |
| 239 | 5.6 |
| 240 | 8.4 |
| 241 | 7.3 |
| 242 | 17 |
| 243 | 8.0 |
| 244 | 4.3 |
| 245 | 5.8 |
| 246 | 19 |
| 247 | 7.2 |
| 248 | 5.5 |
| 249 | 5.1 |
| 250 | 7.7 |
| 251 | 9.2 |
| 252 | 17 |
| 253 | 5.8 |
| 254 | 3.0 |
| 255 | 18 |
| 256 | 8.2 |
| 257 | 5.6 |
| 258 | 3.4 |
| 259 | 4.2 |
| 260 | 4.4 |
| 261 | 8.7 |
| 262 | 22 |
| 263 | 5.2 |
| 264 | 6.9 |
| 265 | 9.8 |
| 266 | 11 |
| 267 | 8.0 |
| 268 | 18 |
| 269 | 5.0 |
| 270 | 20 |
| 271 | 7.0 |
| 272 | 5.7 |
| 273 | 14 |
| 274 | 670 |
| 275 | 25 |
| 276 | 6.1 |
| 277 | 10 |

While the foregoing specification teaches the principles of the present invention, with examples provided for the purpose of illustration, the practice of the invention encompasses all of the usual variations, adaptations and/or modifications that come within the scope of the following claims. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All publications, patents and patent applications cited herein are incorporated by reference in their entirety into the disclosure.

What is claimed is:

1. A compound of structural Formula I:

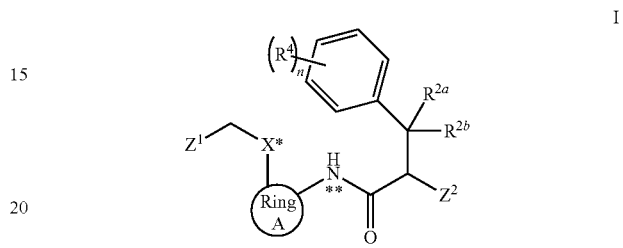

or a pharmaceutically acceptable salt thereof, wherein:
X is O or $CH_2$;
Ring A is

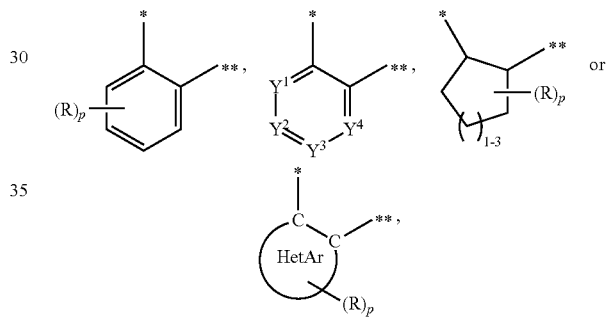

wherein * indicates the point of attachment to X* in Formula I and  indicates the point of attachment to N in Formula I;
one, two or three of $Y^1$, $Y^2$, $Y^3$ and $Y^4$ are N and the others are C(R);
HetAr is:
  (a) a 5-membered (including the two carbons that are the points of attachment to X* and N** in Formula I) monocyclic heteroaromatic ring containing from 1 to 3 heteroatoms independently selected from N, O and S, or
  (b) a 9-, 10- or 11-membered (including the two carbons that are the points of attachment to X* and N** in Formula I) bicyclic heteroaromatic ring system containing from 1 to 4 heteroatoms independently selected from N, O and S;
p is an integer selected from 1, 2 or 3;
R is independently selected at each occurrence from,
  (a) —H,
  (b) halo, —OH, —SH, —CN, —$NO_2$, or —N($R^{3a}$)$_2$,
  (c) —$C_{1-6}$alkyl unsubstituted or substituted with (i) 1 to 6 of —F, or (ii) —OH, —C(O)O$C_{1-6}$alkyl, —O—$C_{1-6}$alkyl or —O—$C_{1-3}$ alkyl-phenyl,
  (d) —O$C_{1-6}$alkyl unsubstituted or substituted with (i) 1 to 6 of —F, or (ii) —OH, —C(O)O$C_{1-6}$alkyl, —O—$C_{1-6}$alkyl or —O—$C_{1-3}$ alkyl-phenyl, (e) —C$_{1-6}$alkyl-O—C$_{1-3}$alkyl unsubstituted or substituted with 1 to 6 of —F,
(f) —C(O)OC$_{1-6}$alkyl unsubstituted or substituted with 1-6 of —F, or
(g) —C(O)C$_{1-6}$alkyl unsubstituted or substituted with 1-6 of —F;

Z$^1$ is

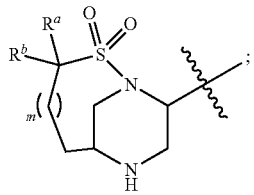

R$^a$ and R$^b$ are independently selected from —H and —C$_{1-3}$alkyl;
R$^c$ is —C$_{1-3}$alkyl or —C$_{3-6}$cycloalkyl and R$^c$ is unsubstituted or substituted with 1-3 of —F;
R$^d$ is —C$_{1-6}$alkyl unsubstituted or substituted with 1-6 of —F or —C$_{3-6}$cycloalkyl unsubstituted or substituted with 1-3 of —F;
m is the integer 1;
Z$^2$ is —H or —NHR$^3$;
R$^{2a}$ is (a) —C$_{1-6}$alkyl unsubstituted or substituted with one to four substituents independently selected at each occurrence from halo; —OH; —C$_{1-6}$alkyl unsubstituted or substituted with 1-3 of —F; or —OR$^c$;
(b) —C$_{3-6}$cycloalkyl unsubstituted or substituted with one to four substituents independently selected at each occurrence from halo; —OH; —C$_{1-6}$alkyl unsubstituted or substituted with 1-6 of —F; —C$_{1-3}$alkyl —OR$^c$; —OR$^d$; —COOH; or —C(O)OR$^d$;
(c) phenyl unsubstituted or substituted with one to four substituents independently selected at each occurrence from halo; —OH; —C$_{1-6}$alkyl unsubstituted or substituted with 1-6 of —F; —C$_{1-3}$alkyl-O—R$^c$; —OR$^d$; —COOH; —C(O)OR$^d$; or —C$_{3-6}$cycloalkyl unsubstituted or substituted with 1-3 of —F;

(d)

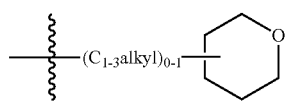

wherein the tetrahydropyran is unsubstituted or substituted with one to four substituents independently selected at each occurrence from halo —OH; —C$_{1-6}$alkyl unsubstituted or substituted with 1-6 of —F; or —OC$_{1-6}$alkyl unsubstituted or substituted with 1-6 of —F;

(e) pyridinyl unsubstituted or substituted with one to four substituents independently selected at each occurrence from
(i) halo, (ii) —OH,
(iii) —C$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$ alkyl-phenyl,
(iv) —OC$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$ alkyl-phenyl,
(v) —C$_{1-6}$alkyl-O—C$_{1-3}$alkyl unsubstituted or substituted with 1 to 6 of —F,
(vi) =O (oxo),
(vii) —C(O)OC$_{1-6}$alkyl optionally substituted with 1-6 of —F, or
(viii) —C(O)C$_{1-6}$alkyl optionally substituted with 1-6 of —F;

(f) pyrimidinyl, unsubstituted or substituted with one to four substituents independently selected at each occurrence from
(i) halo, (ii) —OH,
(iii) —C$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$ alkyl-phenyl,
(iv) —OC$_{1-6}$alkyl unsubstituted or substituted with (i) 1 to 6 of —F, or (ii) —OH, —C(O)OC$_{1-6}$alkyl, —O—C$_{1-6}$alkyl, or —O—C$_{1-3}$ alkyl-phenyl,
(v) —C$_{1-6}$alkyl-O—C$_{1-3}$alkyl unsubstituted or substituted with 1 to 6 of —F,
(vi) =O (oxo),
(vii) —C(O)OC$_{1-6}$alkyl optionally substituted with 1-6 of —F, or
(viii) —C(O)C$_{1-6}$alkyl optionally substituted with 1-6 of —F;

(g)

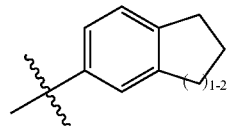

unsubstituted or substituted with one to four substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C$_{3-6}$cycloalkyl unsubstituted or substituted with 1-3 of —F;

(h)

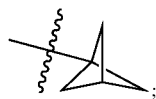

(i) morpholinyl;
(j) piperidinyl, unsubstituted or substituted with one to four substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C(O)OR$^1$;
(k) pyrazinyl, unsubstituted or substituted with one to four substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C(O)OR$^1$;
(l) thiazolyl, unsubstituted or substituted with one to three substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C(O)OR$^1$;

(m) pyrazolyl, unsubstituted or substituted halo; —OH; —C$_{1-6}$alkyl unsubstituted or substituted with 1-6 of —F; —OC$_{1-6}$alkyl unsubstituted or substituted with 1-6 of —F; or —C(O)OR$^1$; or (n)
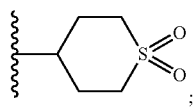
;

R$^1$ is (i) —C$_{1-6}$alkyl unsubstituted or substituted with 1-6 of —F, phenyl or —C$_{3-6}$cycloalkyl, or (ii) —S(O)$_2$—C$_{1-6}$alkyl;

R$^{2b}$ is —H, —C$_{1-6}$alkyl or —OC$_{1-6}$alkyl, wherein each of —C$_{1-6}$alkyl or —OC$_{1-6}$alkyl is unsubstituted or substituted with 1 to 3 substituents independently selected from halo, —OH, or —OC$_{1-6}$alkyl;

or R$^{2a}$ and R$^{2b}$ are joined together with the carbon to which they are both attached to form (a) —C$_{3-6}$cycloalkyl, (b) piperidinyl, or (c) tetrahydro-(2H)-furanyl;

wherein each of cycloalkyl, piperidinyl and tetrahydro-(2H)-furan is unsubstituted or substituted with one to four substituents independently selected at each occurrence from halo;

—OH; —C$_{1-6}$alkyl unsubstituted or substituted with 1-6 of —F; —OC$_{1-6}$alkyl unsubstituted or substituted with 1-6 of —F; or —COOC$_{1-3}$ alkyl unsubstituted or substituted with 1-6 of —F;

R$^3$ and R$^{3a}$ are independently selected at each occurrence from (a) —H, (b) —C$_{1-6}$alkyl unsubstituted or substituted with (i) 1 to 6 of —F, (ii) —OH, (iii) —C(O)OC$_{1-3}$alkyl, (iv) —O—C$_{1-3}$ alkyl, or (v) —O—C$_{1-3}$ alkyl-phenyl, (c) —C(O)OC$_{1-6}$alkyl unsubstituted or substituted with (i) 1-6 of —F, (ii) —C$_{3-6}$cycloalkyl or (iii) —NH$_2$, or (d) —C(O)C$_{1-6}$alkyl unsubstituted or substituted with (i) 1-6 of —F, (ii) —C$_{3-6}$cycloalkyl or (iii) —NH$_2$;

n is an integer selected from 1, 2 or 3;

R$^4$ is independently selected at each occurrence from:

(a) —H, —OH, halo, —CN, —C$_{1-6}$alkyl, —O—C$_{1-6}$alkyl, —C$_{3-6}$cycloalkyl, —O—C$_{3-6}$cycloalkyl, —C$_{2-6}$alkenyl-SR$^5$, —S—C$_{3-6}$cycloalkyl, —SO$_2$R$^5$, —N(R$^5$)$_2$, —N(H)C(O)—C$_{1-6}$alkyl, —C(O)OR$^5$, —C(O)—C$_{1-6}$alkyl, —C$_{1-6}$haloalkyl, —O—C$_{1-6}$haloalkyl, —S—C$_{1-6}$haloalkyl, —NO$_2$, —N(H)CH(O), —CH(O), —C(O)N(R$^5$)$_2$, —C(O)N(H)C(O)R$^5$, or trimethylsilyl, (b) phenyl, benzyl or phenoxy, each being unsubstituted or substituted with 1 to 5 substituents selected from halogen and, —OH, halo, —CN, —C$_{1-6}$alkyl, —C$_{1-6}$haloalkyl, —O—C$_{1-6}$alkyl, —O—C$_{1-6}$haloalkyl, —S—C$_{1-6}$haloalkyl, —NO$_2$, —SO$_2$R$^5$, —N(R$^5$)$_2$, —C(O)OR$^5$, or —C(O)—C$_{1-6}$alkyl, or (c) HetA, —O-HetA or —CH$_2$—HetA, optionally substituted with 1 to 5 substituents selected from halogen and C$_{1-6}$alkyl;

wherein —C$_{1-6}$ alkyl when present within any R$^4$ group is unsubstituted or substituted with 1 to 6 substituents independently selected at each occurrence from:

-halo, —CF3, —CN, —NO$_2$, —OH, —O—C$_{1-6}$alkyl, —O—C$_{1-6}$haloalkyl, —O—C$_{3-6}$cycloalkyl, —SR$^5$, —N(R$^5$)$_2$, —C(O)—C$_{1-6}$alkyl, —C(O)OR$^5$, or —SO$_2$—C$_{1-6}$alkyl;

R$^5$ is independently selected at each occurrence from —H and C$_{1-6}$alkyl; and HetA is independently selected from (i) a 5- or 6-membered monocyclic heteroaromatic ring containing from 1 to 3 heteroatoms independently selected from N, O and S, or (ii) a 9-, 10- or 11-membered bicyclic fused heteroaromatic ring system containing from 1 to 4 heteroatoms independently selected from N, O and S.

2. The compound of claim 1 having structural Formula II or a pharmaceutically acceptable salt thereof:

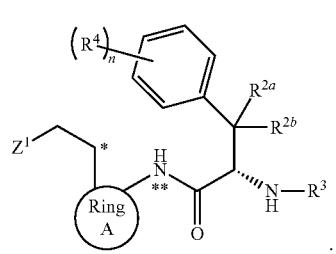

II

3. The compound of claim 1 having structural Formula III or a pharmaceutically acceptable salt thereof:

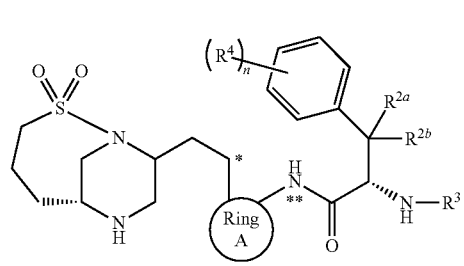

III

4. The compound of claim 1 or a pharmaceutically acceptable salt thereof wherein Z$^2$ is —NHR$^3$.

5. The compound of claim 2, or a pharmaceutically acceptable salt thereof wherein Z$^1$ is

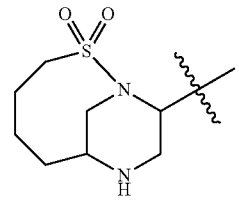

.

6. The compound of claim 1, or a pharmaceutically acceptable salt thereof wherein Ring A is

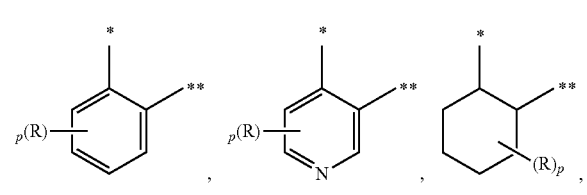

-continued

[structures: cyclopentyl and HetAr-containing ring, both with (R)ₚ]

7. The compound of claim 6 or a pharmaceutically acceptable salt thereof wherein Ring A is

[structures: phenyl with (R)ₚ, or pyridinyl with (R)ₚ]

8. The compound of claim 6 or a pharmaceutically acceptable salt thereof wherein Ring A is

[structures: cyclohexyl with (R)ₚ, or cyclopentyl with (R)ₚ]

9. The compound of claim 6 or a pharmaceutically acceptable salt thereof wherein Ring A is

[structure: HetAr-containing ring with (R)ₚ]

and HetAr is

[structures: various 5-membered heteroaryl rings — oxadiazole, thiadiazole, isoxazole, isoxazole variant, thiazole, thiazole variant, oxazole, oxazole variant, isothiazole, and isothiazole variant]

10. The compound of claim 2, or a pharmaceutically acceptable salt thereof wherein $R^{2a}$ is:
(a) —$C_{1-6}$alkyl unsubstituted or substituted with one or two substituents independently selected at each occurrence from halo; —OH; —$C_{1-6}$alkyl unsubstituted or substituted with 1-3 of —F; or —O$r^c$, (b) —$C_{3-6}$cycloalkyl unsubstituted or substituted with one or two substituents independently selected at each occurrence from halo; —OH; —$C_{1-6}$alkyl unsubstituted or substituted with 1-6 of —F; —$C_{1-3}$alkyl-O$R^c$; —O$R^d$; —COOH; or —C(O)O$r^d$, (c) phenyl unsubstituted or substituted with one or two substituents independently selected at each occurrence from halo; —OH; —$C_{1-6}$alkyl unsubstituted or substituted with 1-6 of —F; —$C_{1-3}$alkyl-O—$R^c$; —O$R^d$; —COOH; —C(O)O$R^d$; or —$C_{3-6}$cycloalkyl unsubstituted or substituted with 1-3 of —F, (d)

[structure: tetrahydropyran connected via —($C_{1-3}$alkyl)$_{0-1}$—]

wherein the tetrahydropyran is unsubstituted or substituted with one or two substituents independently selected at each occurrence from halo —OH; —$C_{1-6}$alkyl unsubstituted or substituted with 1-6 of —F; or —O$C_{1-6}$alkyl unsubstituted or substituted with 1-6 of —F, (e) pyridinyl unsubstituted or substituted with one or two substituents independently selected at each occurrence from
(i) halo, (ii) —OH,
(iii) —$C_{1-6}$alkyl unsubstituted or substituted with (i) 1 to 6 of —F, or (ii) —OH, —C(O)O$C_{1-6}$alkyl, —O—$C_{1-6}$alkyl, or —O—$C_{1-3}$ alkyl-phenyl,
(iv) —O$C_{1-6}$alkyl unsubstituted or substituted with (i) 1 to 6 of —F, or (ii) —OH, —C(O)O$C_{1-6}$alkyl, —O—$C_{1-6}$alkyl, or —O—$C_{1-3}$ alkyl-phenyl,
(v) —$C_{1-6}$alkyl-O—$C_{1-3}$alkyl unsubstituted or substituted with 1 to 6 of —F,
(vi) =O (oxo),
(vii) —C(O)O$C_{1-6}$alkyl optionally substituted with 1-6 of —F, or
(viii) —C(O)$C_{1-6}$alkyl optionally substituted with 1-6 of —F, (f) pyrimidinyl unsubstituted or substituted with one or two substituents independently selected at each occurrence from
(i) halo, (ii) —OH,
(iii) —$C_{1-6}$alkyl unsubstituted or substituted with (i) 1 to 6 of —F, or (ii) —OH, —C(O)O$C_{1-6}$alkyl, —O—$C_{1-6}$alkyl, or —O—$C_{1-3}$ alkyl-phenyl,
(iv) —O$C_{1-6}$alkyl unsubstituted or substituted with (i) 1 to 6 of —F, or (ii) —OH, —C(O)O$C_{1-6}$alkyl, —O—$C_{1-6}$alkyl, or —O—$C_{1-3}$ alkyl-phenyl,
(v) —$C_{1-6}$alkyl-O—$C_{1-3}$alkyl unsubstituted or substituted with 1 to 6 of —F,
(vi) =O (oxo),
(vii) —C(O)O$C_{1-6}$alkyl optionally substituted with 1-6 of —F, or
(viii) —C(O)$C_{1-6}$alkyl optionally substituted with 1-6 of —F, or (g)

[structure: indanyl group with ($)_{1-2}$]

unsubstituted or substituted with one or two substituents independently selected at each occurrence from halo; —OH; —C$_{1-6}$alkyl unsubstituted or substituted with 1-6 of —F; —OC$_{1-6}$alkyl unsubstituted or substituted with 1-6 of —F; or —C$_{3-6}$cycloalkyl unsubstituted or substituted with 1-3 of —F.

11. The compound of claim 10, or a pharmaceutically acceptable salt thereof wherein R$^{2b}$ is —H, —C$_{1-3}$alkyl or —OC$_{1-3}$alkyl wherein each of —C$_{1-3}$alkyl or —OC$_{1-3}$alkyl is unsubstituted or substituted with 1 to 3 substituents independently selected from halo, —OH, or —OC$_{1-6}$alkyl.

12. The compound of claim 2, or a pharmaceutically acceptable salt thereof wherein R$^{2a}$ and R$^{2b}$ are joined together with the carbon to which they are both attached to form (a) cyclohexyl, (b) piperidinyl, or (c) tetrahydro-(2H)-furan; wherein each group is unsubstituted or substituted with one or two substituents independently selected at each occurrence from halo; —OH; —C$_{1-3}$alkyl unsubstituted or substituted with 1-3 of —F; —OC$_{1-3}$alkyl unsubstituted or substituted with 1-3 of —F; or —C(O)OC$_{1-3}$ alkyl unsubstituted or substituted with 1-3 of —F.

13. The compound of claim 2, or a pharmaceutically acceptable salt thereof wherein R$^4$ is independently selected at each occurrence from halo.

14. The compound of claim 1, or a pharmaceutically acceptable salt thereof wherein p is 1 or 2.

15. The compound of claim 4 or a pharmaceutically acceptable salt thereof wherein R$^3$ is —H or —C(O)OC$_{1-6}$alkyl.

16. The compound of claim 1 having structural Formula IV, or a pharmaceutically acceptable salt thereof,

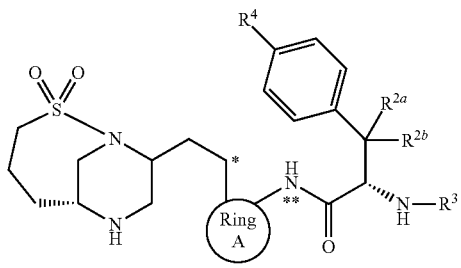

IV wherein R$^{2a}$ is:
(a) —C$_{1-4}$alkyl unsubstituted or substituted with (a) 1 to 3 of —F, (b) —OH or —OC$_{1-3}$alkyl;
(b) cyclohexyl unsubstituted or substituted with (a) 1 to 3 of —F, or (b) —OH or —OC$_{1-3}$alkyl;
(c) phenyl unsubstituted or substituted with 1 to 2 of halo;
(d) pyridyl unsubstituted or substituted with —F, —Cl, —OC$_{1-3}$alkyl, or —C$_{1-3}$alkyl substituted with 1-3 of —F; or (e)

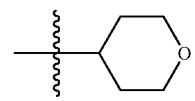

unsubstituted or substituted with 1 to 3 of —C$_{1-3}$alkyl;
R$^{2b}$ is —H;
or R$^{2a}$ and R$^{2b}$ are joined together with the carbon to which they are both attached to form cyclohexyl unsubstituted or substituted with —OC$_{1-3}$ alkyl;
R$^3$ is —H or —C(O)OC$_{1-3}$alkyl;
R$^4$ is —F or —Cl; and
Ring A is (a) cyclohexyl, (b) phenyl substituted with 1-2 of —F, or (c) pyridyl substituted with F.

17. The compound of claim 1 which is:

1) (βS)-N-{2-[2-(2,2-Dioxido-2-thia-1,7-diazabicyclo[4.3.1]dec-9-yl)ethyl]-3-fluorophenyl}-3,5-difluoro-β-(4-fluorophenyl)-L-phenylalaninamide
2) (βS)-N-{2-[2-(2,2-Dioxido-2-thia-1,7-diazabicyclo[4.3.1]dec-9-yl)ethyl]-3-fluorophenyl}-β-(4-fluorophenyl)-3-(trifluoromethyl)-L-phenylalaninamide
3) Methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-3-methylbutyl]carbamate
4) Methyl [(1S,2R)-2-(4-chlorophenyl)-2-(3,3-difluorocyclobutyl)-1-({2-[2-(2,2-dioxido-2-thia-1,7-diazabicyclo[4.3.1]dec-9-yl)ethyl]-3-fluorophenyl}carbamoyl)ethyl]carbamate
5) Methyl [(1S,2R)-2-(4-chlorophenyl)-2-(4,4-difluorocyclohexyl)-1-({2-[2-(2,2-dioxido-2-thia-1,7-diazabicyclo[4.3.1]dec-9-yl)ethyl]-3-fluorophenyl}carbamoyl)ethyl]carbamate
6) (2S,3R)-2-amino-3-(4-chlorophenyl)-N-(2-(2-((6R,9S)-2,2-dioxido-2-thia-1,7-diazabicyclo[4.3.1]decan-9-yl)ethyl)-3-fluorophenyl)-3-((1r,4R)-4-ethoxycyclohexyl)propanamide
7) (βR)-4-Chloro-N-(2-{2-[(6R,9S)-2,2-dioxido-2-thia-1,7-diazabicyclo[4.3.1]dec-9-yl]ethyl}-3-fluorophenyl)-β-[(1r,4R)-4-methoxycyclohexyl]-L-phenylalaninamide
8) Methyl (1R,2S)-1-(4-chlorophenyl)-3-((2-(2-((6R,9S)-2,2-dioxido-2-thia-1,7-diazabicyclo[4.3.1]dec-9-yl)-3-fluorophenyl)amino)-3-oxo-1-((2R,4S)-2-(2,2,2-trifluoroethyl)tetrahydro-2H-pyran-4-yl)propan-2-yl)carbamate
9) Methyl [(1S,2R)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-4-(tetrahydro-2H-pyran-4-yl)butyl]carbamate
10) (2S, 3R)-2-amino-3-(4-chlorophenyl)-3-((S)-2,2-dimethyltetrahydro-2H-pyran-4-yl)-N-(2-(2-((6R,9S)-2,2-dioxido-2-thia-1,7-diazabicyclo[4.3.1]decan-9-yl)ethyl)-3-fluorophenyl)propanamide
11) (βS)-4-Chloro-N-{2-[2-(2,2-dioxido-2-thia-1,7-diazabicyclo[4.3.1]dec-9-yl)ethyl]-3-fluorophenyl}-β-[6-(1-methylethoxy)pyridin-3-yl]L-phenylalaninamide
12) (2S,3S)-2-amino-3-(4-chlorophenyl)-3-(6-(1,1-difluoroethyl)pyridin-3-yl)-N-(2-(2-((6R,9S)-2,2-dioxido-2-thia-1,7-diazabicyclo[4.3.1]decan-9-yl)ethyl)-3-fluorophenyl)propanamide -continued 13) Methyl {(1S)-1-[trans-1-(4-chlorophenyl)-4-methoxycyclohexyl]-2-[(2-2-[(6R,9S)-2,2-dioxido-2-thia-1,7-diazabicyclo[4.3.1]dec-9-yl]ethyl}-3-fluorophenyl)amino]-2-oxoethyl}carbamate
14) Methyl 4-{(1S)-1-amino-2-[(2-{2-[(6R,9S)-2,2-dioxido-2-thia-1,7-diazabicyclo[4.3.1]dec-9-yl]ethyl}]-3-fluorophenyl)amino]-2-oxoethyl}-4-(4-chlorophenyl)piperidine-1-carboxylate
15) β-[(2R,4r,6S)-2,6-Dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-4-fluoro-L-phenylalaninamide
16) Methyl {(1S,2R)-2-(4-chloro-3-fluorophenyl)-2-[(2R,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate
17) (βS)-4-Chloro-N-{2-[2-(2,2-dioxido-2-thia-1,7-diazabicyclo[4.3.1]dec-9-yl)ethyl]-3-fluorophenyl}-β-[2-(1-methylethoxy)pyridin-4-yl]-L-phenylalaninamide
18) Methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(trifluoromethyl)pyridin-4-yl]ethyl}carbamate
19) Methyl {(1S,2S)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-2-[5-(trifluoromethyl)pyridin-3-yl]ethyl}carbamate
20) (βS)-4-Chloro-β-[5-(1,1-difluoroethyl)pyridin-3-yl]-N-{2-[2-(2,2-dioxido-2-thia-1,7-diazabicyclo[4.3.1]dec-9-yl)ethyl]-3-fluorophenyl}-L-phenylalaninamide
21) Methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl-carbamoyl)-2-[6-(trifluoromethyl)pyridin-3-yl]ethyl}carbamate
22) Methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(S)-(4-fluorophenyl)[2-(trifluoromethyl)pyrimidin-5-yl]methyl}-2-oxoethyl]carbamate
23) (βS)-N-(2-{2-[(6R,9S)-2,2-Dioxido-2-thia-1,7-diazabicyclo[4.3.1]dec-9-yl]ethyl}-3-fluorophenyl)-4-fluoro-β-[2-(1-methylethoxy)pyrimidin-5-yl]-L-phenylalaninamide
24) (βR)-4-Chloro-N-[(1S,2R)-2-{2-[(6R,9S)-2,2-dioxido-2-thia-1,7-diazabicyclo[4.3.1]dec-9-yl]ethyl}cyclohexyl]-β-(tetrahydro-2H-pyran-4-yl)-L-phenylalaninamide
25) Methyl [(1S,2R)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-(tetrahydro-2H-pyran-4-yl)ethyl]carbamate
26) Methyl ((2S,3R)-1-((2-(2-((6R,9S)-2,2-dioxido-2-thia-1,7-diazabicyclo[4.3.1]decan-9-yl)ethyl)-3,4-difluorophenyl)amino)-3-(4-fluorophenyl)-3-((1r,4R)-4-methoxycyclohexyl)-1-oxopropan-2-yl)carbamate
27) (2S,3R)-2-Amino-N-(4-(2-((6R,9S)-2,2-dioxido-2-thia-1,7-diazabicyclo[4.3.1]decan-9-yl)ethyl)-5-fluoropyridin-3-yl)-3-(4-fluorophenyl)-3-((1r,4R)-4-methoxycyclohexyl)propanamide
28) Methyl [(1S,2R)-2-(2,2-dimethyltetrahydro-2H-pyran-4-yl)-1-[(2-{2-[(6R,9S)-2,2-dioxido-2-thia-1,7-diazabicyclo[4.3.1dec-9-yl]]ethyl}-3,4-difluorophenyl)carbamoyl]-2-(4-fluorophenyl)ethyl]carbamate
29) Methyl [(1S,2R)-2-(4-chlorophenyl)-2-(2,2-dimethyltetrahydro-2H-pyran-4-yl)-1-{[(1S,2R)-2-{2-[(6R,9S)-2,2-dioxido-2-thia-1,7-diazabicyclo[4.3.1]dec-9-yl]ethyl}cyclopentyl]carbamoyl}ethyl]carbamate
30) Methyl [(1S,2R)-2-[(2R,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-5-fluorophenyl)carbamoyl]-2-(4-fluorophenyl)ethyl]carbamate
31) (2S,3R)-2-Amino-3-(4-chlorophenyl)-3-((2R,4r,6S)-2,6-dimethyltetrahydro-2H-pyran-4-yl)-N-(4-((6R,9S)-2,2-dioxido-2-thia-1,7-diazabicyclo[4.3.1]decan-9-yl)ethyl)-5-fluoropyridin-3-yl)propanamide
32) Methyl [(1S,2R)-2-(4-chlorophenyl)-1-[(2-{2-[(6R,9S)-2,2-dioxido-2-thia-1,7-diazabicyclo[4.3.1]dec-9-yl]ethyl}-3,6-difluorophenyl)carbamoyl]-2-(tetrahydro-2H-pyran-4-yl)ethyl]carbamate
33) (βR)-N-{2-[2-(2,2-Dioxido-2-thia-1,7-diazabicyclo[4.3.1]dec-9-yl)ethyl]-3-fluorophenyl}-β-(4-fluorophenyl)-4-(trifluoromethyl)-L-phenylalaninamide
34) Methyl [(1S,2S)-2-(2,3-dihydro-1H-inden-5-yl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
35) methyl [(1S,2S)-2-(3,5-difluorophenyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
36) (βR)-4-chloro-N-{2-[2-(2,2-dioxido-2-thia-1,7-diazabicyclo[4.3.1]dec-9-yl)ethyl]-3-fluorophenyl}-β-(tetrahydro-2H-pyran-4-yl)-L-phenylalaninamide
37) methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-(tetrahydro-2H-pyran-4-yl)ethyl]carbamate
38) (βR)-4-chloro-N-{2-[2-(2,2-dioxido-2-thia-1,7-diazabicyclo[4.3.1]dec-9-yl)ethyl]-3-fluorophenyl}-β-(1-methylethyl)-L-phenylalaninamide
39) (2S)-2-amino-2-[4,4-difluoro-1-(4-fluorophenyl)cyclohexyl]-N-(2-{2-[(9S)-2,2-dioxido-2-thia-1,7-diazabicyclo[4.3.1]dec-9-yl]ethyl}-3-fluorophenyl)ethanamide
40) (2S)-2-amino-2-[4-(4-chlorophenyl)tetrahydro-2H-pyran-4-yl]-N-(2-{2-[(9S)-2,2-dioxido-2-thia-1,7-diazabicyclo[4.3.1]dec-9-yl]ethyl}-3-fluorophenyl)ethanamide
41) methyl {(1S)-1-[4,4-difluoro-1-(4-fluorophenyl)cyclohexyl]-2-[(2-{2-[(9S)-2,2-dioxido-2-thia-1,7-diazabicyclo[4.3.1]dec-9-yl]ethyl}-3-fluorophenyl)amino]-2-oxoethyl}carbamate 42) methyl {(1S)-1-[4-(4-chlorophenyl)tetrahydro-2H-pyran-4-yl]-2-[(2-{2-[(9S)-2,2-dioxido-2-thia-1,7-diazabicyclo[4.3.1]dec-9-yl]ethyl}-3-fluorophenyl)amino]-2-oxoethyl}carbamate
43) methyl {(1S,2R)-2-(4-chlorophenyl)-2-[(4S)-2,2-dimethyltetrahydro-2H-pyran-4-yl]-1-[(2-{2-[(9S)-2,2-dioxido-2-thia-1,7-diazabicyclo[4.3.1]dec-9-yl]ethyl}-3-fluorophenyl)carbamoyl]ethyl}carbamate
44) (βS)-4-chloro-N-{2-[2-(2,2-dioxido-2-thia-1,7-diazabicyclo[4.3.1]dec-9-yl)ethyl]-3-fluorophenyl}-3-fluoro-β-(5-fluoropyridin-3-yl)-L-phenylalaninamide
45) (βS)-4-chloro-N-{2-[2-(2,2-dioxido-2-thia-1,7-diazabicyclo[4.3.1]dec-9-yl)ethyl]-3-fluorophenyl}-β-(6-methoxypyridin-3-yl)-L-phenylalaninamide
46) methyl [(1S,2S)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-2-(5-fluoropyridin-3-yl)ethyl]carbamate
47) methyl [(1S,2S)-2-(4-chlorophenyl)-1-({2-[2-(2,2-dioxido-2-thia-1,7-diazabicyclo[4.3.1]dec-9-yl)ethyl-fluorophenyl}carbamoyl)-2-(6-methoxypyridin-3-yl)ethyl]carbamate
48) (βR)-4-chloro-β-(3,3-difluorocyclobutyl)-N-{2-[2-(2,2-dioxido-2-thia-1,7-diazabicyclo[4.3.1]dec-9-yl)ethyl]-3-fluorophenyl}-L-phenylalaninamide
49) methyl [(1S)-1-[bis(4-fluorophenyl)methyl]-2-{[(1S,2R)-2-{2-[(6R,9S)-2,2-dioxido-2-thia-1,7-diazabicyclo[4.3.1]dec-9-yl]ethyl}cyclopentyl]amino}-2-oxoethyl]carbamate
50) methyl [(1S,2R)-2-(2,2-dimethyltetrahydro-2H-pyran-4-yl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(4-fluorophenyl)ethyl]carbamate
51) (βS)-3-cyclopropyl-N-{2-[2-(2,2-dioxido-2-thia-1,7-diazabicyclo[4.3.1]dec-9-yl)ethyl]-3-fluorophenyl}-β-(4-fluorophenyl)-L-phenylalaninamide
52) methyl [(1S,2S)-2-(3-cyclopropylphenyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
53) (βR)-4-chloro-β-(4,4-difluorocyclohexyl)-N-{2-[2-(2,2-dioxido-2-thia-1,7-diazabicyclo[4.3.1]dec-9-yl)ethyl]-3-fluorophenyl}-L-phenylalaninamide
54) (βR)-β-(2,2-dimethyltetrahydro-2H-pyran-4-yl)-N-[(1S,2R)-2-{2-{(6R,9S)-2,2-dioxido-2-thia-1,7-diazabicyclo[4.3.1]dec-9-yl]ethyl}cyclopentyl]-4-fluoro-L-phenylalaninamide
55) (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide
56) methyl [(1S,2S)-2-(3,5-difluorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(4-fluorophenyl)ethyl]carbamate
57) (βS)-β-(3,5-difluorophenyl)-N-[(1S,2R)-2-{2-[(6R,9S)-2,2-dioxido-2-thia-1,7-diazabicyclo[4.3.1]dec-9-yl]ethyl}cyclopentyl]-4-fluoro-L-phenylalaninamide
58) methyl [(1S,2R)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(tetrahydro-2H-pyran-4-yl)ethyl]carbamate
59) (βR)-4-cyclopropyl-N-{2-[2-(2,2-dioxido-2-thia-1,7-diazabicyclo[4.3.1]dec-9-yl)ethyl]-3-fluorophenyl}-β-(4-fluorophenyl)-L-phenylalaninamide
60) methyl [(1S,2R)-2-(4-cyclopropylphenyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
61) (βS)-β-(4,4-difluorocyclohexyl)-N-{2-[2-(2,2-dioxido-2-thia-1,7-diazabicyclo[4.3.1]dec-9-yl)ethyl]-3-fluorophenyl}-4-fluoro-L-phenylalaninamide
62) methyl [(1S,2S)-2-(4,4-difluorocyclohexyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
63) methyl [(1S)-2-({2-[2-(2,2-dioxido-2-thia-1,7-diazabicyclo[4.3.1]dec-9-yl)ethyl]-3-fluorophenyl}amino)-1-{(S)-(4-fluorophenyl)[3-(trifluoromethyl)phenyl]methyl}-2-oxoethyl]carbamate
64) (βS)-β-(3,3-difluorocyclobutyl)-N-{2-[2-(2,2-dioxido-2-thia-1,7-diazabicyclo[4.3.1]dec-9-yl)ethyl]-3-fluorophenyl}-4-fluoro-L-phenylalaninamide
65) methyl [(1S,2S)-2-(3,3-difluorocyclobutyl)-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
66) (βS)-N-{2-[2-(2,2-dioxido-2-thia-1,7-diazabicyclo[4.3.1]dec-9-yl)ethyl]-3-fluorophenyl}-3,4-difluoro-β-(6-methoxypyridin-3-yl)-L-phenylalaninamide
67) (βR)-4-chloro-N-{2-[2-(2,2-dioxido-2-thia-1,7-diazabicyclo[4.3.1]dec-9-yl)ethyl]-3-fluorophenyl}-3-fluoro-β-(2-methoxypyridin-4-yl)-L-phenylalaninamide
68) methyl [(1S,2S)-2-(3,4-difluorophenyl)-1-({2-[2-(2,2-dioxido-2-thia-1,7-diazabicyclo[4.3.1]dec-9-yl)ethyl]-3-fluorophenyl}carbamoyl)-2-(6-methoxypyridin-3-yl)ethyl]carbamate
69) methyl [(1S,2R)-2-(4-chloro-3-fluorophenyl)-1-({2-[2-(2,2-dioxido-2-thia-1,7-diazabicyclo[4.3.1]dec-9-yl)ethyl]-3-fluorophenyl}carbamoyl)-2-(2-methoxypyridin-4-yl)ethyl]carbamate
70) (βR)-4-chloro-N-{2-[2-(2,2-dioxido-2-thia-1,7-diazabicyclo[4.3.1]dec-9-yl)ethyl]-3-fluorophenyl}-β-(1-ethylpropyl)-L-phenylalaninamide
71) methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-3-ethylpentyl]carbamate
72) (βS)-4-chloro-β-(5-chloropyridin-3-yl)-N-{2-[2-(2,2-dioxido-2-thia-1,7-diazabicyclo[4.3.1]dec-9-yl)ethyl]-3-fluorophenyl}-3-fluoro-L-phenylalaninamide -continued 73) methyl [(1S,2S)-2-(4-chloro-3-fluorophenyl)-2-(5-chloropyridin-3-yl)-1-({2-[2-(2,2-dioxido-2-thia-1,7-diazabicyclo[4.3.1]dec-9-yl)ethyl]-3-fluorophenyl}carbamoyl)ethyl]carbamate
74) (βR)-4-chloro-N-{2-[2-(2,2-dioxido-2-thia-1,7-diazabicyclo[4.3.1]dec-9-yl)ethyl]-3-fluorophenyl}-3-fluoro-β-[2-(tetrahydro-2H-pyran-4-yl)ethyl]-L-phenylalaninamide
75) (3S)-3-(4-chloro-3-fluorophenyl)-N-[(1S,2R)-2-{2-[(6R,9S)-2,2-dioxido-2-thia-1,7-diazabicyclo[4.3.1]dec-9-yl]ethyl}cyclopentyl]-3-morpholin-4-ylpropanamide
76) (βS)-4-chloro-N-[(1S,2R)-2-{2-[(6R,9S)-2,2-dioxido-2-thia-1,7-diazabicyclo[4.3.1]dec-9-yl]ethyl}cyclopentyl]-3-fluoro-β-[5-(trifluoromethyl)pyridin-3-yl]-L-phenylalaninamide
77) methyl [(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(5-fluoropyridin-3-yl)ethyl]carbamate
78) methyl [(1S,2S)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(6-methoxypyridin-3-yl)ethyl]carbamate
79) methyl {(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-[5-(trifluoromethyl)pyridin-3-yl]ethyl}carbamate
80) (βS)-4-chloro-N-[(1S,2R)-2-{2-[(6R,9S)-2,2-dioxido-2-thia-1,7-diazabicyclo[4.3.1]dec-9-yl]ethyl}cyclopentyl]-β-(6-methoxypyridin-3-yl)-L-phenylalaninamide
81) (βS)-4-chloro-N-[(1S,2R)-2-{2-[(6R,9S)-2,2-dioxido-2-thia-1,7-diazabicyclo[4.3.1]dec-9-yl]ethyl}cyclopentyl]-3-fluoro-β-(5-fluoropyridin-3-yl)-L-phenylalaninamide
82) methyl {(1S)-2-{[(1S,2R)-2-{2-[(6R,9S)-2,2-dioxido-2-thia-1,7-diazabicyclo[4.3.1]dec-9-yl]ethyl}cyclopentyl]amino}-1-[(S)-(6-methoxypyridin-3-yl)(phenyl)methyl]-2-oxoethyl}carbamate
83) methyl [(1S)-2-[(2R,4r,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]-2-(4-fluorophenyl)ethyl]carbamate
84) (βS)-β-(3,5-difluorophenyl)-N-{2-[(2,2-dioxido-2-thia-1,7-diazabicyclo[4.3.1]dec-9-yl)methoxy]-3-fluorophenyl}-4-fluoro-L-phenylalaninamide
85) methyl [(1S,2S)-2-(3,5-difluorophenyl)-1-({2-[(2,2-dioxido-2-thia-1,7-diazabicyclo[4.3.1]dec-9-yl)methoxy]-3-fluorophenyl}carbamoyl)-2-(4-fluorophenyl)ethyl]carbamate
86) (βR)-β-bicyclo[1.1.1]pent-1-yl-N-{2-[2-(2,2-dioxido-2-thia-1,7-diazabicyclo[4.3.1]dec-9-yl)ethyl]-3-fluorophenyl}-4-fluoro-L-phenylalaninamide
87) methyl [(1S,2R)-2-bicyclo[1.1.1]pent-1-yl-1-({2-[2-(2,2-dioxido-2-thia-1,7-diazabicyclo[4.3.1]dec-9-yl)ethyl]-3-fluorophenyl}carbamoyl)-2-(4-fluorophenyl)ethyl]carbamate
88) (βR)-N-(2-{2-[(6R)-2,2-dioxido-2-thia-1,7-diazabicyclo[4.3.1]dec-9-yl]ethyl}-3-fluorophenyl)-4-fluoro-β-[(1R)-1-methoxy-2-methylpropyl]-L-phenylalaninamide
89) (βS)-4-chloro-N-{2-[2-(2,2-dioxido-2-thia-1,7-diazabicyclo[4.3.1]dec-9-yl)ethyl]-3-fluorophenyl}-β-[6-(trifluoromethyl)pyridin-3-yl]-L-phenylalaninamide
90) methyl [(1S,2R)-1-[(2-{2-[(6R)-2,2-dioxido-2-thia-1,7-diazabicyclo[4.3.1]dec-9-yl]ethyl}-3-fluorophenyl)carbamoyl]-2-(4-fluorophenyl)-4-methylpentyl]carbamate
91) (βR)-4-chloro-N-(2-{2-[(6R,9S)-2,2-dioxido-2-thia-1,7-diazabicyclo[4.3.1]dec-9-yl]ethyl}-3,6-difluorophenyl)-β-(tetrahydro-2H-pyran-4-yl)-L-phenylalaninamide
92) methyl [(1S)-1-[bis(4-fluorophenyl)methyl]-2-{[(1S,2R)-2-{2-[(6R,9S)-2,2-dioxido-2-thia-1,7-diazabicyclo[4.3.1]dec-9-yl]ethyl}cyclohexyl]amino}-2-oxoethyl]carbamate
93) N-[(1S,2R)-2-{2-[(6R,9S)-2,2-dioxido-2-thia-1,7-diazabicyclo[4.3.1]dec-9-yl]ethyl}cyclohexyl]-4-fluoro-β-(4-fluorophenyl)-L-phenylalaninamide
94) methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[6-(1-methylethoxy)pyridin-3-yl]ethyl}carbamate
95) (βS)-4-chloro-N-{2-[2-(2,2-dioxido-2-thia-1,7-diazabicyclo[4.3.1]dec-9-yl)ethyl]-3-fluorophenyl}-β-[1-(1-methylethyl)-6-oxo-1,6-dihydropyridin-3-yl]-L-phenylalaninamide
96) methyl [(1S,2R)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-3-methylbutyl]carbamate
97) methyl {(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-[5-(trifluoromethyl)pyridin-3-yl]ethyl}carbamate
98) methyl [(1S,2S)-2-(4-chlorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-(6-methoxypyridin-3-yl)ethyl]carbamate
99) methyl [(1S,2S)-2-(4-chloro-3-fluorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}-2-(5-fluoropyridin-3-yl)ethyl]carbamate
100) methyl [(1S,2S)-2-(4-chlorophenyl)-2-(3,5-difluorophenyl)-1-{[(1S,2R)-2-{2-[(6R,9S)-2,2-dioxido-2-thia-1,7-diazabicyclo[4.3.1]dec-9-yl]ethyl}cyclohexyl]carbamoyl}ethyl]carbamate
101) methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[1-(1-methylethyl)-6-oxo-1,6-dihydropyridin-3-yl]ethyl}carbamate
102) methyl {(1S)-2-[(2-{2-[(6R,9S)-3,3-dimethyl-2,2-dioxido-2-thia-1,7-diazabicyclo[4.3.1]dec-9-yl]ethyl}-3-fluorophenyl)amino]-1-[(R)-[(2R,4r,6S)-2,6-dimethyltetrahydro-2H-pyran-4-yl](4-fluorophenyl)methyl]-2-oxoethyl}carbamate 103) methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-(4-fluorophenyl)(tetrahydro-2H-pyran-2-yl)methyl]-2-oxoethyl}carbamate
104) (βR)-N-(2-{2-[(6R,9S)-2,2-dioxido-2-thia-1,7-diazabicyclo[4.3.1]dec-9-yl]ethyl}-3-fluorophenyl)-4-fluoro-β-(tetrahydro-2H-pyran-2-yl)-L-phenylalaninamide
105) methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(R)-(4-fluorophenyl)[(1s,3S)-3-methoxycyclobutyl]methyl}-2-oxoethyl]carbamate
106) (βR)-N-(2-{2-[(6R,9S)-2,2-dioxido-2-thia-1,7-diazabicyclo[4.3.1]dec-9-yl]ethyl}-3-fluorophenyl)-4-fluoro-β-[(1s,3S)-3-methoxycyclobutyl]-L-phenylalaninamide
107) (βR)-β-[(2R,4s,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclopentyl]-4-fluoro-L-phenylalaninamide
108) methyl [(1S,2R)-2-[(2R,4s,6S)-2,6-dimethyltetrahydro-2H-pyran-4-yl]-1-{[(1S,2R)-2-{2-[(6R,9S)-2,2-dioxido-2-thia-1,7-diazabicyclo[4.3.1]dec-9-yl]ethyl}cyclopentyl]carbamoyl}-2-(4-fluorophenyl)ethyl]carbamate
109) methyl [(1S,2R)-2-[(2R,6S)-2,6-dimethyltetrahydro-2H-pyran-4-yl]-1-[(3-fluoro-2-{2-[(6R,9S)-3-methyl-2,2-dioxido-2-thia-1,7-diazabicyclo[4.3.1]dec-9-yl]ethyl}phenyl)carbamoyl]-2-(4-fluorophenyl)ethyl]carbamate
110) (βR)-β-[(2R,6S)-2,6-dimethyltetrahydro-2H-pyran-4-yl]-4-fluoro-N-(3-fluoro-2-{2-[(6R,9S)-3-methyl-2,2-dioxido-2-thia-1,7-diazabicyclo[4.3.1]dec-9-yl]ethyl}phenyl)-L-phenylalaninamide
112) methyl [(1S,2R)-2-[(2R,6R)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]-2-(4-fluorophenyl)ethyl]carbamate
113) (βR)-β-[(2R,6R)-2,6-dimethyltetrahydro-2H-pyran-4-yl]N-(2-{2-[(6R,9S)-2,2-dioxido-2-thia-1,7-diazabicyclo[4.3.1]dec-9-yl]ethyl}-3-fluorophenyl)-4-fluoro-L-phenylalaninamide
114) methyl [(1S,2S)-2-(4-chlorophenyl)-2-[5-(1,1-difluoroethyl)pyridin-3-yl]-1-({2-[2-(2,2-dioxido-2-thia-1,7-diazabicyclo[4.3.1]dec-9-yl)ethyl]-3-fluorophenyl}carbamoyl)ethyl]carbamate
115) methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-(4-fluorophenyl)(tetrahydro-2H-pyran-2-yl)methyl]-2-oxoethyl}carbamate
116) methyl [(1S,2S)-2-(4-chlorophenyl)-2-[6-(1,1-difluoroethyl)pyridin-3-yl]-1-({2-[2-(2,2-dioxido-2-thia-1,7-diazabicyclo[4.3.1]dec-9-yl)ethyl]-3-fluorophenyl}carbamoyl)ethyl]carbamate
117) methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(R)-(4-fluorophenyl)[(1r,4R)-4-methoxycyclohexyl]methyl}-2-oxoethyl]carbamate
118) (βR)-N-(2-{2-[(6R,9S)-2,2-dioxido-2-thia-1,7-diazabicyclo[4.3.1]dec-9-yl]ethyl}-3-fluorophenyl)-4-fluoro-β-[(1r,4R)-4-methoxycyclohexyl]-L-phenylalaninamide
119) (βR)-N-(2-{2-[(6R,9S)-2,2-dioxido-2-thia-1,7-diazabicyclo[4.3.1]dec-9-yl]ethyl}-3-fluorophenyl)-4-fluoro-β-(tetrahydro-2H-pyran-2-yl)-L-phenylalaninamide
120) methyl {(1S,2R)-2-(4-chlorophenyl)-2-[(2R,4r,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate
121) (βR)-4-chloro-β-[(2R,4r,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-L-phenylalaninamide
122) methyl {(1S,2S)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethoxy)pyridin-4-yl]ethyl}carbamate
123) (βS)-4-chloro-N-{2-[2-(2,2-dioxido-2-thia-1,7-diazabicyclo[4.3.1]dec-9-yl)ethyl]-3-fluorophenyl}-β-[2-(trifluoromethyl)pyridin-4-yl]-L-phenylalaninamide
124) (βR)-4-chloro-N-{2-[2-(2,2-dioxido-2-thia-1,7-diazabicyclo[4.3.1]dec-9-yl)ethyl]-3-fluorophenyl}-β-[2-(1-methylethyl)tetrahydro-2H-pyran-4-yl]-L-phenylalaninamide
125) methyl {(1S)-1-[cis-1-(4-chlorophenyl)-4-methoxycyclohexyl]-2-[(2-{2-[(6R,9S)-2,2-dioxido-2-thia-1,7-diazabicyclo[4.3.1]dec-9-yl]ethyl}-3-fluorophenyl)amino]-2-oxoethyl}carbamate
126) (2S)-2-amino-2-[cis-1-(4-chlorophenyl)-4-methoxycyclohexyl]-N-(2-{2-[(6R,9S)-2,2-dioxido-2-thia-1,7-diazabicyclo[4.3.1]dec-9-yl]ethyl}-3-fluorophenyl)ethanamide
128) methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(1-methylethyl)tetrahydro-2H-pyran-4-yl]ethyl}carbamate
129) (βR)-4-chloro-β-[(4S)-2,2-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-L-phenylalaninamide
131) methyl [(1S,2R)-2-(4-chlorophenyl)-2-[(4R)-2,2-dimethyltetrahydro-2H-pyran-4-yl]-1-{[(1S,2R)-2-{2-[(6R,9S)-2,2-dioxido-2-thia-1,7-diazabicyclo[4.3.1]dec-9-yl]ethyl}cyclohexyl]carbamoyl}ethyl]carbamate
132) (βS)-N-(2-{2-[(6R,9S)-2,2-dioxido-2-thia-1,7-diazabicyclo[4.3.1]dec-9-yl]ethyl}-3-fluorophenyl)-4-fluoro-β-[2-(trifluoromethyl)pyrimidin-5-yl]-L-phenylalaninamide
137) benzyl 4-{(1R,2R)-1-(4-chlorophenyl)-3-{[(1S,2R)-2-{2-[(6R,9S)-2,2-dioxido-2-thia-1,7-diazabicyclo[4.3.1]dec-9-yl]ethyl}cyclopentyl]amino}-2-[(methoxycarbonyl)amino]-3-oxopropyl}piperidine-1-carboxylate
138) 1-methylcyclopropyl 4-{(1R,2R)-1-(4-chlorophenyl)-3-{[(1S,2R)-2-{2-[(6R,9S)-2,2-dioxido-2-thia-1,7-diazabicyclo[4.3.1]dec-9-yl]ethyl}cyclopentyl]amino}-2-[(methoxycarbonyl)amino]-3-oxopropyl}piperidine-1-carboxylate -continued 139) N-(2-{2-[(9S)-2,2-dioxido-2-thia-1,7-diazabicyclo[4.3.1]dec-9-yl]ethyl}-3-fluorophenyl)-4-fluoro-β-(3-fluoropropyl)-β-(methoxymethyl)-L-phenylalaninamide
141) methyl [(1S)-1-[(2-{2-[(9S)-2,2-dioxido-2-thia-1,7-diazabicyclo[4.3.1]dec-9-yl]ethyl}-3-fluorophenyl)carbamoyl]-5-fluoro-2-(4-fluorophenyl)-2-(methoxymethyl)pentyl]carbamate
143) (βR)-4-chloro-N-(2-{2-[(6R,9S)-2,2-dioxido-2-thia-1,7-diazabicyclo[4.3.1]dec-9-yl]ethyl}-3,5-difluorophenyl)-β-(tetrahydro-2H-pyran-4-yl)-L-phenylalaninamide
144) methyl [(1S,2R)-2-(4-chlorophenyl)-1-[(2-{2-[(6R,9S)-2,2-dioxido-2-thia-1,7-diazabicyclo[4.3.1]dec-9-yl]ethyl}-3,5-difluorophenyl)carbamoyl]-2-(tetrahydro-2H-pyran-4-yl)ethyl]carbamate
145) (βS)-4-chloro-N-[(1S,2R)-2-{2-[(6R,9S)-2,2-dioxido-2-thia-1,7-diazabicyclo[4.3.1]dec-9-yl]ethyl}cyclohexyl]-3-fluoro-β-(5-fluoropyridin-3-yl)-L-phenylalaninamide
146) (βR)-β-[(2R,4r,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3,6-difluorophenyl)-4-fluoro-L-phenylalaninamide
147) methyl [(1S,2R)-2-[(2R,4r,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3,6-difluorophenyl)carbamoyl]-2-(4-fluorophenyl)ethyl]carbamate
148) (βR)-β-[(4S)-2,2-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-4-fluoro-L-phenylalaninamide
149) (βR)-β-[(2R,4r,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-4-fluoro-L-phenylalaninamide
150) (βS)-4-chloro-N-[(1S,2R)-2-{2-[(6R,9S)-2,2-dioxido-2-thia-1,7-diazabicyclo[4.3.1]dec-9-yl]ethyl}6cyclohexyl]-3-fluoro-β-[5-(trifluoromethyl)pyridin-3-yl]-L-phenylalaninamide
151) (βR)-4-chloro-N-{2-[2-(2,2-dioxido-2-thia-1,7-diazabicyclo[4.3.1]dec-9-yl)ethyl]-3-fluorophenyl}-β-[2-(tetrahydro-2H-pyran-2-yl)ethyl]-L-phenylalaninamide
153) methyl [(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl]-4-(tetrahydro-2H-pyran-2-yl)butyl]carbamate
155) (βS)-4-chloro-N-[(1S,2R)-2-{2-[(6R,9S)-2,2-dioxido-2-thia-1,7-diazabicyclo[4.3.1]dec-9-yl]ethyl}cyclohexyl]-β-(6-methoxypyridin-3-yl)-L-phenylalaninamide
156) (βR)-N-[(1S,2R)-2-{2-[(6R,9S)-2,2-dioxido-2-thia-1,7-diazabicyclo[4.3.1]dec-9-yl]ethyl}cyclohexyl]-4-fluoro-β-(tetrahydro-2H-pyran-4-yl)-L-phenylalaninamide
157) (βR)-4-chloro-β-(1,1-dioxidotetrahydro-2H-thiopyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide
158) (βR)-4-chloro-β-(1,1-dioxidotetrahydro-2H-thiopyran-4-yl)-N-(2-{2-[(9S)-2,2-dioxido-2-thia-1,7-diazabicyclo[4.3.1]dec-9-yl]ethyl}-3-fluorophenyl)-L-phenylalaninamide
159) methyl {(1S,2R)-2-(4-chlorophenyl)-2-(1,1-dioxidotetrahydro-2H-thiopyran-4-yl)-1-[(2-{2-[(9S)-2,2-dioxido-2-thia-1,7-diazabicyclo[4.3.1]dec-9-yl]ethyl}-3-fluorophenyl)carbamoyl]ethyl}carbamate
160) (βS)-β-(4-chlorophenyl)-N-[(1S,2R)-2-{2-[(6R,9S)-2,2-dioxido-2-thia-1,7-diazabicyclo[4.3.1]dec-9-yl]ethyl}cyclohexyl]-3,5-difluoro-L-phenylalaninamide
161) (βR)-4-chloro-N-[(1S,2R)-2-{2-[(6R,9S)-2,2-dioxido-2-thia-1,7-diazabicyclo[4.3.1]dec-9-yl]ethyl}cyclohexyl]-β-(1-methylethyl)-L-phenylalaninamide
162) (βR)-4-chloro-β-[(2R,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]-L-phenylalaninamide
163) (βR)-4-chloro-N-{2-[2-(2,2-dioxido-2-thia-1,7-diazabicyclo[4.3.1]dec-9-yl)ethyl]-3-fluorophenyl}-β-[2-(2,2,2-trifluoroethyl)tetrahydro-2H-pyran-4-yl]-L-phenylalaninamide
165) (βR)-4-chloro-β-[(2R,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)-3-fluoro-L-phenylalaninamide
166) (βR)-β-[(2R,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3,4-difluorophenyl)-4-fluoro-L-phenylalaninamide
167) methyl {(1S)-1-[(2R,4r,6S)-4-(4-chlorophenyl)-2,6-dimethyltetrahydro-2H-pyran-4-yl]-2-[(2-{2-[(6R,9S)-2,2-dioxido-2-thia-1,7-diazabicyclo[4.3.1]dec-9-yl]ethyl}-3-fluorophenyl)amino]-2-oxoethyl}carbamate
168) (2S)-2-amino-2-[(2R,4r,6S)-4-(4-chlorophenyl)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-3-fluorophenyl)ethanamide
169) methyl [(1S)-1-[(2R,4r,6S)-4-(4-chlorophenyl)-2,6-dimethyltetrahydro-2H-pyran-4-yl]-2-{[(1S,2R)-2-{2-[(6R,9S)-2,2-dioxido-2-thia-1,7-diazabicyclo[4.3.1]dec-9-yl]ethyl}cyclohexyl]amino}-2-oxoethyl]carbamate
170) (2S)-2-amino-2-[(2R,4r,6S)-4-(4-chlorophenyl)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclohexyl]ethanamide
171) (2S)-2-amino-2-[trans-1-(4-chlorophenyl)-4-methoxycyclohexyl]-N-(2-{2-[(6R,9S)-2,2-dioxido-2-thia-1,7-diazabicyclo[4.3.1]dec-9-yl]ethyl}-3-fluorophenyl)ethanamide
172) methyl {(1S,2R)-2-(4-chlorophenyl)-1-({2-[2-(2,2-dioxido-2-thia-1,7-diazabicyclo[4.3.1]dec-9-yl)ethyl]-3-fluorophenyl}carbamoyl)-2-[2-(2,2,2-trifluoroethyl)tetrahydro-2H-pyran-4-yl]ethyl}carbamate
173) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-(tetrahydro-2H-pyran-4-yl)-L-phenylalaninamide 174) methyl [(1S,2R)-2-(4-chlorophenyl)-1-[(4-{2-[(6R,9S)-2,2-dioxido-2-thia-1,7-diazabicyclo[4.3.1]dec-9-yl]ethyl}-5-fluoropyridin-3-yl)carbamoyl]-2-(tetrahydro-2H-pyran-4-yl)ethyl]carbamate
177) (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-propyl-L-phenylalaninamide
178) methyl {(1S)-2-[(4-{2-[(6R,9S)-2,2-dioxido-2-thia-1,7-diazabicyclo[4.3.1]dec-9-yl]ethyl}-5-fluoropyridin-3-yl)amino]-1-[(R)-(4-fluorophenyl)(tetrahydro-2H-pyran-4-yl)methyl]-2-oxoethyl}carbamate
179) (βR)-β-(2,2-dimethyltetrahydro-2H-pyran-4-yl)-N-(2-{2-[(6R,9S)-2,2-dioxido-2-thia-1,7-diazabicyclo[4.3.1]dec-9-yl]ethyl}-3,4-difluorophenyl)-4-fluoro-L-phenylalaninamide
180) (βR)-N-(2-{2-[(6R,9S)-2,2-dioxido-2-thia-1,7-diazabicyclo[4.3.1]dec-9-yl]ethyl}-3,4-difluorophenyl)-4-fluoro-β-[(1r,4R)-4-methoxycyclohexyl]-L-phenylalaninamide
182) (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-(2-methoxyethyl)-L-phenylalaninamide
183) (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-[(1S)-1-methylpropyl]-L-phenylalaninamide
184) (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-(4,4,4-trifluorobutyl)-L-phenylalaninamide
185) (2S)-2-amino-2-[4-(4-chlorophenyl)piperidin-4-yl]-N-(2-{2-[(6R,9S)-2,2-dioxido-2-thia-1,7-diazabicyclo[4.3.1]dec-9-yl]ethyl}-3-fluorophenyl)ethanamide
187) methyl {(1S,2R)-2-(4-chlorophenyl)-1-[(2-{2-[(6R,9S)-2,2-dioxido-2-thia-1,7-diazabicyclo[4.3.1]dec-9-yl]ethyl}-3-fluorophenyl)carbamoyl]-2-[(1r,4R)-4-methoxycyclohexyl]ethyl}carbamate
188) (βR)-β-[(2R,6S)-2,6-dimethyltetrahydro-2H-pyran-4-yl]-N-(2-{2-[(6R,9S)-2,2-dioxido-2-thia-1,7-diazabicyclo[4.3.1]dec-9-yl]ethyl}-5-fluorophenyl)-4-fluoro-L-phenylalaninamide
189) (βR)-N-[(1S,2R)-2-{2-[(6R,9S)-2,2-dioxido-2-thia-1,7-diazabicyclo[4.3.1]dec-9-yl]ethyl}cyclohexyl]-4-fluoro-β-[(1r,4R)-4-methoxycyclohexyl]-L-phenylalaninamide
190) methyl {(1S)-2-[(2-{2-[(6R,9S)-2,2-dioxido-2-thia-1,7-diazabicyclo[4.3.1]dec-9-yl]ethyl}-3-fluorophenyl)amino]-[(R)-[(2S,4S)-2-ethyltetrahydro-2H-pyran-4-yl](4-fluorophenyl)methyl]-2-oxoethyl}carbamate
191) (βR)-N-(2-{2-[(6R,9S)-2,2-dioxido-2-thia-1,7-diazabicyclo[4.3.1]dec-9-yl]ethyl}-3-fluorophenyl)-β-[(2S,4S)-2-ethyltetrahydro-2H-pyran-4-yl]-4-fluoro-L-phenylalaninamide
194) (βR)-4-chloro-β-[(4S)-2,2-dimethyltetrahydro-2H-pyran-4-yl]-N-(2-{2-[(6R,9S)-2,2-dioxido-2-thia-1,7-diazabicyclo[4.3.1]dec-9-yl]ethyl}-3,6-difluorophenyl)-L-phenylalaninamide
195) (βR)-N-(4-{2-[(6R,9S)-2,2-dioxido-2-thia-1,7-diazabicyclo[4.3.1]dec-9-yl]ethyl}-5-fluoropyridin-3-yl)-4-fluoro-β-(tetrahydro-2H-pyran-4-yl)-L-phenylalaninamide
196) (βR)-4-chloro-β-[(2R,4s,6S)-2,6-dimethyltetrahydro-2H-pyran-4-yl]-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide
197) (βR)-4-chloro-N-(2-{2-[(9S)-2,2-dioxido-2-thia-1,7-diazabicyclo[4.3.1]dec-9-yl]ethyl}-3-fluorophenyl)-β-(3-methoxycyclohexyl)-L-phenylalaninamide
200) methyl {(1S,2R)-2-(4-chlorophenyl)-2-[(4S)-2,2-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3,6-difluorophenyl)carbamoy]ethyl}carbamate
201) methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(R)-(4-fluorophenyl)[(1r,4R)-4-hydroxycyclohexyl]methyl}-2-oxoethyl]carbamate
202) (βR)-N-(2-{2-[(6R,9S)-2,2-dioxido-2-thia-1,7-diazabicyclo[4.3.1]dec-9-yl]ethyl}-3-fluorophenyl)-4-fluoro-β-[(1r,4R)-4-hydroxycyclohexyl]-L-phenylalaninamide
203) methyl [(1S,2R)-2-[(2R,6S)-2,6-dimethyltetrahydro-2H-pyran-4-yl]-1-{[2-{2-[6R,9S)-2,2-dioxido-2-thia-1,7-diazabicyclo[4.3.1]dec-9-yl]ethyl}-3-(trifluoromethyl)phenyl]carbamoyl}-2-(4-fluorophenyl)ethyl]carbamate
204) (βR)-β-[(2R,6S)-2,6-dimethyltetrahydro-2H-pyran-4-yl]-N-[2-{2-[(6R,9S)-2,2-dioxido-2-thia-1,7-diazabicyclo[4.3.1]dec-9-yl]ethyl}-3-(trifluoromethyl)phenyl]-4-fluoro-L-phenylalaninamide
205) (2S)-2-amino-N-(2-{2-[(6R,9S)-2,2-dioxido-2-thia-1,7-diazabicyclo[4.3.1]dec-9-yl]ethyl}-3-fluorophenyl)-2-[trans-1-(4-fluorophenyl)-4-methoxycyclohexyl]ethanamide
206) methyl [(1S)-2-[(2-{2-[(6R,9S)-2,2-dioxido-2-thia-1,7-diazabicyclo[4.3.1]dec-9-yl]ethyl}-3-fluorophenyl)amino]-1-{(S)-(4-fluorophenyl)[2-(1-methylethoxy)pyrimidin-5-yl]methyl}-2-oxoethyl]carbamate
207) (βR)-4-chloro-N-[(1S,2R)-2-{2-[(6R,9S)-2,2-dioxido-2-thia-1,7-diazabicyclo[4.3.1]dec-9-yl]ethyl}cyclohexyl]-β-[(1r,4R)-4-methoxycyclohexyl]-L-phenylalaninamide
208) 1-methylcyclopropyl 4-[(1R,2S)-2-amino-1-(4-chlorophenyl)-3-{[(1S,2R)-2-{2-[(6R,9S)-2,2-dioxido-2-thia-1,7-diazabicyclo[4.3.1]dec-9-yl]ethyl}cyclopentyl]amino}-3-oxopropyl]piperidine-1-carboxylate
209) N-(2-{2-[(6R,9S)-2,2-dioxido-2-thia-1,7-diazabicyclo[4.3.1]dec-9-yl]ethyl}-3-fluorophenyl)-4-fluoro-β-[5-(trifluoromethyl)pyridin-2-yl]phenylalaninamide -continued 210) methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[trans-1-(4-fluorophenyl)-4-methoxycyclohexyl]-2-oxoethyl}carbamate
211) methyl {(1S)-2-[(2-{2-[(6R,9S)-2,2-dioxido-2-thia-1,7-diazabicyclo[4.3.1]dec-9-yl]ethyl}-3-fluorophenyl)amino]-1-[(R)-[(1r,4R)-4-ethoxycyclohexyl](4-fluorophenyl)methyl]-2-oxoethyl}carbamate
212) (βR)-N-(2-{2-[(6R,9S)-2,2-dioxido-2-thia-1,7-diazabicyclo[4.3.1]dec-9-yl]ethyl}-3-fluorophenyl)-β-[(1r,4R)-4-ethoxycyclohexyl]-4-fluoro-L-phenylalaninamide
215) (βR)-4-chloro-β-[(4S)-2,2-dimethyltetrahydro-2H-pyran-4-yl]-N-(4-{2-[(6R,9S)-2,2-dioxido-2-thia-1,7-diazabicyclo[4.3.1]dec-9-yl]ethyl}-5-fluoropyridin-3-yl)-L-phenylalaninamide
216) methyl (2-[(2-{2-[(6R,9S)-2,2-dioxido-2-thia-1,7-diazabicyclo[4.3.1]dec-9-yl]ethyl}-3-fluorophenyl)amino]-1-{(4-fluorophenyl)[5-(trifluoromethyl)pyridin-2-yl]methyl}-2-oxoethyl)carbamate
217) (βR)-4-chloro-N-(2-{2-[(6R,9S)-2,2-dioxido-2-thia-1,7-diazabicyclo[4.3.1]dec-9-yl]ethyl}-3-fluorophenyl)-β-[(1r,4R)-4-hydroxycyclohexyl]-L-phenylalaninamide
224) Methyl [(1S)-2-({2-[2-(2,2-dioxido-2-thia-1,7-diazabicyclo[4.3.1]dec-9-yl]ethyl]-3-fluorophenyl}amino)-1-{(R)-(4-fluorophenyl)[4-(trifluoromethyl)phenyl]methyl}-2-oxoethyl]carbamate
225) (2S,3S)-2-Amino-3-(2,3-dihydro-1H-inden-5-yl)-N-{2-[2-(2,2-dioxido-2-thia-1,7-diazabicyclo[4.3.1]dec-9-yl)ethyl]-3-fluorophenyl}-3-(4-fluorophenyl)propanamide
227) (βS)-4-Chloro-N-{2-[2-(2,2-dioxido-2-thia-1,7-diazabicyclo[4.3.1]dec-9-yl)ethyl]-3-fluorophenyl}-3-fluoro-β-[5-(trifluoromethyl)pyridin-3-yl]-L-phenylalaninamide
228) Methyl [(1S,2R)-2-[(2R,6S)-2,6-dimethyltetrahydro-2H-pyran-4-yl]-1-[(2-{2-[(6R,9S)-2,2-dioxido-2-thia-1,7-diazabicyclo[4.3.1]dec-9-yl]ethyl}-3,4-difluorophenyl)carbamoyl]-2-(4-fluorophenyl)ethyl]carbamate
229) methyl 4-{[(1S,2R)-2-(4-chlorophenyl)-2-(2,2-dimethyltetrahydro-2H-pyran-4-yl)-1-{[(1S,2R)-2-{2-[(6R,9S)-2,2-dioxido-2-thia-1,7-diazabicyclo[4.3.1]dec-9-yl]ethyl}cyclopentyl]carbamoyl}ethyl]amino}butanoate
230) (βR)-Nα-[2-(benzyloxy)ethyl]-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide
231) (βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-Nα-(2-hydroxyethyl)-L-phenylalaninamide
232) glycyl-(βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide
233) (2S)-2-amino-2-[4-(4-chlorophenyl)tetrahydro-2H-pyran-4-yl]-N-(4-{2-[(6R,9S)-2,2-dioxido-2-thia-1,7-diazabicyclo[4.3.1]dec-9-yl]ethyl}-5-fluoropyridin-3-yl)ethanamide
234) (βS)-4-chloro-N-(4-{2-[(6R,9S)-2,2-dioxido-2-thia-1,7-diazabicyclo[4.3.1]dec-9-yl]ethyl}-5-fluoropyridin-3-yl)-3-fluoro-β-(5-fluoropyridin-3-yl)-L-phenylalaninamide
235) (2S)-2-amino-N-(4-{2-[(6R,9S)-2,2-dioxido-2-thia-1,7-diazabicyclo[4.3.1]dec-9-yl]ethyl}-5-fluoropyridin-3-yl)-2-[trans-1-(4-fluorophenyl)-4-methoxycyclohexyl]ethanamide
236) (βS)-β-(4-chlorophenyl)-N-(4-{2-[(6R,9S)-2,2-dioxido-2-thia-1,7-diazabicyclo[4.3.1]dec-9-yl]ethyl}-5-fluoropyridin-3-yl)-3,5-difluoro-L-phenylalaninamide
237) 2-methylalanyl-(βR)-4-chloro-β-(2,2-dimethyltetrahydro-2H-pyran-4-yl)-N-[(1S,2R)-2-{2-[(6R,9S)-2,2-dioxido-2-thia-1,7-diazabicyclo[4.3.1]dec-9-yl]ethyl}cyclopentyl]-L-phenylalaninamide
238) (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-4-methylpentanamide
239) (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-3-((1r,4R)-4-methoxycyclohexyl)propanamide
240) (2S,3S)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-3-(6-isopropoxypyridin-3-yl)propanamide
241) (2S,3R)-2-amino-3-(4-chlorophenyl)-3-(4,4-difluorocyclohexyl)-N-(4-(24(6R,9S)-2,2-dioxido-2-thia-1,7-diazabicyclo[4.3.1]decan-9-yl)ethyl)-5-fluoropyridin-3-yl)propanamide
242) (2S,3R)-2-amino-3-(4-chlorophenyl)-N-(4-(2-((6R,9S)-2,2-dioxido-2-thia-1,7-diazabicyclo[4.3.1]decan-9-yl)ethyl)-5-fluoropyridin-3-yl)-4-ethylhexanamide
243) (2S,3R)-2-amino-3-(4-chloro-3-fluorophenyl)-3-((S)-2,2-dimethyltetrahydro-2H-pyran-4-yl)-N-(4-(2-((6R,9S)-2,2-dioxido-2-thia-1,7-diazabicyclo[4.3.1]decan-9-yl)ethyl)-5-fluoropyridin-3-yl)propanamide
244) (2S,3R)-2-amino-3-(4-chloro-3-fluorophenyl)-3-cyclohexyl-N-(4-(2-((6R,9S)-2,2-dioxido-2-thia-1,7-diazabicyclo[4.3.1]decan-9-yl)ethyl)-5-fluoropyridin-3-yl)propanamide
245) (2S,3R)-2-amino-3-(4-chloro-3-fluorophenyl)-3-((2R,6S)-2,6-dimethyltetrahydro-2H-pyran-4-yl)-N-(4-(2-((6R,9S)-2,2-dioxido-2-thia-1,7-diazabicyclo[4.3.1]decan-9-yl)ethyl)-5-fluoropyridin-3-yl)propanamide
246) (2S,3S)-2-amino-3-(4-chlorophenyl)-3-(6-(1,1-difluoroethyl)pyridin-3-yl)-N-(4-(2-((6R,9S)-2,2-dioxido-2-thia-1,7-diazabicyclo[4.3.1]decan-9-yl)ethyl)-5-fluoropyridin-3-yl)propanamide
247) (βS)-4-chloro-N-(2-{2-[(6R,9S)-2,2-dioxido-2-thia-1,7-diazabicyclo[4.3.1]dec-9-yl]ethyl}-3-fluorophenyl)-β-[2-(1-methylethoxy)pyrimidin-5-yl]-L-phenylalaninamide 248) (βR)-4-chloro-N-(2-{2-[(6R,9S)-2,2-dioxido-2-thia-1,7-diazabicyclo[4.3.1]dec-9-yl]ethyl}-3-fluorophenyl)-β-[(1r,4R)-4-ethoxycyclohexyl]-3-fluoro-L-phenylalaninamide
249) (βS)-4-chloro-N-(2-{2-[(6R,9S)-2,2-dioxido-2-thia-1,7-diazabicyclo[4.3.1]dec-9-yl]ethyl}-3-fluorophenyl)-3-fluoro-β-[2-(trifluoromethyl)pyrimidin-5-yl]-L-phenylalaninamide
250) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-(1-methylethoxy)cyclohexyl]-L-phenylalaninamide
251) (βR)-4-chloro-N-(2-{2-[(6R,9S)-2,2-dioxido-2-thia-1,7-diazabicyclo[4.3.1]dec-9-yl]ethyl}-3-fluorophenyl)-β-[2-(trifluoromethyl)-1,3-thiazol-4-yl]-L-phenylalaninamide
252) methyl {(1S,2R)-2-(4-chlorophenyl)-1-[(2-{2-[(6R,9S)-2,2-dioxido-2-thia-1,7-diazabicyclo[4.3.1]dec-9-yl]ethyl}-3-fluorophenyl)carbamoyl]-2-[2-(trifluoromethyl)-1,3-thiazol-4-yl]ethyl}carbamate
253) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-ethoxycyclohexyl]-3-fluoro-L-phenylalaninamide
254) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-(methoxymethyl)cyclohexyl]-L-phenylalaninamide
255) ethyl 4-(4-chlorophenyl)-4-{(1S)-2-[(2-{2-[(6R,9S)-2,2-dioxido-2-thia-1,7-diazabicyclo[4.3.1]dec-9-yl]ethyl}-3-fluorophenyl)amino]-1-[(methoxycarbonyl)amino]-2-oxoethyl}piperidine-1-carboxylate
256) methyl {(1S,2R)-2-(4-chlorophenyl)-1-[(4-{2-[(6R,9S)-2,2-dioxido-2-thia-1,7-diazabicyclo[4.3.1]dec-9-yl]ethyl}-5-fluoropyridin-3-yl)carbamoyl]-2-[(1r,4R)-4-(trifluoromethyl)cyclohexyl]ethyl}carbamate
257) methyl {(1S,2R)-2-(4-chlorophenyl)-2-[(1r,4R)-4-(cyclopropyloxy)cyclohexyl]-1-[(2-{2-[(6R,9S)-2,2-dioxido-2-thia-1,7-diazabicyclo[4.3.1]dec-9-yl]ethyl}-3-fluorophenyl)carbamoylethyl}carbamate
258) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[(1r,4R)-4-(ethoxymethyl)cyclohexyl]-L-phenylalaninamide
259) (βR)-4-chloro-N-(2-{2-[(6R,9S)-2,2-dioxido-2-thia-1,7-diazabicyclo[4.3.1]dec-9-yl]ethyl}-3-fluorophenyl)-β-[5-(1-methylethoxy)pyrazin-2-yl]-L-phenylalaninamide
260) (βR)-4-chloro-N-(2-{2-[(6R,9S)-2,2-dioxido-2-thia-1,7-diazabicyclo[4.3.1]dec-9-yl]ethyl}-3-fluorophenyl)-β-[1-methyl-5-(trifluoromethyl)-1H-pyrazol-3-yl]-L-phenylalaninamide
261) (βR)-4-chloro-N-(2-{2-+(6R,9S)-2,2-dioxido-2-thia-1,7-diazabicyclo[4.3.1]dec-9-yl]ethyl}-3-fluorophenyl)-β-[1-methyl-3-(trifluoromethyl)-1H-pyrazol-5-yl]-L-phenylalaninamide
262) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[1-methyl-3-(trifluoromethyl)-1H-pyrazol-5-yl]-L-phenylalaninamide
263) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[5-(1-methylethoxy)pyrazin-2-yl]-L-phenylalaninamide
264) (βR)-4-chloro-N-(2-{2-[(6R,9S)-2,2-dioxido-2-thia-1,7-diazabicyclo[4.3.1]dec-9-yl]ethyl}-3-fluorophenyl)-β-[4-(trifluoromethyl)-1,3-thiazol-2-yl]-L-phenylalaninamide
265) (βR)-4-chloro-N-(2{2-[(6R,9S)-2,2-dioxido-2-thia-1,7-diazabicyclo[4.3.1]dec-9-yl]ethyl}-3-fluorophenyl)-3-fluoro-β-[1-methyl-5-(trifluoromethyl)-1H-pyrazol-3-yl]-L-phenylalaninamide
266) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-3-fluoro-β-[1-methyl-5-(trifluoromethyl)-1H-pyrazol-3-yl]-L-phenylalaninamide
267) (βR)-4-chloro-N-(2-{2-[(6R,9S)-2,2-dioxido-2-thia-1,7-diazabicyclo[4.3.1]dec-9-yl]ethyl}-3-fluorophenyl)-3-fluoro-β-[1-methyl-3-(trifluoromethyl)-1H-pyrazol-5-yl]-L-phenylalaninamide
268) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-3-fluoro-β-[1-methyl-3-(trifluoromethyl)-1H-pyrazol-5-yl]-L-phenylalaninamide
269) (βR)-4-chloro-N-(4-{2-[(6R,9S)-2,2-dioxido-2-thia-1,7-diazabicyclo[4.3.1]dec-9-yl]ethyl}-5-fluoropyridin-3-yl)-β-[2-(trifluoromethyl)-1,3-thiazol-4-yl]-L-phenylalaninamide
270) methyl {(1S)-1-[cis-1-(4-chlorophenyl)-4-(trifluoromethyl)cyclohexyl]-2-[(4-{2-[(6R,9S)-2,2-dioxido-2-thia-1,7-diazabicyclo[4.3.1]dec-9-yl]ethyl}-5-fluoropyridin-3-yl)amino]-2-oxoethyl}carbamate
271) methyl {(1S,2R)-2-(4-chlorophenyl)-2-(6,6-dimethyltetrahydro-2H-pyran-3-yl)-1-[(2-{2-[(6R,9S)-2,2-dioxido-2-thia-1,7-diazabicyclo[4.3.1]dec-9-yl]ethyl}-3-fluorophenyl)carbamoyl]ethyl}carbamate
272) (βR)-4-chloro-β-(3,3-difluorocyclohexyl)-N-(4-{2-[(6R,9S)-2,2-dioxido-2-thia-1,7-diazabicyclo[4.3.1]dec-9-yl]ethyl}-5-fluoropyridin-3-yl)-L-phenylalaninamide, or

| |
|---|
| 273) methyl {(1S,2R)-2-(4-chlorophenyl)-1-[(2-{2-[(6R,9S)-2,2-dioxido-2-thia-1,7-diazabicyclo[4.3.1]dec-9-yl]ethyl}-3-fluorophenyl)carbamoyl]-2-[6-(trifluoromethyl)tetrahydro-2H-pyran-3-yl]ethyl}carbamate; | or a pharmaceutically acceptable salt thereof.

18. A pharmaceutical composition comprising an effective amount of a compound according to claim 1, or a pharmaceutically acceptable salt thereof, and a pharmaceutically acceptable carrier.

19. A method for the treatment of infection by HIV or for the treatment or delay in the onset of AIDS in a subject in need thereof, which comprises administering to the subject an effective amount of the compound of claim 1, or a pharmaceutically acceptable salt thereof.

* * * * *